(12) United States Patent
Matern et al.

(10) Patent No.: US 10,323,075 B2
(45) Date of Patent: Jun. 18, 2019

(54) COMPOSITIONS AND METHODS OF USE FOR TREATING METABOLIC DISORDERS

(71) Applicant: NGM Biopharmaceuticals, Inc., South San Francisco, CA (US)

(72) Inventors: Hugo Matern, San Mateo, CA (US); Darrin Anthony Lindhout, Mountain View, CA (US); Raj Haldankar, Redwood City, CA (US); Geoffrey Horner, San Francisco, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/789,679

(22) Filed: Oct. 20, 2017

(65) Prior Publication Data

US 2018/0100003 A1 Apr. 12, 2018

Related U.S. Application Data

(62) Division of application No. 14/763,262, filed as application No. PCT/US2014/013232 on Jan. 27, 2014, now Pat. No. 9,828,415.

(60) Provisional application No. 61/882,542, filed on Sep. 25, 2013, provisional application No. 61/758,456, filed on Jan. 30, 2013.

(51) Int. Cl.
| | |
|---|---|
| *A61K 38/00* | (2006.01) |
| *A61K 38/18* | (2006.01) |
| *C07K 14/495* | (2006.01) |
| *C07K 14/765* | (2006.01) |
| *A61K 38/16* | (2006.01) |
| *A61K 38/17* | (2006.01) |
| *C07K 14/435* | (2006.01) |

(52) U.S. Cl.
CPC ........ *C07K 14/495* (2013.01); *A61K 38/1841* (2013.01); *C07K 14/765* (2013.01); *A61K 38/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,194,596 | A | 3/1993 | Tischer |
| 5,350,836 | A | 9/1994 | Kopchick |
| 5,876,969 | A | 3/1999 | Fleer et al. |
| 5,994,102 | A | 11/1999 | Hudson et al. |
| 6,051,424 | A | 4/2000 | Kato et al. |
| 6,107,476 | A | 8/2000 | Erlander et al. |
| 6,165,470 | A | 12/2000 | Becquart et al. |
| 6,180,602 | B1 | 1/2001 | Kato et al. |
| 6,420,543 | B1 | 7/2002 | Lee et al. |
| 6,465,181 | B2 | 10/2002 | Biling-Medel et al. |
| 6,500,638 | B2 | 12/2002 | Hudson et al. |
| 6,521,227 | B1 | 2/2003 | Hudson et al. |
| 6,524,802 | B1 | 2/2003 | Lee et al. |
| 6,686,179 | B2 | 2/2004 | Fleer et al. |
| 6,905,688 | B2 | 6/2005 | Rosen et al. |
| 6,972,322 | B2 | 12/2005 | Fleer et al. |
| 6,989,365 | B2 | 1/2006 | Fleer et al. |
| 7,056,701 | B2 | 6/2006 | Fleer et al. |
| 7,081,354 | B2 | 7/2006 | Fleer et al. |
| 7,094,577 | B2 | 8/2006 | Fleer et al. |
| 7,141,661 | B2 | 11/2006 | Eling et al. |
| 7,157,235 | B2 | 1/2007 | Breit et al. |
| 7,244,833 | B2 | 7/2007 | Yu et al. |
| 7,276,593 | B2 | 10/2007 | Vernet et al. |
| 7,282,351 | B2 | 10/2007 | Hudson et al. |
| 7,348,004 | B2 | 3/2008 | Peters et al. |
| 7,410,779 | B2 | 8/2008 | Fleer et al. |
| 7,435,410 | B2 | 10/2008 | Fleer et al. |
| 7,442,371 | B2 | 10/2008 | Yu et al. |
| 7,514,221 | B2 | 4/2009 | Breit et al. |
| 7,754,689 | B2 | 7/2010 | Lu et al. |
| 7,833,521 | B2 | 11/2010 | Fleer et al. |
| 7,863,239 | B2 | 1/2011 | Timmerman et al. |
| 7,919,084 | B2 | 4/2011 | Breit et al. |
| 7,968,303 | B2 | 6/2011 | Breit et al. |
| 8,021,880 | B2 | 9/2011 | Peters et al. |
| 8,067,548 | B2 | 11/2011 | Wang et al. |
| 8,084,021 | B2 | 12/2011 | Yu et al. |
| 8,192,735 | B2 | 6/2012 | Breit et al. |
| 8,222,384 | B2 | 7/2012 | Wolfman et al. |
| 8,252,739 | B2 | 8/2012 | Rosen et al. |
| 8,592,532 | B2 | 11/2013 | Kodate et al. |
| 8,946,146 | B2 | 2/2015 | Breit et al. |
| 8,986,698 | B2 | 3/2015 | Arnason et al. |

(Continued)

FOREIGN PATENT DOCUMENTS

| | | |
|---|---|---|
| EP | 1179067 | 12/2006 |
| EP | 1279039 | 1/2008 |

(Continued)

OTHER PUBLICATIONS

Bauskin et al. (2000) "The Propeptide of Macrophage Inhibitory Cytokine (MIC-1) a TGF-b Superfamily Member Acts as a Quality Control Determinant for Correctly Folded MIC-1" *EMBO J* 19:2212-2220.

Bauskin et al. (2005) "The Propeptide Mediates Formation of Stromal Stores of PROMIC-1: Role in Determining Prostate Cancer Outcome" *Cancer Research* 65(6) 2330-2336.

Bauskin et al. (2010) The TGF-β superfamily cytokine MIC-1GDF15: secretory mechanisms facilitate creation of latent stromal stores Journal of Interferon & Cytokine Research 2010 V. 30 N. 6 p. 389-397.

Benjamin et al. (1998) "A plasticity window for blood vessel remodeling is defined by pericyte coverage of the preformed endothelial network and is regulated by PDGF-B and VEGF" Development 125:1591-1598.

(Continued)

*Primary Examiner* — Elizabeth C. Kemmerer
(74) *Attorney, Agent, or Firm* — Shweta Chandra; Bozicevic, Field & Francis LLP

(57) ABSTRACT

Methods of treating individuals with a glucose metabolism disorder and/or a body weight disorder, and compositions associated therewith, are provided.

34 Claims, 43 Drawing Sheets

Specification includes a Sequence Listing.

(56) References Cited

U.S. PATENT DOCUMENTS

| | | |
|---|---|---|
| 9,161,966 B2 | 10/2015 | Matern et al. |
| 9,550,819 B2 | 1/2017 | Lindhout et al. |
| 2001/0011077 A1 | 8/2001 | Albone et al. |
| 2003/0023073 A1 | 1/2003 | Hsiao et al. |
| 2003/0053431 A1 | 3/2003 | Madour et al. |
| 2003/0232347 A1 | 12/2003 | Anderson et al. |
| 2003/0232385 A1 | 12/2003 | Breit et al. |
| 2004/0029770 A1 | 2/2004 | Baek et al. |
| 2004/0053325 A1 | 3/2004 | Breit et al. |
| 2004/0253207 A1 | 12/2004 | Hruska et al. |
| 2006/0148709 A1 | 7/2006 | Unsicker et al. |
| 2006/0253913 A1 | 11/2006 | Huang et al. |
| 2007/0077598 A1 | 4/2007 | Breit et al. |
| 2007/0166310 A1 | 7/2007 | Hudson et al. |
| 2009/0004181 A1 | 1/2009 | Breit et al. |
| 2009/0042780 A1 | 2/2009 | Knopf et al. |
| 2009/0291889 A1 | 11/2009 | Breit et al. |
| 2010/0112692 A1 | 5/2010 | Rezania et al. |
| 2010/0184217 A1 | 7/2010 | Cegilski et al. |
| 2010/0221777 A1 | 9/2010 | Choe et al. |
| 2010/0261284 A1 | 10/2010 | Spanuth |
| 2010/0266707 A1 | 10/2010 | Breit et al. |
| 2010/0278843 A1 | 11/2010 | Breit et al. |
| 2010/0286067 A1 | 11/2010 | DeFrees |
| 2011/0033886 A1 | 2/2011 | Hess et al. |
| 2011/0039284 A1 | 2/2011 | Breit et al. |
| 2011/0065204 A1 | 3/2011 | Wollert et al. |
| 2011/0107821 A1 | 5/2011 | Hess et al. |
| 2011/0123454 A1 | 5/2011 | Breit et al. |
| 2011/0257022 A1 | 10/2011 | Hess et al. |
| 2011/0262444 A1 | 10/2011 | Kim et al. |
| 2011/0263443 A1 | 10/2011 | Hess et al. |
| 2011/0300562 A1 | 12/2011 | Lambrecht et al. |
| 2012/0107420 A1 | 5/2012 | Breit et al. |
| 2012/0128624 A1 | 5/2012 | Yu et al. |
| 2012/0309697 A1 | 12/2012 | Breit et al. |
| 2013/0004484 A1 | 1/2013 | Demeule et al. |
| 2013/0071935 A1 | 3/2013 | Bergman et al. |
| 2013/0323835 A1 | 12/2013 | McDonald et al. |
| 2014/0213511 A1 | 1/2014 | Matern et al. |
| 2014/0044674 A1 | 2/2014 | Duerner et al. |
| 2014/0086915 A1 | 3/2014 | Breit et al. |
| 2014/0113370 A1 | 4/2014 | Camphausen et al. |
| 2014/0193427 A1 | 7/2014 | Lerner et al. |
| 2014/0199294 A1 | 7/2014 | Mimoto et al. |
| 2014/0314711 A1 | 10/2014 | Scheer et al. |
| 2015/0023960 A1 | 1/2015 | Lindhout et al. |
| 2015/0322081 A1 | 11/2015 | Hoehn |
| 2016/0031960 A1 | 2/2016 | Lindhout et al. |
| 2016/0120999 A1 | 5/2016 | Shen et al. |
| 2016/0129082 A1 | 5/2016 | Matern et al. |
| 2016/0193295 A1 | 7/2016 | Kannan |
| 2016/0200787 A1 | 7/2016 | Matern et al. |

FOREIGN PATENT DOCUMENTS

| | | |
|---|---|---|
| EP | 1914554 | 4/2008 |
| EP | 0833912 | 2/2009 |
| EP | 2383571 | 11/2011 |
| EP | 2439535 | 4/2012 |
| EP | 2441466 | 4/2012 |
| EP | 2774620 A1 | 9/2014 |
| EP | 2929891 A1 | 10/2015 |
| JP | 07-258293 | 10/1995 |
| JP | 1995250688 | 10/1995 |
| JP | 2003532079 | 10/2003 |
| JP | 2006505617 | 2/2006 |
| JP | 2009539767 | 11/2009 |
| WO | WO199403599 | 2/1994 |
| WO | WO199618730 | 6/1996 |
| WO | WO199700958 | 1/1997 |
| WO | WO199736926 | 10/1997 |
| WO | WO199811224 | 3/1998 |
| WO | WO199906445 | 2/1999 |
| WO | WO200181928 | 11/2001 |
| WO | WO2002092620 | 11/2002 |
| WO | WO2005099746 | 10/2005 |
| WO | WO2005113585 | 12/2005 |
| WO | WO2006000448 | 1/2006 |
| WO | 2007143161 | 12/2007 |
| WO | WO2008013454 | 1/2008 |
| WO | WO2009021293 | 2/2009 |
| WO | WO2009046495 | 4/2009 |
| WO | WO2009089004 | 7/2009 |
| WO | WO2009141357 | 11/2009 |
| WO | WO2010019263 | 2/2010 |
| WO | WO2010048670 | 5/2010 |
| WO | WO2010093925 | 8/2010 |
| WO | WO2010099219 | 9/2010 |
| WO | WO2010129503 | 11/2010 |
| WO | WO2011005621 | 1/2011 |
| WO | 2011057120 | 5/2011 |
| WO | WO2011050407 | 5/2011 |
| WO | WO2011057120 | 5/2011 |
| WO | WO2011064758 | 6/2011 |
| WO | WO2011127458 | 10/2011 |
| WO | WO2012025355 | 3/2012 |
| WO | WO2012138919 | 10/2012 |
| WO | WO2013113008 | 8/2013 |
| WO | WO2013148117 | 10/2013 |
| WO | WO2014000042 | 1/2014 |
| WO | WO2014100689 | 6/2014 |
| WO | WO2015017710 | 2/2015 |

OTHER PUBLICATIONS

Bootcov et al. (1997) "MIC-1 a novel macrophage inhibitory cytokine is a divergent member of the TGF-beta superfamily" *Proc. Natl. Acad. Sci. USA* 94:11514-11519.

Bottner et al. (1999) "Characterization of the rat mouse and human genes of growthdifferentiation factor-15macrophage inhibiting cytokine-1 (GDF-15MIC-1)" Gene 237:105-111.

Breit et al. (2011) "The TGF-beta superfamily cytokine MIC-1GDF15: a pleotrophic cytokine with roles in inflammation cancer and metabolism" *Growth Factors* 29(5):187-95.

Chen et al. (1994) "Substitution of asparagine residues in Aspergillus awamori glucoamylase by site-directed mutagenesis to eliminate N-glycosylation and inactivation by deamidation" *Biochem J.* 301: 275-81.

Clee et al. (2007) "The Genetic Landscape of Type 2 Diabetes in Mice" *Endocrine Reviews* 28(1): 48-83.

Dostalova et al. (2009) "Increased serum concentrations of macrophage inhibitory cytokine-1 in patients with obesity and type 2 diabetes mellitus: the influence of very low calorie diet" *Eur. J. Endocrinol.* 161:397-404.

Ehses et al. (2007) "Increased Number of Islet-Associated Macrophages in Type 2 Diabetes" *Diabetes* 56:2356-2370.

Fairlie et al. (2000) "Expression of a TGF-β superfamily protein macrophage inhibitory cytokine-1 in the yeast Pichia pastoris" *Gene* 254:67-76.

Fairlie et al. (2001) "Epitope Mapping of the Transforming Growth Factor-b Superfamily Protein Macrophage Inhibitory Cytokine-1 (MIC-1): Identification of at Least Five Distinct Epitope Specificities" *Biochem* 40:65-73.

Fairlie W D et al (2001) "The Propeptide of the Transforming Growth Factor-[beta] Superfamily Member Macrophage Inhibitory Cytokine-1 (MIC-1) Is a Multifunctional Domain That Can Facilitate Protein Folding and Secretion" Priority Journal of Biological Chemistry 20010518 American Society for Biochemistry and Molecular Biology Inc. 276(20):16911-16918.

Friedman et al. (1991) "Degradation of growth hormone releasing factor analogs in neutral aqueous solution is related to deamidation of asparagine residues" *Int. J. Peptide Protein Res.* 37:14-20.

"Glucose metabolism disroders" http:ctdbase.orgdetail.go?type=disease&acc=MESH%3AD044882 Mar. 25, 2016 1 page.

Hamann et al. (1996) "Regulation of energy balance by leptin" *Exp Endocrinol Diabetes* 104:293-200.

Hromas et al. (1997) "PLAB a novel placental bone morphogenetic protein" *Biochim. Biophys. Acta* 1354:40-4.

(56) References Cited

OTHER PUBLICATIONS

Johnen et al. (2007) "Tumor-induced anorexia and weight loss are mediated by the TGF-b superfamily cytokine MIC-1" *Nature Medicine* 13 (11): 1333-1340.

Lajer et al. (2010) "Plasma growth differentiation factor-15 independently predicts all-cause and cardiovascular mortality as well as deterioration of kidney function in type 1 diabetic patients with nephropathy" *Diabetes Care* 33(7)1567-1572.

Lind et al. (2009) "Growth-differentiation factor-15 is an independent marker of cardiovascular dysfunction and disease in the elderly: results from the Prospective Investigation of the Vasculature in Uppsala Seniors (PIVUS) Study" *European Heart Journal* 30(19)2346-2353.

Lingvay Ildiko et al. (2016) "Effect of Insulin Glargine Up-titration vs Insulin DegludecLiraglutide on Glycated Hemoglobin Levels in Patients with Uncontrolled Type 2 Diabetes" JAMA 315(9):898-907.

Liu Yan et al. (2009) "Enhancing the Secretion of Recombinant Proteins by Engineering N-Glycosylation Sites" Biotechnol. Prog. 25(5):1468-1475.

Macia et al. (2012) "Macrophage Inhibitory Cytokine 1 (MIC-1GDF15) Decreases Food Intake Body Weight and Improves Glucose Tolerance in Mice on Normal & Obesogenic Diets" PLoS ONE 7(4):1-8.

Massague (1987) "The TGF-beta Family of Growth and Differentiation Factors" Cell 49:437-8.

Ngo et al. (1994) "Computational Complexity Protein Structure Prediction and Levinthal Paradox" *The Protein Folding Problem and Tertiary Structure Prediction* Birkhauser Boston 492-495.

Oliveira Neto et al. (2008) "Interleukin-22 Forms Dimers that are Recognized by Two Interleukin-22R1 Receptor Chains" *Biophysical Journal* 94:1754-1765.

Paralkar et al. (1998) "Cloning and characterization of a novel member of the transforming growth factor[beta]bone morphogenetic protein family" *J. Biol. Chem* 273:13760-13767.

Robinson et al. (2004) "Prediction of primary structure deamidation rates of asparaginyl and glutaminyl peptides through steric and catalytic effects" *J. Pepide Res.* 63:437-448.

Shen et al. (2004) "Bone morphogenetic proteins regulate ionotropic glutamate receptors in human retina" Eur. J. Neurosci. 20:2031-2037.

Soler et al. (2012) "New Experimental Models of Diabetic Nephropathy in Mice Models of Type2 Diabetes: Efforts to Replicate Human Nephropathy" *Experimental Diabetes Research* vol. 2012 Art. ID 616313.

Tokuriki et al. (2009) "Stability effects of mutations and protein evolvability" *Curr. Opin. Struc. Biol.*19:596-604.

Vila et al. (2011) "The Relationship between Insulin Resistance and the Cardiovascular Biomarker Growth Differentiation Factor-15 in Obese Patients" *Clinical Chemistry* 57(2):309-316.

Vukicevic et al. (1996) "Induction of nephrogenic mesenchyme by osteogenic protein 1 (bone morphogenetic protein 7)" PNAS 93:9021-9026.

Wells (1990) "Additivity of Mutational Effects in Proteins" *Biochemistry* 29(37):8509-8517.

Welsh et al (2003) "Large-scale delineation of secreted protein biomarkers overexpressed in cancer tissue and serum" PNAS 100(6):3410-3415.

Yokoyama-Kobayashi et al. (1997) "Human cDNA encoding a novel TGF-beta superfamily protein highly expressed in placenta" *J. Biochem* 122:622-626.

Figure 1A
Human GDF15 Precursor Amino Acid Sequence (GenBank Accession No. NP_004855.2; SEQ ID NO:1)

```
  1  MPGQELRTVN GSQMLLVLLV LSWLPHGGAL SLAEASRASF PGPSELHSED SRFRELRKRY
 61  EDLLTRLRAN QSWEDSNTDL VPAPAVRILT PEVRLGSSGH LHLRISRAAL PEGLPEASRL
121  HRALFRLSPT ASRSWDVTRP LRRQLSLARP QAPALHLRLS PPPSQSDQLL AESSSARPQL
181  ELHLRPQAAR GRRRARARNG DHCPLGPGRC CRLHTVRASL EDLGWADWVL SPREVQVTMC
241  IGACPSQFRA ANMHAQIKTS LHRLKPDTVP APCCVPASYN PMVLIQKTDT GVSLQTYDDL
301  LAKDCHCI
```

Human GDF15 Precursor Nucleic Acid Sequence (GenBank Accession No. NM_004864.2; SEQ ID NO:2)

```
   1  AGTCCCAGCT CAGAGCCGCA ACCTGCACAG CCATGCCCGG GCAAGAACTC AGGACGGTGA
  61  ATGGCTCTCA GATGCTCCTG GTGTTGCTGG TGCTCTCGTG GCTGCCGCAT GGGGGCGCCC
 121  TGTCTCTGGC CGAGGCGAGC CGCGCAAGTT TCCGGGACC CTCAGAGTTG CACTCCGAAG
 181  ACTCCAGATT CCGAGAGTTG GGAAGATTCG AGGAGGACCT GCTAACCAGG CTGCGGGCCA
 241  ACCAGAGCTG GGAAGATTCG AACACCGACC TCGTCCCGGC CCCTGCAGTC CGGATACTCA
 301  CGCCAGAAGT GCGGCTGGGA TCCGGCGGCC ACCTGCACCT GCGTATCTCT CGGGCCGCCC
 361  TTCCCGAGGG GCTCCCGGAG GCCTCCCGCC TTCACCGGGC CCTGTTCCGG CTGTCCCCGA
 421  CGGCGTCAAG GTCGTGGGAC GTGACACGAC CGCTGCGGCG TCAGCTCAGC CTTGCAAGAC
 481  CCCAGGCGCC CGCGCTGCAC CTGCGACTGT CGCCCCCAGC GTCGCAGTCG GACCAACTGC
 541  TGGCAGAATC TTCGTCCGCA CGGCCCCCAGC TGGAGTTGCA CTTGCGGCCG CAAGCCGCCA
 601  GGGGGCGCCG CAGAGCGCGT GCGCGCAACG GGGACCACTG TCCGCTCGGG CCCGGGCGTT
 661  GCTGCCGTCT GCACACGGTC CGCGCGTCGC TGGAAGACCT GGGCTGGGCC GATTGGGTGC
 721  TGTCGCCACG GGAGGTGCAA GTGACCATGT GCATCGGCGC GTGCCCGAGC CAGTTCCGGG
 781  CGGCAAACAT GCACGCGCAG GCCAAGACGA GCCTGCACCG CCTGAAGCCC GACACGGTGC
 841  CAGCGCCCTG CTGCGTGCCC CTGCGCTACA ATCCCATGGT GCTCATTCAA AAGACCGACA
 901  CCGGGGTGTC GCTCCAGACC TATGATGACT TGTTAGCCAA AGACTGCCAC TGCATATGAG
 961  CAGTCCTGGT CCTTCCACTG TGCACCTGCG CGGAGGACGC GACCTCAGTT GTCCTGCCCT
1021  GTGGAATGGG CTCAAGGTTC CTGAGACACC CCAAACAGCT CCAAACAGCT GTATTTATAT
1081  AAGTCTGTTA TTTATTATTA ATTTATTGGG GTGACCTTCT TGGGGACTCG GGGGCTGTC
1141  TGATGGAACT GTGTATTTAT TTAAAACTCT GGTGATAAAA ATAAAGCTGT CTGAACTGTT
1201  AAAAAAAAAA AAAAAAAAAA
```

Figure 1B

Mature Human GDF15 Amino Acid Sequence (GenBank Accession No. NP_004855.2; SEQ ID NO:3)

ARNGDHCPLGPGRCCRLHTVRASLEDLGWADWVLSPREVQVTMCIGACPSQFRAANMHAQIKTSLHRLKPDTVPAPCCVPASYNPMVLIQKTDTGVSL
QTYDDLLAKDCHCI

Mature Human GDF15 Nucleic Acid Sequence (GenBank Accession No. NM_004864.2; SEQ ID NO:4)

GCGCGTAACGGGGATCACTGTCCGCTCGGGCCCGGCGTTGCTGCCGTCTGCACACGGTCCGCGCGT
CGCTGGAAGACCTGGGCTGGGCCGATTGGGTCGTGCCACGGAGGTGCAAGTGACCATGTGCATCGG
CGCGTGCCCGAGCCAGTTCCGGGCGGCAAACATGCACGCGCAGATCAAGACGAGCCTGCACCGCCTGAAG
CCCGACACGGTGCCAGCGCCCTGCTGCGTGCCCGCCAGCTACAATCCCATGGTGCTCATTCAAAAGACCG
ACACCGGGGTGTCGCTCCAGACCTATGATGACTTGTTAGCCAAAGACTGCCACTGCATATAA

Figure 1C

Amino Acid Sequence of Precursor (Endogenous Signal Peptide and Small Prodomain) and Mature Human Serum Albumin (GenBank Accession No. AAA98797.1; SEQ ID NO:5)

MKWVTFISLLFLFSSAYSRGVFRRDAHKSEVAHRFKDLGEENFKALVLIAFAQYLQQCPFEDHVKLVNEVTEFAKTCVADESAENCDKSLHTLFGDKL
CTVATLRETYGEMADCCAKQEPERNECFLQHKDDNPNLPRLVRPEVDVMCTAFHDNEETFLKKYLYEIARRHPYFYAPELLFFAKRYKAAFTECCQAA
DKAACLLPKLDELRDEGKASSAKQRLKCASLQKFGERAFKAWAVARLSQRFPKAEFAEVSKLVTDLTKVHTECCHGDLLECADDRADLAKYICENQDS
ISSKLKECCEKPLLEKSHCIAEVENDEMPADLPSLAADFVESKDVCKNYAEAKDVFLGMFLYEYARRHPDYSVVLLRLAKTYETTLEKCCAAADPHE
CYAKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEK
TPVSDRVTKCCTESLVNRRPCFSALEVDETYVPKEFNAETFTFHADICTLSEKERQIKKQTALVELVKHKPKATKEQLKAVMDDFAAFVEKCCKADDK
ETCFAEEGKKLVAASQAALGL

Figure 1C, continued
DNA Sequence Encoding Precursor (Endogenous Signal Peptide and Small Prodomain) and Mature Human Serum Albumin (GenBank Accession No. NM_000477.5; SEQ ID NO:6)

```
   1 agtatattag tgctaatttc cctccgtttg tcctagcttt tctcttctgt caacccaca
  61 cgcctttggc acaatgaagt gggtaacctt tatttccctt cttttctct ttagctcggc
 121 ttattccagg ggtgtgtttc gtcgagatgc acacaagagt gaggttgctc atcggtttaa
 181 agatttggga gaagaaaatt tcaaagcctt ggtgttgatt gcctttgctc agtatcttca
 241 gcagtgtcca tttgaagatc atgtaaaatt agtgaatgaa gtaactgaat ttgcaaaaac
 301 atgtgttgct gatgagtcag ctgaaaattg tgacaaatca cttcataccc tttttggaga
 361 caattatgc acagttgcaa ctcttcgtga aacctatggt gaaatggctg actgctgtgc
 421 aaaacaagaa cctgagagaa atgaatgctt cttgcaacac aaagatgaca acccaaacct
 481 cccccgattg gtgagaccag aggttgatgt gatgtgcact gcttttcatg acaatgaaga
 541 gacattttg aaaaatact tatatgaaat tgccagaaga agctgctttt acagaatgtt tttatgcccc
 601 ggaactcctt ttctttgcta aaggtataaa agctgctttt acagaatgtt gccaagctgc
 661 tgataaagct gcctgcctgt tgccaaagct cgatgaactt cgggatgaag ggaaggcttc
 721 gtctgccaaa cagagactca agtgtgccag tctccaaaaa tttggagaaa gagctttcaa
 781 agcatgggca gtagctcgcc tgagccagag atttcccaaa gctgagtttg cagaagtttc
 841 caagttagtg acagatctta cacttcca cacggaatgc tgccatggag atctgcttga
 901 atgtgctgat gacaggcgg accttgccaa gtatatctgt gaaaatcaag attcgatctc
 961 cagtaaactg aaggaatgct gtgaaaaacc tctgttggaa aaatcccact gcattgccga
1021 agtggaaaat gatgagatgc ctgctgactt gcctcatta gctgctgatt ttgttgaaag
1081 taaggatgtt tgcaaaaact atgctgaggc aaaggatgtc ttcctgggca tgtttttgta
1141 tgaatatgca agaaggcatc ctgattactc tgtcgtgctg ctgctgagac ttgccaagac
1201 atatgaaacc actctagaga agtgctgtgc cgctgcagat cctcatgaat gctatgccaa
1261 agtgttcgat gaatttaaac ctcttgtgga agagcctcag aatttaatca acaaaattg
1321 tgagctttt gagcagcttg gagagtacaa attccagaat gcgctattag ttcgttacac
1381 caagaaagta cccaagtgt caactccaac tcttgtagag gtctcaagaa acctaggaaa
1441 agtgggcagc aaatgttgta aacatcctga agcaaaaaga atgccctgtg cagaagacta
1501 tctatccgtg gtcctgaacc agttatgtgt gttgcatgag aaaacgccag taagtgacag
1561 agtcaccaaa tgctgcacag aatccttggt gaacaggcga ccatgctttt cagctctgga
1621 agtcgatgaa acatacgttc ccaaagagtt taatgctgaa acattcacct tccatgcaga
1681 tatatgcaca ctttctgaga aggagacaa aatcaagaaa caaactgcac ttgttgagct
1741 cgtgaaacac aagcccaagg caacaaaga gcaactgaaa gctgttatgg atgatttcgc
```

Figure 1C, continued

```
1801 agctttgta gagaagtgct gcaaggctga cgataaggag acctgctttg ccgaggaggg
1861 taaaaaactt gttgctgcaa gtcaagctgc cttaggctta taacatcaca tttaaaagca
1921 tctcagccta ccatgagaat aagagaaaga aaatgaagat caaaagctta ttcatctgtt
1981 tttcttttc gttggtgtaa agccaacacc ctgtctaaaa aacataaatt tctttaatca
2041 tttgccctct tttctctgtg cttcaattaa taaaaaatgg aaagaatcta atagagtggt
2101 acagcactgt tattttcaa agatgtgttg ctatcctgaa aattctgtag gttctgtgga
2161 agttccagtg ttctctctta ttccacttcg gtagaggatt tctagtttct tgtgggctaa
2221 ttaaataaat cattaatact cttctaaaaa aaaaaaaaaa aaaa
```

Amino Acid Sequence of IgK Signal Peptide and Mature Human Serum Albumin (SEQ ID NO:7)

MDMRVPAQLLGLLLLWLRGARCDAHKSEVAHRFKDLGEENFKALVLIAFAQYLQQCPFEDHVKLVNEVTEFAKTCVADESAENCDKSLHTLFGDKLCT
VATLRETYGEMADCCAKQEPERNECFLQHKDDNPNLPRLVRPEVDVMCTAFHDNEETFLKKYLYEIARRHPYFYAPELLFFAKRYKAAFTECCQAADK
AACLLPKLDELRDEGKASSAKQRLKCASLQKFGERAFKAWAVARLSQRFPKAEFAEVSKLVTDLTKVHTECCHGDLLECADDRADLAKYICENQDSIS
SKLKECCEKPLLEKSHCIAEVENDEMPADLPSLAADFVESKDVCKNYAEAKDVFLGMFLYEYARRHPDYSVVLLLRLAKTYETTLEKCCAAADPHECY
AKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTP
VSDRVTKCCTESLVNRRPCFSALEVDETYVPKEFNAETFTFHADICTLSEKERQIKKQTALVELVKHKPKATKEQLKAVMDDFAAFVEKCCKADDKET
CFAEEGKKLVAASQAALGL

Figure 1C, continued

DNA Sequence Encoding IgK Signal Peptide and Mature Human Serum Albumin (SEQ ID NO:8)

```
ATGGACATGAGGGTCCCCGCTCAGCTCCTGGGGCTCCTGCTACTCTGGCTCCGAGGTGCCAGATGTGATGCACACAAGAGTGAGGTTGCTCATCGGTT
TAAAGATTTGGGAGAAGAAATTTCAAAGCCTTGGTGTTGATTGCCTTTGCCTTTGCCTTGCTCAGTATCTTCAGCAGTGTCCATTGAAGATCATGTAAAATTAGTGA
ATGAAGTAACTGAAATTTGCAAAAACATGTGTTGCTGATGAGTCAGCTGAAAATTGTGACAAATCACTTCATACCCTTTTTGGAGACAAATTATGCACA
GTTGCAACTCTTCGTGAAACCTATGGTGAAATGGCTGACTGCTGTGCAAAACAAGAACCTGAGAGAAATGCTTCTTGCAACACAAAGATGACAA
CCCAAACCTCCCCCGATTGGTGAGACCAGAGTTGATGTGATGGAACTCCTTTCTTTGCACTGCTTTTCATGACAATGAAGAGACATTTTGAAAAATACTTATATGAAA
TTGCCAGAAGACATCCTTACTTTTATGCCCCGCAAGCTCGATGAACTTCGGGATGAAGGAAGGCTTCGTCTGCCAAACAGAGACTCAAGTGTGCCAGTCTCCAAAAATTGG
GCTGCCTGCCTGTTGCCAAAGCTTCCCAAGCATGGGCCAGTAGCTCGCTGAGCCAGAGATTTCCCAAGCTGAGTTTGCCAAGTAGTGACAGATCTTACCA
AGAAAGAGCTTTCAAAGCTTCCCAAGCATGGGCCAGTAGCTCGCTGAGCCAGAGATTTGCCAAGTATATCTCGTGAAAATCAAGATTCGATCTCC
AAGTCCACACGGAATGCTGCCATGCAGCTCTGCTGAAGGATCTGCTGATGACAGGCCGGACCTTGCCAAGTATATCTCGTGAAAATCAAGATTCGATCTCC
AGTAAACTGAAGGAATGCTGTGAAAAAAACCCTCTGTTGAAAAGATGTTTGCAAAAAACTATGCTGAGGCAAAGATGTCTTCCTGGGCATGTTTTGTATGAATATGCAAGAAGC
AGCTGCTGATTTGTTGAAAGTAAGGATGTTGCTGCTGTGCTGAGACTTGCCAAGACTTGCCAAGAGAGTGCTGTGCCGCTGCAGATCCTCATGAATGCTAT
ATCCTGATTACTCTGTCGTGCTGATGAATTTAAACCTCTTGTGAGAAGAGCCTCAGATTTAATCAAACAACTCTTGTAGAGGTCCTGAACCAGTTATGTGAGCTTTTGAGCAGCTTGGAGAGTACAAATT
GCCAAATGTTCGATGAATTAGTTCGTTACACCAAGAAATGCCCTGTGCAGAACAAAAGAATGCCCTGTGCAGAGACTATCTATCCGGTCCTGAACCAGTTATGTGTTGCATGAGAAAGTGGGCAGCA
CCAGAATGCGCTATTAGTTCGTTACACCAAGAAATGCCCTGTGCAGAATCCTTGGTGAAGACAGGCGACCATGCTTTCAGCTCTGAAGTCGATGAAACATACGTTCCCAAAGA
GTAAGTGACAGAGTCACCAGTCACCAAATGCTGCACAGAATCCTTGGTGAAGACAGGCGACCATGCTTTCAGCTCTGAAGTCGATGAAACATACGTTCCCAAAGA
GTTTAATGCTGAAACATTCACCTTCCATGCAGATATATGCAGATATATGCAGACTGAAAGCTGTTATGGATGATTTCGCAGCTTTTGATGATTTTGTAGAGAAGTGCTGCAAGGCTGACGATAAGGAGACC
TGCTTTGCCGAGGAGGTAAAAAACTTGTTGCTGCAAGTCAAGCTGCCTTAGGCTTA
```

Figure 1D

Mature Human Serum Albumin Amino Acid Sequence (Subsequence of Amino Acid Sequence of Figure 1C Lacking the IgK Signal Peptide) (SEQ ID NO:9)

```
DAHKSEVAHRFKDLGEENFKALVLIAFAQYLQQCPFEDHVKLVNEVTEFAKTCVADESAENCDKSLHTLFGDKLCTVATLRETYGEMADCCAKQEPER
NECFLQHKDDNPNLPRLVRPEVDVMCTAFHDNEETFLKKYLYEIARRHPYFYAPELLFFAKRYKAAFTECCQAADKAACLLPKLDELRDEGKASSAKQ
RLKCASLQKFGERAFKAWAVARLSQRFPKAEFAEVSKLVTDLTKVHTECCHGDLLECADDRADLAKYICENQDSISSKLKECCEKPLLEKSHCIAEVE
NDEMPADLPSLAADFVESKDVCKNYAEAKDVFLGMFLYEYARRHPDYSVVLLLRLAKTYETTLEKCCAAADPHECYAKVFDEFKPLVEEPQNLIKQNC
ELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAFVEKCCKADDKETCFAEEGKKLVAASQAALGL
```

Mature Human Serum Albumin DNA Sequence (Subsequence of DNA Sequence of Figure 1C Lacking the IgK Signal Peptide) (SEQ ID NO:10)

```
GATGCACACAAGAGTGCTCATCGGTTGCTGAGGTTGCTCTCAGCAGTGCCTTGGTGTTGATTGCCTTTGCTCAGTATCTTCAGCA
GTGTCCATTTGAAGATCATGTAAAATTAGTGAATGAAGTAACTGAATTTGCAAAACATGTGTTGCTGATGAGTCAGTCAGTGACAAATCAC
TTCATACCCTTTTTGGAGACAGTGCACAGTTGCAACTCTTCGTGAAACCTATGGTGAAATGGCTGCTGTGCAAAACAAGAACCTGAGAGA
AATGAATGCTTCTGCAACACAAGATGACAACAAACCTAATTTGCCCCGATTGGTGAGACCAGAGTTGATGTGCACTCCTTTCATGACAATGA
AGAGACATTTTGAAAAATACTTATATGAAATTGCCAGAAGACATCCTTACTTTTATGCCCCAAAGCTCGATGAACTTCGGATGAAGGCTTCGTCTGCCAAACAG
CTTTTACAGAATGTTGCCAGTCCTCCAAAGTTGGAGAAGATCTTACCAAAGTCCACACGAAACTGAAGGAATGCTGCCATGCCAAAAGCATGTGCTGATGACAGGGGCGACCTTGCCA
AGTATATCTGTGAAAATCAAGATTCGATCTCCAGTTAGCTGCCTTCATTAGCTGCTGCAAGAAGCATCCTGATTTGCTAGTCTCGTGATGAATTAGTTCGTGAAGCGCTATTAGTTCGTTAAACATCCTGAAGCAAAATGTTGTAAACATCCTGAAGCAAAATGTTGT
GGGCATGTTTTGTATGAATATGCAAGAAGCATCCTGATTTGCTAGTCTCGTGATGAATTAGTTCGTGAAGCGCTATTAAACATCCTGAAGCAAAATGTTGT
GCTGTGCCGCTGCAGATGCTTGGAGCAGCTTGGAAAATGTGGGCAGCAAACGCCAGTAAGTGACAGAGTTCCCAAAGAGTTCCCAAAGAGTTCCCAAAGAGTTCCCAAAGAG
GAGCTTTTGAAGAAACCTAGGAGAAAGTGGGCAGCAAACGCCAGTAAGTGACAGAGTTCCCAAAGAGTTCCCAAAGAGTTCCCAAAGAG
GGTCTCAAGAAACCTAGGAGAAAGTGGGCAGCAAACGCCAGTAAGTGACAGAGTTCCCAAAGAGTTCCCAAAGAG
ACCAGTTATGTGTTGCATGAGAACATACGTTCCCAAAGAGTTCCCAAAGAGTTCCCAAAGAG
CTGGAAGTGCGATGAACATACGTTCCCAAAGAGTTCCCAAAGAGTTCCCAAAGAG
CAAGAAACAAACTGCACTTGTTGAGCTCGTGAAACAACAAGCCCAAGCCAACAAGAGACAACAAAGAGCCCAAGCAACAAGAG
AGAAGTGCTGCAAGGCTGACGATAAGGAGACCTGCTTTGCCGAGGAGGTAAAAAACTTGTTGCTGCAAGTCAAGCTGCCTTAGGCTTA
```

Figure 1E

Fusion Molecule Comprising HSA Amino Acid Sequence Having an IgK Signal Sequence Fused to the N-Terminus of Mature Human GDF15 Amino Acid Sequence Through a Protease-sensitive Cleavable Linker (SEQ ID NO:11)

MDMRVPAQLLGLLLLWLRGARCDAHKSEVAHRFKDLGEENFKALVLIAFAQYLQQCPFEDHVKLVNEVTEFAKTCVADESAENCDKSLHTLFGDKLCT
VATLRETYGEMADCCAKQEPERNECFLQHKDDNPNLPRLVRPEVDVMCTAFHDNEETFLKKYLYEIARRHPYFYAPELLFFAKRYKAAFTECCQAADK
AACLLPKLDELRDEGKASSAKQRLKCASLQKFGERAFKAWAVARLSQRFPKAEFAEVSKLVTDLTKVHTECCHGDLLECADDRADLAKYICENQDSIS
SKLKECCEKPLLEKSHCIAEVENDEMPADLPSLAADFVESKDVCKNYAEAKDVFLGMFLYEYARRHPDYSVVLLLRLAKTYETTLEKCCAAADPHECY
AKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTP
VSDRVTKCCTESLVNRRPCFSALEVDETYVPKEFNAETFTFHADICTLSEKERQIKKQTALVELVKHKPKATKEQLKAVMDFAAFVEKCCKADDKET
CFAEEGKKLVAASQAALGLGGGSGGGGSIEGRARNGDHCPLGPGRCCRLHTVRASLEDLGWADWVLSPREVQVTMCIGACPSQFRAANMHAQIKTSL
HRLKPDTVPAPCCVPASYNPMVLIQKTDTGVSLQTYDDLLAKDCHCI

Figure 1E, continued

Nucleic Acid Encoding A Fusion Molecule Comprising HSA Amino Acid Sequence Having an IgK Signal Sequence Fused to the N-Terminus of Mature Human GDF15 Amino Acid Sequence Through a Protease-sensitive Cleavable Linker (SEQ ID NO:12)

ATGGACATGAGGGTCCCCGCTCAGCTCCTGGGCTTCCTGCTACTCTGGCTCCGAGGTGCCAGATGTGATGCACACAAGAGTGAGGTTGCTCATCGGTT
TAAAGATTTGGGAGAAGAAATTTCAAAGCCTTGGTGTTGATGATGCCTTGCCTTTCAGTAGTCTCAGTCTTGAAGATCATGTAAAATTAGTGA
ATGAAGTAACTGAATTTGCAAAAACATGTGTTGCTGATGAGTCAGCTGAAAATTGTGACAAATCACTTCATACCCTTTTTGGAGACAAATTATGCACA
GTTGCAACTCTTCGTGAAACCTATGGTGAAATGGCTGACTGTGTGCAAAACAAGCTGCTTTGCAAATGAATGCTTCTTGCAACACAAAGATGACAA
CCCAAACCTCCCCCGATTGGTGAGACCAGAGGTTGATGTGATGTGCACTGCTTTTCATGACAATGAAGAGACATTTTTGAAAAAATACTTATATGAAA
TTGCCAGAAGACATCCTTACTTTTATGCCCCGGAACTCCTTTCTTGCTAAAGGTATAAAGGCTCCAAGCTGTGCCAAGCTCTCCAAAATTTGG
GCTGCCTGTTGCCAAAGCTCGATGAACTTCGGGATGAAGGCTTCGTCTGCAAACAGCTGAAGAGACTCAAGTGTGCCAGTCTCCAAAATTTGG
AGAAAGAGCTTTCAAAGCATGCTGCCATGCCAGAGATCTGCTTGTTGAATGTGCTGACAGGGCGAGCATTGCCAAGTTTCAGAAGTTTGCAAGATGTTGACAGATCTTACCA
AAGTCCACACGGAATGCTGCCATGCCAGAGATCTGCTTGTTGAATGTGCTGACAGGGCGAGCATTGCCAAGTGGAAAATCCCACTGGAAGTGCCTGCTGACTTGCCTTCATT
AGTAAACTGAATGCTGTGAAAGTAAGGATGTTTGCAAAAACTATGCTGAGGCAACAAGGATGCTCTTCCTGGGCATGTTTTGTATGAATGTCAAGAAGGC
ATCCTGATTACTCTGCGTGCTGAGACTTGCCAAGACATATGGAAGAACCACTCTAGAGAAGTGCTGCCGCTGCAGATCCTCATGAATGCTAT
GCCAAAGTGTTCGATGAATTTAAACCTCTGTGAAGAGCCTCAAGAGCCTCAAGAGAATTGTGAGCTTTTGAGCAGCTTGGAGAGTACAAATT
CCAGAATGGTGCTATTAGTTCGTTACACCAAGACAAAAGAATGCCTGTGCAGAACAAGGAATGCCCTGTGCAGAACAAGGACTACTATCGTGGTCCTGAACCAGTTATGTGTTGCATGAGAAAACGCCA
GTAAGTGACAGAGTCACCAACATTGCTGAAAATGCTGCACAGAATCCTTGGTGACACAGGCGACCATGCTTTCTGAAGTCCTGAAGTCGATGAAACATACGTTCCCAAAGA
GTTTAATGCTGAAACATTCACCTTCCATGCAACAGATATATCGCAGATTGAAAGCTGTTATGGATGATTTCGCAGCTTTTGTAGAGGCGGTAGGTGGAGTATTGAAGGGAG
AACACAAGCCCAAGGCAACAAAAGAGCAACTGAAAACTTGTTGCTGCAAGCCCGGGGTCATCGGCGGTGCTCGGCGCAAACATGCCAAAATCCCATGGCTGCTCGGAGAGGCCAACGCGCAGATCAAGACGAGCCTG
TGCTGTCGCCACGGAGGTGCAAGTGACCATGTGCATCGGCGGTGCCCTGCTGCCGCCAGTCTACAATCCCATGGCTGCTCATTCAAAAGACCGACACCGGGTGTGCT
CCAGACCTATGATGACTTGTTAGCCAAAGACTGCCACTGCCATATAA

Figure 1F

Fusion Molecule Comprising Mature HSA Amino Acid Sequence Fused to the N-Terminus of Mature Human GDF15 Amino Acid Sequence Through a Protease-sensitive Cleavable Linker (SEQ ID NO:13)

DAHKSEVAHRFKDLGEENFKALVLIAFAQYLQQCPFEDHVKLVNEVTEFAKTCVADESAENCDKSLHTLFGDKLCTVATLRETYGEMADCCAKQEPER
NECFLQHKDDNPNLPRLVRPEVDVMCTAFHDNEETFLKKYLYEIARRHPYFYAPELLFFAKRYKAAFTECCQAADKAACLLPKLDELRDEGKASSAKQ
RLKCASLQKFGERAFKAWAVARLSQRFPKAEFAEVSKLVTDLTKVHTECCHGDLLECADDRADLAKYICENQDSISSKLKECCEKPLLEKSHCIAEVE
NDEMPADLPSLAADFVESKDVCKNYAEAKDVFLGMFLYEYARRHPDYSVVLLLRLAKTYETTLEKCCAAADPHECYAKVFDEFKPLVEEPQNLIKQNC
ELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAFVEKCCKADDKETCFAEEGKKLVAASQAALGLGGG
GSGGGGSIEGRARNGDHCPLGPGRCCRLHTVRASLEDLGWADWVLSPREVQVTMCIGACPSQFRAANMHAQIKTSLHRLKPDTVPAPCCVPASYNPMV
LIQKTDTGVSLQTYDDLLAKDCHCI

Figure 1F, continued

Nucleic Acid Encoding A Fusion Molecule Comprising Mature HSA Amino Acid Sequence Fused to the N-Terminus of Mature Human GDF15 Amino Acid Sequence Through a Protease-sensitive Cleavable Linker (SEQ ID NO:14)

```
GATGCACACAAGAGAGTGAGGTTGCTCATCGGTTTAAAGATTTGGGAGAAGAAAATTTCAAAGCCTTGGTGTTGATTGCCTTTGCTCAGTATCTTCAGCA
GTGTCCATTTGAAGATCATGTAAAATTAGTGAATGAAGTAACTGAATTTGCAAAAACATGTGTTGCTGATGAGTCAGCTGAAAATTGTGACAAATCAC
TTCATACCCTTTTTGGAGACAAATTATGCACAGTTGCAACTCTTCGTGAAACCTATGGTGAAATGGCTGACTGCTGTGCAAAACAAGAACCTGAGAGA
AATGAATGCTTCTGCAACACAAAGATGACAACCCCAAACCTCCCCGATTGGTGAGACCAGAGGTTGATGTGATGTGCACTGCTTTTCATGACAATGA
AGAGACATTTTTGAAGAAATGTGCCAAGCTGCTGATAAAGCCTGCTGCCTGTGCCAAAGCTGCTGATATAGCTCGGAGACTTCGGTGCTGAAGGAAGGCTTCGTCTGCCAAACAG
CTTTTACAGAATGTGCCAGTCTCCAAAAATTGGAGAAAGAGCTTCACACGGAATGCTGCCATGGAGATCTGCTTGAATGTCTGATGACAGGGCGGACCTTGCCA
AGAAGTTTCCAAGTTAGTGACAGATCTTACCAAAGTCCAGTAAACTGAAGGAATGCTGTGAAAGTAAGGATGTTTGTTGAAGACTTGCTGAGGCAAAGGATGTCTTCCT
AGTATATCTGTGAAAATCAAGATTCGATCTGCCTTCATTAGCTGCCTGATTACTCTGAAAGTGTTGCTGAGACTTGCCAAGACATATGAAAACCACTCTAGAGAAGT
AATGATGAGATGCCTGCTGATGATGCAAGAGGCATCCTATGCCAAAGTCCTCAGAATTTAAACTCCAAGTGTCAACTCCAACTCTGTAGA
GGGCATGTTTTGTATGCAGATCCTCATGAATGCTTCATGATGAATTAAACCTCTTGTTGAGAGAAAGTACCCCAAGTGTCAACTCCAACTCTGTAGA
GCTGTGCCGCTGCAGATCCCTCATGAATGCTTCATGATGAATTAAACCTCTTGTTGAGAGAAAGTACCCCAAGTGTCAACTCCAACTCTGTAGA
GAGCTTTTGAGCAGCTTGGAGATGCAAATTCCAGATGCGCTATTAGTTCGTTACACCAAAGATGTGAAGACTATCATCCGTGGTCCTGA
GGTCTCAAGAAGAACCTAGGAGAAAAGTGGGCAGCAAATGTGTAAACATCCTGAACGCAAATGCTGCACCAGAATCCTGGTGAACAGGCGACCATGCTTTTCAGCT
ACCAGTTATGTGTTGCATGAGAAAACGCCAGTAAGTGACAGAGTCAAAATGCTGAAACATTCACCTTCTGAGAAGGAGAGACAAAT
CTGGAAGTCGATGAAACATACGTTCCCAAAGAGTTTAATGCTGAAACATTCACCTTCTGAGAAGGAGAGACAAAT
CAAGAAACAAACTGCACTTGTTGAGCTGTGAAACACAAGGCAACAAAGAGCAACTGAAAGCTGTTATGGATGATTTCGCAGCTTTTGTAG
AGAAGTGCTGCAAGGCTGACGATAAGGAGACCTGCTTTGCCGAGGAGGGTAAAAAACTTGTTGCTGCCGGGCGTCAAGCTGCCTTAGGCTTAGGTGGAGGC
GGTAGCGGTGGAGGTGGGAGTATTGAAGGGAGGGGCGCGTAACGGGATCACTGTCCGTCGCGGGGATCAAGTGACCAATGTGCCCATGCCCGTCCTCGC
GTCGCTGAAGACCTGGGCTGGGCTGGGCCGATTGGGTGCTGTCCACGGAGGGTGACACGGTGACCAAGTGACCTGGGGCGTCATGCGCGGCGGGCAGTTCCGGGCGG
CAAACATGCACGCCAGATCAAGACGAGCCTGCCGCCCTGAAGCCCGACACGGTGCCAGCGCCCTGCCCGCCCAGCTACAATCCCATGGTG
CTCATTCAAAAGACCGACACCGGGGTGTCGCTCCAGACCTATGACGACCTTGTTAGCCAAAGACTTGATGACTTGCCACTGCATATAA
```

Figure 1G

Fusion Molecule Comprising HSA Amino Acid Sequence Having an IgK Signal Sequence Fused to the N-Terminus of Mature Human GDF15 Amino Acid Sequence Through a Non-cleavable Linker (SEQ ID NO:15)

MDMRVPAQLLGLLLLWLRGARCDAHKSEVAHRFKDLGEENFKALVLIAFAQYLQQCPFEDHVKLVNEVTEFAKTCVADESAENCDKSLHTLFGDKLCT
VATLRETYGEMADCCAKQEPERNECFLQHKDDNPNLPRLVRPEVDVMCTAFHDNEETFLKKYLYEIARRHPYFYAPELLFFAKRYKAAFTECCQAADK
AACLLPKLDELRDEGKASSAKQRLKCASLQKFGERAFKAWAVARLSQRFPKAEFAEVSKLVTDLTKVHTECCHGDLLECADDRADLAKYICENQDSIS
SKLKECCEKPLLEKSHCIAEVENDEMPADLPSLAADFVESKDVCKNYAEAKDVFLGMFLYEYARRHPDYSVVLLLRLAKTYETTLEKCCAAADPHECY
AKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTP
VSDRVTKCCTESLVNRRPCFSALEVDETYVPKEFNAETFTFHADICTLSEKERQIKKQTALVELVKHKPKATKEQLKAVMDDFAAFVEKCCKADDKET
CFAEEGKKLVAASQAALGLGGGSGGGGSGGGGSARNGDHCPLGPGRCCRLHTVRASLEDLGWADWVLSPREVQVTMCIGACPSQFRAANMHAQIKTS
LHRLKPDTVPAPCCVPASYNPMVLIQKTDTGVSLQTYDDLLAKDCHCI

Figure 1G, continued

Nucleic Acid Encoding A Fusion Molecule Comprising HSA Amino Acid Sequence Having an IfK Signal Sequence Fused to the N-Terminus of Mature Human GDF15 Amino Acid Sequence Through a Non-cleavable Linker (SEQ ID NO:16)

```
ATGGACATGAGGGTCCCCGCTCAGCTCTCTGGGCTCCTCCTGCTACTCTGGCTCCGAGGTGCCAGATGTGATGCACACAAGAGTGAGGTTGCTCATCGGTT
TAAAGATTTGGGAGAAGAAATTTCAAAGCCTTGGTGTTGATTGCCTTGCTCAGTATCTTCAGCAGTGTCCATTGAAGATCATGTAAAATTAGTGA
ATGAAGTAACTGAATTGCAAAAACATGTGTTGCTGATGAGTCAGCTGAAAATTGTGACAAATCACTTCATACCCTTTTGGAGACAAATTATGCACA
GTTGCAACTCTTCGTGAAAACCTATGGTGAAATGGCTGACTGCTGTGCAAAACAAGAACCTGAGACAATGAAATGCTTCTGCAACACAAAGATGACAA
CCCAAACCTCCCCCGATTGGTGAGACCAGAGGTTGATGTGCACTGCTTTCATGACAATGAAGAGACATTTTGAAAAATACTTATATGAAA
TTGCCAGAAGACATCCTTACTTTTATGCCAAAGCTCGATGAACTCGGGATGAAGGCTTCGTCTGCCAAACAGACTCAAGTGTGCCAGTCTCCAAAAATTTGG
GCTGCCTGCCTGTTGCCAAAGCTTCAAAGCATGGCCAGTAGCTCGCCTGAGCCAGAGATTTCCAGACAGGGCGACACTCTGCTGATGACACTCTGCTTGATGAC
AGAAAGAGCTTTCAAACGGAATGCTGCCATGGCAGATCTGCTGTGTGTGATGAGAATCCCAGTGCGACCTTGAGAAATCAAGATTCGATCTCC
AAGTCCACACGGAATGCTGCCATGGCAGATCTGCTGTGTGATGAGAATCCCAGTGCGACCTTGAGAAATCAAGATTCGATCTCC
AGTAAACTGAAGGAATGCTGTGAAAGTAAGGATGTTTGCAAAAACTATGCTGAGGCAAAGGATGTCTTCCTGGACATGTTTTTGTATGAATATGCAAGAAGGC
AGCTGCTGATTTGTTGAAAGTAAGGATGTTTGCAAAAACTATGCTGAGGCAAAGGATGTCTTCCTGGACATGTTTTTGTATGAATATGCAAGAAGGC
ATCCTGATTACTCTGTCGTGATGAATTAAACCTCTGGAAGAGCCTCAGAATTAAATCAAACAAAATGTGAGCTTTTGAGCAGCTTGAGAGTACAAATT
GCCAAAGTGTTCGATGAATTAGTTCGTTACACCAAGAAAATGCCCTGTGCAGAAGACTATCTATCCGTGTCCTGAACCAGTTATGTGTTGCATGAGAAAACGCCA
CCAGAATGCGCTATTAGTTCGTTACACCAAGAAAATGCCCTGTGCAGAAGACTATCTATCCGTGTCCTGAACCAGTTATGTGTTGCATGAGAAAACGCCA
AATGTTGTAAACATCCTGAAGCAAAATGCTGCACAGAATCCTTGGTGAAGAATCCTGAGAAGACAAATCAAGAAGACAAATCAAGAGAAGCTTCCAAAGA
GTAAGTGACAGAGTCACCAAGTCTGAAACATTCACCTTCCATGCAACTAAAAGAGCAACTGAAAGCTGTTATGATGATCAGAGAACATACGTTCCAAAGA
GTTTAATGCTGAAACATTCACCTTCCATGCAACTAAAAGAGCAACTGAAAGCTGTTATGATTCAGAGAGACAAATCAAGAAGACAAATCAAGAAGCTGCTGCAAGGCTGACGATAAGGAGACC
AACAAGCCCAAGGAGGAGGTAAAAACTTGTCTGCCGCTCGGGCGTGCATCGGGCGCTGCCGGGCAGTGCCAGTTCCCGGGCCGCAAACATGCCGGCAGATCAAGACGAGC
TGCTTTGCCGCGTAACGGGCACGGGAGGTGGATCACTGTCCGCTCGGGCGTGCATCGGGCGCTGCCGGGCAGTGCCAGTTCCCGGGCCGCAAACATGCCGGCAGATCAAGACGAGC
GAGTGCGCGTGCTGCTCGCCGAGGGTGCAAGTGCATGTGACCATGTGCCGGCCCCCTGCTCGCTGCCCGCCAGCTACAATCCCATGGTGCTCATTCAAAAGACCGACACCGGGGTGTC
GCTCCAGACCTATGATGACTTGTTAGCCAAAGACTGCCACTGCATATAA
```

Figure 1H

Fusion Molecule Containing Mature HSA Amino Acid Sequence Fused to the N-Terminus of Mature Human GDF15 Amino Acid Sequence Through a Non-cleavable Linker (SEQ ID NO:17)

DAHKSEVAHRFKDLGEENFKALVLIAFAQYLQQCPFEDHVKLVNEVTEFAKTCVADESAENCDKSLHTLFGDKLCTVATLRETYGEMADCCAKQEPER
NECFLQHKDDNPNLPRLVRPEVDVMCTAFHDNEETFLKKYLYEIARRHPYFYAPELLFFAKRYKAAFTECCQAADKAACLLPKLDELRDEGKASSAKQ
RLKCASLQKFGERAFKAWAVARLSQRFPKAEFAEVSKLVTDLTKVHTECCHGDLLECADDRADLAKYICENQDSISSKLKECCEKPLLEKSHCIAEVE
NDEMPADLPSLAADFVESKDVCKNYAEAKDVFLGMFLYEYARRHPDYSVVLLLRLAKTYETTLEKCCAAADPHECYAKVFDEFKPLVEEPQNLIKQNC
ELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAFVEKCCKADDKETCFAEEGKKLVAASQAALGLGGG
GSGGGGSGGGGSARNGDHCPLGPGRCCRLHTVRASLEDLGWADWVLSPREVQVTMCIGACPSQFRAANMHAQIKTSLHRLKPDTVPAPCCVPASYNPM
VLIQKTDTGVSLQ TYDDLLAKDCHCI

Figure 1H, continued

Nucleic Acid Encoding Fusion Molecule Containing Mature HSA Amino Acid Sequence Fused to the N-Terminus of Mature Human GDF15 Amino Acid Sequence Through a Non-cleavable Linker (SEQ ID NO:18)

```
GATGCACACAAGAGTGAGGTTGCTCATCGGTTTAAAGATTTGGGAGAAGAAATTTCAAAGCCTTGGTGTTGATTGCCTTTGCTCAGTATCTTCAGCA
GTGTCCATTTGAAGATCATGTAAAATTAGTGACAAATTATGCACAGTTGCAACTCTTCGTGAATGAAGTAACTGAATTGCAAAAACATGTGTTGCTGATGAGTCAGCTGAAAATTGTGACAAATCAC
TTCATACCCTTTTTGGAGACAAATTATGCACAGTTGCAACTCTTCGTGAAACCTATGGTGTGAAATGGCTGACTGCTGTGCAAAACAAGAACCTGAGAGA
AATGAATGCTTCTGCAACACAAGATGACAACCCAAACCTCCCCCGATTGGTGAGACCAGAGGTTGATGTGATGCACTGCTTTTCATGACAATGA
AGAGACATTTTTGAAAAATACTTATATGAAATTGCCAGAAGACATCCTTGCCAGTGCCTGTGCCAAAGCTGCCTGTTGCCAATGAACTCGGGATGAACTTCGGGATGAACTCGGGATGAACTTCGGGATGAACTCGGGATGAACTTCGGGATGAACTCGGGATGAACTTCGGGATGAACTCGGGATGAACTTCGGGATGAACTCGGGATGAACTTCGGGATGAACTCGGGATGAACTTCGGGATGAACTCGGGATGAACTTCGGGATGAACTCGGGATGAACTTCGGGATGAACTCGGGATGAACTTCGGGATGAACTCGGGATGAACTTCGGGATGAACTCGGGATGAACTTCGGGATGAACTCGGGATGAACTTCGGGATGAACTCGGG
```

(SEQ ID NO:18)

Figure 2A – Effect of a Single Acute Dose of a Fusion Molecule Comprising Mature HSA Fused to Mature Human GDF15 on Body Weight
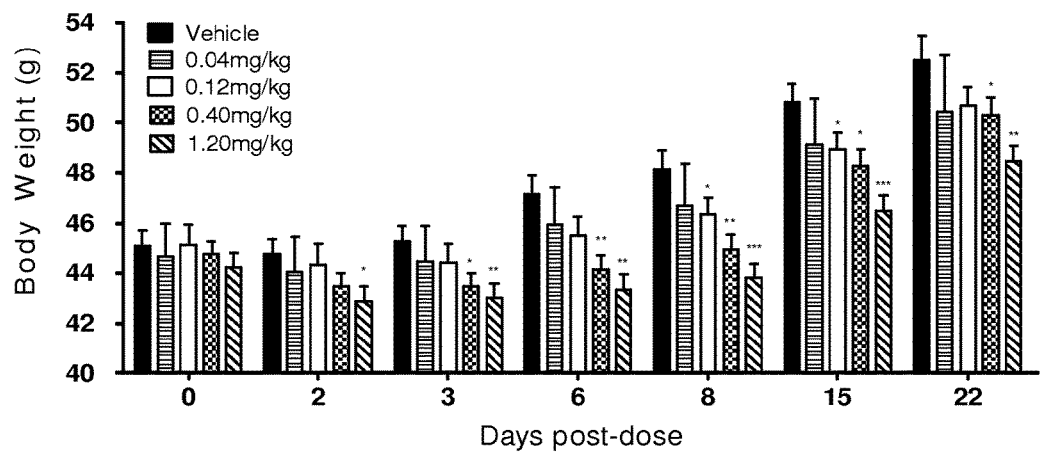
Figure 2B – Effect of a Single Acute Dose of a Fusion Molecule Comprising Mature HSA Fused to Mature Human GDF15 on Food Intake
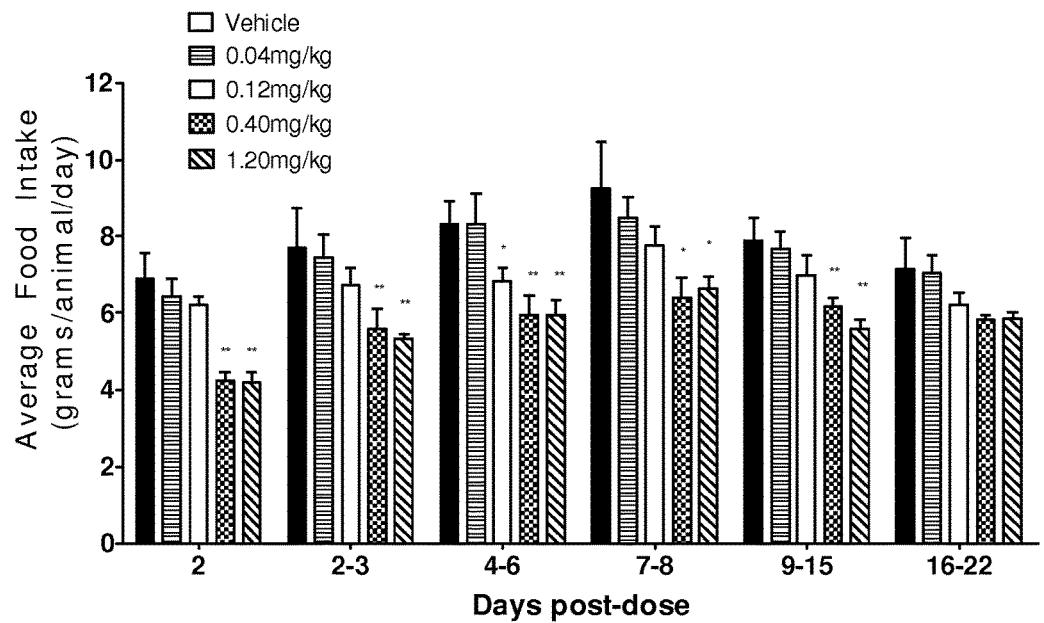

Figure 2C – Effect of a Single Acute Dose of a Fusion Molecule Comprising Mature HSA Fused to Mature Human GDF15 on Blood Glucose
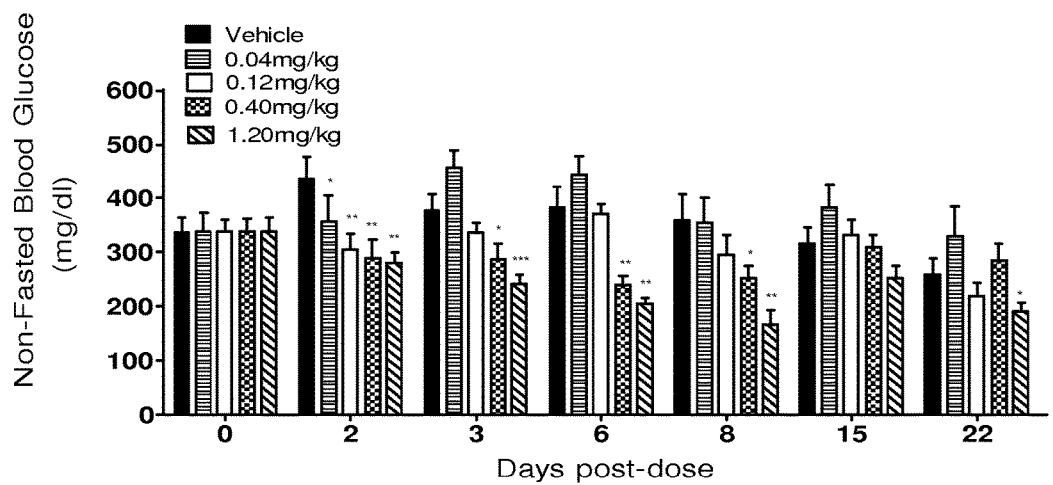

Figure 3 – GDF15 Muteins Generated by Alanine Mutagenesis

```
w29 -(SEQ ID NO:19):
ARNG DHCPLGPGRC CRLHTVRASL EDLGAADWVL SPREVQVTMC IGACPSQFRA
ANMHAQIKTS LHRLKPDTVP APCCVPASYN PMVLIQKTDT GVSLQTYDDL LAKDCHCI w32 -(SEQ ID NO:20):
ARNG DHCPLGPGRC CRLHTVRASL EDLGWADAVL SPREVQVTMC IGACPSQFRA
ANMHAQIKTS LHRLKPDTVP APCCVPASYN PMVLIQKTDT GVSLQTYDDL LAKDCHCI w52 -(SEQ ID NO:21):
ARNG DHCPLGPGRC CRLHTVRASL EDLGWADWVL SPREVQVTMC IGACPSQARA
ANMHAQIKTS LHRLKPDTVP APCCVPASYN PMVLIQKTDT GVSLQTYDDL LAKDCHCI w65 -(SEQ ID NO:22):
ARNG DHCPLGPGRC CRLHTVRASL EDLGWADWVL SPREVQVTMC IGACPSQFRA
ANMHAQIKTS AHRLKPDTVP APCCVPASYN PMVLIQKTDT GVSLQTYDDL LAKDCHCI w68 -(SEQ ID NO:23):
ARNG DHCPLGPGRC CRLHTVRASL EDLGWADWVL SPREVQVTMC IGACPSQFRA
ANMHAQIKTS LHRAKPDTVP APCCVPASYN PMVLIQKTDT GVSLQTYDDL LAKDCHCI w89 -(SEQ ID NO:24):
ARNG DHCPLGPGRC CRLHTVRASL EDLGWADWVL SPREVQVTMC IGACPSQFRA
ANMHAQIKTS LHRLKPDTVP APCCVPASYN PMVLAQKTDT GVSLQTYDDL LAKDCHCI
```

Figure 4 – Identification of GDF15 Mutein Residues for Assessment of Physical Properties

| Mutein | Residue | Mutein | Dimer |
|--------|---------|--------|-------|
| w29 | TRP | ALA | YES |
| w32 | TRP | ALA | YES |
| w52 | PHE | ALA | YES |
| w65 | LEU | ALA | NO |
| w68 | LEU | ALA | YES |
| w89 | ILE | ALA | YES |

Figure 5 – GDF15 Muteins for Evaluation of Physical Properties Relative to GDF15 w113 – (SEQ ID NO:25):
ARNG DHCPLGPGRC CRLHTVRASL AALGWAAWVL SPREVQVTMC IGACPSQFRA
ANMHAQIKTS LHRLKPDTVP APCCVPASYN PMVLIQKTDT GVSLQTYDDL
LAKDCHCI w114 – (SEQ ID NO:26):
ARNG DHCPLGPGRC CRLHTVRASL AALGWAAWVL SPRAVQVTMC IGACPSQFRA
ANMHAQIKTS LHRLKPDTVP APCCVPASYN PMVLIQKTDT GVSLQTYDDL LAKDCHCI w115 – (SEQ ID NO:27):
ARNG DHCPLGPGRC CRLHTVRASL EDLGWADWVL SPREVQVTMC IGACPSQFRA
ANMHAQIKTS LHRLKPDTVP APCCVPASYN PMVLIQKTDT GVSLQTYAAL LAKACHCI w116 – (SEQ ID NO:28):
ARNG DHCPLGPGRC CRLHTVRASL EDLGWADWVL SPREVQVTMC IGACPSQFRA
ANMHAQIKTS LHRLKPDTVP APCCVPASYN PMVLIQKTAT GVSLQTYAAL LAKACHCI w117 – (SEQ ID NO:29):
ARNG DHCPLGPGRC CRLHTVRASL EDLGWADWVL SPREVQVTMC IGACPSQFRA
ANMHAQIKTS LHRLKPDTVP APCCVPASYN PMVLIQKTAT GVSLQTYDDL LAKDCHCI

Figure 6 – Engineered N-Glycan Muteins for Evaluation of Improved Physical Properties Relative to GDF15

```
w118 - (SEQ ID NO:30):
ARNG THCPLGPGRC CRLHTVRASL EDLGWADWVL SPREVQVTMC IGACPSQFRA
ANMHAQIKTS LHRLKPDTVP APCCVPASYN PMVLIQKTDT GVSLQTYDDL LAKDCHCI w119 - (SEQ ID NO:31):
ARNG DHCPLGPGRC CRNHTVRASL EDLGWADWVL SPREVQVTMC IGACPSQFRA
ANMHAQIKTS LHRLKPDTVP APCCVPASYN PMVLIQKTDT GVSLQTYDDL LAKDCHCI w120 - (SEQ ID NO:32):
ARNG DHCPLGPGRC CRLHTVNASL EDLGWADWVL SPREVQVTMC IGACPSQFRA
ANMHAQIKTS LHRLKPDTVP APCCVPASYN PMVLIQKTDT GVSLQTYDDL LAKDCHCI w121 - (SEQ ID NO:33):
ARNG DHCPLGPGRC CRLHTVRASL EDLGWADWNL SPREVQVTMC IGACPSQFRA
ANMHAQIKTS LHRLKPDTVP APCCVPASYN PMVLIQKTDT GVSLQTYDDL LAKDCHCI w122 - (SEQ ID NO:34):
ARNG DHCPLGPGRC CRLHTVRASL EDLGWADWVL SPREVNVTMC IGACPSQFRA
ANMHAQIKTS LHRLKPDTVP APCCVPASYN PMVLIQKTDT GVSLQTYDDL LAKDCHCI w123 - (SEQ ID NO:35):
ARNG DHCPLGPGRC CRLHTVRASL EDLGWADWVL SPREVQVTMC IGACPSQFRA
ANMTAQIKTS LHRLKPDTVP APCCVPASYN PMVLIQKTDT GVSLQTYDDL LAKDCHCI w124 - (SEQ ID NO:36):
ARNG DHCPLGPGRC CRLHTVRASL EDLGWADWVL SPREVQVTMC IGACPSQFRA
ANMHAQNKTS LHRLKPDTVP APCCVPASYN PMVLIQKTDT GVSLQTYDDL LAKDCHCI w125 - (SEQ ID NO:37):
ARNG DHCPLGPGRC CRLHTVRASL EDLGWADWVL SPREVQVTMC IGACPSQFRA
ANMHAQINTS LHRLKPDTVP APCCVPASYN PMVLIQKTDT GVSLQTYDDL LAKDCHCI w126 - (SEQ ID NO:38):
ARNG DHCPLGPGRC CRLHTVRASL EDLGWADWVL SPREVQVTMC IGACPSQFRA
ANMHAQIKTS LHRLKNDTVP APCCVPASYN PMVLIQKTDT GVSLQTYDDL LAKDCHCI w127 - (SEQ ID NO:39):
ARNG DHCPLGPGRC CRLHTVRASL EDLGWADWVL SPREVQVTMC IGACPSQFRA
ANMHAQIKTS LHRLKPDTVP APCCVNASYN PMVLIQKTDT GVSLQTYDDL LAKDCHCI w128 - (SEQ ID NO:40):
ARNG DHCPLGPGRC CRLHTVRASL EDLGWADWVL SPREVQVTMC IGACPSQFRA
ANMHAQIKTS LHRLKPDTVP APCCVPASYN PMVLINKTDT GVSLQTYDDL LAKDCHCI w129 - (SEQ ID NO:41):
ARNG DHCPLGPGRC CRLHTVRASL EDLGWADWVL SPREVQVTMC IGACPSQFRA
ANMHAQIKTS LHRLKPDTVP APCCVPASYN PMVLIQKNDT GVSLQTYDDL LAKDCHCI
```

Figure 6, continued w130 - (SEQ ID NO:42):
ARNG DHCPLGPGRC CRLHTVRASL EDLGWADWVL SPREVQVTMC IGACPSQFRA
ANMHAQIKTS LHRLKPDTVP APCCVPASYN PMVLIQKTDT NVSLQTYDDL LAKDCHCI w131 - (SEQ ID NO:43):
ARNG DHCPLGPGRC CRLHTVRASL EDLGWADWVL SPREVQVTMC IGACPSQFRA
ANMHAQIKTS LHRLKPDTVP APCCVPASYN PMVLIQKTDT GVSNQTYDDL LAKDCHCI w132 - (SEQ ID NO:44):
ARNG THCPLGPGRC CRLHTVRASL EDLGWADWVL SPREVQVTMC IGACPSQFRA
ANMHAQIKTS LHRLKPDTVP APCCVPASYN PMVLINKTDT GVSLQTYDDL LAKDCHCI w133 - (SEQ ID NO:45):
ARNG THCPLGPGRC CRLHTVRASL EDLGWADWVL SPREVQVTMC IGACPSQFRA
ANMHAQIKTS LHRLKPDTVP APCCVPASYN PMVLIQKTDT NVSLQTYDDL LAKDCHCI w134 - (SEQ ID NO:46):
ARNG DHCPLGPGRC CRLHTVRASL EDLGWADWVL SPREVNVTMC IGACPSQFRA
ANMHAQIKTS LHRLKPDTVP APCCVPASYN PMVLINKTDT GVSLQTYDDL LAKDCHCI w135 - (SEQ ID NO:47):
ARNG DHCPLGPGRC CRLHTVRASL EDLGWADWVL SPREVNVTMC IGACPSQFRA
ANMHAQIKTS LHRLKPDTVP APCCVPASYN PMVLIQKTDT NVSLQTYDDL LAKDCHCI w136 - (SEQ ID NO:48):
ARNG DHCPLGPGRC CRLHTVRASL EDLGWADWVL SPREVQVTMC IGACPSQFRA
ANMHAQIKTS LHRLKNDTVP APCCVPASYN PMVLINKTDT GVSLQTYDDL LAKDCHCI w137 - (SEQ ID NO:49):
ARNG DHCPLGPGRC CRLHTVRASL EDLGWADWVL SPREVQVTMC IGACPSQFRA
ANMHAQIKTS LHRLKNDTVP APCCVPASYN PMVLIQKTDT NVSLQTYDDL LAKDCHCI w138 - (SEQ ID NO:50):
ARNG DHCPLGPGRC CRLHTVRASL EDLGWADWVL SPREVQVTMC IGACPSQFRA
ANMHAQIKTS LHRLKPDTVP APCCVPASYN PMVLINKTDT NVSLQTYDDL LAKDCHCI w139 - (SEQ ID NO:51):
ARNG DHCPLGPGRC CRLHTVRASL EDLGWADWVL SPREVQVTMC IGACPSQFRA
ANMHAQIKTS LHRLKPDTVP APCCVPASYN PMVLINKTDT GVSNQTYDDL LAKDCHCI w140 - (SEQ ID NO:52):
ARNG DHCPLGPGRC CRLHTVRASL EDLGWADWVL SPREVQVTMC IGACPSQFRA
ANMHAQIKTS LHRLKPDTVP APCCVPASYN PMVLIQKTDT NVSNQTYDDL LAKDCHCI

Figure 7 – Human GDF15 Mutein Dimer Formation and N-Glycan Site Occupancy

| Mutein | Dimer | N-Glyc |
|--------|-------|--------|
| w118   | YES   | YES    |
| w119   | YES   | YES    |
| w120   | YES   | YES    |
| w121   | YES   | NO     |
| w122   | YES   | YES    |
| w123   | NO    | -      |
| w124   | YES   | NO     |
| w125   | NO    | -      |
| w126   | YES   | YES    |
| w127   | NO    | -      |
| w128   | YES   | YES    |
| w129   | NO    | -      |
| w130   | YES   | YES    |
| w131   | YES   | YES    |
| w132   | YES   | YES    |
| w133   | YES   | YES    |
| w134   | YES   | YES    |
| w135   | YES   | YES    |
| w136   | YES   | YES    |
| w137   | YES   | YES    |
| w138   | YES   | YES    |
| w139   | YES   | YES    |
| w140   | YES   | YES    |

Figure 8A – Maximum Solubility of Human GDF15 Muteins Using Centrifugal Concentrators

| Mutein | Max solubility in PBS |
|---|---|
| hGDF15 | + |
| w29 | + |
| w32 | + |
| w52 | + |
| w68 | + |
| w89 | ++ |
| w113 | + |
| w115 | + |
| w116 | ++ |
| w118 | +++ |
| w120 | ++++ |
| w122 | ++ |

| Mutein | Max solubility in PBS |
|---|---|
| w126 | +++ |
| w128 | ++++ |
| w130 | ++++ |
| w131 | ++++ |
| w132 | ++++ |
| w133 | ++++ |
| w134 | ++++ |
| w135 | +++++ |
| w136 | ++++ |
| w137 | ++++ |
| w138 | +++++ |
| w139 | +++++ |
| w140 | +++++ |

Figure 8B – Maximum Solubility of Human GDF15 Muteins using Turbidity Assessment

| Mutein | Max solubility in PBS |
|---|---|
| hGDF15 | + |
| w120 | ++++ |
| w122 | ++ |
| w126 | ++++ |
| w128 | ++++ |
| w130 | +++++ |
| w131 | ++++ |

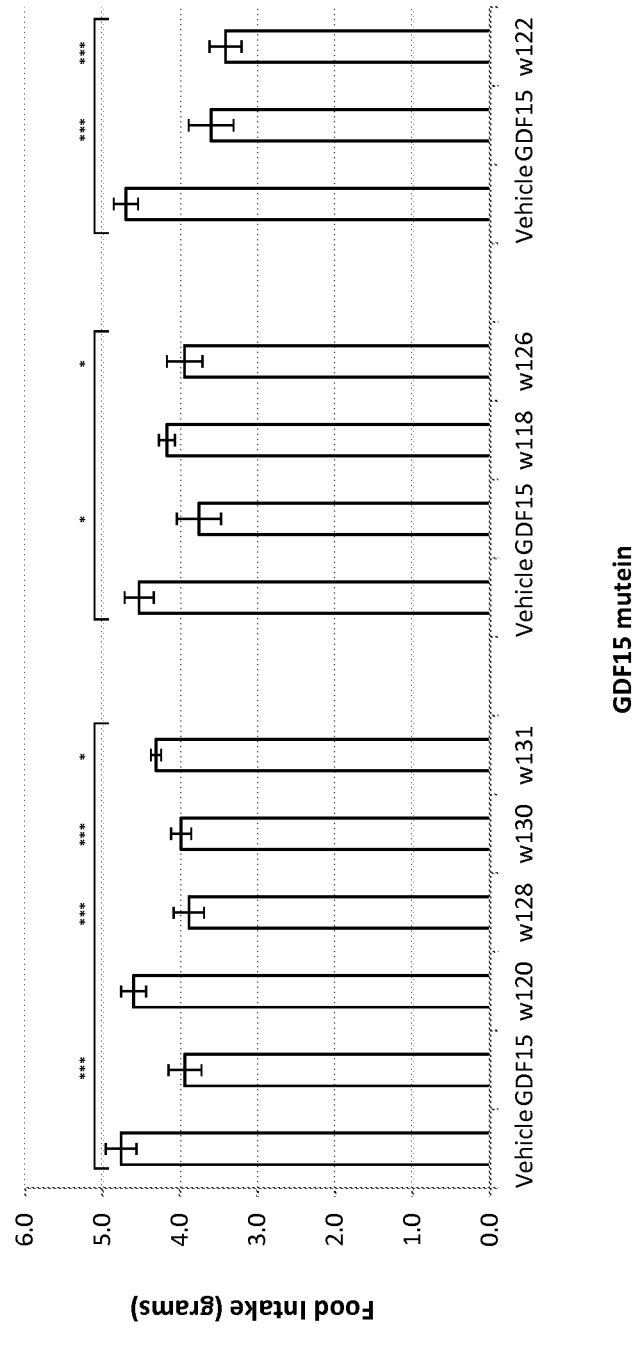
Figure 9A – Acute in vivo Efficacy of Human GDF15 N-Glycan Muteins on Food Intake in *ob/ob* mice

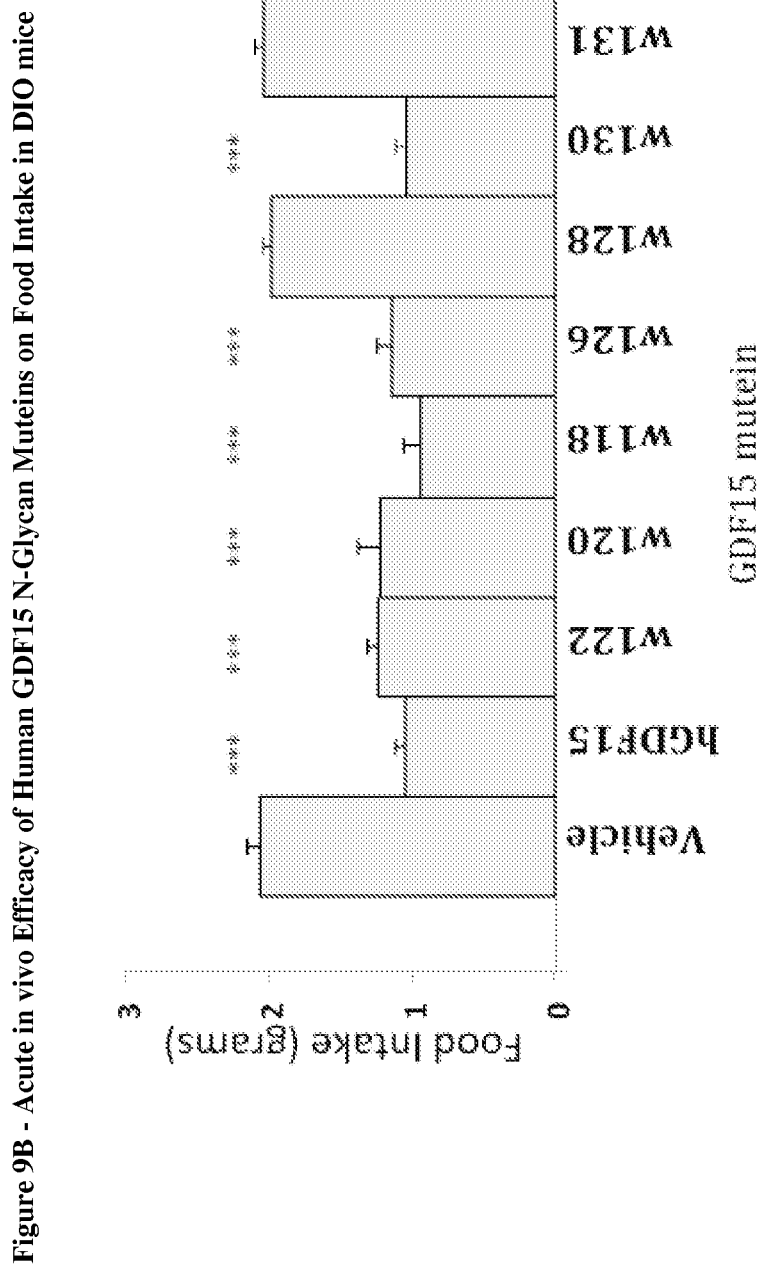
Figure 9B - Acute in vivo Efficacy of Human GDF15 N-Glycan Muteins on Food Intake in DIO mice Figure 10 – Analytical Gel Filtration of N-Glycan Muteins and Mature Human GDF15

| Mutein | Elution time (min) |
|---|---|
| hGDF15 | 10.837 |
| w118 | 10.029 |
| w120 | 9.201 |
| w122 | 9.123 |
| w126 | 10.011 |
| w128 | 9.854 |
| w130 | 9.198 |
| w131 | 9.153 |
| w132 | 9.342 |
| w133 | 8.810 |
| w134 | 8.967 |
| w135 | 8.667 |
| w136 | 9.787 |
| w138 | 9.221 |
| w139 | 9.281 |

Figure 11A -
Amino Acid Sequences of Fusion Molecules Comprising HSA having an Igk Signal Sequence (signal sequence underlined; SEQ ID NO:53) Fused to the N-Terminus of Species Orthologs of Mature GDF15 Mus musculus (bold; SEQ ID NO:54) And Macaca mulatta (bold; SEQ ID NO:55) Through a Cleavable Linker (bold and underlined; SEQ ID NO:56)

Mus musculus (NP_035949.2)

<u>MDMRVPAQLLGLLLLWLRGARC</u>DAHKSEVAHRFKDLGEENFKALVLIAFAQYLQQCPFEDHVKL
VNEVTEFAKTCVADESAENCDKSLHTLFGDKLCTVATLRETYGEMADCCAKQEPERNECFLQHK
DDNPNLPRLVRPEVDVMCTAFHDNEETFLKKYLYEIARRHPYFYAPELLFFAKRYKAAFTECCQ
AADKAACLLPKLDELRDEGKASSAKQRLKCASLQKFGERAFKAWAVARLSQRFPKAEFAEVSKL
VTDLTKVHTECCHGDLLECADDRADLAKYICENQDSISSKLKECCEKPLLEKSHCIAEVENDEM
PADLPSLAADFVESKDVCKNYAEAKDVFLGMFLYEYARRHPDYSVVLLLRLAKTYETTLEKCCA
AADPHECYAKVFDEFKPLVEEPQNLIKQNCELFEQLGEYKFQNALLVRYTKKVPQVSTPTLVEV
SRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAF
VEKCCKADDKETCFAEEGKKLVAASQAALGL<u>GGGGSGGGGSIEGR</u>**SAHAHPRDSCPLGPGRCCH
LETVQATLEDLGWSDWVLSPRQLQLSMCVGECPHLYRSANTHAQIKARLHGLQPDKVPAPCCVP
SSYTPVVLMHRTDSGVSLQTYDDLVARGCHCA** (SEQ ID NO:57)

Macaca mulatta (EHH29815.1)

<u>MDMRVPAQLLGLLLLWLRGARC</u>DAHKSEVAHRFKDLGEENFKALVLIAFAQYLQQCPFEDHVKL
VNEVTEFAKTCVADESAENCDKSLHTLFGDKLCTVATLRETYGEMADCCAKQEPERNECFLQHK
DDNPNLPRLVRPEVDVMCTAFHDNEETFLKKYLYEIARRHPYFYAPELLFFAKRYKAAFTECCQ
AADKAACLLPKLDELRDEGKASSAKQRLKCASLQKFGERAFKAWAVARLSQRFPKAEFAEVSKL
VTDLTKVHTECCHGDLLECADDRADLAKYICENQDSISSKLKECCEKPLLEKSHCIAEVENDEM
PADLPSLAADFVESKDVCKNYAEAKDVFLGMFLYEYARRHPDYSVVLLLRLAKTYETTLEKCCA
AADPHECYAKVFDEFKPLVEEPQNLIKQNCELFEQLGEYKFQNALLVRYTKKVPQVSTPTLVEV
SRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAF
VEKCCKADDKETCFAEEGKKLVAASQAALGL<u>GGGGSGGGGSIEGR</u>**ARNGDRCPLGPGRCCRLHT
VHASLEDLGWADWVLSPREVQVTMCIGACPSQFREANMHAQIKMNLHRLKPDTVPAPCCVPASY
NPMVLIQKTDTGVSLQTYDDLLAKDCHCV** (SEQ ID NO:58)

Figure 11B - Amino Acid Sequences of Fusion Molecules Comprising HSA having an IgK Signal Sequence (signal sequence underlined; SEQ ID NO:53) Fused to the N-terminus of Mature Human TGF-β1 (bold; SEQ ID NO:59) and Mature Human BMP2 (bold; SEQ ID NO:60) through a Cleavable Linker (bold and underlined; SEQ ID NO:61)

Human TGF-β1 (CAA26580.1)

<u>MDMRVPAQLLGLLLLWLRGARC</u>DAHKSEVAHRFKDLGEENFKALVLIAFAQYLQQCPFEDHVKL
VNEVTEFAKTCVADESAENCDKSLHTLFGDKLCTVATLRETYGEMADCCAKQEPERNECFLQHK
DDNPNLPRLVRPEVDVMCTAFHDNEETFLKKYLYEIARRHPYFYAPELLFFAKRYKAAFTECCQ
AADKAACLLPKLDELRDEGKASSAKQRLKCASLQKFGERAFKAWAVARLSQRFPKAEFAEVSKL
VTDLTKVHTECCHGDLLECADDRADLAKYICENQDSISSKLKECCEKPLLEKSHCIAEVENDEM
PADLPSLAADFVESKDVCKNYAEAKDVFLGMFLYEYARRHPDYSVVLLLRLAKTYETTLEKCCA
AADPHECYAKVFDEFKPLVEEPQNLIKQNCELFEQLGEYKFQNALLVRYTKKVPQVSTPTLVEV
SRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAF
VEKCCKADDKETCFAEEGKKLVAASQAALGL**GGGGSIEGRDYKDDDDKALDTNYCFSSTEKNCC
VRQLYIDFRKDLGWKWIHEPKGYHANFCLGPCPYIWSLDTQYSKVLALYNQHNPGASAAPCCVP
QALEPLPIVYYVGRKPKVEQLSNMIVRSCKCS** (SEQ ID NO:62)

Human BMP2 (NM_001200):

<u>MDMRVPAQLLGLLLLWLRGARC</u>DAHKSEVAHRFKDLGEENFKALVLIAFAQYLQQCPFEDHVKL
VNEVTEFAKTCVADESAENCDKSLHTLFGDKLCTVATLRETYGEMADCCAKQEPERNECFLQHK
DDNPNLPRLVRPEVDVMCTAFHDNEETFLKKYLYEIARRHPYFYAPELLFFAKRYKAAFTECCQ
AADKAACLLPKLDELRDEGKASSAKQRLKCASLQKFGERAFKAWAVARLSQRFPKAEFAEVSKL
VTDLTKVHTECCHGDLLECADDRADLAKYICENQDSISSKLKECCEKPLLEKSHCIAEVENDEM
PADLPSLAADFVESKDVCKNYAEAKDVFLGMFLYEYARRHPDYSVVLLLRLAKTYETTLEKCCA
AADPHECYAKVFDEFKPLVEEPQNLIKQNCELFEQLGEYKFQNALLVRYTKKVPQVSTPTLVEV
SRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAF
VEKCCKADDKETCFAEEGKKLVAASQAALGL**GGGGSIEGRDYKDDDDKQAKHKQRKRLKSSCKR
HPLYVDFSDVGWNDWIVAPPGYHAFYCHGECPFPLADHLNSTNHAIVQTLVNSVNSKIPKACCV
PTELSAISMLYLDENEKVVLKNYQDMVVEGCGCR** (SEQ ID NO:63)

Figure 12 – Secretion of Fusion Molecules Comprising HSA Fused to the N-Terminus of Mature GDF15 Species Orthologs, Human TGFβ1 and Human BMP2

| Construct | Dimer Secretion |
|---|---|
| Mus musculus - GDF15 | YES |
| Macaca mulatta - GDF15 | YES |
| Human TGF-β1 | NO |
| Human BMP2 | NO |

Figure 13 – Amino Acid Sequences of Fusion Molecules Comprising HSA Having an IgK Signal Sequence (signal sequence underlined; SEQ ID NO:53) Fused to the N-Terminus of Mature Human GDF15 Muteins Generated by Alanine-scan Through a Non-cleavable Linker (bold and underlined; (SEQ ID NO:64)

<u>MDMRVPAQLLGLLLLWLRGARC</u>DAHKSEVAHRFKDLGEENFKALVLIAFAQYLQQCPFEDHVKLV
NEVTEFAKTCVADESAENCDKSLHTLFGDKLCTVATLRETYGEMADCCAKQEPERNECFLQHKDD
NPNLPRLVRPEVDVMCTAFHDNEETFLKKYLYEIARRHPYFYAPELLFFAKRYKAAFTECCQAAD
KAACLLPKLDELRDEGKASSAKQRLKCASLQKFGERAFKAWAVARLSQRFPKAEFAEVSKLVTDL
TKVHTECCHGDLLECADDRADLAKYICENQDSISSKLKECCEKPLLEKSHCIAEVENDEMPADLP
SLAADFVESKDVCKNYAEAKDVFLGMFLYEYARRHPDYSVVLLLRLAKTYETTLEKCCAAADPHE
CYAKVFDEFKPLVEEPQNLIKQNCELFEQLGEYKFQNALLVRYTKKVPQVSTPTLVEVSRNLGKV
GSKCCKHPEAKRMPCAEDYLSVVLNQLCVLHEKTPVSDRVTKCCTESLVNRRPCFSALEVDETYV
PKEFNAETFTFHADICTLSEKERQIKKQTALVELVKHKPKATKEQLKAVMDDFAAFVEKCCKADD
KETCFAEEGKKLVAASQAALGL**GGGGSGGGGSGGGGSARNGDHCPLGPGRCCRLHTVRASLEDLG
WADWVLSPREVQVTMCIGACPSQFRAANMHAQIKTSLHRLKPDTVPAPCCVPASYNPMVLIQKTD
TGVSLQTYDDLLAKDCHCI** (SEQ ID NO:15)

Muteins of Bolded sequence above are as follows:

w2 (SEQ ID NO:65):
AANG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w3 -(SEQ ID NO:66):
ARAG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w4 -(SEQ ID NO:67):
ARNA DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w5 - (SEQ ID NO:68):
ARNG AHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w6 - (SEQ ID NO:69):
ARNG DAPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w8 - (SEQ ID NO:70):
ARNG DHCALGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w9 - (SEQ ID NO:71):
ARNG DHCPAGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w10 - (SEQ ID NO:72):
ARNG DHCPLAPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI

Figure 13, continued

```
w11 - (SEQ ID NO:73):
ARNG DHCPLGAGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w12 - (SEQ ID NO:74):
ARNG DHCPLGPARC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w13 - (SEQ ID NO:75):
ARNG DHCPLGPGAC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w16 - (SEQ ID NO:76):
ARNG DHCPLGPGRC CALHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w17 - (SEQ ID NO:77):
ARNG DHCPLGPGRC CRAHTVRASL EDLGWADWVL SPREVQVTMC IGACPSQFRA ANMHAQIKTS
LHRLKPDTVP APCCVPASYN PMVLIQKTDT GVSLQTYDDL LAKDCHCI w18 - (SEQ ID NO:78):
ARNG DHCPLGPGRC CRLATVRASL EDLGWADWVL SPREVQVTMC IGACPSQFRA ANMHAQIKTS
LHRLKPDTVP APCCVPASYN PMVLIQKTDT GVSLQTYDDL LAKDCHCI w19 - (SEQ ID NO:79):
ARNG DHCPLGPGRC CRLHAVRASL EDLGWADWVL SPREVQVTMC IGACPSQFRA ANMHAQIKTS
LHRLKPDTVP APCCVPASYN PMVLIQKTDT GVSLQTYDDL LAKDCHCI w20 - (SEQ ID NO:80):
ARNG DHCPLGPGRC CRLHTARASL EDLGWADWVL SPREVQVTMC IGACPSQFRA ANMHAQIKTS
LHRLKPDTVP APCCVPASYN PMVLIQKTDT GVSLQTYDDL LAKDCHCI w21 - (SEQ ID NO:81):
ARNG DHCPLGPGRC CRLHTVAASL EDLGWADWVL SPREVQVTMC IGACPSQFRA ANMHAQIKTS
LHRLKPDTVP APCCVPASYN PMVLIQKTDT GVSLQTYDDL LAKDCHCI w23 - (SEQ ID NO:82):
ARNG DHCPLGPGRC CRLHTVRAAL EDLGWADWVL SPREVQVTMC IGACPSQFRA ANMHAQIKTS
LHRLKPDTVP APCCVPASYN PMVLIQKTDT GVSLQTYDDL LAKDCHCI w24 - (SEQ ID NO:83):
ARNG DHCPLGPGRC CRLHTVRASA EDLGWADWVL SPREVQVTMC IGACPSQFRA ANMHAQIKTS
LHRLKPDTVP APCCVPASYN PMVLIQKTDT GVSLQTYDDL LAKDCHCI w25 - (SEQ ID NO:84):
ARNG DHCPLGPGRC CRLHTVRASL ADLGWADWVL SPREVQVTMC IGACPSQFRA ANMHAQIKTS
LHRLKPDTVP APCCVPASYN PMVLIQKTDT GVSLQTYDDL LAKDCHCI w26 - (SEQ ID NO:85):
ARNG DHCPLGPGRC CRLHTVRASL EALGWADWVL SPREVQVTMC IGACPSQFRA ANMHAQIKTS
LHRLKPDTVP APCCVPASYN PMVLIQKTDT GVSLQTYDDL LAKDCHCI
```

Figure 13, continued w27 - (SEQ ID NO:86):
ARNG DHCPLGPGRC CRLHTVRASL EDAGWADWVL SPREVQVTMC IGACPSQFRA ANMHAQIKTS
LHRLKPDTVP APCCVPASYN PMVLIQKTDT GVSLQTYDDL LAKDCHCI w28 - (SEQ ID NO:87):
ARNG DHCPLGPGRC CRLHTVRASL EDLAWADWVL SPREVQVTMC IGACPSQFRA ANMHAQIKTS
LHRLKPDTVP APCCVPASYN PMVLIQKTDT GVSLQTYDDL LAKDCHCI w29 - (SEQ ID NO:88):
ARNG DHCPLGPGRC CRLHTVRASL EDLGAADWVL SPREVQVTMC IGACPSQFRA ANMHAQIKTS
LHRLKPDTVP APCCVPASYN PMVLIQKTDT GVSLQTYDDL LAKDCHCI w31 - (SEQ ID NO:89):
ARNG DHCPLGPGRC CRLHTVRASL EDLGWAAWVL SPREVQVTMC IGACPSQFRA ANMHAQIKTS
LHRLKPDTVP APCCVPASYN PMVLIQKTDT GVSLQTYDDL LAKDCHCI w32 - (SEQ ID NO:90):
ARNG DHCPLGPGRC CRLHTVRASL EDLGWADAVL SPREVQVTMC IGACPSQFRA ANMHAQIKTS
LHRLKPDTVP APCCVPASYN PMVLIQKTDT GVSLQTYDDL LAKDCHCI w33 - (SEQ ID NO:91):
ARNG DHCPLGPGRC CRLHTVRASL EDLGWADWAL SPREVQVTMC IGACPSQFRA ANMHAQIKTS
LHRLKPDTVP APCCVPASYN PMVLIQKTDT GVSLQTYDDL LAKDCHCI w34 - (SEQ ID NO:92):
ARNG DHCPLGPGRC CRLHTVRASL EDLGWADWVA SPREVQVTMC IGACPSQFRA ANMHAQIKTS
LHRLKPDTVP APCCVPASYN PMVLIQKTDT GVSLQTYDDL LAKDCHCI w35 - (SEQ ID NO:93):
ARNG DHCPLGPGRC CRLHTVRASL EDLGWADWVL APREVQVTMC IGACPSQFRA ANMHAQIKTS
LHRLKPDTVP APCCVPASYN PMVLIQKTDT GVSLQTYDDL
LAKDCHCI w36 - (SEQ ID NO:94):
ARNG DHCPLGPGRC CRLHTVRASL EDLGWADWVL SAREVQVTMC IGACPSQFRA ANMHAQIKTS
LHRLKPDTVP APCCVPASYN PMVLIQKTDT GVSLQTYDDL LAKDCHCI w37 - (SEQ ID NO:95):
ARNG DHCPLGPGRC CRLHTVRASL EDLGWADWVL SPAEVQVTMC IGACPSQFRA ANMHAQIKTS
LHRLKPDTVP APCCVPASYN PMVLIQKTDT GVSLQTYDDL LAKDCHCI w38 - (SEQ ID NO:96):
ARNG DHCPLGPGRC CRLHTVRASL EDLGWADWVL SPRAVQVTMC IGACPSQFRA ANMHAQIKTS
LHRLKPDTVP APCCVPASYN PMVLIQKTDT GVSLQTYDDL LAKDCHCI w39 - (SEQ ID NO:97):
ARNG DHCPLGPGRC CRLHTVRASL EDLGWADWVL SPREAQVTMC IGACPSQFRA ANMHAQIKTS
LHRLKPDTVP APCCVPASYN PMVLIQKTDT GVSLQTYDDL LAKDCHCI w40 - (SEQ ID NO:98):
ARNG DHCPLGPGRC CRLHTVRASL EDLGWADWVL SPREVAVTMC IGACPSQFRA ANMHAQIKTS
LHRLKPDTVP APCCVPASYN PMVLIQKTDT GVSLQTYDDL LAKDCHCI

Figure 13, continued w41 - (SEQ ID NO:99):
ARNG DHCPLGPGRC CRLHTVRASL EDLGWADWVL SPREVQATMC IGACPSQFRA ANMHAQIKTS
LHRLKPDTVP APCCVPASYN PMVLIQKTDT GVSLQTYDDL LAKDCHCI w42 - (SEQ ID NO:100):
ARNG DHCPLGPGRC CRLHTVRASL EDLGWADWVL SPREVQVAMC IGACPSQFRA ANMHAQIKTS
LHRLKPDTVP APCCVPASYN PMVLIQKTDT GVSLQTYDDL LAKDCHCI w43 - (SEQ ID NO:101):
ARNG DHCPLGPGRC CRLHTVRASL EDLGWADWVL SPREVQVTAC IGACPSQFRA ANMHAQIKTS
LHRLKPDTVP APCCVPASYN PMVLIQKTDT GVSLQTYDDL LAKDCHCI w45 - (SEQ ID NO:102):
ARNG DHCPLGPGRC CRLHTVRASL EDLGWADWVL SPREVQVTMC AGACPSQFRA ANMHAQIKTS
LHRLKPDTVP APCCVPASYN PMVLIQKTDT GVSLQTYDDL LAKDCHCI w46 - (SEQ ID NO:103):
ARNG DHCPLGPGRC CRLHTVRASL EDLGWADWVL SPREVQVTMC IAACPSQFRA ANMHAQIKTS
LHRLKPDTVP APCCVPASYN PMVLIQKTDT GVSLQTYDDL LAKDCHCI w49 - (SEQ ID NO:104):
ARNG DHCPLGPGRC CRLHTVRASL EDLGWADWVL SPREVQVTMC IGACASQFRA ANMHAQIKTS
LHRLKPDTVP APCCVPASYN PMVLIQKTDT GVSLQTYDDL LAKDCHCI w50 - (SEQ ID NO:105):
ARNG DHCPLGPGRC CRLHTVRASL EDLGWADWVL SPREVQVTMC IGACPAQFRA ANMHAQIKTS
LHRLKPDTVP APCCVPASYN PMVLIQKTDT GVSLQTYDDL LAKDCHCI w51 - (SEQ ID NO:106):
ARNG DHCPLGPGRC CRLHTVRASL EDLGWADWVL SPREVQVTMC IGACPSAFRA ANMHAQIKTS
LHRLKPDTVP APCCVPASYN PMVLIQKTDT GVSLQTYDDL LAKDCHCI w52 - (SEQ ID NO:107):
ARNG DHCPLGPGRC CRLHTVRASL EDLGWADWVL SPREVQVTMC IGACPSQARA ANMHAQIKTS
LHRLKPDTVP APCCVPASYN PMVLIQKTDT GVSLQTYDDL LAKDCHCI w53 - R53A (SEQ ID NO:108):
ARNG DHCPLGPGRC CRLHTVRASL EDLGWADWVL SPREVQVTMC IGACPSQFAA ANMHAQIKTS
LHRLKPDTVP APCCVPASYN PMVLIQKTDT GVSLQTYDDL LAKDCHCI w56 - N56A (SEQ ID NO:109):
ARNG DHCPLGPGRC CRLHTVRASL EDLGWADWVL SPREVQVTMC IGACPSQFRA AAMHAQIKTS
LHRLKPDTVP APCCVPASYN PMVLIQKTDT GVSLQTYDDL LAKDCHCI w57 - (SEQ ID NO:110):
ARNG DHCPLGPGRC CRLHTVRASL EDLGWADWVL SPREVQVTMC IGACPSQFRA ANAHAQIKTS
LHRLKPDTVP APCCVPASYN PMVLIQKTDT GVSLQTYDDL LAKDCHCI w58 - (SEQ ID NO:111):
ARNG DHCPLGPGRC CRLHTVRASL EDLGWADWVL SPREVQVTMC IGACPSQFRA ANMAAQIKTS
LHRLKPDTVP APCCVPASYN PMVLIQKTDT GVSLQTYDDL LAKDCHCI

Figure 13, continued w60 - (SEQ ID NO:112):
ARNG DHCPLGPGRC CRLHTVRASL EDLGWADWVL SPREVQVTMC IGACPSQFRA ANMHAAIKTS
LHRLKPDTVP APCCVPASYN PMVLIQKTDT GVSLQTYDDL LAKDCHCI w61 - (SEQ ID NO:113):
ARNG DHCPLGPGRC CRLHTVRASL EDLGWADWVL SPREVQVTMC IGACPSQFRA ANMHAQAKTS
LHRLKPDTVP APCCVPASYN PMVLIQKTDT GVSLQTYDDL LAKDCHCI w62 - (SEQ ID NO:114):
ARNG DHCPLGPGRC CRLHTVRASL EDLGWADWVL SPREVQVTMC IGACPSQFRA ANMHAQIATS
LHRLKPDTVP APCCVPASYN PMVLIQKTDT GVSLQTYDDL LAKDCHCI w63 - (SEQ ID NO:115):
ARNG DHCPLGPGRC CRLHTVRASL EDLGWADWVL SPREVQVTMC IGACPSQFRA ANMHAQIKAS
LHRLKPDTVP APCCVPASYN PMVLIQKTDT GVSLQTYDDL LAKDCHCI w64 - (SEQ ID NO:116):
ARNG DHCPLGPGRC CRLHTVRASL EDLGWADWVL SPREVQVTMC IGACPSQFRA ANMHAQIKTA
LHRLKPDTVP APCCVPASYN PMVLIQKTDT GVSLQTYDDL LAKDCHCI w65 - (SEQ ID NO:117):
ARNG DHCPLGPGRC CRLHTVRASL EDLGWADWVL SPREVQVTMC IGACPSQFRA ANMHAQIKTS
AHRLKPDTVP APCCVPASYN PMVLIQKTDT GVSLQTYDDL LAKDCHCI w66 - (SEQ ID NO:118):
ARNG DHCPLGPGRC CRLHTVRASL EDLGWADWVL SPREVQVTMC IGACPSQFRA ANMHAQIKTS
LARLKPDTVP APCCVPASYN PMVLIQKTDT GVSLQTYDDL LAKDCHCI w67 - (SEQ ID NO:119):
ARNG DHCPLGPGRC CRLHTVRASL EDLGWADWVL SPREVQVTMC IGACPSQFRA ANMHAQIKTS
LHALKPDTVP APCCVPASYN PMVLIQKTDT GVSLQTYDDL LAKDCHCI w68 - (SEQ ID NO:120):
ARNG DHCPLGPGRC CRLHTVRASL EDLGWADWVL SPREVQVTMC IGACPSQFRA ANMHAQIKTS
LHRAKPDTVP APCCVPASYN PMVLIQKTDT GVSLQTYDDL LAKDCHCI w69 - (SEQ ID NO:121):
ARNG DHCPLGPGRC CRLHTVRASL EDLGWADWVL SPREVQVTMC IGACPSQFRA ANMHAQIKTS
LHRLAPDTVP APCCVPASYN PMVLIQKTDT GVSLQTYDDL LAKDCHCI w70 - (SEQ ID NO:122):
ARNG DHCPLGPGRC CRLHTVRASL EDLGWADWVL SPREVQVTMC IGACPSQFRA ANMHAQIKTS
LHRLKADTVP APCCVPASYN PMVLIQKTDT GVSLQTYDDL LAKDCHCI w71 - (SEQ ID NO:123):
ARNG DHCPLGPGRC CRLHTVRASL EDLGWADWVL SPREVQVTMC IGACPSQFRA ANMHAQIKTS
LHRLKPATVP APCCVPASYN PMVLIQKTDT GVSLQTYDDL LAKDCHCI w72 - (SEQ ID NO:124):
ARNG DHCPLGPGRC CRLHTVRASL EDLGWADWVL SPREVQVTMC IGACPSQFRA ANMHAQIKTS
LHRLKPDAVP APCCVPASYN PMVLIQKTDT GVSLQTYDDL LAKDCHCI

Figure 13, continued

```
w73 - (SEQ ID NO:125):
ARNG DHCPLGPGRC CRLHTVRASL EDLGWADWVL SPREVQVTMC IGACPSQFRA ANMHAQIKTS
LHRLKPDTAP APCCVPASYN PMVLIQKTDT GVSLQTYDDL LAKDCHCI w74 - (SEQ ID NO:126):
ARNG DHCPLGPGRC CRLHTVRASL EDLGWADWVL SPREVQVTMC IGACPSQFRA ANMHAQIKTS
LHRLKPDTVA APCCVPASYN PMVLIQKTDT GVSLQTYDDL LAKDCHCI w76 - (SEQ ID NO:127):
ARNG DHCPLGPGRC CRLHTVRASL EDLGWADWVL SPREVQVTMC IGACPSQFRA ANMHAQIKTS
LHRLKPDTVP AACCVPASYN PMVLIQKTDT GVSLQTYDDL LAKDCHCI w79 - (SEQ ID NO:128):
ARNG DHCPLGPGRC CRLHTVRASL EDLGWADWVL SPREVQVTMC IGACPSQFRA ANMHAQIKTS
LHRLKPDTVP APCCAPASYN PMVLIQKTDT GVSLQTYDDL LAKDCHCI w80 - (SEQ ID NO:129):
ARNG DHCPLGPGRC CRLHTVRASL EDLGWADWVL SPREVQVTMC IGACPSQFRA ANMHAQIKTS
LHRLKPDTVP APCCVAASYN PMVLIQKTDT GVSLQTYDDL LAKDCHCI w82 - (SEQ ID NO:130):
ARNG DHCPLGPGRC CRLHTVRASL EDLGWADWVL SPREVQVTMC IGACPSQFRA ANMHAQIKTS
LHRLKPDTVP APCCVPAAYN PMVLIQKTDT GVSLQTYDDL LAKDCHCI w83 - Y83A (SEQ ID NO:131):
ARNG DHCPLGPGRC CRLHTVRASL EDLGWADWVL SPREVQVTMC IGACPSQFRA ANMHAQIKTS
LHRLKPDTVP APCCVPASAN PMVLIQKTDT GVSLQTYDDL LAKDCHCI w84 - (SEQ ID NO:132):
ARNG DHCPLGPGRC CRLHTVRASL EDLGWADWVL SPREVQVTMC IGACPSQFRA ANMHAQIKTS
LHRLKPDTVP APCCVPASYA PMVLIQKTDT GVSLQTYDDL LAKDCHCI w85 - (SEQ ID NO:133):
ARNG DHCPLGPGRC CRLHTVRASL EDLGWADWVL SPREVQVTMC IGACPSQFRA ANMHAQIKTS
LHRLKPDTVP APCCVPASYN AMVLIQKTDT GVSLQTYDDL LAKDCHCI w86 - (SEQ ID NO:134):
ARNG DHCPLGPGRC CRLHTVRASL EDLGWADWVL SPREVQVTMC IGACPSQFRA ANMHAQIKTS
LHRLKPDTVP APCCVPASYN PAVLIQKTDT GVSLQTYDDL LAKDCHCI w87 - (SEQ ID NO:135):
ARNG DHCPLGPGRC CRLHTVRASL EDLGWADWVL SPREVQVTMC IGACPSQFRA ANMHAQIKTS
LHRLKPDTVP APCCVPASYN PMALIQKTDT GVSLQTYDDL LAKDCHCI w88 - (SEQ ID NO:136):
ARNG DHCPLGPGRC CRLHTVRASL EDLGWADWVL SPREVQVTMC IGACPSQFRA ANMHAQIKTS
LHRLKPDTVP APCCVPASYN PMVAIQKTDT GVSLQTYDDL LAKDCHCI w89 - (SEQ ID NO:137):
ARNG DHCPLGPGRC CRLHTVRASL EDLGWADWVL SPREVQVTMC IGACPSQFRA ANMHAQIKTS
LHRLKPDTVP APCCVPASYN PMVLAQKTDT GVSLQTYDDL LAKDCHCI
```

Figure 13, continued w90 - (SEQ ID NO:138):
ARNG DHCPLGPGRC CRLHTVRASL EDLGWADWVL SPREVQVTMC IGACPSQFRA ANMHAQIKTS
LHRLKPDTVP APCCVPASYN PMVLIAKTDT GVSLQTYDDL LAKDCHCI w91 - (SEQ ID NO:139):
ARNG DHCPLGPGRC CRLHTVRASL EDLGWADWVL SPREVQVTMC IGACPSQFRA ANMHAQIKTS
LHRLKPDTVP APCCVPASYN PMVLIQATDT GVSLQTYDDL LAKDCHCI w92 - (SEQ ID NO:140):
ARNG DHCPLGPGRC CRLHTVRASL EDLGWADWVL SPREVQVTMC IGACPSQFRA ANMHAQIKTS
LHRLKPDTVP APCCVPASYN PMVLIQKADT GVSLQTYDDL LAKDCHCI w93 - (SEQ ID NO:141):
ARNG DHCPLGPGRC CRLHTVRASL EDLGWADWVL SPREVQVTMC IGACPSQFRA ANMHAQIKTS
LHRLKPDTVP APCCVPASYN PMVLIQKTAT GVSLQTYDDL LAKDCHCI w94 - (SEQ ID NO:142):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDA GVSLQTYDDL LAKDCHCI w95 - (SEQ ID NO:143):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT AVSLQTYDDL LAKDCHCI w96 - (SEQ ID NO:144):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GASLQTYDDL LAKDCHCI w97 - (SEQ ID NO:145):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVALQTYDDL LAKDCHCI w98 - (SEQ ID NO:146):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSAQTYDDL LAKDCHCI w99 - (SEQ ID NO:147):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLATYDDL LAKDCHCI w100 - (SEQ ID NO:148):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQAYDDL LAKDCHCI w101 - (SEQ ID NO:149):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTADDL LAKDCHCI w102 - (SEQ ID NO:150):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYADL LAKDCHCI

Figure 13, continued

```
w103 - (SEQ ID NO:151):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDAL LAKDCHCI w104 - (SEQ ID NO:152):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDA LAKDCHCI w105 - (SEQ ID NO:153):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL AAKDCHCI w107 - (SEQ ID NO:154):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAADCHCI w108 - (SEQ ID NO:155):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKACHCI w110 - (SEQ ID NO:156):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCACI w112 - (SEQ ID NO:157):
ARNG DHCPLGPGRC CRLHTVRASL EDLGWADWVL SPREVQVTMC IGACPSQFRA ANMHAQIKTS
LHRLKPDTVP APCCVPASYN PMVLIQKTDT GVSLQTYDDL LAKDCHCA
```

Figure 14 – Identification of GDF15 Mutein Residues Available for Mutagenesis and Assessment of Secretion Properties Using HSA Fusions Comprising a Non-cleavable Linker

| Mutein | Residue | Mutein | Dimer | Mutein | Residue | Mutein | Dimer | Mutein | Residue | Mutein | Dimer |
|---|---|---|---|---|---|---|---|---|---|---|---|
| w2 | ARG | ALA | YES | w39 | VAL | ALA | YES | w80 | PRO | ALA | YES |
| w3 | ASN | ALA | YES | w40 | GLN | ALA | YES | w82 | SER | ALA | YES |
| w4 | GLY | ALA | YES | w41 | VAL | ALA | YES | w83 | TYR | ALA | NO |
| w5 | ASP | ALA | YES | w42 | THR | ALA | YES | w84 | ASN | ALA | YES |
| w6 | HIS | ALA | YES | w43 | MET | ALA | YES | w85 | PRO | ALA | YES |
| w8 | PRO | ALA | YES | w45 | ILE | ALA | YES | w86 | MET | ALA | YES |
| w9 | LEU | ALA | YES | w46 | GLY | ALA | NO | w87 | VAL | ALA | YES |
| w10 | GLY | ALA | YES | w49 | PRO | ALA | YES | w88 | LEU | ALA | YES |
| w11 | PRO | ALA | YES | w50 | SER | ALA | YES | w89 | ILE | ALA | YES |
| w12 | GLY | ALA | YES | w51 | GLN | ALA | YES | w90 | GLN | ALA | YES |
| w13 | ARG | ALA | YES | w52 | PHE | ALA | YES | w91 | LYS | ALA | YES |
| w16 | ARG | ALA | YES | w53 | ARG | ALA | YES | w92 | THR | ALA | YES |
| w17 | LEU | ALA | YES | w56 | ASN | ALA | YES | w93 | ASP | ALA | YES |
| w18 | HIS | ALA | YES | w57 | MET | ALA | YES | w94 | THR | ALA | YES |
| w19 | THR | ALA | YES | w58 | HIS | ALA | YES | w95 | GLY | ALA | YES |
| w20 | VAL | ALA | YES | w60 | GLN | ALA | YES | w96 | VAL | ALA | YES |
| w21 | ARG | ALA | YES | w61 | ILE | ALA | YES | w97 | SER | ALA | YES |
| w23 | SER | ALA | YES | w62 | LYS | ALA | NO | w98 | LEU | ALA | YES |
| w24 | LEU | ALA | YES | w63 | THR | ALA | YES | w99 | GLN | ALA | YES |
| w25 | GLU | ALA | YES | w64 | SER | ALA | YES | w100 | THR | ALA | YES |
| w26 | ASP | ALA | YES | w65 | LEU | ALA | NO | w101 | TYR | ALA | YES |
| w27 | LEU | ALA | YES | w66 | HIS | ALA | YES | w102 | ASP | ALA | YES |
| w28 | GLY | ALA | YES | w67 | ARG | ALA | YES | w103 | ASP | ALA | YES |
| w29 | TRP | ALA | YES | w68 | LEU | ALA | YES | w104 | LEU | ALA | YES |
| w31 | ASP | ALA | YES | w69 | LYS | ALA | YES | w105 | LEU | ALA | YES |
| w32 | TRP | ALA | YES | w70 | PRO | ALA | YES | w107 | LYS | ALA | YES |
| w33 | VAL | ALA | YES | w71 | ASP | ALA | YES | w108 | ASP | ALA | YES |
| w34 | LEU | ALA | YES | w72 | THR | ALA | YES | w110 | HIS | ALA | YES |
| w35 | SER | ALA | YES | w73 | VAL | ALA | YES | w112 | ILE | ALA | YES |
| w36 | PRO | ALA | NO | w74 | PRO | ALA | YES | | | | |
| w37 | ARG | ALA | YES | w76 | PRO | ALA | YES | | | | |
| w38 | GLU | ALA | YES | w79 | VAL | ALA | YES | | | | |

Figures 15A-15E
Amino Acid Sequences of Fusion Molecules Comprising a Signal Sequence Fused to Fc (IgG), ABD, and MBD; Fused to the N-Terminus of Mature GDF15 Through a Variable Linker

Figure 15A: Schematic of Fusion Molecules

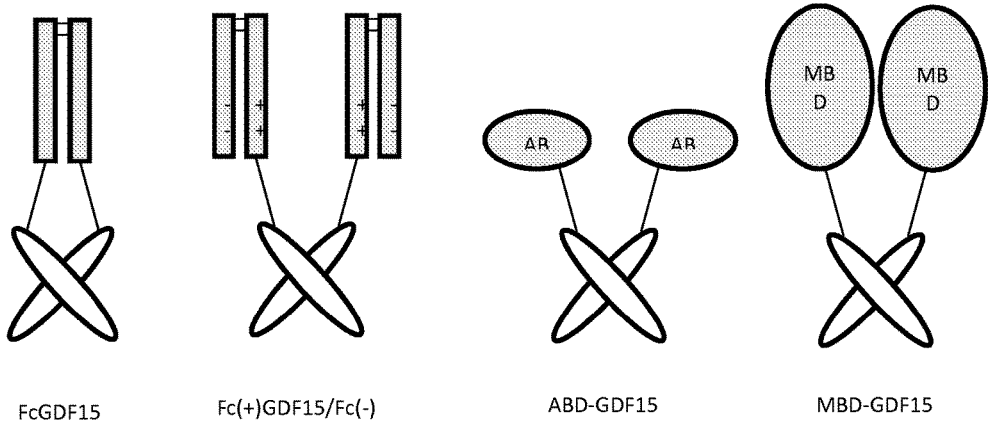

FcGDF15    Fc(+)GDF15/Fc(-)    ABD-GDF15    MBD-GDF15

Figure 15B: FcGDF15 containing a 3X(Glu-3Gly-Ser) linker:

MGVKVLFALI CIAVAEADKT HTCPPCPAPE LLGGPSVFLF PPKPKDTLMI
SRTPEVTCVV VDVSHEDPEV KFNWYVDGVE VHNAKTKPRE EQYNSTYRVV
SVLTVLHQDW LNGKEYKCKV SNKALPAPIE KTISKAKGQP REPQVYTLPP
SRDELTKNQV SLTCLVKGFY PSDIAVEWES NGQPENNYKT TPPVLDSDGS
FFLYSKLTVD KSRWQQGNVF SCSVMHEALH NHYTQKSLSL SPGK**EGGGSE
GGGSEGGGSA RNGDHCPLGP GRCCRLHTVR ASLEDLGWAD WVLSPREVQV
TMCIGACPSQ FRAANMHAQI KTSLHRLKPD TVPAPCCVPA SYNPMVLIQK
TDTGVSLQTY DDLLAKDCHC I** (SEQ ID NO:158)

Figure 15C: Fc(+)GDF15/Fc(-) charged pair containing Fc(+)-3X(Glu-3Gly-Ser)-GDF15 and hFc(-)

MDMRVPAQLL GLLLLWLRGA RCDKTHTCPP CPAPELLGGP SVFLFPPKPK
DTLMISRTPE VTCVVVDVSH EDPEVKFNWY VDGVEVHNAK TKPREEQYNS
TYRVVSVLTV LHQDWLNGKE YKCKVSNKAL PAPIEKTISK AKGQPREPQV
YTLPPSRKEL TKNQVSLTCL VKGFYPSDIA VEWESNGQPE NNYKTTPPVL
KSDGSFFLYS KLTVDKSRWQ QGNVFSCSVM HEALHNHYTQ KSLSLSPGK**E
GGGSEGGGSE GGGSARNGDH CPLGPGRCCR LHTVRASLED LGWADWVLSP
REVQVTMCIG ACPSQFRAAN MHAQIKTSLH RLKPDTVPAP CCVPASYNPM
VLIQKTDTGV SLQTYDDLLA KDCHCI**(SEQ ID NO:159)

MDMRVPAQLL GLLLLWLRGA RCDKTHTCPP CPAPELLGGP SVFLFPPKPK
DTLMISRTPE VTCVVVDVSH EDPEVKFNWY VDGVEVHNAK TKPREEQYNS
TYRVVSVLTV LHQDWLNGKE YKCKVSNKAL PAPIEKTISK AKGQPREPQV
YTLPPSRDEL TKNQVSLTCL VKGFYPSDIA VEWESNGQPE NNYDTTPPVL
DSDGSFFLYS DLTVDKSRWQ QGNVFSCSVM HEALHNHYTQ KSLSLSPGK
(SEQ ID NO:160)

Figure 15D: Albumin Binding Domain (ABD) containing a 5XGly linker (ABD-GDF15)

MLAEAKVLAN RELDKYGVSD FYKRLINKAK TVEGVEALKL HILAALPGGG
GGARNGDHCP LGPGRCCRLH TVRASLEDLG WADWVLSPRE VQVTMCIGAC
PSQFRAANMH AQIKTSLHRL KPDTVPAPCC VPASYNPMVL IQKTDTGVSL
QTYDDLLAKD CHCI (SEQ ID NO:161)

Figure 15E: Maltose Binding domain (MBD) containing an Enterokinase cleavable 5XGly linker (MBD-GDF15)

MGVKVLFALI CIAVAEAMKI EEGKLVIWIN GDKGYNGLAE VGKKFEKDTG
IKVTVEHPDK LEEKFPQVAA TGDGPDIIFW AHDRFGGYAQ SGLLAEITPD
KAFQDKLYPF TWDAVRYNGK LIAYPIAVEA LSLIYNKDLL PNPPKTWEEI
PALDKELKAK GKSALMFNLQ EPYFTWPLIA ADGGYAFKYE NGKYDIKDVG
VDNAGAKAGL TFLVDLIKNK HMNADTDYSI AEAAFNKGET AMTINGPWAW
SNIDTSKVNY GVTVLPTFKG QPSKPFVGVL SAGINAASPN KELAKEFLEN
YLLTDEGLEA VNKDKPLGAV ALKSYEEELV KDPRIAATME NAQKGEIMPN
IPQMSAFWYA VRTAVINAAS GRQTVDEALK DAQTNSSSNN NNNNNNNNLG
DDDDKGGGGG ARNGDHCPLG PGRCCRLHTV RASLEDLGWA DWVLSPREVQ
VTMCIGACPS QFRAANMHAQ IKTSLHRLKP DTVPAPCCVP ASYNPMVLIQ
KTDTGVSLQT YDDLLAKDCH CI (SEQ ID NO:162)

Figure 16 --(Panel A) Solubility Improvements of Fusion Molecules Comprising ABD and MBD Fused to the N-Terminus of Mature GDF15; and (Panel B) Reduction in Body Weight in *ob/ob* mice following a single subcutaneous injection of 3mg/kg of ABD-GDF15
(A)
| Construct | Max Solubility in PBS |
|---|---|
| hGDF15 | + |
| ABD-GDF15 | +++++ |
| MBD-GDF15 | ++++ |
(B)
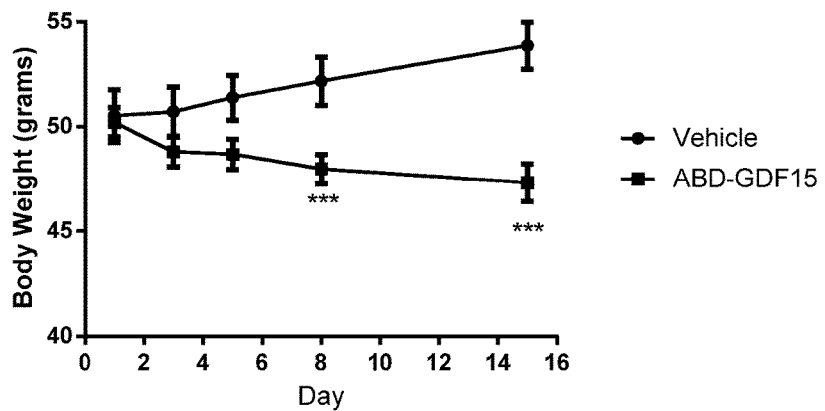

Figure 17A - Platypus (Oa) GDF15 Precursor Amino Acid Sequence

```
MVGSVPGLRL AAAASLLLLL LLLLSPGTEP RALGPQESIN SKSLQHRYEE ALAEMWGNQS RGETGPASRA
IRLLTPKCRA GGKGRLGLQL SRSAVEAGLP WEPQAESLTL DLTPTLQQWL QGSSRPLLRL QLVGPREVME
ALASPGAKPP VLEVQFQELQ SRANRRARAL GQDCEHQGGK CCPRTHHVSF QELGWADWVL APKDYMMKFC
QGSCPHNYKP ASMHSLIKAR MHNLAPGTTP EPCCVPSSYE PMVLMHYNSE GKITLSPFEN MIAKDCHCA
(SEQ ID NO:163)
```

Figure 17B: Reduction in Food Intake and Body Weight in DIO mice Following Subcutaneous Injection of OaGDF15.

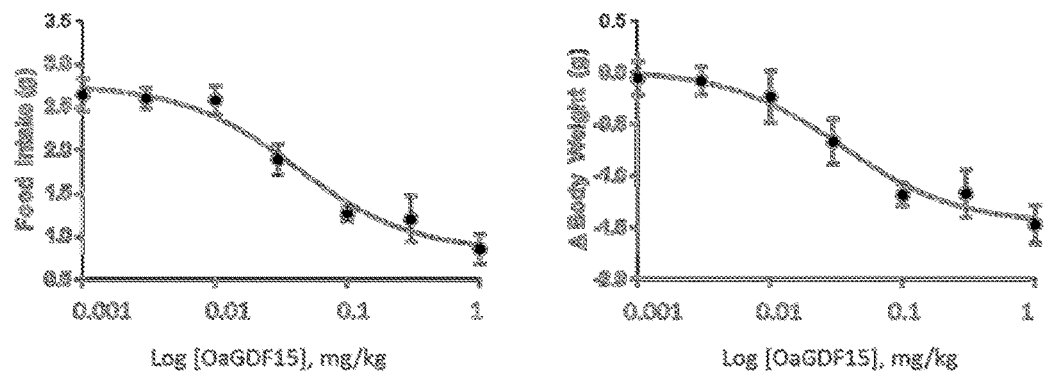

SEQUENCE LISTING

```
<160> NUMBER OF SEQ ID NOS: 231

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
```

```
            210                 215                 220
Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
                260                 265                 270

Cys Cys Val Pro Ala Ser Tyr Asn Pro Met Val Leu Ile Gln Lys Thr
            275                 280                 285

Asp Thr Gly Val Ser Leu Gln Thr Tyr Asp Asp Leu Leu Ala Lys Asp
        290                 295                 300

Cys His Cys Ile
305

<210> SEQ ID NO 2
<211> LENGTH: 1220
<212> TYPE: PRT
<213> ORGANISM: Homo sapiens

<400> SEQUENCE: 2

Ala Gly Thr Cys Cys Ala Gly Cys Thr Cys Ala Gly Ala Gly Cys
1               5                   10                  15

Cys Gly Cys Ala Ala Cys Cys Thr Gly Cys Ala Cys Ala Gly Cys Cys
                20                  25                  30

Ala Thr Gly Cys Cys Gly Gly Gly Cys Ala Ala Gly Ala Ala Cys
            35                  40                  45

Thr Cys Ala Gly Gly Ala Cys Gly Gly Thr Gly Ala Thr Gly Gly
        50                  55                  60

Cys Thr Cys Thr Cys Ala Gly Ala Thr Gly Cys Thr Cys Cys Thr Gly
65                  70                  75                  80

Gly Thr Gly Thr Thr Gly Cys Thr Gly Gly Thr Gly Cys Thr Cys Thr
                85                  90                  95

Cys Gly Thr Gly Gly Cys Thr Gly Cys Cys Gly Cys Ala Thr Gly Gly
            100                 105                 110

Gly Gly Gly Cys Gly Cys Cys Cys Thr Gly Thr Cys Thr Cys Thr Gly
            115                 120                 125

Gly Cys Cys Gly Ala Gly Cys Gly Ala Cys Cys Gly Cys Gly
        130                 135                 140

Cys Ala Ala Gly Thr Thr Cys Cys Gly Gly Ala Cys Cys
145                 150                 155                 160

Cys Thr Cys Ala Gly Ala Gly Thr Cys Ala Cys Thr Cys Cys
            165                 170                 175

Gly Ala Ala Gly Ala Cys Thr Cys Cys Ala Gly Ala Thr Cys Cys
            180                 185                 190

Gly Ala Gly Ala Gly Thr Thr Gly Cys Gly Gly Ala Ala Cys Gly
        195                 200                 205

Cys Thr Ala Cys Gly Ala Gly Gly Ala Cys Cys Thr Gly Cys Thr Ala
            210                 215                 220

Ala Cys Cys Ala Gly Gly Cys Thr Gly Cys Gly Gly Cys Cys Ala
225                 230                 235                 240

Ala Cys Cys Ala Gly Ala Gly Cys Thr Gly Gly Ala Ala Gly Ala
            245                 250                 255

Thr Thr Cys Gly Ala Ala Cys Ala Cys Cys Gly Ala Cys Cys Thr Cys
                260                 265                 270
```

-continued

Gly Thr Cys Cys Cys Gly Gly Cys Cys Cys Cys Thr Gly Cys Ala Gly
275 280 285

Thr Cys Cys Gly Gly Ala Thr Ala Cys Thr Cys Ala Cys Gly Cys Cys
290 295 300

Ala Gly Ala Ala Gly Thr Gly Cys Gly Gly Cys Thr Gly Gly Gly Ala
305 310 315 320

Thr Cys Cys Gly Gly Cys Gly Gly Cys Cys Ala Cys Cys Thr Gly Cys
325 330 335

Ala Cys Cys Thr Gly Cys Gly Thr Ala Thr Cys Thr Cys Thr Cys Gly
340 345 350

Gly Gly Cys Cys Gly Cys Cys Cys Thr Thr Cys Cys Cys Gly Ala Gly
355 360 365

Gly Gly Gly Cys Thr Cys Cys Cys Cys Gly Ala Gly Gly Cys Cys Thr
370 375 380

Cys Cys Cys Gly Cys Cys Thr Thr Cys Ala Cys Cys Gly Gly Gly Cys
385 390 395 400

Thr Cys Thr Gly Thr Thr Cys Cys Gly Gly Cys Thr Gly Thr Cys Cys
405 410 415

Cys Cys Gly Ala Cys Gly Gly Cys Gly Thr Cys Ala Ala Gly Gly Thr
420 425 430

Cys Gly Thr Gly Gly Gly Ala Cys Gly Thr Gly Ala Cys Ala Cys Gly
435 440 445

Ala Cys Cys Gly Cys Thr Gly Cys Gly Gly Cys Gly Thr Cys Ala Gly
450 455 460

Cys Thr Cys Ala Gly Cys Cys Thr Thr Gly Cys Ala Ala Gly Ala Cys
465 470 475 480

Cys Cys Cys Ala Gly Gly Cys Gly Cys Cys Cys Gly Cys Gly Cys Thr
485 490 495

Gly Cys Ala Cys Cys Thr Gly Cys Gly Ala Cys Thr Gly Thr Cys Gly
500 505 510

Cys Cys Gly Cys Cys Gly Cys Cys Gly Thr Cys Gly Cys Ala Gly Thr
515 520 525

Cys Gly Gly Ala Cys Cys Ala Ala Cys Thr Gly Cys Thr Gly Gly Cys
530 535 540

Ala Gly Ala Ala Thr Cys Thr Thr Cys Gly Thr Cys Cys Gly Cys Ala
545 550 555 560

Cys Gly Gly Cys Cys Cys Cys Ala Gly Cys Thr Gly Gly Ala Gly Thr
565 570 575

Thr Gly Cys Ala Cys Thr Thr Gly Cys Gly Gly Cys Cys Gly Cys Ala
580 585 590

Ala Gly Cys Cys Gly Cys Cys Ala Gly Gly Gly Gly Gly Cys Gly Cys
595 600 605

Cys Gly Cys Ala Gly Ala Gly Cys Gly Cys Gly Thr Gly Cys Gly Cys
610 615 620

Gly Cys Ala Ala Cys Gly Gly Gly Gly Ala Cys Cys Ala Cys Thr Gly
625 630 635 640

Thr Cys Cys Gly Cys Thr Cys Gly Gly Gly Cys Cys Cys Gly Gly Gly
645 650 655

Cys Gly Thr Thr Gly Cys Thr Gly Cys Cys Gly Thr Cys Thr Gly Cys
660 665 670

Ala Cys Ala Cys Gly Gly Thr Cys Cys Gly Cys Gly Cys Gly Thr Cys
675 680 685

Gly Cys Thr Gly Gly Ala Ala Gly Ala Cys Cys Thr Gly Gly Gly Cys

-continued

```
            690             695             700
Thr Gly Gly Gly Cys Cys Gly Ala Thr Thr Gly Gly Thr Gly Cys
705             710             715             720

Thr Gly Thr Cys Gly Cys Cys Ala Cys Gly Gly Gly Ala Gly Thr
                725             730             735

Gly Cys Ala Ala Gly Thr Gly Ala Cys Cys Ala Thr Gly Thr Cys
            740             745             750

Ala Thr Cys Gly Gly Cys Gly Cys Gly Thr Gly Cys Cys Gly Ala
        755             760             765

Gly Cys Cys Ala Gly Thr Thr Cys Cys Gly Gly Gly Cys Gly Gly Cys
    770             775             780

Ala Ala Ala Cys Ala Thr Gly Cys Ala Cys Gly Gly Cys Ala Gly
785             790             795             800

Ala Thr Cys Ala Ala Gly Ala Cys Gly Ala Gly Cys Cys Thr Gly Cys
        805             810             815

Ala Cys Cys Gly Cys Cys Thr Gly Ala Ala Gly Cys Cys Cys Gly Ala
            820             825             830

Cys Ala Cys Gly Gly Thr Gly Cys Cys Ala Gly Cys Gly Cys Cys Cys
        835             840             845

Thr Gly Cys Thr Gly Cys Gly Thr Gly Cys Cys Gly Cys Cys Ala
850             855             860

Gly Cys Thr Ala Cys Ala Ala Thr Cys Cys Ala Thr Gly Gly Thr
865             870             875             880

Gly Cys Thr Cys Ala Thr Thr Cys Ala Ala Ala Gly Ala Cys Cys
            885             890             895

Gly Ala Cys Ala Cys Cys Gly Gly Gly Thr Gly Thr Cys Gly Cys
        900             905             910

Thr Cys Cys Ala Gly Ala Cys Cys Thr Ala Thr Gly Ala Thr Gly Ala
            915             920             925

Cys Thr Thr Gly Thr Thr Ala Gly Cys Cys Ala Ala Ala Gly Ala Cys
930             935             940

Thr Gly Cys Cys Ala Cys Thr Gly Cys Ala Thr Ala Thr Gly Ala Gly
945             950             955             960

Cys Ala Gly Thr Cys Cys Thr Gly Gly Thr Cys Cys Thr Cys Cys
        965             970             975

Ala Cys Thr Gly Thr Gly Cys Ala Cys Cys Thr Gly Cys Gly Cys Gly
            980             985             990

Gly Ala Gly Gly Ala Cys Gly Cys  Gly Ala Cys Cys Thr  Cys Ala Gly
        995             1000            1005

Thr Thr  Gly Thr Cys Cys Thr  Gly Cys Cys Cys Thr  Gly Thr Gly
    1010            1015            1020

Gly Ala  Ala Thr Gly Gly Gly  Cys Thr Cys Ala Ala  Gly Gly Thr
    1025            1030            1035

Thr Cys  Cys Thr Gly Ala Gly  Ala Cys Ala Cys Cys  Cys Gly Ala
    1040            1045            1050

Thr Thr  Cys Cys Thr Gly Cys  Cys Cys Ala Ala Ala  Cys Ala Gly
    1055            1060            1065

Cys Thr  Gly Thr Ala Thr Thr  Ala Thr Ala Thr Ala  Ala Gly Gly
    1070            1075            1080

Thr Cys  Thr Gly Thr Thr Ala  Thr Thr Ala Thr  Thr Ala Thr
    1085            1090            1095

Thr Ala  Ala Thr Thr Ala  Thr Thr Gly Gly Gly  Gly Thr Gly
    1100            1105            1110
```

```
Ala Cys Cys Thr Thr Cys Thr Thr Gly Gly Gly Ala Cys Thr
1115                1120                1125

Cys Gly Gly Gly Gly Gly Cys Thr Gly Gly Thr Cys Thr Gly Ala
1130                1135                1140

Thr Gly Gly Ala Ala Cys Thr Gly Thr Gly Thr Ala Thr Thr Thr
1145                1150                1155

Ala Thr Thr Thr Ala Ala Ala Ala Cys Thr Cys Thr Gly Gly Thr
1160                1165                1170

Gly Ala Thr Ala Ala Ala Ala Thr Ala Ala Ala Gly Cys Thr
1175                1180                1185

Gly Thr Cys Thr Gly Ala Ala Cys Thr Gly Thr Thr Ala Ala Ala
1190                1195                1200

Ala Ala Ala Ala Ala Ala Ala Ala Ala Ala Ala Ala Ala Ala
1205                1210                1215

Ala Ala
1220

<210> SEQ ID NO 3
<211> LENGTH: 112
<212> TYPE: PRT
<213> ORGANISM: Homo sapiens

<400> SEQUENCE: 3

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 4
<211> LENGTH: 339
<212> TYPE: DNA
<213> ORGANISM: Homo sapiens

<400> SEQUENCE: 4
gcgcgtaacg gggatcactg tccgctcggg cccgggcgtt gctgccgtct gcacacggtc      60
cgcgcgtcgc tggaagacct gggctgggcc gattgggtgc tgtcgccacg ggaggtgcaa     120
gtgaccatgt gcatcggcgc gtgcccgagc cagttccggg cggcaaacat gcacgcgcag     180
atcaagacga gcctgcaccg cctgaagccc gacacggtgc cagcgccctg ctgcgtgccc     240
gccagctaca atcccatggt gctcattcaa aagaccgaca ccggggtgtc gctccagacc     300
tatgatgact tgttagccaa agactgccac tgcatataa                           339

<210> SEQ ID NO 5
<211> LENGTH: 609
<212> TYPE: PRT
<213> ORGANISM: Homo sapiens
```

<400> SEQUENCE: 5

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
```

```
                        405                 410                 415
Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 6
<211> LENGTH: 2264
<212> TYPE: DNA
<213> ORGANISM: Homo sapiens

<400> SEQUENCE: 6
agtatattag tgctaatttc cctccgtttg tcctagcttt tctcttctgt caaccccaca      60
cgcctttggc acaatgaagt gggtaacctt tatttccctt cttttttctct ttagctcggc    120 ttattccagg ggtgtgtttc gtcgagatgc acacaagagt gaggttgctc atcggtttaa    180
agatttggga agagaaaatt tcaaagccct ggtgttgatt gcctttgctc agtatctcca    240
gcagtgtcca tttgaagatc atgtaaaatt agtgaatgaa gtaactgaat tgcaaaaac     300 atgtgttgct gatgagtcag ctgaaaattg tgacaaatca cttcataccc ttttggaga    360 caaattatgc acagttgcaa ctcttcgtga aacctatggt gaaatggctg actgctgtgc    420
aaaacaagaa cctgagagaa atgaatgctt cttgcaacac aaagatgaca cccaaacct    480 ccccccgattg gtgagaccag aggttgatgt gatgtgcact gcttttcatg acaatgaaga    540 gacattttg aaaaaatact tatatgaaat tgccagaaga catccttact tttatgcccc     600
ggaactcctt ttctttgcta aaaggtataa agctgctttt acagaatgtt gccaagctgc    660
tgataaagct gcctgcctgt tgccaaagct cgatgaactt cgggatgaag gaaggcttc    720 gtctgccaaa cagagactca gtgtgccag tctccaaaaa tttggagaaa gagctttcaa    780
agcatgggca gtagctcgcc tgagccagag atttcccaaa gctgagtttg cagaagtttc    840
caagttagtg acagatctta ccaaagtcca cacggaatgc tgccatggag atctgcttga    900
atgtgctgat gacagggcgg accttgccaa gtatatctgt gaaaatcaag attcgatctc    960
```

```
cagtaaactg aaggaatgct gtgaaaaacc tctgttggaa aaatcccact gcattgccga   1020
agtggaaaat gatgagatgc ctgctgactt gccttcatta gctgctgatt ttgttgaaag   1080
taaggatgtt tgcaaaaact atgctgaggc aaaggatgtc ttcctgggca tgttttttgta  1140 tgaatatgca agaaggcatc ctgattactc tgtcgtgctg ctgctgagac ttgccaagac   1200
atatgaaacc actctagaga agtgctgtgc cgctgcagat cctcatgaat gctatgccaa   1260
agtgttcgat gaatttaaac ctcttgtgga agagcctcag aatttaatca acaaaattg    1320 tgagcttttt gagcagcttg gagagtacaa attccagaat gcgctattag ttcgttacac   1380
caagaaagta ccccaagtgt caactccaac tcttgtagag gtctcaagaa acctaggaaa   1440
agtgggcagc aaatgttgta acatcctga agcaaaaaga atgccctgtg cagaagacta    1500
tctatccgtg gtcctgaacc agttatgtgt gttgcatgag aaaacgccag taagtgacag   1560
agtcaccaaa tgctgcacag aatccttggt gaacaggcga ccatgctttt cagctctgga   1620
agtcgatgaa acatacgttc ccaaagagtt taatgctgaa acattcacct tccatgcaga   1680
tatatgcaca ctttctgaga aggagagaca aatcaagaaa caaactgcac ttgttgagct   1740
cgtgaaacac aagcccaagg caacaaaaga gcaactgaaa gctgttatgg atgatttcgc   1800
agcttttgta gagaagtgct gcaaggctga cgataaggag acctgctttg ccgaggaggg   1860
taaaaaactt gttgctgcaa gtcaagctgc cttaggctta aacatcaca tttaaaagca    1920 tctcagccta ccatgagaat aagagaaaga aaatgaagat caaaagctta ttcatctgtt   1980 tttcttttc gttggtgtaa agccaacacc ctgtctaaaa aacataaatt tctttaatca    2040
ttttgcctct tttctctgtg cttcaattaa taaaaaatgg aaagaatcta atagagtggt   2100
acagcactgt tattttttcaa agatgtgttg ctatcctgaa aattctgtag gttctgtgga  2160
agttccagtg ttctctctta ttccacttcg gtagaggatt tctagtttct tgtgggctaa   2220
ttaaataaat cattaatact cttctaaaaa aaaaaaaaaa aaaa                   2264
```

<210> SEQ ID NO 7
<211> LENGTH: 607
<212> TYPE: PRT
<213> ORGANISM: Homo sapiens

<400> SEQUENCE: 7

```
Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
            20                  25                  30

Phe Lys Asp Leu Gly Glu Glu Asn Phe Lys Ala Leu Val Leu Ile Ala
        35                  40                  45

Phe Ala Gln Tyr Leu Gln Gln Cys Pro Phe Glu Asp His Val Lys Leu
    50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140
```

-continued

```
Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
            165                 170                 175

Leu Phe Phe Ala Lys Arg Tyr Lys Ala Ala Phe Thr Glu Cys Cys Gln
        180                 185                 190

Ala Ala Asp Lys Ala Ala Cys Leu Leu Pro Lys Leu Asp Glu Leu Arg
    195                 200                 205

Asp Glu Gly Lys Ala Ser Ser Ala Lys Gln Arg Leu Lys Cys Ala Ser
210                 215                 220

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
            245                 250                 255

Val Thr Asp Leu Thr Lys Val His Thr Glu Cys Cys His Gly Asp Leu
        260                 265                 270

Leu Glu Cys Ala Asp Asp Arg Ala Asp Leu Ala Lys Tyr Ile Cys Glu
    275                 280                 285

Asn Gln Asp Ser Ile Ser Ser Lys Leu Lys Glu Cys Cys Glu Lys Pro
290                 295                 300

Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
            325                 330                 335

Val Cys Lys Asn Tyr Ala Glu Ala Lys Asp Val Phe Leu Gly Met Phe
        340                 345                 350

Leu Tyr Glu Tyr Ala Arg Arg His Pro Asp Tyr Ser Val Val Leu Leu
    355                 360                 365

Leu Arg Leu Ala Lys Thr Tyr Glu Thr Thr Leu Glu Lys Cys Cys Ala
370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
            405                 410                 415

Phe Glu Gln Leu Gly Glu Tyr Lys Phe Gln Asn Ala Leu Leu Val Arg
        420                 425                 430

Tyr Thr Lys Lys Val Pro Gln Val Ser Thr Pro Thr Leu Val Glu Val
    435                 440                 445

Ser Arg Asn Leu Gly Lys Val Gly Ser Lys Cys Cys Lys His Pro Glu
450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
            485                 490                 495

Lys Cys Cys Thr Glu Ser Leu Val Asn Arg Arg Pro Cys Phe Ser Ala
        500                 505                 510

Leu Glu Val Asp Glu Thr Tyr Val Pro Lys Glu Phe Asn Ala Glu Thr
    515                 520                 525

Phe Thr Phe His Ala Asp Ile Cys Thr Leu Ser Glu Lys Glu Arg Gln
530                 535                 540

Ile Lys Lys Gln Thr Ala Leu Val Glu Leu Val Lys His Lys Pro Lys
545                 550                 555                 560
```

```
        Ala Thr Lys Glu Gln Leu Lys Ala Val Met Asp Asp Phe Ala Ala Phe
                        565                 570                 575

Val Glu Lys Cys Cys Lys Ala Asp Asp Lys Glu Thr Cys Phe Ala Glu
                    580                 585                 590

Glu Gly Lys Lys Leu Val Ala Ala Ser Gln Ala Ala Leu Gly Leu
                595                 600                 605

<210> SEQ ID NO 8
<211> LENGTH: 1821
<212> TYPE: DNA
<213> ORGANISM: Homo sapiens

<400> SEQUENCE: 8
atggacatga gggtccccgc tcagctcctg gggctcctgc tactctggct ccgaggtgcc      60
agatgtgatg cacacaagag tgaggttgct catcggttta agatttgggg agaagaaaat     120
ttcaaagcct tggtgttgat tgcctttgct cagtatcttc agcagtgtcc atttgaagat     180
catgtaaaat tagtgaatga agtaactgaa tttgcaaaaa catgtgttgc tgatgagtca     240
gctgaaaatt gtgacaaatc acttcatacc cttttggag acaaattatg cacagttgca     300
actcttcgtg aaacctatgg tgaaatggct gactgctgtg caaaacaaga acctgagaga     360
aatgaatgct tcttgcaaca caaagatgac aacccaaacc tcccccgatt ggtgagacca     420
gaggttgatg tgatgtgcac tgcttttcat gacaatgaag agacatttt gaaaaaatac     480 ttatatgaaa ttgccagaag acatccttac ttttatgccc cggaactcct tttctttgct     540
aaaaggtata agctgctttt tacagaatgt gccaagctg ctgataaagc tgcctgcctg     600
ttgccaaagc tcgatgaact tcgggatgaa gggaaggctt cgtctgccaa acagagactc     660
aagtgtgcca gtctccaaaa atttggagaa agagctttca agcatgggc agtagctcgc     720 ctgagccaga gatttcccaa agctgagttt gcagaagttt ccaagttagt gacagatctt     780
accaaagtcc acacggaatg ctgccatgga gatctgcttg aatgtgctga tgacagggcg     840
gaccttgcca gtatatctg tgaaaatcaa gattcgatct ccagtaaact gaaggaatgc     900
tgtgaaaaac ctctgttgga aaatccccac tgcattgccg aagtggaaaa tgatgagatg     960
cctgctgact tgccttcatt agctgctgat tttgttgaaa gtaaggatgt ttgcaaaaac    1020
tatgctgagg caaggatgt cttcctgggc atgttttgt atgaatatgc aagaaggcat    1080
cctgattact ctgtcgtgct gctgctgaga cttgccaaga catatgaaac cactctagag    1140
aagtgctgtg ccgctgcaga tcctcatgaa tgctatgcca agtgttcga tgaatttaaa    1200 cctcttgtgg aagagcctca gaatttaatc aaacaaaatt gtgagctttt tgagcagctt    1260
ggagagtaca aattccagaa tgcgctatta gttcgttaca ccaagaaagt accccaagtg    1320
tcaactccaa ctcttgtaga ggtctcaaga aacctaggaa aagtgggcag caaatgttgt    1380
aaacatcctg aagcaaaaag aatgccctgt gcagaagact atctatccgt ggtcctgaac    1440
cagttatgtg tgttgcatga aaaacgcca gtaagtgaca gagtcaccaa atgctgcaca    1500
gaatccttgg tgaacaggcg accatgcttt tcagctctgg aagtcgatga acatacgtt    1560 cccaaagagt ttaatgctga acattcacc ttccatgcag atatatgcac actttctgag    1620
aaggagagac aaatcaagaa acaaactgca cttgttgagc tcgtgaaaca caagcccaag    1680
gcaacaaaag agcaactgaa agctgttatg gatgatttcg cagcttttgt agagaagtgc    1740
tgcaaggctg acgataagga gacctgcttt gccgaggagg gtaaaaaact tgttgctgca    1800
agtcaagctg ccttaggctt a                                              1821
```

<210> SEQ ID NO 9
<211> LENGTH: 585
<212> TYPE: PRT
<213> ORGANISM: Homo sapiens

<400> SEQUENCE: 9

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

```
Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 10
<211> LENGTH: 1755
<212> TYPE: DNA
<213> ORGANISM: Homo sapiens

<400> SEQUENCE: 10
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca atcacttcat acccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca acctcccccc gattggtgag accagaggtt     360
gatgtgatgt gcactgcttt tcatgacaat gaagagacat ttttgaaaaa atacttatat     420
gaaattgcca gaagacatcc ttactttat gccccggaac tccttttctt tgctaaaagg     480
tataaagctg ctttttacaga atgttgccaa gctgctgata agctgcctg cctgttgcca     540 aagctcgatg aacttcggga tgaagggaag gcttcgtctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttgaatgtg ctgatgacag gcggaccctt     780
gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
gacttgcctt cattagctgc tgattttgtt gaaagtaagg atgtttgcaa aaactatgct     960
```

```
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc tcagaatttt aatcaaacaa aattgtgagc tttttgagca gcttggagag   1200
tacaaattcc agaatgcgct attagttcgt tacaccaaga agtacccca agtgtcaact   1260 ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg atgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc caaggcaaca   1620 aaagagcaac tgaaagctgt tatggatgat ttcgcagctt ttgtagagaa gtgctgcaag   1680
gctgacgata aggagacctg cttttgccgag gagggtaaaa aacttgttgc tgcaagtcaa   1740
gctgccttag gctta                                                    1755

<210> SEQ ID NO 11
<211> LENGTH: 733
<212> TYPE: PRT
<213> ORGANISM: Artificial Sequence
<220> FEATURE:
<223> OTHER INFORMATION: synthetic polypeptide

<400> SEQUENCE: 11

Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
                20                  25                  30

Phe Lys Asp Leu Gly Glu Glu Asn Phe Lys Ala Leu Val Leu Ile Ala
            35                  40                  45

Phe Ala Gln Tyr Leu Gln Gln Cys Pro Phe Glu Asp His Val Lys Leu
        50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190

Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
```

```
              210                 215                 220
Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
                    245                 250                 255

Val Thr Asp Leu Thr Lys Val His Thr Glu Cys Cys His Gly Asp Leu
                260                 265                 270

Leu Glu Cys Ala Asp Asp Arg Ala Asp Leu Ala Lys Tyr Ile Cys Glu
            275                 280                 285

Asn Gln Asp Ser Ile Ser Ser Lys Leu Lys Glu Cys Cys Glu Lys Pro
        290                 295                 300

Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
                    325                 330                 335

Val Cys Lys Asn Tyr Ala Glu Ala Lys Asp Val Phe Leu Gly Met Phe
                340                 345                 350

Leu Tyr Glu Tyr Ala Arg Arg His Pro Asp Tyr Ser Val Val Leu Leu
            355                 360                 365

Leu Arg Leu Ala Lys Thr Tyr Glu Thr Thr Leu Glu Lys Cys Cys Ala
        370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
                    405                 410                 415

Phe Glu Gln Leu Gly Glu Tyr Lys Phe Gln Asn Ala Leu Leu Val Arg
                420                 425                 430

Tyr Thr Lys Lys Val Pro Gln Val Ser Thr Pro Thr Leu Val Glu Val
            435                 440                 445

Ser Arg Asn Leu Gly Lys Val Gly Ser Lys Cys Cys Lys His Pro Glu
        450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
                    485                 490                 495

Lys Cys Cys Thr Glu Ser Leu Val Asn Arg Arg Pro Cys Phe Ser Ala
                500                 505                 510

Leu Glu Val Asp Glu Thr Tyr Val Pro Lys Glu Phe Asn Ala Glu Thr
            515                 520                 525

Phe Thr Phe His Ala Asp Ile Cys Thr Leu Ser Glu Lys Glu Arg Gln
        530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
                    565                 570                 575

Val Glu Lys Cys Cys Lys Ala Asp Asp Lys Glu Thr Cys Phe Ala Glu
                580                 585                 590

Glu Gly Lys Lys Leu Val Ala Ala Ser Gln Ala Ala Leu Gly Leu Gly
            595                 600                 605

Gly Gly Gly Ser Gly Gly Gly Ser Ile Glu Gly Arg Ala Arg Asn
        610                 615                 620

Gly Asp His Cys Pro Leu Gly Pro Gly Arg Cys Cys Arg Leu His Thr
625                 630                 635                 640
```

```
Val Arg Ala Ser Leu Glu Asp Leu Gly Trp Ala Asp Trp Val Leu Ser
                645                 650                 655

Pro Arg Glu Val Gln Val Thr Met Cys Ile Gly Ala Cys Pro Ser Gln
            660                 665                 670

Phe Arg Ala Ala Asn Met His Ala Gln Ile Lys Thr Ser Leu His Arg
        675                 680                 685

Leu Lys Pro Asp Thr Val Pro Ala Pro Cys Cys Val Pro Ala Ser Tyr
    690                 695                 700

Asn Pro Met Val Leu Ile Gln Lys Thr Asp Thr Gly Val Ser Leu Gln
705                 710                 715                 720

Thr Tyr Asp Asp Leu Leu Ala Lys Asp Cys His Cys Ile
                725                 730
```

<210> SEQ ID NO 12
<211> LENGTH: 2202
<212> TYPE: DNA
<213> ORGANISM: Artificial sequence
<220> FEATURE:
<223> OTHER INFORMATION: synthetic polynucleotide

<400> SEQUENCE: 12

```
atggacatga gggtccccgc tcagctcctg gggctcctgc tactctggct ccgaggtgcc    60
agatgtgatg cacacaagag tgaggttgct catcggttta agatttggg agaagaaaat    120
ttcaaagcct tggtgttgat gcctttgct cagtatcttc agcagtgtcc atttgaagat    180
catgtaaaat tagtgaatga agtaactgaa tttgcaaaaa catgtgttgc tgatgagtca    240
gctgaaaatt gtgacaaatc acttcatacc cttttggag acaaattatg cacagttgca    300
actcttcgtg aaacctatgg tgaaatggct gactgctgtg caaaacaaga acctgagaga    360
aatgaatgct tcttgcaaca caaagatgac aacccaaacc tccccgatt ggtgagacca    420
gaggttgatg tgatgtgcac tgcttttcat gacaatgaag agacattttt gaaaaaatac    480
ttatatgaaa ttgccagaag acatccttac ttttatgccc cggaactcct tttctttgct    540
aaaaggtata aagctgcttt tacagaatgt tgccaagctg ctgataaagc tgcctgcctg    600
ttgccaaagc tcgatgaact tcgggatgaa gggaaggctt cgtctgccaa acagagactc    660
aagtgtgcca gtctccaaaa atttggagaa agagctttca agcatgggc agtagctcgc    720
ctgagccaga gatttcccaa agctgagttt gcagaagttt ccaagttagt gacagatctc    780
accaaagtcc acacggaatg ctgccatgga gatctgcttg aatgtgctga tgacagggcg    840
gaccttgcca gtatatctg tgaaaatcaa gattcgatct ccagtaaact gaaggaatgc    900
tgtgaaaaac ctctgttgga aaaatcccac tgcattgccg aagtggaaaa tgatgagatg    960
cctgctgact gccttcatt agctgctgat tttgttgaaa gtaaggatgt ttgcaaaaac   1020
tatgctgagg caaaggatgt cttcctgggc atgttttttgt atgaatatgc aagaaggcat   1080
cctgattact ctgtcgtgct gctgctgaga cttgccaaga catatgaaac cactctagag   1140
aagtgctgtg ccgctgcaga tcctcatgaa tgctatgcca aagtgttcga tgaatttaaa   1200
cctcttgtgg aagagcctca gaatttaatc aaacaaaatt gtgagctttt tgagcagctt   1260
ggagagtaca aattccagaa tgcgctatta gttcgttaca ccaagaaagt accccaagtg   1320
tcaactccaa ctcttgtaga ggtctcaaga aacctaggaa aagtgggcag caaatgttgt   1380
aaacatcctg aagcaaaaag aatgccctgt gcagaagact atctatccgt ggtcctgaac   1440
cagttatgtg tgttgcatga gaaaacgcca gtaagtgaca gagtcaccaa atgctgcaca   1500
```

```
gaatccttgg tgaacaggcg accatgcttt tcagctctgg aagtcgatga acatacgtt    1560 cccaaagagt ttaatgctga acattcacc ttccatgcag atatatgcac actttctgag    1620
aaggagagac aaatcaagaa acaaactgca cttgttgagc tcgtgaaaca caagcccaag    1680
gcaacaaaag agcaactgaa agctgttatg gatgatttcg cagcttttgt agagaagtgc    1740
tgcaaggctg acgataagga gacctgcttt gccgaggagg gtaaaaaact tgttgctgca    1800
agtcaagctg ccttaggctt aggtggaggc ggtagcggtg gaggtgggag tattgaaggg    1860
agggcgcgta acgggatca ctgtccgctc gggcccgggc gttgctgccg tctgcacacg    1920
gtccgcgcgt cgctggaaga cctgggctgg gccgattggg tgctgtcgcc acggaggtg    1980 caagtgacca tgtgcatcgg cgcgtgcccg agccagttcc gggcggcaaa catgcacgcg    2040
cagatcaaga cgagcctgca ccgcctgaag cccgacacgg tgccagcgcc ctgctgcgtg    2100
cccgccagct acaatcccat ggtgctcatt caaaagaccg acaccggggt gtcgctccag    2160
acctatgatg acttgttagc caaagactgc cactgcatat aa    2202
```

<210> SEQ ID NO 13
<211> LENGTH: 711
<212> TYPE: PRT
<213> ORGANISM: Artificial sequence
<220> FEATURE:
<223> OTHER INFORMATION: synthetic polypeptide

<400> SEQUENCE: 13

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240
```

```
Val His Thr Glu Cys Cys His Gly Asp Leu Glu Cys Ala Asp Asp
            245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Gly Gly Gly Ser Gly Gly
            580                 585                 590

Gly Gly Ser Ile Glu Gly Arg Ala Arg Asn Gly Asp His Cys Pro Leu
            595                 600                 605

Gly Pro Gly Arg Cys Cys Arg Leu His Thr Val Arg Ala Ser Leu Glu
            610                 615                 620

Asp Leu Gly Trp Ala Asp Trp Val Leu Ser Pro Arg Glu Val Gln Val
625                 630                 635                 640

Thr Met Cys Ile Gly Ala Cys Pro Ser Gln Phe Arg Ala Ala Asn Met
            645                 650                 655

His Ala Gln Ile Lys Thr Ser Leu His Arg Leu Lys Pro Asp Thr Val
```

```
                660             665             670
Pro Ala Pro Cys Cys Val Pro Ala Ser Tyr Asn Pro Met Val Leu Ile
            675                 680                 685

Gln Lys Thr Asp Thr Gly Val Ser Leu Gln Thr Tyr Asp Asp Leu Leu
        690                 695                 700

Ala Lys Asp Cys His Cys Ile
705                 710

<210> SEQ ID NO 14
<211> LENGTH: 2136
<212> TYPE: DNA
<213> ORGANISM: Artificial sequence
<220> FEATURE:
<223> OTHER INFORMATION: synthetic polynucleotide

<400> SEQUENCE: 14
```

| | | | | | |
|---|---|---|---|---|---|
| gatgcacaca | agagtgaggt | tgctcatcgg | tttaaagatt | tgggagaaga | aaatttcaaa | 60 |
| gccttggtgt | tgattgcctt | tgctcagtat | cttcagcagt | gtccatttga | agatcatgta | 120 |
| aaattagtga | atgaagtaac | tgaatttgca | aaaacatgtg | ttgctgatga | gtcagctgaa | 180 |
| aattgtgaca | atcacttca | tacccttttt | ggagacaaat | tatgcacagt | tgcaactctt | 240 |
| cgtgaaacct | atggtgaaat | ggctgactgc | tgtgcaaaac | aagaacctga | gagaaatgaa | 300 |
| tgcttcttgc | aacacaaaga | tgacaaccca | aacctccccc | gattggtgag | accagaggtt | 360 |
| gatgtgatgt | gcactgcttt | tcatgacaat | gaagagacat | ttttgaaaaa | atacttatat | 420 |
| gaaattgcca | agacatcc | ttacttttat | gccccggaac | tccttttctt | tgctaaaagg | 480 |
| tataaagctg | cttttacaga | atgttgccaa | gctgctgata | agctgcctg | cctgttgcca | 540 |
| aagctcgatg | aacttcggga | tgaagggaag | gcttcgtctg | ccaaacagag | actcaagtgt | 600 |
| gccagtctcc | aaaaatttgg | agaaagagct | ttcaaagcat | gggcagtagc | tcgcctgagc | 660 |
| cagagatttc | ccaaagctga | gtttgcagaa | gtttccaagt | tagtgacaga | tcttaccaaa | 720 |
| gtccacacgg | aatgctgcca | tggagatctg | cttgaatgtg | ctgatgacag | ggcggacctt | 780 |
| gccaagtata | tctgtgaaaa | tcaagattcg | atctccagta | aactgaagga | atgctgtgaa | 840 |
| aaacctctgt | tggaaaaatc | ccactgcatt | gccgaagtgg | aaaatgatga | gatgcctgct | 900 |
| gacttgcctt | cattagctgc | tgattttgtt | gaaagtaagg | atgtttgcaa | aaactatgct | 960 |
| gaggcaaagg | atgtcttcct | gggcatgttt | ttgtatgaat | atgcaagaag | gcatcctgat | 1020 |
| tactctgtcg | tgctgctgct | gagacttgcc | aagacatatg | aaaccactct | agagaagtgc | 1080 |
| tgtgccgctg | cagatcctca | tgaatgctat | gccaaagtgt | tcgatgaatt | taaacctctt | 1140 |
| gtggaagagc | tcagaatttt | aatcaaacaa | aattgtgagc | ttttttgagca | gcttggagag | 1200 |
| tacaaattcc | agaatgcgct | attagttcgt | tacaccaaga | aagtaccccca | agtgtcaact | 1260 |
| ccaactcttg | tagaggtctc | aagaaaccta | ggaaaagtgg | gcagcaaatg | ttgtaaacat | 1320 |
| cctgaagcaa | aaagaatgcc | ctgtgcagaa | gactatctat | ccgtggtcct | gaaccagtta | 1380 |
| tgtgtgttgc | atgagaaaac | gccagtaagt | gacagagtca | ccaaatgctg | cacagaatcc | 1440 |
| ttggtgaaca | ggcgaccatg | cttttcagct | ctggaagtcg | atgaaacata | cgttcccaaa | 1500 |
| gagtttaatg | ctgaaacatt | caccttccat | gcagatatat | gcacactttc | tgagaaggag | 1560 |
| agacaaatca | gaaacaaac | tgcacttgtt | gagctcgtga | acacaagcc | caaggcaaca | 1620 |
| aaagagcaac | tgaaagctgt | tatggatgat | ttcgcagctt | ttgtagagaa | gtgctgcaag | 1680 |
| gctgacgata | aggagacctg | ctttgccgag | gagggtaaaa | aacttgttgc | tgcaagtcaa | 1740 |

```
gctgccttag gcttaggtgg aggcggtagc ggtggaggtg ggagtattga agggagggcg    1800
cgtaacgggg atcactgtcc gctcgggccc gggcgttgct gccgtctgca cacggtccgc    1860
gcgtcgctgg aagacctggg ctgggccgat tgggtgctgt cgccacggga ggtgcaagtg    1920
accatgtgca tcggcgcgtg cccgagccag ttccgggcgg caaacatgca cgcgcagatc    1980
aagacgagcc tgcaccgcct gaagcccgac acggtgccag cgccctgctg cgtgcccgcc    2040
agctacaatc ccatggtgct cattcaaaag accgacaccg gggtgtcgct ccagacctat    2100
gatgacttgt tagccaaaga ctgccactgc atataa                              2136
```

<210> SEQ ID NO 15
<211> LENGTH: 734
<212> TYPE: PRT
<213> ORGANISM: Artificial sequence
<220> FEATURE:
<223> OTHER INFORMATION: synthetic polypeptide

<400> SEQUENCE: 15

```
Met Asp Met Arg Val Pro Ala Gln Leu Leu Gly Leu Leu Leu Leu Trp
 1               5                  10                  15

Leu Arg Gly Ala Arg Cys Asp Ala His Lys Ser Glu Val Ala His Arg
            20                  25                  30

Phe Lys Asp Leu Gly Glu Glu Asn Phe Lys Ala Leu Val Leu Ile Ala
        35                  40                  45

Phe Ala Gln Tyr Leu Gln Gln Cys Pro Phe Glu Asp His Val Lys Leu
    50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
           100                 105                 110

Cys Ala Lys Gln Glu Pro Glu Arg Asn Glu Cys Phe Leu Gln His Lys
       115                 120                 125

Asp Asp Asn Pro Asn Leu Pro Arg Leu Val Arg Pro Glu Val Asp Val
130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190

Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
    210                 215                 220

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
                245                 250                 255

Val Thr Asp Leu Thr Lys Val His Thr Glu Cys Cys His Gly Asp Leu
            260                 265                 270

Leu Glu Cys Ala Asp Asp Arg Ala Asp Leu Ala Lys Tyr Ile Cys Glu
        275                 280                 285

Asn Gln Asp Ser Ile Ser Ser Lys Leu Lys Glu Cys Cys Glu Lys Pro
```

-continued

```
            290             295             300
Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
                325                 330                 335

Val Cys Lys Asn Tyr Ala Glu Ala Lys Asp Val Phe Leu Gly Met Phe
            340                 345                 350

Leu Tyr Glu Tyr Ala Arg Arg His Pro Asp Tyr Ser Val Val Leu Leu
        355                 360                 365

Leu Arg Leu Ala Lys Thr Tyr Glu Thr Thr Leu Glu Lys Cys Cys Ala
    370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
                405                 410                 415

Phe Glu Gln Leu Gly Glu Tyr Lys Phe Gln Asn Ala Leu Leu Val Arg
            420                 425                 430

Tyr Thr Lys Lys Val Pro Gln Val Ser Thr Pro Thr Leu Val Glu Val
        435                 440                 445

Ser Arg Asn Leu Gly Lys Val Gly Ser Lys Cys Cys Lys His Pro Glu
    450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
                485                 490                 495

Lys Cys Cys Thr Glu Ser Leu Val Asn Arg Arg Pro Cys Phe Ser Ala
            500                 505                 510

Leu Glu Val Asp Glu Thr Tyr Val Pro Lys Glu Phe Asn Ala Glu Thr
        515                 520                 525

Phe Thr Phe His Ala Asp Ile Cys Thr Leu Ser Glu Lys Glu Arg Gln
    530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
                565                 570                 575

Val Glu Lys Cys Cys Lys Ala Asp Asp Lys Glu Thr Cys Phe Ala Glu
            580                 585                 590

Glu Gly Lys Lys Leu Val Ala Ala Ser Gln Ala Ala Leu Gly Leu Gly
        595                 600                 605

Gly Gly Gly Ser Gly Gly Gly Gly Ser Gly Gly Gly Gly Ser Ala Arg
    610                 615                 620

Asn Gly Asp His Cys Pro Leu Gly Pro Gly Arg Cys Cys Arg Leu His
625                 630                 635                 640

Thr Val Arg Ala Ser Leu Glu Asp Leu Gly Trp Ala Asp Trp Val Leu
                645                 650                 655

Ser Pro Arg Glu Val Gln Val Thr Met Cys Ile Gly Ala Cys Pro Ser
            660                 665                 670

Gln Phe Arg Ala Ala Asn Met His Ala Gln Ile Lys Thr Ser Leu His
        675                 680                 685

Arg Leu Lys Pro Asp Thr Val Pro Ala Pro Cys Cys Val Pro Ala Ser
    690                 695                 700

Tyr Asn Pro Met Val Leu Ile Gln Lys Thr Asp Thr Gly Val Ser Leu
705                 710                 715                 720
```

```
Gln Thr Tyr Asp Asp Leu Leu Ala Lys Asp Cys His Cys Ile
            725                 730
```

```
<210> SEQ ID NO 16
<211> LENGTH: 2205
<212> TYPE: DNA
<213> ORGANISM: Artificial sequence
<220> FEATURE:
<223> OTHER INFORMATION: synthetic polynucleotide

<400> SEQUENCE: 16
```

| | | | | | |
|---|---|---|---|---|---|
| atggacatga | gggtccccgc | tcagctcctg | gggctcctgc | tactctggct | ccgaggtgcc       60 |
| agatgtgatg | cacacaagag | tgaggttgct | catcggttta | aagatttggg | agaagaaaat      120 |
| ttcaaagcct | tggtgttgat | tgcctttgct | cagtatcttc | agcagtgtcc | atttgaagat      180 |
| catgtaaaat | tagtgaatga | agtaactgaa | tttgcaaaaa | catgtgttgc | tgatgagtca      240 |
| gctgaaaatt | gtgacaaatc | acttcatacc | cttttttggag | acaaattatg | cacagttgca      300 |
| actcttcgtg | aaacctatgg | tgaaatggct | gactgctgtg | caaaacaaga | acctgagaga      360 |
| aatgaatgct | tcttgcaaca | caaagatgac | aacccaaacc | tcccccgatt | ggtgagacca      420 |
| gaggttgatg | tgatgtgcac | tgcttttcat | gacaatgaag | agacattttt | gaaaaaatac      480 |
| ttatatgaaa | ttgccagaag | acatccttac | ttttatgccc | cggaactcct | tttctttgct      540 |
| aaaaggtata | aagctgcttt | tacagaatgt | tgccaagctg | ctgataaagc | tgcctgcctg      600 |
| ttgccaaagc | tcgatgaact | tcgggatgaa | gggaaggctt | cgtctgccaa | acagagactc      660 |
| aagtgtgcca | gtctccaaaa | atttggagaa | agagctttca | agcatgggca | gtagctcgc       720 |
| ctgagccaga | gatttcccaa | agctgagttt | gcagaagttt | ccaagttagt | gacagatctt      780 |
| accaaagtcc | acacggaatg | ctgccatgga | gatctgcttg | aatgtgctga | tgacagggcg      840 |
| gaccttgcca | gtatatctg | tgaaaatcaa | gattcgatct | ccagtaaact | gaaggaatgc      900 |
| tgtgaaaaac | ctctgttgga | aaaatcccac | tgcattgccg | aagtggaaaa | tgatgagatg      960 |
| cctgctgact | tgccttcatt | agctgctgat | tttgttgaaa | gtaaggatgt | ttgcaaaaac     1020 |
| tatgctgagg | caaaggatgt | cttcctgggc | atgttttttgt | atgaatatgc | aagaaggcat     1080 |
| cctgattact | ctgtcgtgct | gctgctgaga | cttgccaaga | catatgaaac | cactctagag     1140 |
| aagtgctgtg | ccgctgcaga | tcctcatgaa | tgctatgcca | agtgttcga | tgaatttaaa     1200 |
| cctcttgtgg | aagagcctca | gaatttaatc | aaacaaaatt | gtgagctttt | tgagcagctt     1260 |
| ggagagtaca | aattccagaa | tgcgctatta | gttcgttaca | ccaagaaagt | accccaagtg     1320 |
| tcaactccaa | ctcttgtaga | ggtctcaaga | aacctaggaa | aagtgggcag | caaatgttgt     1380 |
| aaacatcctg | aagcaaaaag | aatgccctgt | gcagaagact | atctatccgt | ggtcctgaac     1440 |
| cagttatgtg | tgttgcatga | aaaacgcca | gtaagtgaca | gagtcaccaa | atgctgcaca     1500 |
| gaatccttgg | tgaacaggcg | accatgcttt | tcagctctgg | aagtcgatga | aacatacgtt     1560 |
| cccaaagagt | ttaatgctga | acattcacc | ttccatgcag | atatatgcac | actttctgag     1620 |
| aaggagagac | aaatcaagaa | acaaactgca | cttgttgagc | tcgtgaaaca | caagcccaag     1680 |
| gcaacaaaag | agcaactgaa | agctgttatg | gatgatttcg | cagcttttgt | agagaagtgc     1740 |
| tgcaaggctg | acgataagga | gacctgcttt | gccgaggagg | gtaaaaaact | tgttgctgca     1800 |
| agtcaagctg | ccttaggctt | aggtggaggc | ggtagcggtg | gaggtgggag | tggtggaggt     1860 |
| gggagtgcgc | gtaacgggga | tcactgtccg | ctcgggcccg | gcgttgctg | ccgtctgcac     1920 |
| acggtccgcg | cgtcgctgga | agacctgggc | tgggccgatt | gggtgctgtc | gccacgggag     1980 |

```
gtgcaagtga ccatgtgcat cggcgcgtgc ccgagccagt tccgggcggc aaacatgcac    2040
gcgcagatca agacgagcct gcaccgcctg aagcccgaca cggtgccagc gccctgctgc    2100
gtgcccgcca gctacaatcc catggtgctc attcaaaaga ccgacaccgg ggtgtcgctc    2160
cagacctatg atgacttgtt agccaaagac tgccactgca tataa                    2205
```

<210> SEQ ID NO 17
<211> LENGTH: 712
<212> TYPE: PRT
<213> ORGANISM: Artificial sequence
<220> FEATURE:
<223> OTHER INFORMATION: synthetic polypeptide

<400> SEQUENCE: 17

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320
```

```
Glu Ala Lys Asp Val Phe Leu Gly Met Phe Leu Tyr Glu Tyr Ala Arg
            325                 330                 335

Arg His Pro Asp Tyr Ser Val Val Leu Leu Arg Leu Ala Lys Thr
        340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly
            580                 585                 590

Gly Gly Ser Gly Gly Gly Gly Ser Ala Arg Asn Gly Asp His Cys Pro
        595                 600                 605

Leu Gly Pro Gly Arg Cys Cys Arg Leu His Thr Val Arg Ala Ser Leu
            610                 615                 620

Glu Asp Leu Gly Trp Ala Asp Trp Val Leu Ser Pro Arg Glu Val Gln
625                 630                 635                 640

Val Thr Met Cys Ile Gly Ala Cys Pro Ser Gln Phe Arg Ala Ala Asn
                645                 650                 655

Met His Ala Gln Ile Lys Thr Ser Leu His Arg Leu Lys Pro Asp Thr
            660                 665                 670

Val Pro Ala Pro Cys Cys Val Pro Ala Ser Tyr Asn Pro Met Val Leu
        675                 680                 685

Ile Gln Lys Thr Asp Thr Gly Val Ser Leu Gln Thr Tyr Asp Asp Leu
            690                 695                 700

Leu Ala Lys Asp Cys His Cys Ile
705                 710

<210> SEQ ID NO 18
<211> LENGTH: 2139
<212> TYPE: DNA
```

<213> ORGANISM: Artificial sequence
<220> FEATURE:
<223> OTHER INFORMATION: synthetic polynucleotide

<400> SEQUENCE: 18

```
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca aatcacttca tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat aagagacat ttttgaaaaa atacttatat      420
gaaattgcca aagacatcc ttactttat gccccggaac tccttttctt tgctaaaagg       480
tataaagctg cttttacaga atgttgccaa gctgctgata agctgcctg cctgttgcca      540
aagctcgatg aacttcggga tgaagggaag cttcgtctg ccaaacagag actcaagtgt      600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttgaatgtg ctgatgacag ggcggacctt     780
gccaagtata tctgtgaaaa tcaagattcg atctccagta aactgaagga atgctgtgaa     840
aaacctctgt tggaaaaatc ccactgcatt gccgaagtgg aaaatgatga tgatgcctgct    900
gacttgcctt cattagctgc tgattttgtt gaaagtaagg atgtttgcaa aaactatgct     960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg cagatcctca tgaatgctat gccaaagtgt tcgatgaatt taaacctctt    1140
gtggaagagc tcagaatttt aatcaaacaa aattgtgagc tttttgagca gcttggagag    1200
tacaaattcc agaatgcgct attagttcgt tacaccaaga aagtacccca agtgtcaact    1260
ccaactcttg tagaggtctc aagaaaccta ggaaaagtgg gcagcaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca agaaacaaac tgcacttgtt gagctcgtga acacaagcc caaggcaaca    1620
aaagagcaac tgaaagctgt tatggatgat ttcgcagctt ttgtagagaa gtgctgcaag    1680
gctgacgata aggagacctg cttttgccgag gagggtaaaa aacttgttgc tgcaagtcaa    1740
gctgccttag gcttaggtgg aggcggtagc ggtggaggtg ggagtggtgg aggtgggagt    1800
gcgcgtaacg gggatcactg tccgctcggg cccgggcgtt gctgccgtct gcacacggtc    1860
cgcgcgtcgc tggaagacct gggctgggcc gattgggtgc tgtcgccacg ggaggtgcaa    1920
gtgaccatgt gcatcggcgc gtgcccgagc cagttccggg cggcaaacat gcacgcgcag    1980
atcaagacga gcctgcaccg cctgaagccc gacacggtgc cagcgccctg ctgcgtgccc    2040
gccagctaca atcccatggt gctcattcaa aagaccgaca ccgggggtgtc gctccagacc    2100
tatgatgact tgttagccaa agactgccac tgcatataa                          2139
```

<210> SEQ ID NO 19
<211> LENGTH: 112
<212> TYPE: PRT
<213> ORGANISM: Artificial sequence
<220> FEATURE:
<223> OTHER INFORMATION: synthetic polypeptide

<400> SEQUENCE: 19

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Ala Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 20
<211> LENGTH: 112
<212> TYPE: PRT
<213> ORGANISM: Artificial sequence
<220> FEATURE:
<223> OTHER INFORMATION: synthetic polypeptide

<400> SEQUENCE: 20

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Ala
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 21
<211> LENGTH: 112
<212> TYPE: PRT
<213> ORGANISM: Artificial sequence
<220> FEATURE:
<223> OTHER INFORMATION: synthetic polypeptide

<400> SEQUENCE: 21

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

```
Pro Ser Gln Ala Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 22
<211> LENGTH: 112
<212> TYPE: PRT
<213> ORGANISM: Artificial sequence
<220> FEATURE:
<223> OTHER INFORMATION: synthetic polypeptide

<400> SEQUENCE: 22

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Ala His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 23
<211> LENGTH: 112
<212> TYPE: PRT
<213> ORGANISM: Artificial sequence
<220> FEATURE:
<223> OTHER INFORMATION: synthetic polypeptide

<400> SEQUENCE: 23

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Ala Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 24
<211> LENGTH: 112
<212> TYPE: PRT
```

<213> ORGANISM: Artificial sequence
<220> FEATURE:
<223> OTHER INFORMATION: synthetic polypeptide

<400> SEQUENCE: 24

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ala Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 25
<211> LENGTH: 112
<212> TYPE: PRT
<213> ORGANISM: Artificial sequence
<220> FEATURE:
<223> OTHER INFORMATION: synthetic polypeptide

<400> SEQUENCE: 25

```
Ala Arg Asn Gly Asp His Cys Pro Leu Gly Pro Gly Arg Cys Cys Arg
1               5                   10                  15

Leu His Thr Val Arg Ala Ser Leu Ala Ala Leu Gly Trp Ala Ala Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 26
<211> LENGTH: 112
<212> TYPE: PRT
<213> ORGANISM: Artificial sequence
<220> FEATURE:
<223> OTHER INFORMATION: synthetic polypeptide

<400> SEQUENCE: 26

```
Ala Arg Asn Gly Asp His Cys Pro Leu Gly Pro Gly Arg Cys Cys Arg
1               5                   10                  15

Leu His Thr Val Arg Ala Ser Leu Ala Ala Leu Gly Trp Ala Ala Trp
            20                  25                  30

Val Leu Ser Pro Arg Ala Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60
```

```
Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110

<210> SEQ ID NO 27
<211> LENGTH: 112
<212> TYPE: PRT
<213> ORGANISM: Artificial sequence
<220> FEATURE:
<223> OTHER INFORMATION: synthetic polypeptide

<400> SEQUENCE: 27

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Ala Ala Leu Leu Ala Lys Ala Cys His Cys Ile
            100                 105                 110

<210> SEQ ID NO 28
<211> LENGTH: 112
<212> TYPE: PRT
<213> ORGANISM: Artificial sequence
<220> FEATURE:
<223> OTHER INFORMATION: synthetic polypeptide

<400> SEQUENCE: 28

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Ala Thr Gly Val
                 85                  90                  95

Ser Leu Gln Thr Tyr Ala Ala Leu Leu Ala Lys Ala Cys His Cys Ile
            100                 105                 110

<210> SEQ ID NO 29
<211> LENGTH: 112
<212> TYPE: PRT
<213> ORGANISM: Artificial sequence
<220> FEATURE:
<223> OTHER INFORMATION: synthetic polypeptide
```

<400> SEQUENCE: 29

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65              70                  75                  80

Ala Ser Tyr Asn Pro Met Val Leu Ile Gln Lys Thr Ala Thr Gly Val
                85                  90                  95

Ser Leu Gln Thr Tyr Asp Asp Leu Leu Ala Lys Asp Cys His Cys Ile
            100                 105                 110
```

<210> SEQ ID NO 30
<211> LENGTH: 112
<212> TYPE: PRT
<213> ORGANISM: Artificial sequence
<220> FEATURE:
<223> OTHER INFORMATION: synthetic polypeptide

<400> SEQUENCE: 30

```
Ala Arg Asn Gly Thr His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65              70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 31
<211> LENGTH: 112
<212> TYPE: PRT
<213> ORGANISM: Artificial sequence
<220> FEATURE:
<223> OTHER INFORMATION: synthetic polypeptide

<400> SEQUENCE: 31

```
Ala Arg Asn Gly Asp His Cys Pro Leu Gly Pro Gly Arg Cys Cys Arg
1               5                   10                  15

Asn His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65              70                  75                  80
```

Ala Ser Tyr Asn Pro Met Val Leu Ile Gln Lys Thr Asp Thr Gly Val
            85                  90                  95

Ser Leu Gln Thr Tyr Asp Asp Leu Leu Ala Lys Asp Cys His Cys Ile
            100                 105                 110

<210> SEQ ID NO 32
<211> LENGTH: 112
<212> TYPE: PRT
<213> ORGANISM: Artificial sequence
<220> FEATURE:
<223> OTHER INFORMATION: synthetic polypeptide

<400> SEQUENCE: 32

Ala Arg Asn Gly Asp His Cys Pro Leu Gly Pro Gly Arg Cys Cys Arg
1               5                   10                  15

Leu His Thr Val Asn Ala Ser Leu Glu Asp Leu Gly Trp Ala Asp Trp
            20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
            85                  90                  95

Ser Leu Gln Thr Tyr Asp Asp Leu Leu Ala Lys Asp Cys His Cys Ile
            100                 105                 110

<210> SEQ ID NO 33
<211> LENGTH: 112
<212> TYPE: PRT
<213> ORGANISM: Artificial sequence
<220> FEATURE:
<223> OTHER INFORMATION: synthetic polypeptide

<400> SEQUENCE: 33

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Asn Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
            85                  90                  95

Ser Leu Gln Thr Tyr Asp Asp Leu Leu Ala Lys Asp Cys His Cys Ile
            100                 105                 110

<210> SEQ ID NO 34
<211> LENGTH: 112
<212> TYPE: PRT
<213> ORGANISM: Artificial sequence
<220> FEATURE:
<223> OTHER INFORMATION: synthetic polypeptide

<400> SEQUENCE: 34

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Asn Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 35
<211> LENGTH: 112
<212> TYPE: PRT
<213> ORGANISM: Artificial sequence
<220> FEATURE:
<223> OTHER INFORMATION: synthetic polypeptide

<400> SEQUENCE: 35

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met Thr Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 36
<211> LENGTH: 112
<212> TYPE: PRT
<213> ORGANISM: Artificial sequence
<220> FEATURE:
<223> OTHER INFORMATION: synthetic polypeptide

<400> SEQUENCE: 36

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Asn Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95
```

```
Ser Leu Gln Thr Tyr Asp Asp Leu Leu Ala Lys Asp Cys His Cys Ile
            100                 105                 110

<210> SEQ ID NO 37
<211> LENGTH: 112
<212> TYPE: PRT
<213> ORGANISM: Artificial sequence
<220> FEATURE:
<223> OTHER INFORMATION: synthetic polypeptide

<400> SEQUENCE: 37

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Asn Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 38
<211> LENGTH: 112
<212> TYPE: PRT
<213> ORGANISM: Artificial sequence
<220> FEATURE:
<223> OTHER INFORMATION: synthetic polypeptide

<400> SEQUENCE: 38

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Asn Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 39
<211> LENGTH: 112
<212> TYPE: PRT
<213> ORGANISM: Artificial sequence
<220> FEATURE:
<223> OTHER INFORMATION: synthetic polypeptide

<400> SEQUENCE: 39

Ala Arg Asn Gly Asp His Cys Pro Leu Gly Pro Gly Arg Cys Cys Arg
1               5                   10                  15
```

```
Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Asn
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 40
<211> LENGTH: 112
<212> TYPE: PRT
<213> ORGANISM: Artificial sequence
<220> FEATURE:
<223> OTHER INFORMATION: synthetic polypeptide

<400> SEQUENCE: 40

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 41
<211> LENGTH: 112
<212> TYPE: PRT
<213> ORGANISM: Artificial sequence
<220> FEATURE:
<223> OTHER INFORMATION: synthetic polypeptide

<400> SEQUENCE: 41

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Asn Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 42
<211> LENGTH: 112
<212> TYPE: PRT
<213> ORGANISM: Artificial sequence
<220> FEATURE:
<223> OTHER INFORMATION: synthetic polypeptide

<400> SEQUENCE: 42

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Asn Val
                85                  90                  95

Ser Leu Gln Thr Tyr Asp Asp Leu Leu Ala Lys Asp Cys His Cys Ile
            100                 105                 110

<210> SEQ ID NO 43
<211> LENGTH: 112
<212> TYPE: PRT
<213> ORGANISM: Artificial sequence
<220> FEATURE:
<223> OTHER INFORMATION: synthetic polypeptide

<400> SEQUENCE: 43

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Asn Gln Thr Tyr Asp Asp Leu Leu Ala Lys Asp Cys His Cys Ile
            100                 105                 110

<210> SEQ ID NO 44
<211> LENGTH: 112
<212> TYPE: PRT
<213> ORGANISM: Artificial sequence
<220> FEATURE:
<223> OTHER INFORMATION: synthetic polypeptide

<400> SEQUENCE: 44

Ala Arg Asn Gly Thr His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

```
Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Gly Val
                 85                  90                  95

Ser Leu Gln Thr Tyr Asp Asp Leu Leu Ala Lys Asp Cys His Cys Ile
            100                 105                 110
```

<210> SEQ ID NO 45
<211> LENGTH: 112
<212> TYPE: PRT
<213> ORGANISM: Artificial sequence
<220> FEATURE:
<223> OTHER INFORMATION: synthetic polypeptide

<400> SEQUENCE: 45

```
Ala Arg Asn Gly Thr His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Asn Val
                 85                  90                  95

Ser Leu Gln Thr Tyr Asp Asp Leu Leu Ala Lys Asp Cys His Cys Ile
            100                 105                 110
```

<210> SEQ ID NO 46
<211> LENGTH: 112
<212> TYPE: PRT
<213> ORGANISM: Artificial sequence
<220> FEATURE:
<223> OTHER INFORMATION: synthetic polypeptide

<400> SEQUENCE: 46

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Asn Val Thr Met Cys Ile Gly Ala Cys
         35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Gly Val
                 85                  90                  95

Ser Leu Gln Thr Tyr Asp Asp Leu Leu Ala Lys Asp Cys His Cys Ile
            100                 105                 110
```

<210> SEQ ID NO 47

<211> LENGTH: 112
<212> TYPE: PRT
<213> ORGANISM: Artificial sequence
<220> FEATURE:
<223> OTHER INFORMATION: synthetic polypeptide

<400> SEQUENCE: 47

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Asn Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Asn Val
                85                  90                  95

Ser Leu Gln Thr Tyr Asp Asp Leu Leu Ala Lys Asp Cys His Cys Ile
            100                 105                 110
```

<210> SEQ ID NO 48
<211> LENGTH: 112
<212> TYPE: PRT
<213> ORGANISM: Artificial sequence
<220> FEATURE:
<223> OTHER INFORMATION: synthetic polypeptide

<400> SEQUENCE: 48

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Asn Asp Thr Val Pro Ala Pro Cys Cys Val Pro
65                  70                  75                  80

Ala Ser Tyr Asn Pro Met Val Leu Ile Asn Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 49
<211> LENGTH: 112
<212> TYPE: PRT
<213> ORGANISM: Artificial sequence
<220> FEATURE:
<223> OTHER INFORMATION: synthetic polypeptide

<400> SEQUENCE: 49

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45
```

```
Pro Ser Gln Phe Arg Ala Ala Asn Met His Ala Gln Ile Lys Thr Ser
    50                  55                  60

Leu His Arg Leu Lys Asn Asp Thr Val Pro Ala Pro Cys Cys Val Pro
65                  70                  75                  80

Ala Ser Tyr Asn Pro Met Val Leu Ile Gln Lys Thr Asp Thr Asn Val
                85                  90                  95

Ser Leu Gln Thr Tyr Asp Asp Leu Leu Ala Lys Asp Cys His Cys Ile
                100                 105                 110

<210> SEQ ID NO 50
<211> LENGTH: 112
<212> TYPE: PRT
<213> ORGANISM: Artificial sequence
<220> FEATURE:
<223> OTHER INFORMATION: synthetic polypeptide

<400> SEQUENCE: 50

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Asn Val
                85                  90                  95

Ser Leu Gln Thr Tyr Asp Asp Leu Leu Ala Lys Asp Cys His Cys Ile
                100                 105                 110

<210> SEQ ID NO 51
<211> LENGTH: 112
<212> TYPE: PRT
<213> ORGANISM: Artificial sequence
<220> FEATURE:
<223> OTHER INFORMATION: synthetic polypeptide

<400> SEQUENCE: 51

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Asn Lys Thr Asp Thr Gly Val
                85                  90                  95

Ser Asn Gln Thr Tyr Asp Asp Leu Leu Ala Lys Asp Cys His Cys Ile
                100                 105                 110

<210> SEQ ID NO 52
<211> LENGTH: 112
<212> TYPE: PRT
<213> ORGANISM: Artificial sequence
```

```
<220> FEATURE:
<223> OTHER INFORMATION: synthetic polypeptide

<400> SEQUENCE: 52

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65              70                  75                  80

Ala Ser Tyr Asn Pro Met Val Leu Ile Gln Lys Thr Asp Thr Asn Val
            85                  90                  95

Ser Asn Gln Thr Tyr Asp Asp Leu Leu Ala Lys Asp Cys His Cys Ile
        100                 105                 110

<210> SEQ ID NO 53
<211> LENGTH: 22
<212> TYPE: PRT
<213> ORGANISM: Homo sapiens

<400> SEQUENCE: 53

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 54
<211> LENGTH: 115
<212> TYPE: PRT
<213> ORGANISM: Mus musculus

<400> SEQUENCE: 54

Ser Ala His Ala His Pro Arg Asp Ser Cys Pro Leu Gly Pro Gly Arg
1               5                   10                  15

Cys Cys His Leu Glu Thr Val Gln Ala Thr Leu Glu Asp Leu Gly Trp
            20                  25                  30

Ser Asp Trp Val Leu Ser Pro Arg Gln Leu Gln Leu Ser Met Cys Val
        35                  40                  45

Gly Glu Cys Pro His Leu Tyr Arg Ser Ala Asn Thr His Ala Gln Ile
    50                  55                  60

Lys Ala Arg Leu His Gly Leu Gln Pro Asp Lys Val Pro Ala Pro Cys
65              70                  75                  80

Cys Val Pro Ser Ser Tyr Thr Pro Val Val Leu Met His Arg Thr Asp
            85                  90                  95

Ser Gly Val Ser Leu Gln Thr Tyr Asp Asp Leu Val Ala Arg Gly Cys
        100                 105                 110

His Cys Ala
    115

<210> SEQ ID NO 55
<211> LENGTH: 112
<212> TYPE: PRT
<213> ORGANISM: Macaca mulatta

<400> SEQUENCE: 55
```

```
Ala Arg Asn Gly Asp Arg Cys Pro Leu Gly Pro Gly Arg Cys Cys Arg
1               5                   10                  15

Leu His Thr Val His Ala Ser Leu Glu Asp Leu Gly Trp Ala Asp Trp
            20                  25                  30

Val Leu Ser Pro Arg Glu Val Gln Val Thr Met Cys Ile Gly Ala Cys
            35                  40                  45

Pro Ser Gln Phe Arg Glu Ala Asn Met His Ala Gln Ile Lys Met Asn
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Val
            100                 105                 110
```

<210> SEQ ID NO 56
<211> LENGTH: 14
<212> TYPE: PRT
<213> ORGANISM: Artificial sequence
<220> FEATURE:
<223> OTHER INFORMATION: synthetic polypeptide

<400> SEQUENCE: 56

```
Gly Gly Gly Gly Ser Gly Gly Gly Gly Ser Ile Glu Gly Arg
1               5                   10
```

<210> SEQ ID NO 57
<211> LENGTH: 736
<212> TYPE: PRT
<213> ORGANISM: Artificial sequence
<220> FEATURE:
<223> OTHER INFORMATION: synthetic polypeptide

<400> SEQUENCE: 57

```
Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
            20                  25                  30

Phe Lys Asp Leu Gly Glu Glu Asn Phe Lys Ala Leu Val Leu Ile Ala
        35                  40                  45

Phe Ala Gln Tyr Leu Gln Gln Cys Pro Phe Glu Asp His Val Lys Leu
    50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
```

```
            180                 185                 190
Ala Ala Asp Lys Ala Ala Cys Leu Leu Pro Lys Leu Asp Glu Leu Arg
        195                 200                 205
Asp Glu Gly Lys Ala Ser Ser Ala Lys Gln Arg Leu Lys Cys Ala Ser
        210                 215                 220
Leu Gln Lys Phe Gly Glu Arg Ala Phe Lys Ala Trp Ala Val Ala Arg
225                 230                 235                 240
Leu Ser Gln Arg Phe Pro Lys Ala Glu Phe Ala Glu Val Ser Lys Leu
                    245                 250                 255
Val Thr Asp Leu Thr Lys Val His Thr Glu Cys Cys His Gly Asp Leu
            260                 265                 270
Leu Glu Cys Ala Asp Asp Arg Ala Asp Leu Ala Lys Tyr Ile Cys Glu
        275                 280                 285
Asn Gln Asp Ser Ile Ser Ser Lys Leu Lys Glu Cys Cys Glu Lys Pro
        290                 295                 300
Leu Leu Glu Lys Ser His Cys Ile Ala Glu Val Glu Asn Asp Glu Met
305                 310                 315                 320
Pro Ala Asp Leu Pro Ser Leu Ala Ala Asp Phe Val Glu Ser Lys Asp
                    325                 330                 335
Val Cys Lys Asn Tyr Ala Glu Ala Lys Asp Val Phe Leu Gly Met Phe
                340                 345                 350
Leu Tyr Glu Tyr Ala Arg Arg His Pro Asp Tyr Ser Val Val Leu Leu
            355                 360                 365
Leu Arg Leu Ala Lys Thr Tyr Glu Thr Thr Leu Glu Lys Cys Cys Ala
        370                 375                 380
Ala Ala Asp Pro His Glu Cys Tyr Ala Lys Val Phe Asp Glu Phe Lys
385                 390                 395                 400
Pro Leu Val Glu Glu Pro Gln Asn Leu Ile Lys Gln Asn Cys Glu Leu
                    405                 410                 415
Phe Glu Gln Leu Gly Glu Tyr Lys Phe Gln Asn Ala Leu Leu Val Arg
                420                 425                 430
Tyr Thr Lys Lys Val Pro Gln Val Ser Thr Pro Thr Leu Val Glu Val
            435                 440                 445
Ser Arg Asn Leu Gly Lys Val Gly Ser Lys Cys Cys Lys His Pro Glu
        450                 455                 460
Ala Lys Arg Met Pro Cys Ala Glu Asp Tyr Leu Ser Val Val Leu Asn
465                 470                 475                 480
Gln Leu Cys Val Leu His Glu Lys Thr Pro Val Ser Asp Arg Val Thr
                    485                 490                 495
Lys Cys Cys Thr Glu Ser Leu Val Asn Arg Arg Pro Cys Phe Ser Ala
                500                 505                 510
Leu Glu Val Asp Glu Thr Tyr Val Pro Lys Glu Phe Asn Ala Glu Thr
            515                 520                 525
Phe Thr Phe His Ala Asp Ile Cys Thr Leu Ser Glu Lys Glu Arg Gln
        530                 535                 540
Ile Lys Lys Gln Thr Ala Leu Val Glu Leu Val Lys His Lys Pro Lys
545                 550                 555                 560
Ala Thr Lys Glu Gln Leu Lys Ala Val Met Asp Asp Phe Ala Ala Phe
                    565                 570                 575
Val Glu Lys Cys Cys Lys Ala Asp Asp Lys Glu Thr Cys Phe Ala Glu
                580                 585                 590
Glu Gly Lys Lys Leu Val Ala Ala Ser Gln Ala Ala Leu Gly Leu Gly
            595                 600                 605
```

```
Gly Gly Gly Ser Gly Gly Gly Ser Ile Glu Gly Arg Ser Ala His
        610             615                 620
Ala His Pro Arg Asp Ser Cys Pro Leu Gly Pro Gly Arg Cys Cys His
625             630                 635                 640
Leu Glu Thr Val Gln Ala Thr Leu Glu Asp Leu Gly Trp Ser Asp Trp
            645                 650                 655
Val Leu Ser Pro Arg Gln Leu Gln Leu Ser Met Cys Val Gly Glu Cys
        660                 665                 670
Pro His Leu Tyr Arg Ser Ala Asn Thr His Ala Gln Ile Lys Ala Arg
            675                 680                 685
Leu His Gly Leu Gln Pro Asp Lys Val Pro Ala Pro Cys Cys Val Pro
        690                 695                 700
Ser Ser Tyr Thr Pro Val Val Leu Met His Arg Thr Asp Ser Gly Val
705                 710                 715                 720
Ser Leu Gln Thr Tyr Asp Asp Leu Val Ala Arg Gly Cys His Cys Ala
            725                 730                 735

<210> SEQ ID NO 58
<211> LENGTH: 733
<212> TYPE: PRT
<213> ORGANISM: Artificial sequence
<220> FEATURE:
<223> OTHER INFORMATION: synthetic polypeptide

<400> SEQUENCE: 58

Met Asp Met Arg Val Pro Ala Gln Leu Leu Gly Leu Leu Leu Leu Trp
1               5                   10                  15
Leu Arg Gly Ala Arg Cys Asp Ala His Lys Ser Glu Val Ala His Arg
            20                  25                  30
Phe Lys Asp Leu Gly Glu Glu Asn Phe Lys Ala Leu Val Leu Ile Ala
        35                  40                  45
Phe Ala Gln Tyr Leu Gln Gln Cys Pro Phe Glu Asp His Val Lys Leu
    50                  55                  60
Val Asn Glu Val Thr Glu Phe Ala Lys Thr Cys Val Ala Asp Glu Ser
65                  70                  75                  80
Ala Glu Asn Cys Asp Lys Ser Leu His Thr Leu Phe Gly Asp Lys Leu
                85                  90                  95
Cys Thr Val Ala Thr Leu Arg Glu Thr Tyr Gly Glu Met Ala Asp Cys
            100                 105                 110
Cys Ala Lys Gln Glu Pro Glu Arg Asn Glu Cys Phe Leu Gln His Lys
        115                 120                 125
Asp Asp Asn Pro Asn Leu Pro Arg Leu Val Arg Pro Glu Val Asp Val
    130                 135                 140
Met Cys Thr Ala Phe His Asp Asn Glu Glu Thr Phe Leu Lys Lys Tyr
145                 150                 155                 160
Leu Tyr Glu Ile Ala Arg Arg His Pro Tyr Phe Tyr Ala Pro Glu Leu
                165                 170                 175
Leu Phe Phe Ala Lys Arg Tyr Lys Ala Ala Phe Thr Glu Cys Cys Gln
            180                 185                 190
Ala Ala Asp Lys Ala Ala Cys Leu Leu Pro Lys Leu Asp Glu Leu Arg
        195                 200                 205
Asp Glu Gly Lys Ala Ser Ser Ala Lys Gln Arg Leu Lys Cys Ala Ser
    210                 215                 220
Leu Gln Lys Phe Gly Glu Arg Ala Phe Lys Ala Trp Ala Val Ala Arg
225                 230                 235                 240
```

```
Leu Ser Gln Arg Phe Pro Lys Ala Glu Phe Ala Glu Val Ser Lys Leu
                245                 250                 255
Val Thr Asp Leu Thr Lys Val His Thr Glu Cys Cys His Gly Asp Leu
            260                 265                 270
Leu Glu Cys Ala Asp Asp Arg Ala Asp Leu Ala Lys Tyr Ile Cys Glu
        275                 280                 285
Asn Gln Asp Ser Ile Ser Ser Lys Leu Lys Glu Cys Cys Glu Lys Pro
    290                 295                 300
Leu Leu Glu Lys Ser His Cys Ile Ala Glu Val Glu Asn Asp Glu Met
305                 310                 315                 320
Pro Ala Asp Leu Pro Ser Leu Ala Ala Asp Phe Val Glu Ser Lys Asp
                325                 330                 335
Val Cys Lys Asn Tyr Ala Glu Ala Lys Asp Val Phe Leu Gly Met Phe
            340                 345                 350
Leu Tyr Glu Tyr Ala Arg Arg His Pro Asp Tyr Ser Val Val Leu Leu
        355                 360                 365
Leu Arg Leu Ala Lys Thr Tyr Glu Thr Thr Leu Glu Lys Cys Cys Ala
    370                 375                 380
Ala Ala Asp Pro His Glu Cys Tyr Ala Lys Val Phe Asp Glu Phe Lys
385                 390                 395                 400
Pro Leu Val Glu Glu Pro Gln Asn Leu Ile Lys Gln Asn Cys Glu Leu
                405                 410                 415
Phe Glu Gln Leu Gly Glu Tyr Lys Phe Gln Asn Ala Leu Leu Val Arg
            420                 425                 430
Tyr Thr Lys Lys Val Pro Gln Val Ser Thr Pro Thr Leu Val Glu Val
        435                 440                 445
Ser Arg Asn Leu Gly Lys Val Gly Ser Lys Cys Cys Lys His Pro Glu
    450                 455                 460
Ala Lys Arg Met Pro Cys Ala Glu Asp Tyr Leu Ser Val Val Leu Asn
465                 470                 475                 480
Gln Leu Cys Val Leu His Glu Lys Thr Pro Val Ser Asp Arg Val Thr
                485                 490                 495
Lys Cys Cys Thr Glu Ser Leu Val Asn Arg Arg Pro Cys Phe Ser Ala
            500                 505                 510
Leu Glu Val Asp Glu Thr Tyr Val Pro Lys Glu Phe Asn Ala Glu Thr
        515                 520                 525
Phe Thr Phe His Ala Asp Ile Cys Thr Leu Ser Glu Lys Glu Arg Gln
    530                 535                 540
Ile Lys Lys Gln Thr Ala Leu Val Glu Leu Val Lys His Lys Pro Lys
545                 550                 555                 560
Ala Thr Lys Glu Gln Leu Lys Ala Val Met Asp Asp Phe Ala Ala Phe
                565                 570                 575
Val Glu Lys Cys Cys Lys Ala Asp Asp Lys Glu Thr Cys Phe Ala Glu
            580                 585                 590
Glu Gly Lys Lys Leu Val Ala Ala Ser Gln Ala Ala Leu Gly Leu Gly
        595                 600                 605
Gly Gly Gly Ser Gly Gly Gly Ser Ile Glu Gly Arg Ala Arg Asn
    610                 615                 620
Gly Asp Arg Cys Pro Leu Gly Pro Gly Arg Cys Cys Arg Leu His Thr
625                 630                 635                 640
Val His Ala Ser Leu Glu Asp Leu Gly Trp Ala Asp Trp Val Leu Ser
                645                 650                 655
```

```
Pro Arg Glu Val Gln Val Thr Met Cys Ile Gly Ala Cys Pro Ser Gln
            660                 665                 670

Phe Arg Glu Ala Asn Met His Ala Gln Ile Lys Met Asn Leu His Arg
            675                 680                 685

Leu Lys Pro Asp Thr Val Pro Ala Pro Cys Cys Val Pro Ala Ser Tyr
            690                 695                 700

Asn Pro Met Val Leu Ile Gln Lys Thr Asp Thr Gly Val Ser Leu Gln
705                 710                 715                 720

Thr Tyr Asp Asp Leu Leu Ala Lys Asp Cys His Cys Val
                725                 730

<210> SEQ ID NO 59
<211> LENGTH: 112
<212> TYPE: PRT
<213> ORGANISM: Homo sapiens

<400> SEQUENCE: 59

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 60
<211> LENGTH: 114
<212> TYPE: PRT
<213> ORGANISM: Homo sapiens

<400> SEQUENCE: 60

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 61
<211> LENGTH: 17
<212> TYPE: PRT
```

<213> ORGANISM: Homo sapiens

<400> SEQUENCE: 61

Gly Gly Gly Gly Ser Ile Glu Gly Arg Asp Tyr Lys Asp Asp Asp
1               5                   10                  15

Lys

<210> SEQ ID NO 62
<211> LENGTH: 736
<212> TYPE: PRT
<213> ORGANISM: Artificial sequence
<220> FEATURE:
<223> OTHER INFORMATION: synthetic polypeptide

<400> SEQUENCE: 62

Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
                20                  25                  30

Phe Lys Asp Leu Gly Glu Glu Asn Phe Lys Ala Leu Val Leu Ile Ala
            35                  40                  45

Phe Ala Gln Tyr Leu Gln Gln Cys Pro Phe Glu Asp His Val Lys Leu
        50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190

Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
    210                 215                 220

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
                245                 250                 255

Val Thr Asp Leu Thr Lys Val His Thr Glu Cys Cys His Gly Asp Leu
            260                 265                 270

Leu Glu Cys Ala Asp Asp Arg Ala Asp Leu Ala Lys Tyr Ile Cys Glu
        275                 280                 285

Asn Gln Asp Ser Ile Ser Ser Lys Leu Lys Glu Cys Cys Glu Lys Pro
    290                 295                 300

Leu Leu Glu Lys Ser His Cys Ile Ala Glu Val Glu Asn Asp Glu Met
305                 310                 315                 320

```
Pro Ala Asp Leu Pro Ser Leu Ala Ala Asp Phe Val Glu Ser Lys Asp
                325                 330                 335

Val Cys Lys Asn Tyr Ala Glu Ala Lys Asp Val Phe Leu Gly Met Phe
            340                 345                 350

Leu Tyr Glu Tyr Ala Arg Arg His Pro Asp Tyr Ser Val Val Leu Leu
        355                 360                 365

Leu Arg Leu Ala Lys Thr Tyr Glu Thr Thr Leu Glu Lys Cys Cys Ala
    370                 375                 380

Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
                405                 410                 415

Phe Glu Gln Leu Gly Glu Tyr Lys Phe Gln Asn Ala Leu Leu Val Arg
            420                 425                 430

Tyr Thr Lys Lys Val Pro Gln Val Ser Thr Pro Thr Leu Val Glu Val
        435                 440                 445

Ser Arg Asn Leu Gly Lys Val Gly Ser Lys Cys Cys Lys His Pro Glu
    450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
                485                 490                 495

Lys Cys Cys Thr Glu Ser Leu Val Asn Arg Arg Pro Cys Phe Ser Ala
            500                 505                 510

Leu Glu Val Asp Glu Thr Tyr Val Pro Lys Glu Phe Asn Ala Glu Thr
        515                 520                 525

Phe Thr Phe His Ala Asp Ile Cys Thr Leu Ser Glu Lys Glu Arg Gln
    530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
                565                 570                 575

Val Glu Lys Cys Cys Lys Ala Asp Asp Lys Glu Thr Cys Phe Ala Glu
            580                 585                 590

Glu Gly Lys Lys Leu Val Ala Ala Ser Gln Ala Ala Leu Gly Leu Gly
        595                 600                 605

Gly Gly Gly Ser Ile Glu Gly Arg Asp Tyr Lys Asp Asp Asp Asp Lys
    610                 615                 620

Ala Leu Asp Thr Asn Tyr Cys Phe Ser Ser Thr Glu Lys Asn Cys Cys
625                 630                 635                 640

Val Arg Gln Leu Tyr Ile Asp Phe Arg Lys Asp Leu Gly Trp Lys Trp
                645                 650                 655

Ile His Glu Pro Lys Gly Tyr His Ala Asn Phe Cys Leu Gly Pro Cys
            660                 665                 670

Pro Tyr Ile Trp Ser Leu Asp Thr Gln Tyr Ser Lys Val Leu Ala Leu
        675                 680                 685

Tyr Asn Gln His Asn Pro Gly Ala Ser Ala Ala Pro Cys Cys Val Pro
    690                 695                 700

Gln Ala Leu Glu Pro Leu Pro Ile Val Tyr Tyr Val Gly Arg Lys Pro
705                 710                 715                 720

Lys Val Glu Gln Leu Ser Asn Met Ile Val Arg Ser Cys Lys Cys Ser
                725                 730                 735
```

-continued

```
<210> SEQ ID NO 63
<211> LENGTH: 738
<212> TYPE: PRT
<213> ORGANISM: Artificial sequence
<220> FEATURE:
<223> OTHER INFORMATION: synthetic polypeptide

<400> SEQUENCE: 63

Met Asp Met Arg Val Pro Ala Gln Leu Leu Gly Leu Leu Leu Leu Trp
1               5                   10                  15

Leu Arg Gly Ala Arg Cys Asp Ala His Lys Ser Glu Val Ala His Arg
            20                  25                  30

Phe Lys Asp Leu Gly Glu Glu Asn Phe Lys Ala Leu Val Leu Ile Ala
        35                  40                  45

Phe Ala Gln Tyr Leu Gln Gln Cys Pro Phe Glu Asp His Val Lys Leu
    50                  55                  60

Val Asn Glu Val Thr Glu Phe Ala Lys Thr Cys Val Ala Asp Glu Ser
65                  70                  75                  80

Ala Glu Asn Cys Asp Lys Ser Leu His Thr Leu Phe Gly Asp Lys Leu
                85                  90                  95

Cys Thr Val Ala Thr Leu Arg Glu Thr Tyr Gly Glu Met Ala Asp Cys
            100                 105                 110

Cys Ala Lys Gln Glu Pro Glu Arg Asn Glu Cys Phe Leu Gln His Lys
        115                 120                 125

Asp Asp Asn Pro Asn Leu Pro Arg Leu Val Arg Pro Glu Val Asp Val
    130                 135                 140

Met Cys Thr Ala Phe His Asp Asn Glu Glu Thr Phe Leu Lys Lys Tyr
145                 150                 155                 160

Leu Tyr Glu Ile Ala Arg Arg His Pro Tyr Phe Tyr Ala Pro Glu Leu
                165                 170                 175

Leu Phe Phe Ala Lys Arg Tyr Lys Ala Ala Phe Thr Glu Cys Cys Gln
            180                 185                 190

Ala Ala Asp Lys Ala Ala Cys Leu Leu Pro Lys Leu Asp Glu Leu Arg
        195                 200                 205

Asp Glu Gly Lys Ala Ser Ser Ala Lys Gln Arg Leu Lys Cys Ala Ser
    210                 215                 220

Leu Gln Lys Phe Gly Glu Arg Ala Phe Lys Ala Trp Ala Val Ala Arg
225                 230                 235                 240

Leu Ser Gln Arg Phe Pro Lys Ala Glu Phe Ala Glu Val Ser Lys Leu
                245                 250                 255

Val Thr Asp Leu Thr Lys Val His Thr Glu Cys Cys His Gly Asp Leu
            260                 265                 270

Leu Glu Cys Ala Asp Asp Arg Ala Asp Leu Ala Lys Tyr Ile Cys Glu
        275                 280                 285

Asn Gln Asp Ser Ile Ser Ser Lys Leu Lys Glu Cys Cys Glu Lys Pro
    290                 295                 300

Leu Leu Glu Lys Ser His Cys Ile Ala Glu Val Glu Asn Asp Glu Met
305                 310                 315                 320

Pro Ala Asp Leu Pro Ser Leu Ala Ala Asp Phe Val Glu Ser Lys Asp
                325                 330                 335

Val Cys Lys Asn Tyr Ala Glu Ala Lys Asp Val Phe Leu Gly Met Phe
            340                 345                 350

Leu Tyr Glu Tyr Ala Arg Arg His Pro Asp Tyr Ser Val Val Leu Leu
        355                 360                 365

Leu Arg Leu Ala Lys Thr Tyr Glu Thr Thr Leu Glu Lys Cys Cys Ala
```

370                 375                 380
Ala Ala Asp Pro His Glu Cys Tyr Ala Lys Val Phe Asp Glu Phe Lys
385                 390                 395                 400

Pro Leu Val Glu Glu Pro Gln Asn Leu Ile Lys Gln Asn Cys Glu Leu
                    405                 410                 415

Phe Glu Gln Leu Gly Glu Tyr Lys Phe Gln Asn Ala Leu Leu Val Arg
                    420                 425                 430

Tyr Thr Lys Lys Val Pro Gln Val Ser Thr Pro Thr Leu Val Glu Val
                    435                 440                 445

Ser Arg Asn Leu Gly Lys Val Gly Ser Lys Cys Cys Lys His Pro Glu
                    450                 455                 460

Ala Lys Arg Met Pro Cys Ala Glu Asp Tyr Leu Ser Val Val Leu Asn
465                 470                 475                 480

Gln Leu Cys Val Leu His Glu Lys Thr Pro Val Ser Asp Arg Val Thr
                    485                 490                 495

Lys Cys Cys Thr Glu Ser Leu Val Asn Arg Arg Pro Cys Phe Ser Ala
                    500                 505                 510

Leu Glu Val Asp Glu Thr Tyr Val Pro Lys Glu Phe Asn Ala Glu Thr
                    515                 520                 525

Phe Thr Phe His Ala Asp Ile Cys Thr Leu Ser Glu Lys Glu Arg Gln
530                 535                 540

Ile Lys Lys Gln Thr Ala Leu Val Glu Leu Val Lys His Lys Pro Lys
545                 550                 555                 560

Ala Thr Lys Glu Gln Leu Lys Ala Val Met Asp Asp Phe Ala Ala Phe
                    565                 570                 575

Val Glu Lys Cys Cys Lys Ala Asp Asp Lys Glu Thr Cys Phe Ala Glu
                    580                 585                 590

Glu Gly Lys Lys Leu Val Ala Ala Ser Gln Ala Ala Leu Gly Leu Gly
                    595                 600                 605

Gly Gly Gly Ser Ile Glu Gly Arg Asp Tyr Lys Asp Asp Asp Asp Lys
                    610                 615                 620

Gln Ala Lys His Lys Gln Arg Lys Arg Leu Lys Ser Ser Cys Lys Arg
625                 630                 635                 640

His Pro Leu Tyr Val Asp Phe Ser Asp Val Gly Trp Asn Asp Trp Ile
                    645                 650                 655

Val Ala Pro Pro Gly Tyr His Ala Phe Tyr Cys His Gly Glu Cys Pro
                    660                 665                 670

Phe Pro Leu Ala Asp His Leu Asn Ser Thr Asn His Ala Ile Val Gln
                    675                 680                 685

Thr Leu Val Asn Ser Val Asn Ser Lys Ile Pro Lys Ala Cys Cys Val
                    690                 695                 700

Pro Thr Glu Leu Ser Ala Ile Ser Met Leu Tyr Leu Asp Glu Asn Glu
705                 710                 715                 720

Lys Val Val Leu Lys Asn Tyr Gln Asp Met Val Val Glu Gly Cys Gly
                    725                 730                 735

Cys Arg

<210> SEQ ID NO 64
<211> LENGTH: 15
<212> TYPE: PRT
<213> ORGANISM: Artificial sequence
<220> FEATURE:
<223> OTHER INFORMATION: synthetic polypeptide

<400> SEQUENCE: 64

```
Gly Gly Gly Gly Ser Gly Gly Gly Ser Gly Gly Gly Ser
1               5               10              15
```

<210> SEQ ID NO 65
<211> LENGTH: 112
<212> TYPE: PRT
<213> ORGANISM: Artificial sequence
<220> FEATURE:
<223> OTHER INFORMATION: synthetic polypeptide

<400> SEQUENCE: 65

```
Ala Ala Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
            85                  90                  95

Ser Leu Gln Thr Tyr Asp Asp Leu Leu Ala Lys Asp Cys His Cys Ile
            100                 105                 110
```

<210> SEQ ID NO 66
<211> LENGTH: 112
<212> TYPE: PRT
<213> ORGANISM: Artificial sequence
<220> FEATURE:
<223> OTHER INFORMATION: synthetic polypeptide

<400> SEQUENCE: 66

```
Ala Arg Ala Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
            85                  90                  95

Ser Leu Gln Thr Tyr Asp Asp Leu Leu Ala Lys Asp Cys His Cys Ile
            100                 105                 110
```

<210> SEQ ID NO 67
<211> LENGTH: 112
<212> TYPE: PRT
<213> ORGANISM: Artificial sequence
<220> FEATURE:
<223> OTHER INFORMATION: synthetic polypeptide

<400> SEQUENCE: 67

```
Ala Arg Asn Ala Asp His Cys Pro Leu Gly Pro Gly Arg Cys Cys Arg
1               5                   10                  15
```

```
Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 68
<211> LENGTH: 112
<212> TYPE: PRT
<213> ORGANISM: Artificial sequence
<220> FEATURE:
<223> OTHER INFORMATION: synthetic polypeptide

<400> SEQUENCE: 68

```
Ala Arg Asn Gly Ala His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 69
<211> LENGTH: 111
<212> TYPE: PRT
<213> ORGANISM: Artificial sequence
<220> FEATURE:
<223> OTHER INFORMATION: synthetic polypeptide

<400> SEQUENCE: 69

```
Ala Arg Asn Gly Asp Ala Pro Leu Gly Pro Gly Arg Cys Cys Arg Leu
1               5                   10                  15

His Thr Val Arg Ala Ser Leu Glu Asp Leu Gly Trp Ala Asp Trp Val
            20                  25                  30

Leu Ser Pro Arg Glu Val Gln Val Thr Met Cys Ile Gly Ala Cys Pro
        35                  40                  45

Ser Gln Phe Arg Ala Ala Asn Met His Ala Gln Ile Lys Thr Ser Leu
    50                  55                  60

His Arg Leu Lys Pro Asp Thr Val Pro Ala Pro Cys Cys Val Pro Ala
65                  70                  75                  80

Ser Tyr Asn Pro Met Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110
```

-continued

<210> SEQ ID NO 70
<211> LENGTH: 112
<212> TYPE: PRT
<213> ORGANISM: Artificial sequence
<220> FEATURE:
<223> OTHER INFORMATION: synthetic polypeptide

<400> SEQUENCE: 70

Ala Arg Asn Gly Asp His Cys Ala Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 71
<211> LENGTH: 112
<212> TYPE: PRT
<213> ORGANISM: Artificial sequence
<220> FEATURE:
<223> OTHER INFORMATION: synthetic polypeptide

<400> SEQUENCE: 71

Ala Arg Asn Gly Asp His Cys Pro Ala Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 72
<211> LENGTH: 112
<212> TYPE: PRT
<213> ORGANISM: Artificial sequence
<220> FEATURE:
<223> OTHER INFORMATION: synthetic polypeptide

<400> SEQUENCE: 72

Ala Arg Asn Gly Asp His Cys Pro Leu Ala Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
                35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110

<210> SEQ ID NO 73
<211> LENGTH: 112
<212> TYPE: PRT
<213> ORGANISM: Artificial sequence
<220> FEATURE:
<223> OTHER INFORMATION: synthetic polypeptide

<400> SEQUENCE: 73

Ala Arg Asn Gly Asp His Cys Pro Leu Gly Ala Gly Arg Cys Cys Arg
 1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
                35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110

<210> SEQ ID NO 74
<211> LENGTH: 112
<212> TYPE: PRT
<213> ORGANISM: Artificial sequence
<220> FEATURE:
<223> OTHER INFORMATION: synthetic polypeptide

<400> SEQUENCE: 74

Ala Arg Asn Gly Asp His Cys Pro Leu Gly Pro Ala Arg Cys Cys Arg
 1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
                35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110

<210> SEQ ID NO 75

```
<211> LENGTH: 112
<212> TYPE: PRT
<213> ORGANISM: Artificial sequence
<220> FEATURE:
<223> OTHER INFORMATION: synthetic polypeptide

<400> SEQUENCE: 75

Ala Arg Asn Gly Asp His Cys Pro Leu Gly Pro Gly Ala Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 76
<211> LENGTH: 112
<212> TYPE: PRT
<213> ORGANISM: Artificial sequence
<220> FEATURE:
<223> OTHER INFORMATION: synthetic polypeptide

<400> SEQUENCE: 76

Ala Arg Asn Gly Asp His Cys Pro Leu Gly Pro Gly Arg Cys Cys Ala
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 77
<211> LENGTH: 112
<212> TYPE: PRT
<213> ORGANISM: Artificial sequence
<220> FEATURE:
<223> OTHER INFORMATION: synthetic polypeptide

<400> SEQUENCE: 77

Ala Arg Asn Gly Asp His Cys Pro Leu Gly Pro Gly Arg Cys Cys Arg
1               5                   10                  15

Ala His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45
```

```
Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 78
<211> LENGTH: 112
<212> TYPE: PRT
<213> ORGANISM: Artificial sequence
<220> FEATURE:
<223> OTHER INFORMATION: synthetic polypeptide

<400> SEQUENCE: 78

```
Ala Arg Asn Gly Asp His Cys Pro Leu Gly Pro Gly Arg Cys Cys Arg
1               5                   10                  15

Leu Ala Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 79
<211> LENGTH: 112
<212> TYPE: PRT
<213> ORGANISM: Artificial sequence
<220> FEATURE:
<223> OTHER INFORMATION: synthetic polypeptide

<400> SEQUENCE: 79

```
Ala Arg Asn Gly Asp His Cys Pro Leu Gly Pro Gly Arg Cys Cys Arg
1               5                   10                  15

Leu His Ala Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 80
<211> LENGTH: 112
<212> TYPE: PRT
<213> ORGANISM: Artificial sequence
<220> FEATURE:
<223> OTHER INFORMATION: synthetic polypeptide

<400> SEQUENCE: 80

Ala Arg Asn Gly Asp His Cys Pro Leu Gly Pro Gly Arg Cys Cys Arg
1               5                   10                  15

Leu His Thr Ala Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 81
<211> LENGTH: 112
<212> TYPE: PRT
<213> ORGANISM: Artificial sequence
<220> FEATURE:
<223> OTHER INFORMATION: synthetic polypeptide

<400> SEQUENCE: 81

Ala Arg Asn Gly Asp His Cys Pro Leu Gly Pro Gly Arg Cys Cys Arg
1               5                   10                  15

Leu His Thr Val Ala Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 82
<211> LENGTH: 112
<212> TYPE: PRT
<213> ORGANISM: Artificial sequence
<220> FEATURE:
<223> OTHER INFORMATION: synthetic polypeptide

<400> SEQUENCE: 82

Ala Arg Asn Gly Asp His Cys Pro Leu Gly Pro Gly Arg Cys Cys Arg
1               5                   10                  15

Leu His Thr Val Arg Ala Ala Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 83
<211> LENGTH: 112
<212> TYPE: PRT
<213> ORGANISM: Artificial sequence
<220> FEATURE:
<223> OTHER INFORMATION: synthetic polypeptide

<400> SEQUENCE: 83

Ala Arg Asn Gly Asp His Cys Pro Leu Gly Pro Gly Arg Cys Cys Arg
1               5                   10                  15

Leu His Thr Val Arg Ala Ser Ala Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 84
<211> LENGTH: 112
<212> TYPE: PRT
<213> ORGANISM: Artificial sequence
<220> FEATURE:
<223> OTHER INFORMATION: synthetic polypeptide

<400> SEQUENCE: 84

Ala Arg Asn Gly Asp His Cys Pro Leu Gly Pro Gly Arg Cys Cys Arg
1               5                   10                  15

Leu His Thr Val Arg Ala Ser Leu Ala Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 85
<211> LENGTH: 112
<212> TYPE: PRT
<213> ORGANISM: Artificial sequence
<220> FEATURE:
<223> OTHER INFORMATION: synthetic polypeptide

```
<400> SEQUENCE: 85

Ala Arg Asn Gly Asp His Cys Pro Leu Gly Pro Gly Arg Cys Cys Arg
1               5                   10                  15

Leu His Thr Val Arg Ala Ser Leu Glu Ala Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 86
<211> LENGTH: 112
<212> TYPE: PRT
<213> ORGANISM: Artificial sequence
<220> FEATURE:
<223> OTHER INFORMATION: synthetic polypeptide

<400> SEQUENCE: 86

Ala Arg Asn Gly Asp His Cys Pro Leu Gly Pro Gly Arg Cys Cys Arg
1               5                   10                  15

Leu His Thr Val Arg Ala Ser Leu Asp Ala Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 87
<211> LENGTH: 112
<212> TYPE: PRT
<213> ORGANISM: Artificial sequence
<220> FEATURE:
<223> OTHER INFORMATION: synthetic polypeptide

<400> SEQUENCE: 87

Ala Arg Asn Gly Asp His Cys Pro Leu Gly Pro Gly Arg Cys Cys Arg
1               5                   10                  15

Leu His Thr Val Arg Ala Ser Leu Glu Asp Leu Ala Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80
```

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 88
<211> LENGTH: 112
<212> TYPE: PRT
<213> ORGANISM: Artificial sequence
<220> FEATURE:
<223> OTHER INFORMATION: synthetic polypeptide

<400> SEQUENCE: 88

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Ala Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 89
<211> LENGTH: 112
<212> TYPE: PRT
<213> ORGANISM: Artificial sequence
<220> FEATURE:
<223> OTHER INFORMATION: synthetic polypeptide

<400> SEQUENCE: 89

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Ala Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 90
<211> LENGTH: 112
<212> TYPE: PRT
<213> ORGANISM: Artificial sequence
<220> FEATURE:
<223> OTHER INFORMATION: synthetic polypeptide

<400> SEQUENCE: 90

Ala Arg Asn Gly Asp His Cys Pro Leu Gly Pro Gly Arg Cys Cys Arg

```
                1               5                  10                   15
Leu His Thr Val Arg Ala Ser Leu Glu Asp Leu Gly Trp Ala Asp Ala
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
             100                 105                 110

<210> SEQ ID NO 91
<211> LENGTH: 112
<212> TYPE: PRT
<213> ORGANISM: Artificial sequence
<220> FEATURE:
<223> OTHER INFORMATION: synthetic polypeptide

<400> SEQUENCE: 91

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Ala Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
             100                 105                 110

<210> SEQ ID NO 92
<211> LENGTH: 112
<212> TYPE: PRT
<213> ORGANISM: Artificial sequence
<220> FEATURE:
<223> OTHER INFORMATION: synthetic polypeptide

<400> SEQUENCE: 92

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Ala Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95
```

Ser Leu Gln Thr Tyr Asp Asp Leu Leu Ala Lys Asp Cys His Cys Ile
            100                 105                 110

<210> SEQ ID NO 93
<211> LENGTH: 112
<212> TYPE: PRT
<213> ORGANISM: Artificial sequence
<220> FEATURE:
<223> OTHER INFORMATION: synthetic polypeptide

<400> SEQUENCE: 93

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ala Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 94
<211> LENGTH: 112
<212> TYPE: PRT
<213> ORGANISM: Artificial sequence
<220> FEATURE:
<223> OTHER INFORMATION: synthetic polypeptide

<400> SEQUENCE: 94

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Ala Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 95
<211> LENGTH: 112
<212> TYPE: PRT
<213> ORGANISM: Artificial sequence
<220> FEATURE:
<223> OTHER INFORMATION: synthetic polypeptide

<400> SEQUENCE: 95

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp

```
                20                  25                  30
Val Leu Ser Pro Ala Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 96
<211> LENGTH: 112
<212> TYPE: PRT
<213> ORGANISM: Artificial sequence
<220> FEATURE:
<223> OTHER INFORMATION: synthetic polypeptide

<400> SEQUENCE: 96

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Ala Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 97
<211> LENGTH: 112
<212> TYPE: PRT
<213> ORGANISM: Artificial sequence
<220> FEATURE:
<223> OTHER INFORMATION: synthetic polypeptide

<400> SEQUENCE: 97

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Ala Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 98
<211> LENGTH: 112
<212> TYPE: PRT
<213> ORGANISM: Artificial sequence
<220> FEATURE:
<223> OTHER INFORMATION: synthetic polypeptide

<400> SEQUENCE: 98

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Ala Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 99
<211> LENGTH: 112
<212> TYPE: PRT
<213> ORGANISM: Artificial sequence
<220> FEATURE:
<223> OTHER INFORMATION: synthetic polypeptide

<400> SEQUENCE: 99

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Ala Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 100
<211> LENGTH: 112
<212> TYPE: PRT
<213> ORGANISM: Artificial sequence
<220> FEATURE:
<223> OTHER INFORMATION: synthetic polypeptide

<400> SEQUENCE: 100

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Ala Met Cys Ile Gly Ala Cys

```
                35                  40                  45

Pro Ser Gln Phe Arg Ala Ala Asn Met His Ala Gln Ile Lys Thr Ser
     50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
                100                 105                 110

<210> SEQ ID NO 101
<211> LENGTH: 112
<212> TYPE: PRT
<213> ORGANISM: Artificial sequence
<220> FEATURE:
<223> OTHER INFORMATION: synthetic polypeptide

<400> SEQUENCE: 101

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Ala Cys Ile Gly Ala Cys
             35                  40                  45

Pro Ser Gln Phe Arg Ala Ala Asn Met His Ala Gln Ile Lys Thr Ser
     50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
                100                 105                 110

<210> SEQ ID NO 102
<211> LENGTH: 112
<212> TYPE: PRT
<213> ORGANISM: Artificial sequence
<220> FEATURE:
<223> OTHER INFORMATION: synthetic polypeptide

<400> SEQUENCE: 102

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ala Gly Ala Cys
             35                  40                  45

Pro Ser Gln Phe Arg Ala Ala Asn Met His Ala Gln Ile Lys Thr Ser
     50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
                100                 105                 110

<210> SEQ ID NO 103
<211> LENGTH: 112
```

```
<212> TYPE: PRT
<213> ORGANISM: Artificial sequence
<220> FEATURE:
<223> OTHER INFORMATION: synthetic polypeptide

<400> SEQUENCE: 103

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Ala Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 104
<211> LENGTH: 112
<212> TYPE: PRT
<213> ORGANISM: Artificial sequence
<220> FEATURE:
<223> OTHER INFORMATION: synthetic polypeptide

<400> SEQUENCE: 104

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Ala Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 105
<211> LENGTH: 112
<212> TYPE: PRT
<213> ORGANISM: Artificial sequence
<220> FEATURE:
<223> OTHER INFORMATION: synthetic polypeptide

<400> SEQUENCE: 105

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ala Gln Phe Arg Ala Ala Asn Met His Ala Gln Ile Lys Thr Ser
```

```
                    50                  55                  60
Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                    85                  90                  95

Ser Leu Gln Thr Tyr Asp Asp Leu Leu Ala Lys Asp Cys His Cys Ile
                   100                 105                 110

<210> SEQ ID NO 106
<211> LENGTH: 112
<212> TYPE: PRT
<213> ORGANISM: Artificial sequence
<220> FEATURE:
<223> OTHER INFORMATION: synthetic polypeptide

<400> SEQUENCE: 106

Ala Arg Asn Gly Asp His Cys Pro Leu Gly Pro Gly Arg Cys Cys Arg
  1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Ala Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                    85                  90                  95

Ser Leu Gln Thr Tyr Asp Asp Leu Leu Ala Lys Asp Cys His Cys Ile
                   100                 105                 110

<210> SEQ ID NO 107
<211> LENGTH: 112
<212> TYPE: PRT
<213> ORGANISM: Artificial sequence
<220> FEATURE:
<223> OTHER INFORMATION: synthetic polypeptide

<400> SEQUENCE: 107

Ala Arg Asn Gly Asp His Cys Pro Leu Gly Pro Gly Arg Cys Cys Arg
  1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Ala Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                    85                  90                  95

Ser Leu Gln Thr Tyr Asp Asp Leu Leu Ala Lys Asp Cys His Cys Ile
                   100                 105                 110

<210> SEQ ID NO 108
<211> LENGTH: 112
<212> TYPE: PRT
<213> ORGANISM: Artificial sequence
<220> FEATURE:
```

<223> OTHER INFORMATION: synthetic polypeptide

<400> SEQUENCE: 108

```
Ala Arg Asn Gly Asp His Cys Pro Leu Gly Pro Gly Arg Cys Cys Arg
1               5                   10                  15
Leu His Thr Val Arg Ala Ser Leu Glu Asp Leu Gly Trp Ala Asp Trp
            20                  25                  30
Val Leu Ser Pro Arg Glu Val Gln Val Thr Met Cys Ile Gly Ala Cys
        35                  40                  45
Pro Ser Gln Phe Ala Ala Ala Asn Met His Ala Gln Ile Lys Thr Ser
    50                  55                  60
Leu His Arg Leu Lys Pro Asp Thr Val Pro Ala Pro Cys Cys Val Pro
65                  70                  75                  80
Ala Ser Tyr Asn Pro Met Val Leu Ile Gln Lys Thr Asp Thr Gly Val
                85                  90                  95
Ser Leu Gln Thr Tyr Asp Asp Leu Leu Ala Lys Asp Cys His Cys Ile
            100                 105                 110
```

<210> SEQ ID NO 109
<211> LENGTH: 112
<212> TYPE: PRT
<213> ORGANISM: Artificial sequence
<220> FEATURE:
<223> OTHER INFORMATION: synthetic polypeptide

<400> SEQUENCE: 109

```
Ala Arg Asn Gly Asp His Cys Pro Leu Gly Pro Gly Arg Cys Cys Arg
1               5                   10                  15
Leu His Thr Val Arg Ala Ser Leu Glu Asp Leu Gly Trp Ala Asp Trp
            20                  25                  30
Val Leu Ser Pro Arg Glu Val Gln Val Thr Met Cys Ile Gly Ala Cys
        35                  40                  45
Pro Ser Gln Phe Arg Ala Ala Met His Ala Gln Ile Lys Thr Ser
    50                  55                  60
Leu His Arg Leu Lys Pro Asp Thr Val Pro Ala Pro Cys Cys Val Pro
65                  70                  75                  80
Ala Ser Tyr Asn Pro Met Val Leu Ile Gln Lys Thr Asp Thr Gly Val
                85                  90                  95
Ser Leu Gln Thr Tyr Asp Asp Leu Leu Ala Lys Asp Cys His Cys Ile
            100                 105                 110
```

<210> SEQ ID NO 110
<211> LENGTH: 112
<212> TYPE: PRT
<213> ORGANISM: Artificial sequence
<220> FEATURE:
<223> OTHER INFORMATION: synthetic polypeptide

<400> SEQUENCE: 110

```
Ala Arg Asn Gly Asp His Cys Pro Leu Gly Pro Gly Arg Cys Cys Arg
1               5                   10                  15
Leu His Thr Val Arg Ala Ser Leu Glu Asp Leu Gly Trp Ala Asp Trp
            20                  25                  30
Val Leu Ser Pro Arg Glu Val Gln Val Thr Met Cys Ile Gly Ala Cys
        35                  40                  45
Pro Ser Gln Phe Arg Ala Ala Asn Ala His Ala Gln Ile Lys Thr Ser
    50                  55                  60
Leu His Arg Leu Lys Pro Asp Thr Val Pro Ala Pro Cys Cys Val Pro
```

65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 111
<211> LENGTH: 112
<212> TYPE: PRT
<213> ORGANISM: Artificial sequence
<220> FEATURE:
<223> OTHER INFORMATION: synthetic polypeptide

<400> SEQUENCE: 111

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met Ala Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 112
<211> LENGTH: 112
<212> TYPE: PRT
<213> ORGANISM: Artificial sequence
<220> FEATURE:
<223> OTHER INFORMATION: synthetic polypeptide

<400> SEQUENCE: 112

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Ala Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 113
<211> LENGTH: 112
<212> TYPE: PRT
<213> ORGANISM: Artificial sequence
<220> FEATURE:
<223> OTHER INFORMATION: synthetic polypeptide

<400> SEQUENCE: 113

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
                35                  40                  45

Pro Ser Gln Phe Arg Ala Ala Asn Met His Ala Gln Ala Lys Thr Ser
            50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110
```

<210> SEQ ID NO 114
<211> LENGTH: 112
<212> TYPE: PRT
<213> ORGANISM: Artificial sequence
<220> FEATURE:
<223> OTHER INFORMATION: synthetic polypeptide

<400> SEQUENCE: 114

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
                35                  40                  45

Pro Ser Gln Phe Arg Ala Ala Asn Met His Ala Gln Ile Ala Thr Ser
            50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110
```

<210> SEQ ID NO 115
<211> LENGTH: 112
<212> TYPE: PRT
<213> ORGANISM: Artificial sequence
<220> FEATURE:
<223> OTHER INFORMATION: synthetic polypeptide

<400> SEQUENCE: 115

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
                35                  40                  45

Pro Ser Gln Phe Arg Ala Ala Asn Met His Ala Gln Ile Lys Ala Ser
            50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
```

```
                85                  90                  95
Ser Leu Gln Thr Tyr Asp Asp Leu Leu Ala Lys Asp Cys His Cys Ile
            100                 105                 110
```

<210> SEQ ID NO 116
<211> LENGTH: 112
<212> TYPE: PRT
<213> ORGANISM: Artificial sequence
<220> FEATURE:
<223> OTHER INFORMATION: synthetic polypeptide

<400> SEQUENCE: 116

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ala
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 117
<211> LENGTH: 112
<212> TYPE: PRT
<213> ORGANISM: Artificial sequence
<220> FEATURE:
<223> OTHER INFORMATION: synthetic polypeptide

<400> SEQUENCE: 117

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Ala His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 118
<211> LENGTH: 112
<212> TYPE: PRT
<213> ORGANISM: Artificial sequence
<220> FEATURE:
<223> OTHER INFORMATION: synthetic polypeptide

<400> SEQUENCE: 118

```
Ala Arg Asn Gly Asp His Cys Pro Leu Gly Pro Gly Arg Cys Cys Arg
1               5                   10                  15
```

```
Leu His Thr Val Arg Ala Ser Leu Glu Asp Leu Gly Trp Ala Asp Trp
         20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
 50                  55                  60

Leu Ala Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110
```

<210> SEQ ID NO 119
<211> LENGTH: 112
<212> TYPE: PRT
<213> ORGANISM: Artificial sequence
<220> FEATURE:
<223> OTHER INFORMATION: synthetic polypeptide

<400> SEQUENCE: 119

```
Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
 50                  55                  60

Leu His Ala Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
            100                 105                 110
```

<210> SEQ ID NO 120
<211> LENGTH: 112
<212> TYPE: PRT
<213> ORGANISM: Artificial sequence
<220> FEATURE:
<223> OTHER INFORMATION: synthetic polypeptide

<400> SEQUENCE: 120

```
Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
             20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
 50                  55                  60

Leu His Arg Ala Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
```

<210> SEQ ID NO 121
<211> LENGTH: 112
<212> TYPE: PRT
<213> ORGANISM: Artificial sequence
<220> FEATURE:
<223> OTHER INFORMATION: synthetic polypeptide

<400> SEQUENCE: 121

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Ala Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 122
<211> LENGTH: 112
<212> TYPE: PRT
<213> ORGANISM: Artificial sequence
<220> FEATURE:
<223> OTHER INFORMATION: synthetic polypeptide

<400> SEQUENCE: 122

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Ala Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 123
<211> LENGTH: 112
<212> TYPE: PRT
<213> ORGANISM: Artificial sequence
<220> FEATURE:
<223> OTHER INFORMATION: synthetic polypeptide

<400> SEQUENCE: 123

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

```
Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
 50                  55                  60

Leu His Arg Leu Lys Pro Ala Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 124
<211> LENGTH: 112
<212> TYPE: PRT
<213> ORGANISM: Artificial sequence
<220> FEATURE:
<223> OTHER INFORMATION: synthetic polypeptide

<400> SEQUENCE: 124

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
 50                  55                  60

Leu His Arg Leu Lys Pro Asp Ala Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 125
<211> LENGTH: 112
<212> TYPE: PRT
<213> ORGANISM: Artificial sequence
<220> FEATURE:
<223> OTHER INFORMATION: synthetic polypeptide

<400> SEQUENCE: 125

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
 50                  55                  60

Leu His Arg Leu Lys Pro Asp Thr Ala Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

-continued

<210> SEQ ID NO 126
<211> LENGTH: 112
<212> TYPE: PRT
<213> ORGANISM: Artificial sequence
<220> FEATURE:
<223> OTHER INFORMATION: synthetic polypeptide

<400> SEQUENCE: 126

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Ala Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 127
<211> LENGTH: 112
<212> TYPE: PRT
<213> ORGANISM: Artificial sequence
<220> FEATURE:
<223> OTHER INFORMATION: synthetic polypeptide

<400> SEQUENCE: 127

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Ala Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 128
<211> LENGTH: 112
<212> TYPE: PRT
<213> ORGANISM: Artificial sequence
<220> FEATURE:
<223> OTHER INFORMATION: synthetic polypeptide

<400> SEQUENCE: 128

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

```
Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Ala Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110
```

<210> SEQ ID NO 129
<211> LENGTH: 112
<212> TYPE: PRT
<213> ORGANISM: Artificial sequence
<220> FEATURE:
<223> OTHER INFORMATION: synthetic polypeptide

<400> SEQUENCE: 129

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Ala
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110
```

<210> SEQ ID NO 130
<211> LENGTH: 112
<212> TYPE: PRT
<213> ORGANISM: Artificial sequence
<220> FEATURE:
<223> OTHER INFORMATION: synthetic polypeptide

<400> SEQUENCE: 130

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ala Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110
```

<210> SEQ ID NO 131
<211> LENGTH: 112
<212> TYPE: PRT

<213> ORGANISM: Artificial sequence
<220> FEATURE:
<223> OTHER INFORMATION: synthetic polypeptide

<400> SEQUENCE: 131

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
50                  55                  60

Leu His Arg Leu Lys Pro Asp Thr Val Pro Ala Pro Cys Cys Val Pro
65                  70                  75                  80

Ala Ser Ala Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110

<210> SEQ ID NO 132
<211> LENGTH: 112
<212> TYPE: PRT
<213> ORGANISM: Artificial sequence
<220> FEATURE:
<223> OTHER INFORMATION: synthetic polypeptide

<400> SEQUENCE: 132

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
50                  55                  60

Leu His Arg Leu Lys Pro Asp Thr Val Pro Ala Pro Cys Cys Val Pro
65                  70                  75                  80

Ala Ser Tyr Ala Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
                100                 105                 110

<210> SEQ ID NO 133
<211> LENGTH: 112
<212> TYPE: PRT
<213> ORGANISM: Artificial sequence
<220> FEATURE:
<223> OTHER INFORMATION: synthetic polypeptide

<400> SEQUENCE: 133

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
50                  55                  60

Leu His Arg Leu Lys Pro Asp Thr Val Pro Ala Pro Cys Cys Val Pro
65                  70                  75                  80

Ala Ser Tyr Asn Ala Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 134
<211> LENGTH: 112
<212> TYPE: PRT
<213> ORGANISM: Artificial sequence
<220> FEATURE:
<223> OTHER INFORMATION: synthetic polypeptide

<400> SEQUENCE: 134

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Ala Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 135
<211> LENGTH: 112
<212> TYPE: PRT
<213> ORGANISM: Artificial sequence
<220> FEATURE:
<223> OTHER INFORMATION: synthetic polypeptide

<400> SEQUENCE: 135

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Ala Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 136
<211> LENGTH: 112
<212> TYPE: PRT
<213> ORGANISM: Artificial sequence
<220> FEATURE:
<223> OTHER INFORMATION: synthetic polypeptide

<400> SEQUENCE: 136

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Ala Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 137
<211> LENGTH: 112
<212> TYPE: PRT
<213> ORGANISM: Artificial sequence
<220> FEATURE:
<223> OTHER INFORMATION: synthetic polypeptide

<400> SEQUENCE: 137

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ala Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 138
<211> LENGTH: 112
<212> TYPE: PRT
<213> ORGANISM: Artificial sequence
<220> FEATURE:
<223> OTHER INFORMATION: synthetic polypeptide

<400> SEQUENCE: 138

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Ala Lys Thr Asp Thr Gly Val
             85                  90                  95

Ser Leu Gln Thr Tyr Asp Asp Leu Leu Ala Lys Asp Cys His Cys Ile
            100                 105                 110

<210> SEQ ID NO 139
<211> LENGTH: 112
<212> TYPE: PRT
<213> ORGANISM: Artificial sequence
<220> FEATURE:
<223> OTHER INFORMATION: synthetic polypeptide

<400> SEQUENCE: 139

Ala Arg Asn Gly Asp His Cys Pro Leu Gly Pro Gly Arg Cys Cys Arg
1               5                  10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Ala Thr Asp Thr Gly Val
             85                  90                  95

Ser Leu Gln Thr Tyr Asp Asp Leu Leu Ala Lys Asp Cys His Cys Ile
            100                 105                 110

<210> SEQ ID NO 140
<211> LENGTH: 112
<212> TYPE: PRT
<213> ORGANISM: Artificial sequence
<220> FEATURE:
<223> OTHER INFORMATION: synthetic polypeptide

<400> SEQUENCE: 140

Ala Arg Asn Gly Asp His Cys Pro Leu Gly Pro Gly Arg Cys Cys Arg
1               5                  10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Ala Asp Thr Gly Val
             85                  90                  95

Ser Leu Gln Thr Tyr Asp Asp Leu Leu Ala Lys Asp Cys His Cys Ile
            100                 105                 110

<210> SEQ ID NO 141
<211> LENGTH: 112
<212> TYPE: PRT
<213> ORGANISM: Artificial sequence
<220> FEATURE:
<223> OTHER INFORMATION: synthetic polypeptide

<400> SEQUENCE: 141

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Ala Thr Gly Val
                85                  90                  95

Ser Leu Gln Thr Tyr Asp Asp Leu Leu Ala Lys Asp Cys His Cys Ile
                100                 105                 110

<210> SEQ ID NO 142
<211> LENGTH: 112
<212> TYPE: PRT
<213> ORGANISM: Artificial sequence
<220> FEATURE:
<223> OTHER INFORMATION: synthetic polypeptide

<400> SEQUENCE: 142

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Ala Gly Val
                85                  90                  95

Ser Leu Gln Thr Tyr Asp Asp Leu Leu Ala Lys Asp Cys His Cys Ile
                100                 105                 110

<210> SEQ ID NO 143
<211> LENGTH: 112
<212> TYPE: PRT
<213> ORGANISM: Artificial sequence
<220> FEATURE:
<223> OTHER INFORMATION: synthetic polypeptide

<400> SEQUENCE: 143

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Ala Val
                85                  90                  95

Ser Leu Gln Thr Tyr Asp Asp Leu Leu Ala Lys Asp Cys His Cys Ile
            100                 105                 110

<210> SEQ ID NO 144
<211> LENGTH: 112
<212> TYPE: PRT
<213> ORGANISM: Artificial sequence
<220> FEATURE:
<223> OTHER INFORMATION: synthetic polypeptide

<400> SEQUENCE: 144

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Ala
                85                  90                  95

Ser Leu Gln Thr Tyr Asp Asp Leu Leu Ala Lys Asp Cys His Cys Ile
            100                 105                 110

<210> SEQ ID NO 145
<211> LENGTH: 112
<212> TYPE: PRT
<213> ORGANISM: Artificial sequence
<220> FEATURE:
<223> OTHER INFORMATION: synthetic polypeptide

<400> SEQUENCE: 145

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ala Leu Gln Thr Tyr Asp Asp Leu Leu Ala Lys Asp Cys His Cys Ile
            100                 105                 110

<210> SEQ ID NO 146
<211> LENGTH: 112
<212> TYPE: PRT
<213> ORGANISM: Artificial sequence
<220> FEATURE:
<223> OTHER INFORMATION: synthetic polypeptide

<400> SEQUENCE: 146

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Ala Gln Thr Tyr Asp Asp Leu Leu Ala Lys Asp Cys His Cys Ile
                100                 105                 110

<210> SEQ ID NO 147
<211> LENGTH: 112
<212> TYPE: PRT
<213> ORGANISM: Artificial sequence
<220> FEATURE:
<223> OTHER INFORMATION: synthetic polypeptide

<400> SEQUENCE: 147

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Ala Thr Tyr Asp Asp Leu Leu Ala Lys Asp Cys His Cys Ile
                100                 105                 110

<210> SEQ ID NO 148
<211> LENGTH: 112
<212> TYPE: PRT
<213> ORGANISM: Artificial sequence
<220> FEATURE:
<223> OTHER INFORMATION: synthetic polypeptide

<400> SEQUENCE: 148

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Ala Tyr Asp Asp Leu Leu Ala Lys Asp Cys His Cys Ile
                100                 105                 110

<210> SEQ ID NO 149
<211> LENGTH: 112
<212> TYPE: PRT
<213> ORGANISM: Artificial sequence
<220> FEATURE:
<223> OTHER INFORMATION: synthetic polypeptide

<400> SEQUENCE: 149

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Ala Asp Asp Leu Leu Ala Lys Asp Cys His Cys Ile
            100                 105                 110

<210> SEQ ID NO 150
<211> LENGTH: 112
<212> TYPE: PRT
<213> ORGANISM: Artificial sequence
<220> FEATURE:
<223> OTHER INFORMATION: synthetic polypeptide

<400> SEQUENCE: 150

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Ala Asp Leu Leu Ala Lys Asp Cys His Cys Ile
            100                 105                 110

<210> SEQ ID NO 151
<211> LENGTH: 112
<212> TYPE: PRT
<213> ORGANISM: Artificial sequence
<220> FEATURE:
<223> OTHER INFORMATION: synthetic polypeptide

<400> SEQUENCE: 151

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

```
Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                 85                  90                  95

Ser Leu Gln Thr Tyr Asp Ala Leu Ala Lys Asp Cys His Cys Ile
                100                 105                 110
```

<210> SEQ ID NO 152
<211> LENGTH: 112
<212> TYPE: PRT
<213> ORGANISM: Artificial sequence
<220> FEATURE:
<223> OTHER INFORMATION: synthetic polypeptide

<400> SEQUENCE: 152

```
Ala Arg Asn Gly Asp His Cys Pro Leu Gly Pro Gly Arg Cys Cys Arg
1                5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Ala Leu Ala Lys Asp Cys His Cys Ile
                100                 105                 110
```

<210> SEQ ID NO 153
<211> LENGTH: 112
<212> TYPE: PRT
<213> ORGANISM: Artificial sequence
<220> FEATURE:
<223> OTHER INFORMATION: synthetic polypeptide

<400> SEQUENCE: 153

```
Ala Arg Asn Gly Asp His Cys Pro Leu Gly Pro Gly Arg Cys Cys Arg
1                5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
         35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Ala Ala Lys Asp Cys His Cys Ile
                100                 105                 110
```

<210> SEQ ID NO 154

```
<211> LENGTH: 112
<212> TYPE: PRT
<213> ORGANISM: Artificial sequence
<220> FEATURE:
<223> OTHER INFORMATION: synthetic polypeptide

<400> SEQUENCE: 154

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Ala Asp Cys His Cys Ile
            100                 105                 110

<210> SEQ ID NO 155
<211> LENGTH: 112
<212> TYPE: PRT
<213> ORGANISM: Artificial sequence
<220> FEATURE:
<223> OTHER INFORMATION: synthetic polypeptide

<400> SEQUENCE: 155

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Ala Cys His Cys Ile
            100                 105                 110

<210> SEQ ID NO 156
<211> LENGTH: 112
<212> TYPE: PRT
<213> ORGANISM: Artificial sequence
<220> FEATURE:
<223> OTHER INFORMATION: synthetic polypeptide

<400> SEQUENCE: 156

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45
```

```
Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys Ala Cys Ile
            100                 105                 110

<210> SEQ ID NO 157
<211> LENGTH: 112
<212> TYPE: PRT
<213> ORGANISM: Artificial sequence
<220> FEATURE:
<223> OTHER INFORMATION: synthetic polypeptide

<400> SEQUENCE: 157

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ala
            100                 105                 110

<210> SEQ ID NO 158
<211> LENGTH: 371
<212> TYPE: PRT
<213> ORGANISM: Artificial sequence
<220> FEATURE:
<223> OTHER INFORMATION: synthetic polypeptide

<400> SEQUENCE: 158

Met Gly Val Lys Val Leu Phe Ala Leu Ile Cys Ile Ala Val Ala Glu
1               5                   10                  15

Ala Asp Lys Thr His Thr Cys Pro Pro Cys Pro Ala Pro Glu Leu Leu
                20                  25                  30

Gly Gly Pro Ser Val Phe Leu Phe Pro Pro Lys Pro Lys Asp Thr Leu
            35                  40                  45

Met Ile Ser Arg Thr Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140
```

Val Tyr Thr Leu Pro Pro Ser Arg Asp Glu Leu Thr Lys Asn Gln Val
145                 150                 155                 160

Ser Leu Thr Cys Leu Val Lys Gly Phe Tyr Pro Ser Asp Ile Ala Val
            165                 170                 175

Glu Trp Glu Ser Asn Gly Gln Pro Glu Asn Asn Tyr Lys Thr Thr Pro
        180                 185                 190

Pro Val Leu Asp Ser Asp Gly Ser Phe Phe Leu Tyr Ser Lys Leu Thr
                195                 200                 205

Val Asp Lys Ser Arg Trp Gln Gln Gly Asn Val Phe Ser Cys Ser Val
210                 215                 220

Met His Glu Ala Leu His Asn His Tyr Thr Gln Lys Ser Leu Ser Leu
225                 230                 235                 240

Ser Pro Gly Lys Glu Gly Gly Ser Glu Gly Gly Ser Glu Gly
            245                 250                 255

Gly Gly Ser Ala Arg Asn Gly Asp His Cys Pro Leu Gly Pro Gly Arg
            260                 265                 270

Cys Cys Arg Leu His Thr Val Arg Ala Ser Leu Glu Asp Leu Gly Trp
            275                 280                 285

Ala Asp Trp Val Leu Ser Pro Arg Glu Val Gln Val Thr Met Cys Ile
290                 295                 300

Gly Ala Cys Pro Ser Gln Phe Arg Ala Ala Asn Met His Ala Gln Ile
305                 310                 315                 320

Lys Thr Ser Leu His Arg Leu Lys Pro Asp Thr Val Pro Ala Pro Cys
                325                 330                 335

Cys Val Pro Ala Ser Tyr Asn Pro Met Val Leu Ile Gln Lys Thr Asp
            340                 345                 350

Thr Gly Val Ser Leu Gln Thr Tyr Asp Asp Leu Leu Ala Lys Asp Cys
            355                 360                 365

His Cys Ile
    370

<210> SEQ ID NO 159
<211> LENGTH: 376
<212> TYPE: PRT
<213> ORGANISM: Artificial sequence
<220> FEATURE:
<223> OTHER INFORMATION: synthetic polypeptide

<400> SEQUENCE: 159

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
    50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Lys Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
                180                 185                 190

Tyr Lys Thr Thr Pro Pro Val Leu Lys Ser Asp Gly Ser Phe Phe Leu
                195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys Glu Gly Gly Ser Glu Gly
                245                 250                 255

Gly Gly Ser Glu Gly Gly Gly Ser Ala Arg Asn Gly Asp His Cys Pro
                260                 265                 270

Leu Gly Pro Gly Arg Cys Cys Arg Leu His Thr Val Arg Ala Ser Leu
                275                 280                 285

Glu Asp Leu Gly Trp Ala Asp Trp Val Leu Ser Pro Arg Glu Val Gln
290                 295                 300

Val Thr Met Cys Ile Gly Ala Cys Pro Ser Gln Phe Arg Ala Ala Asn
305                 310                 315                 320

Met His Ala Gln Ile Lys Thr Ser Leu His Arg Leu Lys Pro Asp Thr
                325                 330                 335

Val Pro Ala Pro Cys Cys Val Pro Ala Ser Tyr Asn Pro Met Val Leu
                340                 345                 350

Ile Gln Lys Thr Asp Thr Gly Val Ser Leu Gln Thr Tyr Asp Asp Leu
                355                 360                 365

Leu Ala Lys Asp Cys His Cys Ile
                370                 375

<210> SEQ ID NO 160
<211> LENGTH: 249
<212> TYPE: PRT
<213> ORGANISM: Artificial sequence
<220> FEATURE:
<223> OTHER INFORMATION: synthetic polypeptide

<400> SEQUENCE: 160

Met Asp Met Arg Val Pro Ala Gln Leu Leu Gly Leu Leu Leu Leu Trp
1               5                   10                  15

Leu Arg Gly Ala Arg Cys Asp Lys Thr His Thr Cys Pro Pro Cys Pro
                20                  25                  30

Ala Pro Glu Leu Leu Gly Gly Pro Ser Val Phe Leu Phe Pro Pro Lys
                35                  40                  45

Pro Lys Asp Thr Leu Met Ile Ser Arg Thr Pro Glu Val Thr Cys Val
                50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Asp Thr Thr Pro Pro Val Leu Asp Ser Asp Gly Ser Phe Phe Leu
        195                 200                 205

Tyr Ser Asp Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 161
<211> LENGTH: 164
<212> TYPE: PRT
<213> ORGANISM: Artificial sequence
<220> FEATURE:
<223> OTHER INFORMATION: synthetic polypeptide

<400> SEQUENCE: 161

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
            20                  25                  30

Glu Gly Val Glu Ala Leu Lys Leu His Ile Leu Ala Ala Leu Pro Gly
        35                  40                  45

Gly Gly Gly Gly Ala Arg Asn Gly Asp His Cys Pro Leu Gly Pro Gly
    50                  55                  60

Arg Cys Cys Arg Leu His Thr Val Arg Ala Ser Leu Glu Asp Leu Gly
65                  70                  75                  80

Trp Ala Asp Trp Val Leu Ser Pro Arg Glu Val Gln Val Thr Met Cys
                85                  90                  95

Ile Gly Ala Cys Pro Ser Gln Phe Arg Ala Ala Asn Met His Ala Gln
            100                 105                 110

Ile Lys Thr Ser Leu His Arg Leu Lys Pro Asp Thr Val Pro Ala Pro
        115                 120                 125

Cys Cys Val Pro Ala Ser Tyr Asn Pro Met Val Leu Ile Gln Lys Thr
    130                 135                 140

Asp Thr Gly Val Ser Leu Gln Thr Tyr Asp Asp Leu Leu Ala Lys Asp
145                 150                 155                 160

Cys His Cys Ile

<210> SEQ ID NO 162
<211> LENGTH: 522
<212> TYPE: PRT
<213> ORGANISM: Artificial sequence
<220> FEATURE:
<223> OTHER INFORMATION: synthetic polypeptide

<400> SEQUENCE: 162

```
Met Gly Val Lys Val Leu Phe Ala Leu Ile Cys Ile Ala Val Ala Glu
1               5                   10                  15

Ala Met Lys Ile Glu Glu Gly Lys Leu Val Ile Trp Ile Asn Gly Asp
                20                  25                  30

Lys Gly Tyr Asn Gly Leu Ala Glu Val Gly Lys Lys Phe Glu Lys Asp
            35                  40                  45

Thr Gly Ile Lys Val Thr Val Glu His Pro Asp Lys Leu Glu Glu Lys
        50                  55                  60

Phe Pro Gln Val Ala Ala Thr Gly Asp Gly Pro Asp Ile Ile Phe Trp
65                  70                  75                  80

Ala His Asp Arg Phe Gly Gly Tyr Ala Gln Ser Gly Leu Leu Ala Glu
                85                  90                  95

Ile Thr Pro Asp Lys Ala Phe Gln Asp Lys Leu Tyr Pro Phe Thr Trp
                100                 105                 110

Asp Ala Val Arg Tyr Asn Gly Lys Leu Ile Ala Tyr Pro Ile Ala Val
            115                 120                 125

Glu Ala Leu Ser Leu Ile Tyr Asn Lys Asp Leu Leu Pro Asn Pro Pro
130                 135                 140

Lys Thr Trp Glu Glu Ile Pro Ala Leu Asp Lys Glu Leu Lys Ala Lys
145                 150                 155                 160

Gly Lys Ser Ala Leu Met Phe Asn Leu Gln Glu Pro Tyr Phe Thr Trp
                165                 170                 175

Pro Leu Ile Ala Ala Asp Gly Gly Tyr Ala Phe Lys Tyr Glu Asn Gly
            180                 185                 190

Lys Tyr Asp Ile Lys Asp Val Gly Val Asp Asn Ala Gly Ala Lys Ala
            195                 200                 205

Gly Leu Thr Phe Leu Val Asp Leu Ile Lys Asn Lys His Met Asn Ala
210                 215                 220

Asp Thr Asp Tyr Ser Ile Ala Glu Ala Ala Phe Asn Lys Gly Glu Thr
225                 230                 235                 240

Ala Met Thr Ile Asn Gly Pro Trp Ala Trp Ser Asn Ile Asp Thr Ser
                245                 250                 255

Lys Val Asn Tyr Gly Val Thr Val Leu Pro Thr Phe Lys Gly Gln Pro
            260                 265                 270

Ser Lys Pro Phe Val Gly Val Leu Ser Ala Gly Ile Asn Ala Ala Ser
            275                 280                 285

Pro Asn Lys Glu Leu Ala Lys Glu Phe Leu Glu Asn Tyr Leu Leu Thr
            290                 295                 300

Asp Glu Gly Leu Glu Ala Val Asn Lys Asp Lys Pro Leu Gly Ala Val
305                 310                 315                 320

Ala Leu Lys Ser Tyr Glu Glu Glu Leu Val Lys Asp Pro Arg Ile Ala
                325                 330                 335

Ala Thr Met Glu Asn Ala Gln Lys Gly Glu Ile Met Pro Asn Ile Pro
                340                 345                 350

Gln Met Ser Ala Phe Trp Tyr Ala Val Arg Thr Ala Val Ile Asn Ala
            355                 360                 365

Ala Ser Gly Arg Gln Thr Val Asp Glu Ala Leu Lys Asp Ala Gln Thr
            370                 375                 380

Asn Ser Ser Ser Asn Asn Asn Asn Asn Asn Asn Asn Asn Asn Leu Gly
385                 390                 395                 400

Asp Asp Asp Asp Lys Gly Gly Gly Gly Ala Arg Asn Gly Asp His
                405                 410                 415
```

Cys Pro Leu Gly Pro Gly Arg Cys Cys Arg Leu His Thr Val Arg Ala
            420                 425                 430

Ser Leu Glu Asp Leu Gly Trp Ala Asp Trp Val Leu Ser Pro Arg Glu
            435                 440                 445

Val Gln Val Thr Met Cys Ile Gly Ala Cys Pro Ser Gln Phe Arg Ala
        450                 455                 460

Ala Asn Met His Ala Gln Ile Lys Thr Ser Leu His Arg Leu Lys Pro
465                 470                 475                 480

Asp Thr Val Pro Ala Pro Cys Cys Val Pro Ala Ser Tyr Asn Pro Met
                485                 490                 495

Val Leu Ile Gln Lys Thr Asp Thr Gly Val Ser Leu Gln Thr Tyr Asp
            500                 505                 510

Asp Leu Leu Ala Lys Asp Cys His Cys Ile
            515                 520

<210> SEQ ID NO 163
<211> LENGTH: 279
<212> TYPE: PRT
<213> ORGANISM: Artificial sequence
<220> FEATURE:
<223> OTHER INFORMATION: synthetic polypeptide

<400> SEQUENCE: 163

Met Val Gly Ser Val Pro Gly Leu Arg Leu Ala Ala Ala Ser Leu
1               5                   10                  15

Leu Leu Leu Leu Leu Leu Leu Ser Pro Gly Thr Glu Pro Arg Ala
            20                  25                  30

Leu Gly Pro Gln Glu Ser Ile Asn Ser Lys Ser Leu Gln His Arg Tyr
            35                  40                  45

Glu Glu Ala Leu Ala Glu Met Trp Gly Asn Gln Ser Arg Gly Glu Thr
50                  55                  60

Gly Pro Ala Ser Arg Ala Ile Arg Leu Leu Thr Pro Lys Cys Arg Ala
65                  70                  75                  80

Gly Gly Lys Gly Arg Leu Gly Leu Gln Leu Ser Arg Ser Ala Val Glu
                85                  90                  95

Ala Gly Leu Pro Trp Glu Pro Gln Ala Glu Ser Leu Thr Leu Asp Leu
            100                 105                 110

Thr Pro Thr Leu Gln Gln Trp Leu Gln Gly Ser Ser Arg Pro Leu Leu
            115                 120                 125

Arg Leu Gln Leu Val Gly Pro Arg Glu Val Met Glu Ala Leu Ala Ser
130                 135                 140

Pro Gly Ala Lys Pro Pro Val Leu Glu Val Gln Phe Gln Glu Leu Gln
145                 150                 155                 160

Ser Arg Ala Asn Arg Arg Ala Arg Ala Leu Gly Gln Asp Cys Glu His
                165                 170                 175

Gln Gly Gly Lys Cys Cys Pro Arg Thr His His Val Ser Phe Gln Glu
            180                 185                 190

Leu Gly Trp Ala Asp Trp Val Leu Ala Pro Lys Asp Tyr Met Met Lys
            195                 200                 205

Phe Cys Gln Gly Ser Cys Pro His Asn Tyr Lys Pro Ala Ser Met His
210                 215                 220

Ser Leu Ile Lys Ala Arg Met His Asn Leu Ala Pro Gly Thr Thr Pro
225                 230                 235                 240

Glu Pro Cys Cys Val Pro Ser Ser Tyr Glu Pro Met Val Leu Met His
                245                 250                 255

```
Tyr Asn Ser Glu Gly Lys Ile Thr Leu Ser Pro Phe Glu Asn Met Ile
            260                 265                 270

Ala Lys Asp Cys His Cys Ala
        275

<210> SEQ ID NO 164
<211> LENGTH: 18
<212> TYPE: PRT
<213> ORGANISM: Artificial sequence
<220> FEATURE:
<223> OTHER INFORMATION: synthetic polypeptide

<400> SEQUENCE: 164

Met Lys Trp Val Thr Phe Ile Ser Leu Leu Phe Leu Phe Ser Ser Ala
1               5                   10                  15

Tyr Ser

<210> SEQ ID NO 165
<211> LENGTH: 6
<212> TYPE: PRT
<213> ORGANISM: Artificial sequence
<220> FEATURE:
<223> OTHER INFORMATION: synthetic polypeptide

<400> SEQUENCE: 165

Arg Gly Val Phe Arg Arg
1               5

<210> SEQ ID NO 166
<211> LENGTH: 112
<212> TYPE: PRT
<213> ORGANISM: Artificial sequence
<220> FEATURE:
<223> OTHER INFORMATION: synthetic polypeptide

<400> SEQUENCE: 166

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 167
<211> LENGTH: 112
<212> TYPE: PRT
<213> ORGANISM: Artificial sequence
<220> FEATURE:
<223> OTHER INFORMATION: synthetic polypeptide

<400> SEQUENCE: 167

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
```

```
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 168
<211> LENGTH: 112
<212> TYPE: PRT
<213> ORGANISM: Artificial sequence
<220> FEATURE:
<223> OTHER INFORMATION: synthetic polypeptide

<400> SEQUENCE: 168

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 169
<211> LENGTH: 112
<212> TYPE: PRT
<213> ORGANISM: Artificial sequence
<220> FEATURE:
<223> OTHER INFORMATION: synthetic polypeptide

<400> SEQUENCE: 169

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Lys Asp Cys His Cys Ile
            100                 105                 110
```

```
<210> SEQ ID NO 170
<211> LENGTH: 112
<212> TYPE: PRT
<213> ORGANISM: Artificial sequence
<220> FEATURE:
<223> OTHER INFORMATION: synthetic polypeptide

<400> SEQUENCE: 170

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 171
<211> LENGTH: 112
<212> TYPE: PRT
<213> ORGANISM: Artificial sequence
<220> FEATURE:
<223> OTHER INFORMATION: synthetic polypeptide

<400> SEQUENCE: 171

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 172
<211> LENGTH: 112
<212> TYPE: PRT
<213> ORGANISM: Artificial sequence
<220> FEATURE:
<223> OTHER INFORMATION: synthetic polypeptide

<400> SEQUENCE: 172

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
```

```
              35                  40                  45
Pro Ser Gln Phe Arg Ala Ala Asn Met His Ala Gln Ile Lys Thr Ser
     50                  55                  60
Leu His Arg Leu Gln Pro Asp Thr Val Pro Ala Pro Cys Cys Val Pro
 65                  70                  75                  80
Ala Ser Tyr Asn Pro Met Val Leu Ile Gln Arg Thr Asp Thr Gly Val
                 85                  90                  95
Ser Leu Gln Thr Tyr Asp Asp Leu Leu Ala Lys Asp Cys His Cys Ile
                100                 105                 110

<210> SEQ ID NO 173
<211> LENGTH: 112
<212> TYPE: PRT
<213> ORGANISM: Artificial sequence
<220> FEATURE:
<223> OTHER INFORMATION: synthetic polypeptide

<400> SEQUENCE: 173

Ala Arg Asn Gly Asp His Cys Pro Leu Gly Pro Gly Arg Cys Cys Arg
 1               5                  10                  15
Leu Gln Ser Leu Arg Ala Ser Leu Glu Asp Leu Gly Trp Ala Asp Trp
                 20                  25                  30
Val Leu Ser Pro Arg Glu Val Gln Val Thr Met Cys Ile Gly Ala Cys
             35                  40                  45
Pro Ser Gln Phe Arg Ala Ala Asn Met His Ala Gln Ile Gln Thr Ser
     50                  55                  60
Leu His Arg Leu Gln Pro Asp Thr Val Pro Ala Pro Cys Cys Val Pro
 65                  70                  75                  80
Ala Ser Tyr Asn Pro Met Val Leu Ile Gln Arg Thr Asp Thr Gly Val
                 85                  90                  95
Ser Leu Gln Thr Tyr Asp Asp Leu Leu Ala Arg Asp Cys His Cys Ile
                100                 105                 110

<210> SEQ ID NO 174
<211> LENGTH: 112
<212> TYPE: PRT
<213> ORGANISM: Artificial sequence
<220> FEATURE:
<223> OTHER INFORMATION: synthetic polypeptide

<400> SEQUENCE: 174

Ala Arg Asn Gly Asp His Cys Pro Leu Gly Pro Gly Arg Cys Cys Arg
 1               5                  10                  15
Leu Gln Ser Leu Arg Ala Ser Leu Glu Asp Leu Gly Trp Ala Asp Trp
                 20                  25                  30
Val Leu Ser Pro Arg Glu Val Gln Val Thr Met Cys Ile Gly Ala Cys
             35                  40                  45
Pro Ser Gln Phe Arg Ala Ala Asn Met His Ala Gln Ile Gln Thr Ser
     50                  55                  60
Leu His Arg Leu Lys Pro Asp Thr Val Pro Ala Pro Cys Cys Val Pro
 65                  70                  75                  80
Ala Ser Tyr Asn Pro Met Val Leu Ile Gln Arg Thr Asp Thr Gly Val
                 85                  90                  95
Ser Leu Gln Thr Tyr Asp Asp Leu Leu Ala Arg Asp Cys His Cys Ile
                100                 105                 110

<210> SEQ ID NO 175
<211> LENGTH: 112
```

<212> TYPE: PRT
<213> ORGANISM: Artificial sequence
<220> FEATURE:
<223> OTHER INFORMATION: synthetic polypeptide

<400> SEQUENCE: 175

Ala Arg Asn Gly Asp His Cys Pro Leu Gly Pro Gly Arg Cys Cys Arg
1               5                   10                  15
Leu Gln Ser Leu Arg Ala Ser Leu Glu Asp Leu Gly Trp Ala Asp Trp
            20                  25                  30
Val Leu Ser Pro Arg Glu Val Gln Val Thr Met Cys Ile Gly Ala Cys
        35                  40                  45
Pro Ser Gln Phe Arg Ala Ala Asn Met His Ala Gln Ile Gln Thr Ser
    50                  55                  60
Leu His Arg Leu Gln Pro Asp Thr Val Pro Ala Pro Cys Cys Val Pro
65                  70                  75                  80
Ala Ser Tyr Asn Pro Met Val Leu Ile Gln Lys Thr Asp Thr Gly Val
                85                  90                  95
Ser Leu Gln Thr Tyr Asp Asp Leu Leu Ala Arg Asp Cys His Cys Ile
            100                 105                 110

<210> SEQ ID NO 176
<211> LENGTH: 112
<212> TYPE: PRT
<213> ORGANISM: Artificial sequence
<220> FEATURE:
<223> OTHER INFORMATION: synthetic polypeptide

<400> SEQUENCE: 176

Ala Arg Asn Gly Asp His Cys Pro Leu Gly Pro Gly Arg Cys Cys Arg
1               5                   10                  15
Leu Gln Ser Leu Arg Ala Ser Leu Glu Asp Leu Gly Trp Ala Asp Trp
            20                  25                  30
Val Leu Ser Pro Arg Glu Val Gln Val Thr Met Cys Ile Gly Ala Cys
        35                  40                  45
Pro Ser Gln Phe Arg Ala Ala Asn Met His Ala Gln Ile Gln Thr Ser
    50                  55                  60
Leu His Arg Leu Gln Pro Asp Thr Val Pro Ala Pro Cys Cys Val Pro
65                  70                  75                  80
Ala Ser Tyr Asn Pro Met Val Leu Ile Gln Arg Thr Asp Thr Gly Val
                85                  90                  95
Ser Leu Gln Thr Tyr Asp Asp Leu Leu Ala Lys Asp Cys His Cys Ile
            100                 105                 110

<210> SEQ ID NO 177
<211> LENGTH: 11
<212> TYPE: PRT
<213> ORGANISM: Artificial sequence
<220> FEATURE:
<223> OTHER INFORMATION: synthetic polypeptide

<400> SEQUENCE: 177

Tyr Gly Arg Lys Lys Arg Arg Gln Arg Arg Arg
1               5                   10

<210> SEQ ID NO 178
<211> LENGTH: 12
<212> TYPE: PRT
<213> ORGANISM: Artificial sequence
<220> FEATURE:
<223> OTHER INFORMATION: synthetic polypeptide

<400> SEQUENCE: 178

Arg Arg Gln Arg Arg Thr Ser Lys Leu Met Lys Arg
1               5                   10

<210> SEQ ID NO 179
<211> LENGTH: 27
<212> TYPE: PRT
<213> ORGANISM: Artificial sequence
<220> FEATURE:
<223> OTHER INFORMATION: synthetic polypeptide

<400> SEQUENCE: 179

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 180
<211> LENGTH: 33
<212> TYPE: PRT
<213> ORGANISM: Artificial sequence
<220> FEATURE:
<223> OTHER INFORMATION: synthetic polypeptide

<400> SEQUENCE: 180

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 181
<211> LENGTH: 16
<212> TYPE: PRT
<213> ORGANISM: Artificial sequence
<220> FEATURE:
<223> OTHER INFORMATION: synthetic polypeptide

<400> SEQUENCE: 181

Arg Gln Ile Lys Ile Trp Phe Gln Asn Arg Arg Met Lys Trp Lys Lys
1               5                   10                  15

<210> SEQ ID NO 182
<211> LENGTH: 9
<212> TYPE: PRT
<213> ORGANISM: Artificial sequence
<220> FEATURE:
<223> OTHER INFORMATION: synthetic polypeptide

<400> SEQUENCE: 182

Arg Lys Lys Arg Arg Gln Arg Arg Arg
1               5

<210> SEQ ID NO 183
<211> LENGTH: 8
<212> TYPE: PRT
<213> ORGANISM: Artificial sequence
<220> FEATURE:
<223> OTHER INFORMATION: synthetic polypeptide

<400> SEQUENCE: 183

Arg Lys Lys Arg Arg Gln Arg Arg
1               5

<210> SEQ ID NO 184
<211> LENGTH: 11
<212> TYPE: PRT
<213> ORGANISM: Artificial sequence
<220> FEATURE:
<223> OTHER INFORMATION: synthetic polypeptide

<400> SEQUENCE: 184

Tyr Ala Arg Ala Ala Ala Arg Gln Ala Arg Ala
1               5                   10

<210> SEQ ID NO 185
<211> LENGTH: 11
<212> TYPE: PRT
<213> ORGANISM: Artificial sequence
<220> FEATURE:
<223> OTHER INFORMATION: synthetic polypeptide

<400> SEQUENCE: 185

Thr His Arg Leu Pro Arg Arg Arg Arg Arg Arg
1               5                   10

<210> SEQ ID NO 186
<211> LENGTH: 11
<212> TYPE: PRT
<213> ORGANISM: Artificial sequence
<220> FEATURE:
<223> OTHER INFORMATION: synthetic polypeptide

<400> SEQUENCE: 186

Gly Gly Arg Arg Ala Arg Arg Arg Arg Arg Arg
1               5                   10

<210> SEQ ID NO 187
<211> LENGTH: 50
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (6)..(50)
<223> OTHER INFORMATION: amino acids in this region may be present or
      absent

<400> SEQUENCE: 187

Gly Gly Gly Gly Ser Gly Gly Gly Gly Ser Gly Gly Gly Gly Ser Gly
1               5                   10                  15

Gly Gly Ser Gly Gly Gly Ser Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 188
<211> LENGTH: 12
<212> TYPE: PRT
<213> ORGANISM: Artificial sequence
<220> FEATURE:
<223> OTHER INFORMATION: synthetic polypeptide

<400> SEQUENCE: 188

Gly Gly Gly Ser Gly Gly Gly Ser Ile Glu Gly Arg
1               5                   10

```
<210> SEQ ID NO 189
<211> LENGTH: 5
<212> TYPE: PRT
<213> ORGANISM: Artificial sequence
<220> FEATURE:
<223> OTHER INFORMATION: synthetic polypeptide

<400> SEQUENCE: 189

Gly Gly Gly Gly Gly
1               5

<210> SEQ ID NO 190
<211> LENGTH: 50
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (6)..(50)
<223> OTHER INFORMATION: amino acids in this region may be present or
      absent

<400> SEQUENCE: 190

Glu Gly Gly Gly Ser Glu Gly Gly Gly Ser Glu Gly Gly Gly Ser Glu
1               5                   10                  15

Gly Gly Gly Ser Glu Gly Gly Gly Ser Glu Gly Gly Gly Ser Glu Gly
            20                  25                  30

Gly Gly Ser Glu Gly Gly Gly Ser Glu Gly Gly Gly Ser Glu Gly Gly
        35                  40                  45

Gly Ser
    50

<210> SEQ ID NO 191
<211> LENGTH: 4
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (2)..(3)
<223> OTHER INFORMATION: amino acids Xaa can be any amino acid
<220> FEATURE:
<221> NAME/KEY: MISC_FEATURE
<222> LOCATION: (4)..(4)
<223> OTHER INFORMATION: amino acid Xaa is a hydrophobic amino acid

<400> SEQUENCE: 191

Pro Xaa Xaa Xaa
1

<210> SEQ ID NO 192
<211> LENGTH: 5
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (2)..(3)
<223> OTHER INFORMATION: amino acids Xaa can be any amino acid
<220> FEATURE:
<221> NAME/KEY: MISC_FEATURE
<222> LOCATION: (4)..(4)
<223> OTHER INFORMATION: amino acid Xaa is a hydrophobic amino acid
<220> FEATURE:
<221> NAME/KEY: MISC_FEATURE
<222> LOCATION: (5)..(5)
```

```
<223> OTHER INFORMATION: amino acid Xaa can be either Ser or Thr

<400> SEQUENCE: 192

Pro Xaa Xaa Xaa Xaa
1               5

<210> SEQ ID NO 193
<211> LENGTH: 6
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: amino acid Xaa can be Leu or Gln

<400> SEQUENCE: 193

Pro Xaa Gly Met Thr Ser
1               5

<210> SEQ ID NO 194
<211> LENGTH: 5
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (2)..(2)
<223> OTHER INFORMATION: where amino acid Xaa can be Leu or Gln

<400> SEQUENCE: 194

Pro Xaa Gly Met Thr
1               5

<210> SEQ ID NO 195
<211> LENGTH: 10
<212> TYPE: PRT
<213> ORGANISM: Artificial sequence
<220> FEATURE:
<223> OTHER INFORMATION: synthetic polypeptide

<400> SEQUENCE: 195

Cys Gly Leu Val Pro Ala Gly Ser Gly Pro
1               5                   10

<210> SEQ ID NO 196
<211> LENGTH: 12
<212> TYPE: PRT
<213> ORGANISM: Artificial sequence
<220> FEATURE:
<223> OTHER INFORMATION: synthetic polypeptide

<400> SEQUENCE: 196

Ser Leu Leu Lys Ser Arg Met Val Pro Asn Phe Asn
1               5                   10

<210> SEQ ID NO 197
<211> LENGTH: 12
<212> TYPE: PRT
<213> ORGANISM: Artificial sequence
<220> FEATURE:
<223> OTHER INFORMATION: synthetic polypeptide

<400> SEQUENCE: 197

Ser Leu Leu Ile Ala Arg Arg Met Pro Asn Phe Asn
1               5                   10
```

<210> SEQ ID NO 198
<211> LENGTH: 12
<212> TYPE: PRT
<213> ORGANISM: Artificial sequence
<220> FEATURE:
<223> OTHER INFORMATION: synthetic polypeptide

<400> SEQUENCE: 198

Ser Lys Leu Val Gln Ala Ser Ala Ser Gly Val Asn
1               5                   10

<210> SEQ ID NO 199
<211> LENGTH: 12
<212> TYPE: PRT
<213> ORGANISM: Artificial sequence
<220> FEATURE:
<223> OTHER INFORMATION: synthetic polypeptide

<400> SEQUENCE: 199

Ser Ser Tyr Leu Lys Ala Ser Asp Ala Pro Asp Asn
1               5                   10

<210> SEQ ID NO 200
<211> LENGTH: 12
<212> TYPE: PRT
<213> ORGANISM: Artificial sequence
<220> FEATURE:
<223> OTHER INFORMATION: synthetic polypeptide

<400> SEQUENCE: 200

Arg Pro Lys Pro Gln Gln Phe Phe Gly Leu Met Asn
1               5                   10

<210> SEQ ID NO 201
<211> LENGTH: 12
<212> TYPE: PRT
<213> ORGANISM: Artificial sequence
<220> FEATURE:
<223> OTHER INFORMATION: synthetic polypeptide

<400> SEQUENCE: 201

Ser Leu Arg Pro Leu Ala Leu Trp Arg Ser Phe Asn
1               5                   10

<210> SEQ ID NO 202
<211> LENGTH: 12
<212> TYPE: PRT
<213> ORGANISM: Artificial sequence
<220> FEATURE:
<223> OTHER INFORMATION: synthetic polypeptide

<400> SEQUENCE: 202

Ser Pro Gln Gly Ile Ala Gly Gln Arg Asn Phe Asn
1               5                   10

<210> SEQ ID NO 203
<211> LENGTH: 14
<212> TYPE: PRT
<213> ORGANISM: Artificial sequence
<220> FEATURE:
<223> OTHER INFORMATION: synthetic polypeptide

<400> SEQUENCE: 203

Asp Val Asp Glu Arg Asp Val Arg Gly Phe Ala Ser Phe Leu
1               5                   10

<210> SEQ ID NO 204
<211> LENGTH: 12
<212> TYPE: PRT
<213> ORGANISM: Artificial sequence
<220> FEATURE:
<223> OTHER INFORMATION: synthetic polypeptide

<400> SEQUENCE: 204

Ser Leu Pro Leu Gly Leu Trp Ala Pro Asn Phe Asn
1               5                   10

<210> SEQ ID NO 205
<211> LENGTH: 12
<212> TYPE: PRT
<213> ORGANISM: Artificial sequence
<220> FEATURE:
<223> OTHER INFORMATION: synthetic polypeptide

<400> SEQUENCE: 205

Ser Leu Leu Ile Phe Arg Ser Trp Ala Asn Phe Asn
1               5                   10

<210> SEQ ID NO 206
<211> LENGTH: 12
<212> TYPE: PRT
<213> ORGANISM: Artificial sequence
<220> FEATURE:
<223> OTHER INFORMATION: synthetic polypeptide

<400> SEQUENCE: 206

Ser Gly Val Val Ile Ala Thr Val Ile Val Ile Thr
1               5                   10

<210> SEQ ID NO 207
<211> LENGTH: 12
<212> TYPE: PRT
<213> ORGANISM: Artificial sequence
<220> FEATURE:
<223> OTHER INFORMATION: synthetic polypeptide

<400> SEQUENCE: 207

Ser Leu Gly Pro Gln Gly Ile Trp Gly Gln Phe Asn
1               5                   10

<210> SEQ ID NO 208
<211> LENGTH: 12
<212> TYPE: PRT
<213> ORGANISM: Artificial sequence
<220> FEATURE:
<223> OTHER INFORMATION: synthetic polypeptide

<400> SEQUENCE: 208

Lys Lys Ser Pro Gly Arg Val Val Gly Gly Ser Val
1               5                   10

<210> SEQ ID NO 209
<211> LENGTH: 12
<212> TYPE: PRT
<213> ORGANISM: Artificial sequence
<220> FEATURE:
<223> OTHER INFORMATION: synthetic polypeptide

<400> SEQUENCE: 209

Pro Gln Gly Leu Leu Gly Ala Pro Gly Ile Leu Gly
1               5                   10

```
<210> SEQ ID NO 210
<211> LENGTH: 31
<212> TYPE: PRT
<213> ORGANISM: Artificial sequence
<220> FEATURE:
<223> OTHER INFORMATION: synthetic polypeptide

<400> SEQUENCE: 210

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 211
<211> LENGTH: 12
<212> TYPE: PRT
<213> ORGANISM: Artificial sequence
<220> FEATURE:
<223> OTHER INFORMATION: synthetic polypeptide

<400> SEQUENCE: 211

Gly Pro Gln Gly Leu Ala Gly Gln Arg Gly Ile Val
1               5                   10

<210> SEQ ID NO 212
<211> LENGTH: 12
<212> TYPE: PRT
<213> ORGANISM: Artificial sequence
<220> FEATURE:
<223> OTHER INFORMATION: synthetic polypeptide

<400> SEQUENCE: 212

Gly Gly Ser Gly Gln Arg Gly Arg Lys Ala Leu Glu
1               5                   10

<210> SEQ ID NO 213
<211> LENGTH: 12
<212> TYPE: PRT
<213> ORGANISM: Artificial sequence
<220> FEATURE:
<223> OTHER INFORMATION: synthetic polypeptide

<400> SEQUENCE: 213

Ser Leu Ser Ala Leu Leu Ser Ser Asp Ile Phe Asn
1               5                   10

<210> SEQ ID NO 214
<211> LENGTH: 12
<212> TYPE: PRT
<213> ORGANISM: Artificial sequence
<220> FEATURE:
<223> OTHER INFORMATION: synthetic polypeptide

<400> SEQUENCE: 214

Ser Leu Pro Arg Phe Lys Ile Ile Gly Gly Phe Asn
1               5                   10

<210> SEQ ID NO 215
<211> LENGTH: 12
<212> TYPE: PRT
<213> ORGANISM: Artificial sequence
<220> FEATURE:
<223> OTHER INFORMATION: synthetic polypeptide

<400> SEQUENCE: 215

Ser Leu Leu Gly Ile Ala Val Pro Gly Asn Phe Asn
1               5                   10
```

<210> SEQ ID NO 216
<211> LENGTH: 12
<212> TYPE: PRT
<213> ORGANISM: Artificial sequence
<220> FEATURE:
<223> OTHER INFORMATION: synthetic polypeptide

<400> SEQUENCE: 216

Phe Phe Lys Asn Ile Val Thr Pro Arg Thr Pro Pro
1               5                   10

<210> SEQ ID NO 217
<211> LENGTH: 51
<212> TYPE: DNA
<213> ORGANISM: Artificial sequence
<220> FEATURE:
<223> OTHER INFORMATION: synthetic polynucleotide

<400> SEQUENCE: 217
tggctccgag gtgccagatg tgatgcacac aagagtgagg ttgctcatcg g         51

<210> SEQ ID NO 218
<211> LENGTH: 39
<212> TYPE: DNA
<213> ORGANISM: Artificial sequence
<220> FEATURE:
<223> OTHER INFORMATION: synthetic polynucleotide

<400> SEQUENCE: 218
gctaccgcct ccacctaagc ctaaggcagc ttgacttgc                       39

<210> SEQ ID NO 219
<211> LENGTH: 90
<212> TYPE: DNA
<213> ORGANISM: Artificial sequence
<220> FEATURE:
<223> OTHER INFORMATION: synthetic polynucleotide

<400> SEQUENCE: 219
gctgccttag gcttaggtgg aggcggtagc ggtggaggtg ggagtggagg tggaggcagt    60
gcgcgcaacg gggaccactg tccgctcggg                                    90

<210> SEQ ID NO 220
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 220
cagaggtcga ggtcggggga tcctcatatg cagtggcagt ctttggctaa caa           53

<210> SEQ ID NO 221
<211> LENGTH: 14
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (12)..(12)
<223> OTHER INFORMATION: where amino acid Xaa can be either Glu or Asp

<400> SEQUENCE: 221

Gly Gly Gly Gly Ser Gly Gly Gly Gly Ser Ile Xaa Gly Arg

```
1               5                   10
```

<210> SEQ ID NO 222
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 222

Arg Gly Arg Arg
1

<210> SEQ ID NO 223
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 223

Arg Lys Arg Lys Lys Arg
1               5

<210> SEQ ID NO 224
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 224

Arg Lys Lys Arg
1

<210> SEQ ID NO 225
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 225

Arg Arg Arg Lys Lys Arg
1               5

<210> SEQ ID NO 226
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 226

Gly Gly Ser Gly
1

<210> SEQ ID NO 227
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 227

Gly Gly Ser Gly Gly
1               5

```
<210> SEQ ID NO 228
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 228

Gly Ser Gly Ser Gly
1               5

<210> SEQ ID NO 229
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 229

Gly Ser Gly Gly Gly
1               5

<210> SEQ ID NO 230
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 230

Gly Gly Gly Ser Gly
1               5

<210> SEQ ID NO 231
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 231

Gly Ser Ser Ser Gly
1               5
```

COMPOSITIONS AND METHODS OF USE FOR TREATING METABOLIC DISORDERS

CROSS-REFERENCE TO RELATED APPLICATIONS

This application claims priority benefit of U.S. provisional application Ser. No. 61/758,456, filed Jan. 30, 2013, and of U.S. provisional application Ser. No. 61/882,542, filed Sep. 25, 2013, each of which applications is incorporated herein by reference in its entirety.

FIELD OF THE INVENTION

The present invention relates to, among other things, growth differentiation factor muteins and modifications thereof which are useful in treating obesity, diabetes and other metabolic-related disorders.

BACKGROUND

Obesity is most commonly caused by excessive food intake coupled with limited energy expenditure and/or lack of physical exercise. Obesity increases the likelihood of development of various diseases, such as diabetes mellitus, hypertension, atherosclerosis, coronary artery disease, sleep apnea, gout, rheumatism and arthritis. Moreover, mortality risk directly correlates with obesity, such that, for example, a body-mass index in excess of 40 results in an average decreased life expectancy of more than 10 years.

Current pharmacological treatment modalities include appetite suppressors targeting receptor classes (e.g., CB1, 5-HT$_{2C}$, and NPY); regulators of the appetite circuits in the hypothalamus and the molecular actions of ghrelin; and nutrient-absorption inhibitors targeting lipases. Unfortunately, none of the current modalities has been shown to effectively treat obesity without causing adverse effects, some of which can be very severe.

High blood glucose levels stimulate the secretion of insulin by pancreatic beta-cells. Insulin in turn stimulates the entry of glucose into muscles and adipose cells, leading to the storage of glycogen and triglycerides and to the synthesis of proteins. Activation of insulin receptors on various cell types diminishes circulating glucose levels by increasing glucose uptake and utilization, and by reducing hepatic glucose output. Disruptions within this regulatory network can result in diabetes and associated pathologic syndromes that affect a large and growing percentage of the human population.

Patients who have a glucose metabolism disorder can suffer from hyperglycemia, hyperinsulinemia, and/or glucose intolerance. An example of a disorder that is often associated with the aberrant levels of glucose and/or insulin is insulin resistance, in which liver, fat, and muscle cells lose their ability to respond to normal blood insulin levels.

In view of the prevalence and severity of obesity, diabetes and associated metabolic and non-metabolic disorders, along with the shortcomings of current treatment options, alternative treatment modalities that modulate, for example, appetite, glucose and/or insulin levels and enhance the biological response to fluctuating glucose levels in a patient remain of interest.

In addition, in the pharmaceutical sciences it is frequently beneficial, and sometimes imperative, to improve one of more physical properties of the treatment modality (e.g., a protein, peptide, or hydrophobic molecule) of interest and/or the manner in which it is administered. Improvements of physical properties include, for example, methods of increasing water solubility, bioavailability, serum half-life, and/or therapeutic half-life; modulating immunogenicity and/or biological activity; and/or extending the circulation time. Such improvements must be imparted without adversely impacting the bioactivity of the treatment modality. Thus, it may be advantageous for alternatives to current treatment options for obesity, diabetes and associated metabolic and non-metabolic disorders, to possess one or more improved physical properties.

SUMMARY

The present disclosure contemplates the use of the agents described herein, and compositions thereof, to treat and/or prevent various diseases, disorders and conditions, and/or the symptoms thereof. In some embodiments, the diseases, disorders and conditions, and/or the symptoms thereof, relate to glucose metabolism disorders and other metabolic-related disorders, whereas in other embodiments they relate to body weight disorders. By way of example, but not limitation, the agents, and compositions thereof, can be used for the treatment and/or prevention of diabetes mellitus (e.g., Type 2 diabetes), insulin resistance and diseases, disorders and conditions characterized by insulin resistance, decreased insulin production, hyperglycemia, hypoinsulinemia, and metabolic syndrome. The agents, and compositions thereof, can also be used for the treatment and/or prevention of obesity and other body weight disorders by, for example, effecting appetite suppression.

In certain embodiments, the agents are human Growth Differentiation Factor 15 (GDF15)-related polypeptides, and homologues, variants (e.g., muteins), fragments and other modified forms thereof. In particular embodiments, the agents contemplated by the present disclosure are modified human GDF15 molecules, whereas in other embodiments the agents are modified GDF15 muteins. The present disclosure also contemplates nucleic acid molecules encoding the foregoing. For the sake of convenience, the modified human GDF15 molecules and the modified GDF15 variants (e.g., muteins) described henceforward are collectively referred to hereafter as the "Polypeptide(s)". It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it may correspond to a sequence of a naturally occurring human polypeptide or nucleic acid molecule. In addition to the human polypeptides and the nucleic acid molecules which encode them, the present disclosure contemplates GDF15-related polypeptides and corresponding nucleic acid molecules from other species.

The present disclosure also contemplates other GDF15-related agents capable of eliciting a biological response comparable to (or greater than) that of the Polypeptides, and/or agents capable of enhancing the activity of the Polypeptides.

In some embodiments of the present disclosure, a subject having, or at risk of having, a disease or disorder treatable by one or more Polypeptides is administered in an amount effective for treating the disease or disorder. In some embodiments, the disease or disorder is a hyperglycemic condition, insulin resistance, hyperinsulinemia, glucose intolerance or metabolic syndrome. In other embodiments the disease or disorder is a body weight disorder (e.g., obesity), while in still other embodiments the Polypeptides cause, to at least some extent, appetite suppression.

Other aspects of the present disclosure include cell-based expression systems, vectors, engineered cell lines, and methods and uses related to the foregoing.

As described in detail hereafter, one embodiment of the present disclosure relates to a polypeptide comprising a) a polypeptide comprising at least one modification to the sequence depicted in FIG. 1B (SEQ ID NO:3); wherein the modification does not alter the amino acid sequence of the polypeptide, or b) a mutein polypeptide of the sequence depicted in FIG. 1B (SEQ ID NO:3), wherein the mutein polypeptide comprises at least one modification that does not alter the amino acid sequence of the mutein polypeptide; and wherein the modification set forth in a) and b) improves at least one physical property of the polypeptide or the mutein polypeptide.

In certain embodiments of the present disclosure, a polypeptide comprises a mutein polypeptide of any one of the sequences depicted in, for example, FIGS. 3, 5, 6 and 13.

In some embodiments, the polypeptide has a length of from about 10 amino acids to about 113 amino acids. In other embodiments, a polypeptide of the present disclosure may have fewer than 100 amino acid residues, fewer than 75 amino acid residues, fewer than 50 amino acid residues, fewer than 25 amino acid residues, or fewer than 20 amino acid residues.

In still further embodiments, a polypeptide of the present disclosure comprises an amino acid sequence having at least 85% amino acid identity, at least 90% amino acid identity, at least 93% amino acid identity, at least 95% amino acid identity, at least 97% amino acid identity, at least 98% amino acid identity, or at least 99% amino acid identity to the amino acid sequence depicted in FIG. 1B (SEQ ID NO:3)

According to the present disclosure, the polypeptide may be produced recombinantly.

In some embodiments of the present disclosure, the modification to a Polypeptide comprises pegylation, glycosylation, polysialylation, hesylation, albumin fusion, albumin binding through a conjugated fatty acid chain, Fc-fusion, or fusion with a PEG mimetic.

In particular embodiments, the modification to a polypeptide comprises glycosylation, and in some of those embodiments the glycosylation is N-glycosylation. The N-glycosylation may occur at more than one amino acid residue of the polypeptide.

In other embodiments, the modification to a polypeptide comprises an albumin fusion wherein an albumin, an albumin variant, or an albumin fragment is conjugated to the polypeptide. In some embodiments, the albumin, albumin variant, or albumin fragment is human serum albumin (HSA), a human serum albumin variant, or a human serum albumin fragment, whereas in other embodiments the albumin, albumin variant, or albumin fragment is bovine serum albumin, a bovine serum albumin variant, or a bovine serum albumin fragment.

The full-length HSA has a signal peptide of 18 amino acids (MKWVTFISLLFLFSSAYS; SEQ ID NO:164) followed by a pro-domain of 6 amino acids (RGVFRR; SEQ II NO:165); this 24 amino acid residue peptide may be referred to as the pre-pro domain. The mature HSA polypeptide spans residues D25-L609 of the sequence depicted in FIG. 1C (SEQ II NO:5). In a construct used to generate the experimental data presented herein, the endogenous signal peptide was replaced with human IgK signal peptide, and the endogenous pro-domain was left out entirely.

In still further embodiments, the albumin, albumin variant, or albumin fragment is conjugated to the polypeptide at the carboxyl terminus, the amino terminus, both the carboxyl and amino termini, or internally. Particular embodiments entail conjugation of the albumin, albumin variant, or albumin fragment to the polypeptide at the amino terminus.

In particular embodiments, the albumin, albumin variant, or albumin fragment is conjugated to a polypeptide comprising the 167 amino acid pro-domain and the 112 amino acid mature domain of the 308 amino acid GDF15 precursor polypeptide; thus, the present disclosure contemplates a GDF15 polypeptide that has a length of from about amino acid residue 30 to about amino acid residue 308 of the sequence depicted in FIG. 1A (SEQ ID NO:1).

The present disclosure contemplates direct expression and production of the 112 amino acid mature domain of GDF15 as depicted in FIG. 1B (SEQ ID NO:3), absent the 167 amino acid pro-domain, using a signal peptide of appropriate length to confer secretion from mammalian tissue culture. An example of a suitable signal peptide to facilitate expression and secretion includes IgK. The art describes mechanisms by which other appropriate signal peptides can be identified [see, e.g., Ng et al. (January 2013) "Engineering Signal Peptides for Enhanced Protein Secretion from *Lactococcus lactis*.", Appl. Environ. Microbiol. 79(1):347-56; Chou (2001) "Using Subsite Coupling to Predict Signal Peptides", Protein Engineering 14(2):75-79; Leversen et al. (July 2009) "Evaluation of Signal Peptide Prediction Algorithms for Identification of Mycobacterial Signal Peptides Using Sequence Data from Proteomic Methods" Microbiology 155(7):2357-83; and Shen et al., (2007) "Signal-3L: a 3-layer Approach for Predicting Signal Peptides", Biochemical and Biophysical Res. Comm. 363: 297-303].

The present disclosure contemplates albumin fusion molecules wherein the albumin, albumin variant, or albumin fragment is conjugated to the polypeptide via a linker. Examples of suitable linkers are described herein. By way of example, the linker may be a peptide linker of, for example, four-to-six amino acids. In some embodiments, the linker is a non-cleavable linker (e.g., a 3×(4Gly-Ser) linker; SEQ ID NO:64). In other embodiments, the linker is a cleavable linker, and in further embodiments the cleavable linker can be cleaved by a protease (e.g., a 2×(4Gly-Ser) Factor Xa-cleavable linker (GGGGSGGGGSIXGR where X can be either E or D (SEQ ID NO:221)).

In particular embodiments, the albumin, albumin variant, or albumin fragment of an albumin fusion molecule is excised prior to the albumin fusion molecule being secreted from a cell, whereas in other embodiments the albumin fusion molecule is excised subsequent to the albumin fusion molecule being secreted from a cell.

The present disclosure encompasses embodiments wherein the physical property of the recited polypeptide is selected from the group consisting of solubility, bioavailability, serum half-life, therapeutic half-life, circulation time, and immunogenicity. In particular embodiments, the physical property is solubility.

Furthermore, the present disclosure contemplates nucleic acid molecules encoding the aforementioned polypeptides. In some embodiments, a nucleic acid molecule is operably linked to an expression control element that confers expression of the nucleic acid molecule encoding the polypeptide in vitro, in a cell or in vivo.

In some embodiments, a vector (e.g., a viral vector) contains one or more of the nucleic acid molecules.

Some embodiments include transformed or host cells that express one or more of the aforementioned polypeptides.

In particular embodiments of the present disclosure, one or more of the aforementioned polypeptides is formulated to yield a pharmaceutical composition, wherein the composition also includes one or more pharmaceutically acceptable diluents, carriers or excipients. In certain embodiments, a pharmaceutical composition also includes at least one additional prophylactic or therapeutic agent.

Still further embodiments of the present disclosure comprise an antibody that binds specifically to one of the aforementioned mutein polypeptides. In some embodiments, the antibody comprises a light chain variable region and a heavy chain variable region present in separate polypeptides or in a single polypeptide. An antibody of the present disclosure binds the polypeptide with an affinity of from about $10^7 M^{-1}$ to about $10^{12} M^{-1}$ in certain embodiments. In still other embodiments, the antibody comprises a heavy chain constant region of the isotype IgG1, IgG2, IgG3, or IgG4. In additional embodiments, the antibody is detectably labeled, while it is a Fv, scFv, Fab, F(ab')$_2$, or Fab' in other embodiments.

The present disclosure also contemplates antibodies that comprise a covalently linked non-polypeptide polymer (e.g., a poly(ethylene glycol) polymer). In other embodiments, the antibody comprises a covalently linked moiety selected from a lipid moiety, a fatty acid moiety, a polysaccharide moiety, and a carbohydrate moiety.

The antibody is a single chain Fv (scFv) antibody in some embodiments, and the scFv is multimerized in others.

The antibodies of the present disclosure may be, but are not limited to, monoclonal antibodies, polyclonal antibodies, or humanized antibodies.

Furthermore, the present disclosure contemplates pharmaceutical compositions comprising an antibody as described above formulated with at least one pharmaceutically acceptable excipient, carrier or diluent. Such pharmaceutical compositions may also contain at least one additional prophylactic or therapeutic agent.

Certain embodiments of the present disclosure contemplate a sterile container that contains one of the above-mentioned pharmaceutical compositions and optionally one or more additional components. By way of example, but not limitation, the sterile container may be a syringe. In still further embodiments, the sterile container is one component of a kit; the kit may also contain, for example, a second sterile container that contains at least one prophylactic or therapeutic agent.

The present disclosure also contemplates a method of treating or preventing a glucose metabolism disorder in a subject (e.g., a human) by administering to the subject a therapeutically effective amount of a polypeptide. In some methods, the treating or preventing results in a reduction in plasma glucose in the subject, a reduction in plasma insulin in the subject, a reduction in body weight and/or food intake, or an increase in glucose tolerance in the subject. In particular embodiments, the glucose metabolism disorder is diabetes mellitus. In some embodiments, the subject is obese and/or has a body weight disorder.

Though not limited to any particular route of administration or dosing regimen, in some embodiments the administering is by parenteral (e.g., subcutaneous) injection.

BRIEF DESCRIPTION OF THE DRAWINGS

FIG. 1A depicts the human GDF15 precursor amino acid sequence and the corresponding nucleic acid encoding the human GDF15 precursor amino acid sequence.

FIG. 1B depicts the mature human GDF15 amino acid sequence and the corresponding nucleic acid sequence encoding mature human GDF15.

FIG. 1C depicts a human serum albumin precursor sequence comprising endogenous signal peptide and prodomain, and mature human serum albumin (D25-L609), and the corresponding nucleic acid sequence; and a human serum albumin precursor sequence comprising IgK signal peptide and mature human serum albumin (D25-L609), and the corresponding nucleic acid sequence.

FIG. 1D depicts the mature human serum albumin amino acid sequence (subsequence of the amino acid sequence of FIG. 1C lacking the IgK Signal Peptide, and the corresponding nucleic acid sequence).

FIG. 1E depicts a fusion molecule wherein the human serum albumin amino acid sequence having an IgK signal sequence is fused to the N-terminus of the mature human GDF15 amino acid sequence through a protease-sensitive 2×(4Gly-Ser) Factor Xa-cleavable linker (SEQ ID NO:56), and the corresponding nucleic acid encoding the fusion molecule.

FIG. 1F depicts a fusion molecule wherein the mature human serum albumin amino acid sequence is fused to the N-terminus of the mature human GDF15 amino acid sequence through a protease-sensitive 2×(4Gly-Ser) Factor Xa-cleavable linker (SEQ ID NO:56), and the corresponding nucleic acid encoding the fusion molecule.

FIG. 1G depicts a fusion molecule wherein the human serum albumin amino acid sequence having an IgK signal sequence is fused to the N-terminus of the mature human GDF15 amino acid sequence through a non-cleavable 3×(4Gly-Ser) linker (SEQ ID NO:64), and the corresponding nucleic acid encoding the fusion molecule.

FIG. 1H depicts a fusion molecule wherein the mature human serum albumin amino acid sequence is fused to the N-terminus of the mature human GDF15 amino acid sequence through a non-cleavable 3×(4Gly-Ser) linker (SEQ ID NO:64), and the corresponding nucleic acid encoding the fusion molecule.

FIGS. 2A-2C depicts the effect on body weight (FIG. 2A), food take (FIG. 2B), and blood glucose (FIG. 2C) in ob/ob mice following administration of the fusion molecule described in FIG. 1H as a single subcutaneous dose at the indicated concentrations (PBS (vehicle), 0.04 mg/kg, 0.12 mg/kg, 0.4 mg/kg, and 1.2 mg/kg). As noted in the figure, the indicated parameters were determined on various days over a 22-day period. In each group of mice, n=7 and p-values (*, $p<0.05$; , $p<0.01$; *, $p<0.001$) were determined by student's unpaired T-test comparing the body weight, food intake and blood glucose groups at the various concentrations to vehicle control group at each specified time point.

FIG. 3 depicts the amino acid sequences of the GDF15 muteins generated via mutagenesis of predicted solvent-accessible hydrophobic residues within mature human GDF15. Fusion molecules were generated wherein each GDF15 mutein sequence was fused to HSA through the linker depicted in FIG. 1H (a non-cleavable 3×(4Gly-Ser) linker; (SEQ ID NO:64)); the sequences set forth in FIG. 3 neither depict the HSA component nor the linker component of the fusion molecules.

FIG. 4 is a table summarizing whether each GDF15 mutein set forth in FIG. 3 is secreted as a disulfide-linked homodimer.

FIG. 5 depicts the amino acid sequences of GDF15 muteins having alanine substitutions for evaluation of their improvement in physical properties relative to GDF15.

FIG. 6 depicts the amino acid sequences of single-point glycosylation muteins and additional di-glycosylation muteins for introduction of N-linked glycosylation consensus sites (Asn-Xxx-Ser/Thr) for evaluation of improved physical properties relative to GDF15. Fusion molecules were generated wherein each GDF15 mutein sequence was fused to HSA through the linker depicted in FIG. 1E (a Factor Xa-cleavable linker); the sequences set forth in FIG. 6 depict neither the HSA component nor the linker component of the fusion molecules.

FIG. 7 provides a summary of secretion and dimer formation data, along with N-glycan site occupancy, for each engineered N-glycosylated human GDF15 mutein set forth in FIG. 6.

FIGS. 8A and 8B set forth engineered human GDF15 muteins, following expression and purification, having improved physical properties compared to mature human GDF15.

FIG. 9A depicts the effect on overnight food intake reduction in ob/ob mice following a single, subcutaneous acute dose of 0.3 mg/kg of mature human GDF15, N-glycosylated human GDF15 muteins, and vehicle (PBS) control. In each group of mice, n=7 and p-values (*, $p<0.05$; , $p<0.01$; *, $p<0.001$) were determined by student's unpaired T-test comparing food intake of GDF15 mutein-treated mice relative to vehicle control group.

FIG. 9B depicts the effect on overnight food intake reduction in DIO mice following a single, subcutaneous acute dose of 1.0 mg/kg of mature human GDF15, N-glycosylated human GDF15 muteins, and vehicle (PBS) control. In each group of mice, n=9 and p-values (*, $p<0.05$; , $p<0.01$; *, $p<0.001$) were determined by student's unpaired T-test comparing food intake of GDF15 mutein-treated mice relative to vehicle control group.

FIG. 10 indicates that the hydrodynamic radii of GDF15 N-Glycan muteins are increased relative to mature human GDF15, as determined by analytical gel filtration chromatography measuring elution time.

FIG. 11A depicts the amino acid sequences of fusion molecules comprising HSA having an IgK signal sequence fused to the N-terminus of species orthologs of mature GDF15 *Mus musculus* and *Macaca mulatta* through a 2×(4Gly-Ser) Factor Xa-cleavable linker (SEQ ID NO:56).

FIG. 11B depicts the amino acid sequences of fusion molecules comprising HSA having an IgK signal sequence fused to the N-terminus of mature human TGF-β1 and mature human BMP2 through a 2×(4Gly-Ser) Factor Xa-cleavable linker (SEQ ID NO:56).

FIG. 12 provides a summary of secretion and dimer formation for fusion molecules comprising HSA fused to either the N-terminus of species orthologs of mature GDF15, or to the N-terminus of mature human TGF-β1 or human BMP2 through a cleavable linker.

FIG. 13 provides amino acid sequences of fusion molecules comprising HSA having an IgK signal sequence fused to the N-terminus of mature human GDF15 muteins generated by Alanine-scan through a non-cleavable 3×(4Gly-Ser) linker (SEQ ID NO:64).

FIG. 14 provides a summary of secretion and dimer formation for an Alanine scan of GDF15 using fusion molecules comprising HSA amino acid sequence fused to the N-terminus of mature human GDF15 amino acid sequence through a non-cleavable linker. This summary provides a template for sites available for mutagenesis that do not impact fold of GDF15 or secretion parameters.

FIGS. 15A-15E provides multiple sequences of solubility-enhanced, half-life extension molecules comprising fusion to the N-terminus of mature GDF15 amino acid sequence through various linkers. FIG. 15A): Schematic of fusion molecules comprising a signal sequence fused to Fc (IgG), ABD, and MBD; fused to the N-terminus of mature GDF15 through a variable Linker; FIG. 15B): FcGDF15 containing a 3×(Glu-3Gly-Ser) linker; FIG. 15C): Fc(+) GDF15/Fc(−) charged pair containing Fc(+)-3×(Glu-3Gly-Ser)-GDF15 and hFc(−); FIG. 15D): Albumin Binding Domain (ABD) containing a 5×Gly linker (ABD-GDF15); and FIG. 15E): Maltose Binding domain (MBD) containing an Enterokinase cleavable 5×Gly linker (MBD-GDF15).

FIG. 16 provides a summary of (A) the solubility improvements in PBS buffer of each of the respective fusion constructs described in FIG. 15 relative to mature GDF15; and (B) reduction in body weight in ob/ob mouse model following a single subcutaneous injection of 3 mg/kg albumin binding domain fusion to mature GDF15 (ABD-GDF15).

FIG. 17A depicts the amino acid sequence utilized to generate recombinant platypus (Oa) mature GDF15.

FIG. 17B depicts the effect on overnight food intake and body weight reduction in DIO mice (n=8) following a single, subcutaneous dose of 0.001, 0.003, 0.01, 0.03, 0.1, 0.3 and 1.0 mg/kg of mature OaGDF15.

DETAILED DESCRIPTION

Before the methods and compositions of the present disclosure are further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. Thus, for example, reference to "the Human Polypeptide" includes reference to one or more Human Polypeptides, and so forth. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

The present disclosure contemplates the use of the agents described herein, and compositions thereof, to treat and/or prevent various diseases, disorders and conditions, and/or the symptoms thereof. In some embodiments, the diseases, disorders and conditions, and/or the symptoms thereof, pertain to glucose metabolism disorders, while in other embodiments they pertain to body weight disorders. By way of example, but not limitation, the agents, and compositions thereof, can be used for the treatment and/or prevention of Type 2 diabetes, insulin resistance and diseases, disorders and conditions characterized by insulin resistance, decreased insulin production, hyperglycemia, metabolic syndrome, or obesity.

In particular embodiments, the agents contemplated by the present disclosure are modified human Growth Differentiation Factor 15 (GDF15), whereas in other embodiments the agents are modified GDF15 variants (e.g., muteins). The modified human GDF15 and modified GDF15 variants (e.g., muteins) have sufficient homology to human GDF15 such that they have the ability to bind the GDF15 receptor(s) and initiate a signal transduction pathway resulting in, for example, reduced body weight and/or the other physiological effects described herein. The present disclosure also contemplates nucleic acid molecules encoding the foregoing. As indicated above, the modified human GDF15 molecules and the modified GDF15 variants described henceforward are collectively referred to as the "Polypeptide(s)".

Examples of various GDF15 muteins that may be modified are described hereafter. In some embodiments, one or more GDF15 amino acid residues are substituted with another amino acid. In other embodiments, one or more GDF15 native lysine residues are substituted with another amino acid (however, changes involving K62Q are inactive). In some embodiments of the present disclosure, alanine scanning may be used to generate GDF15 muteins, and modifications to those muteins can then be assessed for their ability to enhance one or more desirable properties of the muteins themselves. Examples of modified GDF15 molecules and modified GDF15 muteins are described hereafter.

The present disclosure contemplates modifications to GDF15 and GDF15 muteins, including, for example, pegylation, glycosylation, and albumin conjugates. In particular embodiments, strategies are employed such that pegylation is effected only at specific lysine residues (i.e., site-specific pegylation). In other embodiments, albumin fusions may be generated whereby mature albumin, or an altered form thereof (e.g., a fragment), is conjugated directly or indirectly (e.g., via a linker) to GDF15 or a GDF15 mutein. As indicated above, the modifications may, for example, improve the serum half-life and/or the solubility of the Polypeptides. Examples of particular modified GDF15 molecules and modified GDF15 muteins are described hereafter.

Definitions

The terms "patient" or "subject" are used interchangeably to refer to a human or a non-human animal (e.g., a mammal).

The terms "treat", "treating", treatment" and the like refer to a course of action (such as administering a Polypeptide or a pharmaceutical composition comprising a Polypeptide) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (i.e., arresting the development or further development of the disease, disorder or condition or clinical symptoms association therewith) an active disease (e.g., so as to decrease the level of insulin and/or glucose in the bloodstream, to increase glucose tolerance so as to minimize fluctuation of glucose levels, and/or so as to protect against diseases caused by disruption of glucose homeostasis).

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering a Polypeptide or a pharmaceutical composition comprising a Polypeptide) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects. For example, in the case of a hyperglycemic condition, a lowering or reduction of blood glucose or an improvement in glucose tolerance test can be used to determine whether the amount of an agent is effective to treat the hyperglycemic condition. For example, a therapeutically effective amount is an amount sufficient to reduce or decrease any level (e.g., a baseline level) of fasting plasma glucose (FPG), wherein, for example, the amount is sufficient to reduce a FPG level greater than 200 mg/dl to less than 200 mg/dl, wherein the amount is sufficient to reduce a FPG level between 175 mg/dl and 200 mg/dl to less than the starting level, wherein the amount is sufficient to reduce a FPG level between 150 mg/dl and 175 mg/dl to less than the starting level, wherein the amount is sufficient to reduce a FPG level between 125 mg/dl and 150 mg/dl to less than the starting level, and so on (e.g., reducing FPG levels to less than 125 mg/dl, to less than 120 mg/dl, to less than 115 mg/dl, to less than 110 mg/dl, etc.). In the case of HbAlc levels, the effective amount is an amount sufficient to reduce or decrease levels by more than about 10% to 9%, by more than about 9% to 8%, by more than about 8% to 7%, by more than about 7% to 6%, by more than about 6% to 5%, and so on. More particularly, a reduction or decrease of HbAlc levels by about 0.1%, 0.25%, 0.4%, 0.5%, 0.6%, 0.7%, 0.8%, 0.9%, 1%, 1.5%, 2%, 3%, 4%, 5%, 10%, 20%, 30%, 33%, 35%, 40%, 45%, 50%, or more is contemplated by the present disclosure. The therapeutically effective amount can be adjusted in connection with the dosing regimen and diagnostic analysis of the subject's condition and the like.

The phrase "in a sufficient amount to effect a change" means that there is a detectable difference between a level of an indicator measured before (e.g., a baseline level) and after administration of a particular therapy. Indicators include any objective parameter (e.g., level of glucose or insulin) or subjective parameter (e.g., a subject's feeling of well-being).

The phrase "glucose tolerance", as used herein, refers to the ability of a subject to control the level of plasma glucose and/or plasma insulin when glucose intake fluctuates. For example, glucose tolerance encompasses the subject's ability to reduce, within about 120 minutes, the level of plasma glucose back to a level determined before the intake of glucose.

Broadly speaking, the terms "diabetes" and "diabetic" refer to a progressive disease of carbohydrate metabolism involving inadequate production or utilization of insulin, frequently characterized by hyperglycemia and glycosuria. The terms "pre-diabetes" and "pre-diabetic" refer to a state wherein a subject does not have the characteristics, symptoms and the like typically observed in diabetes, but does have characteristics, symptoms and the like that, if left untreated, may progress to diabetes. The presence of these conditions may be determined using, for example, either the fasting plasma glucose (FPG) test or the oral glucose tolerance test (OGTT). Both usually require a subject to fast for at least 8 hours prior to initiating the test. In the FPG test, a subject's blood glucose is measured after the conclusion of the fasting; generally, the subject fasts overnight and the blood glucose is measured in the morning before the subject eats. A healthy subject would generally have a FPG concentration between about 90 and about 100 mg/dl, a subject with "pre-diabetes" would generally have a FPG concentration between about 100 and about 125 mg/dl, and a subject with "diabetes" would generally have a FPG level above about 126 mg/dl. In the OGTT, a subject's blood glucose is measured after fasting and again two hours after drinking a glucose-rich beverage. Two hours after consumption of the glucose-rich beverage, a healthy subject generally has a blood glucose concentration below about 140 mg/dl, a pre-diabetic subject generally has a blood glucose concentration about 140 to about 199 mg/dl, and a diabetic subject generally has a blood glucose concentration about 200 mg/dl or above. While the aforementioned glycemic values pertain to human subjects, normoglycemia, moderate hyperglycemia and overt hyperglycemia are scaled differently in murine subjects. A healthy murine subject after a four-hour fast would generally have a FPG concentration between about 100 and about 150 mg/dl, a murine subject with "pre-diabetes" would generally have a FPG concentration between about 175 and about 250 mg/dl and a murine subject with "diabetes" would generally have a FPG concentration above about 250 mg/dl.

The term "insulin resistance" as used herein refers to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" refers to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of Type 2 diabetes and/or other disorders (e.g., atherosclerosis).

The phrase "glucose metabolism disorder" encompasses any disorder characterized by a clinical symptom or a combination of clinical symptoms that is associated with an elevated level of glucose and/or an elevated level of insulin in a subject relative to a healthy individual. Elevated levels of glucose and/or insulin may be manifested in the following diseases, disorders and conditions: hyperglycemia, type II diabetes, gestational diabetes, type I diabetes, insulin resistance, impaired glucose tolerance, hyperinsulinemia, impaired glucose metabolism, pre-diabetes, other metabolic disorders (such as metabolic syndrome, which is also referred to as syndrome X), and obesity, among others. The Polypeptides of the present disclosure, and compositions thereof, can be used, for example, to achieve and/or maintain glucose homeostasis, e.g., to reduce glucose level in the bloodstream and/or to reduce insulin level to a range found in a healthy subject.

The term "hyperglycemia", as used herein, refers to a condition in which an elevated amount of glucose circulates in the blood plasma of a subject relative to a healthy individual. Hyperglycemia can be diagnosed using methods known in the art, including measurement of fasting blood glucose levels as described herein.

The term "hyperinsulinemia", as used herein, refers to a condition in which there are elevated levels of circulating insulin when, concomitantly, blood glucose levels are either elevated or normal. Hyperinsulinemia can be caused by insulin resistance which is associated with dyslipidemia, such as high triglycerides, high cholesterol, high low-density lipoprotein (LDL) and low high-density lipoprotein (HDL); high uric acids levels; polycystic ovary syndrome; type II diabetes and obesity. Hyperinsulinemia can be diagnosed as having a plasma insulin level higher than about 2 $\mu$U/mL.

As used herein, the phrase "body weight disorder" refers to conditions associated with excessive body weight and/or enhanced appetite. Various parameters are used to determine whether a subject is overweight compared to a reference healthy individual, including the subject's age, height, sex and health status. For example, a subject may be considered overweight or obese by assessment of the subject's Body Mass Index (BMI), which is calculated by dividing a subject's weight in kilograms by the subject's height in meters squared. An adult having a BMI in the range of ~18.5 to ~24.9 kg/m$^2$ is considered to have a normal weight; an adult having a BMI between ~25 and ~29.9 kg/m$^2$ may be considered overweight (pre-obese); and an adult having a BMI of ~30 kg/m$^2$ or higher may be considered obese. Enhanced appetite frequently contributes to excessive body weight. There are several conditions associated with enhanced appetite, including, for example, night eating syndrome, which is characterized by morning anorexia and evening polyphagia often associated with insomnia, but which may be related to injury to the hypothalamus.

The term "Activators" refers to agents that, for example, stimulate, increase, activate, facilitate, enhance activation, sensitize or up-regulate the function or activity of one or more Polypeptides. In addition, Activators include agents that operate through the same mechanism of action as the Polypeptides (i.e., agents that modulate the same signaling pathway as the Polypeptides in a manner analogous to that of the Polypeptides) and are capable of eliciting a biological response comparable to (or greater than) that of the Polypeptides. Examples of Activators include agonists such as small molecule compounds.

The term "Modulators" collectively refers to the Polypeptides and the Activators.

The terms "modulate", "modulation" and the like refer to the ability of an agent (e.g., an Activator) to increase the function or activity of one or more Polypeptides (or the nucleic acid molecules encoding them), either directly or indirectly; or to the ability of an agent to produce an effect comparable to that of one or more Polypeptides.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants (e.g., homologs and allelic variants) and non-naturally-occurring variants (e.g., muteins). Naturally-occurring variants include homologs, i.e., nucleic acids and polypeptides that differ in nucleotide or amino acid sequence, respectively, from one species to another. Naturally-occurring variants include allelic variants, i.e., nucleic acids and polypeptides that differ in nucleotide or amino acid sequence, respectively, from one individual to another within a species. Non-naturally-occurring variants include nucleic acids and polypeptides that comprise a change in nucleotide or amino acid sequence, respectively, where the change in sequence is artificially introduced, e.g., the change is generated in the laboratory or other facility by human intervention ("hand of man").

The term "native", in reference to GDF15, refers to biologically active, naturally-occurring GDF15, including biologically active, naturally-occurring GDF15 variants. The term includes the 112 amino acid human GDF15 mature sequence.

The term "muteins" as used herein refers broadly to mutated recombinant proteins, i.e., a polypeptide comprising an artificially introduced change in amino acid sequence, e.g., a change in amino acid sequence generated in the laboratory or other facility by human intervention ("hand of man"). These proteins usually carry single or multiple amino acid substitutions and are frequently derived from cloned genes that have been subjected to site-directed or random mutagenesis, or from completely synthetic genes. "Muteins" of the present disclosure thus encompass, for example, amino acid substitutions and/or amino acid deletions (e.g., N-terminal truncations of 1, 2, 3, 4, 5, or 6 or more amino acids) relative to a reference polypeptide, e.g., relative to mature human GDF15.

As used herein in reference to native human GDF15 or a GDF15 mutein, the terms "modified", "modification" and the like refer to one or more changes that enhance a desired property of human GDF15, a naturally-occurring GDF15 variant, or a GDF15 mutein, where the change does not alter the primary amino acid sequence of the GDF15. "Modification" includes a covalent chemical modification that does not alter the primary amino acid sequence of the GDF15 polypeptide itself. Such desired properties include, for example, enhancing solubility, prolonging the circulation half-life, increasing the stability, reducing the clearance, altering the immunogenicity or allergenicity, improving aspects of manufacturability (e.g., cost and efficiency), and enabling the raising of particular antibodies (e.g., by introduction of unique epitopes) for use in detection assays. Changes to human GDF15, a naturally-occurring GDF15 variant, or a GDF15 mutein that may be carried out include, but are not limited to, pegylation (covalent attachment of one or more molecules of polyethylene glycol (PEG), or derivatives thereof); glycosylation (e.g., N-glycosylation), polysialylation and hesylation; maltose binding protein fusion; albumin fusion (e.g., HSA fusion); albumin binding through, for example, a conjugated fatty acid chain (acylation); Fc-fusion; and fusion with a PEG mimetic. Some particular embodiments entail modifications involving polyethylene glycol, other particular embodiments entail modifications involving albumin, and still other particular modifications entail modifications involving glycosylation.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

The term "probe" refers to a fragment of DNA or RNA corresponding to a gene or sequence of interest, wherein the fragment has been labeled radioactively (e.g., by incorporating $32^P$ or $35^S$) or with some other detectable molecule, such as biotin, digoxygenin or fluorescein. As stretches of DNA or RNA with complementary sequences will hybridize, a probe can be used, for example, to label viral plaques, bacterial colonies or bands on a gel that contain the gene of interest. A probe can be cloned DNA or it can be a synthetic DNA strand; the latter can be used to obtain a cDNA or genomic clone from an isolated protein by, for example, microsequencing a portion of the protein, deducing the nucleic acid sequence encoding the protein, synthesizing an oligonucleotide carrying that sequence, radiolabeling the sequence and using it as a probe to screen a cDNA library or a genomic library.

The term "heterologous" refers to two components that are defined by structures derived from different sources. For example, in the context of a polypeptide, a "heterologous" polypeptide may include operably linked amino acid sequences that are derived from different polypeptides (e.g., a first component comprising a recombinant polypeptide and a second component derived from a native GDF15 polypeptide). Similarly, in the context of a polynucleotide encoding a chimeric polypeptide, a "heterologous" polynucleotide may include operably linked nucleic acid sequences that can be derived from different genes (e.g., a first component from a nucleic acid encoding a polypeptide according to an embodiment disclosed herein and a second component from a nucleic acid encoding a carrier polypeptide). Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin than the promoter, the coding sequence or both). For example, a T7 promoter operably linked to a polynucleotide encoding a GDF15 polypeptide or domain thereof is said to be a heterologous nucleic acid. In the context of recombinant cells, "heterologous" can refer to the presence of a nucleic acid (or gene product, such as a polypeptide) that is of a different genetic origin than the host cell in which it is present.

The term "operably linked" refers to linkage between molecules to provide a desired function. For example, "operably linked" in the context of nucleic acids refers to a functional linkage between nucleic acid sequences. By way of example, a nucleic acid expression control sequence (such as a promoter, signal sequence, or array of transcription factor binding sites) may be operably linked to a second polynucleotide, wherein the expression control sequence affects transcription and/or translation of the second polynucleotide. In the context of a polypeptide, "operably linked" refers to a functional linkage between amino acid sequences (e.g., different domains) to provide for a described activity of the polypeptide.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" a GDF15 polypeptide), is meant to indicate that the polypeptide or nucleic acid has a sequence that is based on that of a reference polypeptide or nucleic acid (e.g., a naturally occurring GDF15 polypeptide or a GDF15-encoding nucleic acid), and is not meant to be limiting as to the source or method in which the protein or nucleic acid is made. By way of example, the term "derived from" includes homologues or variants of reference amino acid or DNA sequences.

In the context of a polypeptide, the term "isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates the polypeptide has been separated from an environment in which it was made by either synthetic or recombinant means.

"Enriched" means that a sample is non-naturally manipulated (e.g., by a scientist or a clinician) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "antibodies" (Abs) and "immunoglobulins" (Igs) refer to glycoproteins having the same structural characteristics. While antibodies exhibit binding specificity to a specific antigen, immunoglobulins include both antibodies and other antibody-like molecules which lack antigen specificity. Antibodies are described in detail hereafter.

The term "monoclonal antibody" refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. In contrast to polyclonal antibody preparations, which can include different antibodies directed against different determinants (epitopes), each monoclonal antibody is directed against a single determinant on the antigen.

In the context of an antibody, the term "isolated" refers to an antibody that has been separated and/or recovered from contaminant components of its natural environment; such contaminant components include materials which might interfere with diagnostic or therapeutic uses for the antibody, and may include enzymes, hormones, and other proteinaceous or nonproteinaceous solutes.

Growth Differentiation Factor 15 (GDF15)

GDF15, also known as MIC-1 (macrophage inhibitory cytokine-1), PDF, PLAB, NAG-1, TGF-PL, and PTGFB, is a member of the transforming growth factor β (TGF-β) super-family. GDF15, which is synthesized as a 62 kDa intracellular precursor protein that is subsequently cleaved by a furin-like protease, is secreted as a 25 kDa disulfide-linked protein. [See, e.g., Fairlie et al., J. Leukoc. Biol 65:2-5 (1999)]. GDF15 mRNA is seen in several tissues, including liver, kidney, pancreas, colon and placenta, and GDF15 expression in liver can be significantly up-regulated during injury of organs such as the liver, kidneys, heart and lungs.

The GDF15 precursor is a 308 amino acid polypeptide (NCBI Ref. Seq. NP_004855.2) containing a 29 amino acid signal peptide, a 167 amino acid pro-domain, and a mature domain of 112 amino acids which is excised from the pro-domain by furin-like proteases. A 308-amino acid GDF15 polypeptide is referred to as a "full-length" GDF15 polypeptide; a 112-amino acid GDF15 polypeptide (e.g., amino acids 197-308 of the amino acid sequence depicted in FIG. 1A) is a "mature" GDF15 polypeptide. Unless otherwise indicated, the term "GDF15" refers to the 112 amino acid mature sequence. In addition, numerical references to particular GDF15 residues refer to the 112 amino acid mature sequence (i.e., residue 1 is Ala (A), and residue 112 is Ile (I); see FIG. 1B). Of note, while the GDF15 precursor amino acid sequence predicts three excision sites, resulting in three putative forms of "mature" human GDF15 (i.e., 110, 112 and 115 amino acids), the 112 amino acid mature sequence is accepted as being correct.

The scope of the present disclosure includes GDF15 orthologs, and modified forms thereof, from other mammalian species, and their use, including mouse (NP_035949), chimpanzee (XP_524157), orangutan (XP_002828972), Rhesus monkey (EHH29815), giant panda (XP_002912774), gibbon (XP_003275874), guinea pig (XP_003465238), ferret (AER98997), cow (NP_001193227), pig (NP_001167527), dog (XP_541938) and platypus (*Ornithorhynchus anatinus*; AFV61279. The mature form of human GDF15 has approximately 67% amino acid identity to the mouse ortholog.

A. Modified GDF15 Muteins Having Desired Physical Properties

The present disclosure contemplates, in part, modified GDF15 muteins, wherein one or more amino acid residues of the mature GDF15 polypeptide are substituted with one or more other residues. For example, the GDF15 mutein component of a modified GDF15 mutein may include one or more substitutions of native lysine residues (i.e., residues 62, 69, 91 and 107) with any other amino acid, with the exception that GDF15 muteins containing K62Q are inactive. As such, a modified GDF15 containing K62Q may be specifically excluded from the GDF15 muteins of the present disclosure. GDF15 muteins retaining K62 but incorporating any combination of K69Q, K91R and/or K107R are active in lowering body weight to a level comparable to that of mature human GDF15 control.

In other GDF15 muteins, one or more GDF15 residue is substituted with another amino acid, including, for example, the following substitutions: H18Q, T19S or V20L. Such GDF15 muteins are candidates for modification to improve one or more inherent physical properties (e.g., stability, serum half-life, and generation of particular antibodies for use in detection assays and protein purification).

Examples of other candidate GDF15 muteins include, but are not limited to, the following:
  mutein v1) K69Q, K91R, K107R (SEQ ID NO:166);
  mutein v2) K62Q, K91R, K107R (SEQ ID NO:167);
  mutein v3) K62Q, K69Q, K107R (SEQ ID NO:168);
  mutein v4) K62Q, K69Q, K91R (SEQ ID NO:169);
  mutein v5) K91R, K107R (SEQ ID NO:170);
  mutein v6) K69Q, K107R (SEQ ID NO:171);
  mutein v7) K69Q, K91R (SEQ ID NO:172);
  mutein v8) H18Q, T19S, V20L, K62Q, K69Q, K91R, K107R (SEQ ID NO:173);
  mutein v9) H18Q, T19S, V20L, K62Q, K91R, K107R (SEQ ID NO:174);
  mutein v10) H18Q, T19S, V20L, K62Q, K69Q, K107R (SEQ ID NO:175); and
  mutein v11) H18Q, T19S, V20L, K62Q, K69Q, K91R (SEQ ID NO:176).

Further examples of GDF15 muteins include, but are not limited to, a human GDF15 polypeptide comprising an amino acid substitution at one, two, three, four or more of R2, N3, G4, D5, H6, P8, L9, G10, P11, G12, R13, R16, L17, H18, T19, V20, R21, S23, L24, E25, D26, L27, G28, W29, D31, W32, V33, L34, S35, R37, E38, V39, Q40, V41, T42, M43, I45, P49, S50, Q51, F52, R53, N56, M57, H58, Q60, I61, T63, S64, H66, R67, L68, K69, P70, D71, T72, V73, P74, P76, V79, P80, S82, N84, P85, M86, V87, L88, I89, Q90, K91, T92, D93, T94, G95, V96, S97, L98, Q99, T100, Y101, D102, D103, L104, L105, K107, D108, H110, and I112, wherein the amino acid substitution may be a conservative amino acid substitution or a nonconservative amino acid substitution. In one example, the GDF15 muteins contain an alanine substituted for one, two three, four or more of R2, N3, G4, D5, H6, P8, L9, G10, P11, G12, R13, R16, L17, H18, T19, V20, R21, S23, L24, E25, D26, L27, G28, W29, D31, W32, V33, L34, S35, R37, E38, V39, Q40, V41, T42, M43, I45, P49, S50, Q51, F52, R53, N56, M57, H58, Q60, I61, T63, S64, H66, R67, L68, K69, P70, D71, T72, V73, P74, P76, V79, P80, S82, N84, P85, M86, V87, L88, I89, Q90, K91, T92, D93, T94, G95, V96, S97, L98, Q99, T100, Y101, D102, D103, L104, L105, K107, D108, H110, and I112. In some embodiments, the GDF15 muteins do not have an amino acid substitution at P36, G46, K62, L65, and/or Y83. In some embodiments, the GDF15 muteins do not have an amino acid substitution at C7, C14, C15, C44, C48, C77, C78, C109 and/or C111.

As indicated above and as described in more detail below, native GDF15 and GDF15 muteins may be modified through, for example, pegylation (covalent attachment of one or more molecules of polyethylene glycol (PEG), or derivatives thereof); glycosylation (e.g., N-glycosylation); polysialylation; albumin fusion molecules comprising serum albumin (e.g., human serum albumin (HSA), cyno serum albumin, or bovine serum albumin (BSA)); albumin binding through, for example, a conjugated fatty acid chain (acylation); Fc-fusion; and fusion with a PEG mimetic. In certain embodiments, the modifications are introduced in a site-specific manner. In other embodiments, the modifications include a linker.

In particular embodiments, the present disclosure contemplates modification of mature human GDF15 and GDF15 muteins by conjugation with albumin. In other embodiments, the present disclosure contemplates modification of mature human GDF15 and GDF15 muteins via N-glycosylation. The characteristics of albumins and GDF15/GDF15 mutein conjugates thereof (e.g., fusion proteins), and N-glycosylated GDF15/GDF15 muteins are described further hereafter.

Example 1 indicates the effects on body weight, food intake, and fasted blood glucose of a fusion molecule comprising mature HSA fused to the N-terminus of mature human GDF15 through a non-cleavable 3×(4Gly-Ser) linker (SEQ ID NO:64). Administration of the fusion molecule (which exhibited improved half-life, expression, secretion and solubility relative to unconjugated recombinant human GDF15) resulted in significant improvement in body weight (FIG. 2A), food intake (FIG. 2B), and non-fasted blood glucose (FIG. 2C) compared to vehicle control. These data demonstrate that an HSA fusion with GDF15 is active, and that such fusion molecules represent a viable approach for enhancing certain beneficial properties of GDF15 muteins. The data also indicate that measurement of the indicated parameters may be useful as a platform for high-throughput screening of muteins.

Example 2 describes the methodology used to identify means for improving the physical properties (e.g., solubility and stability) of mature human GDF15. A set of six hydrophobic residues predicted to be surface-accessible were mutated to alanine as a means of increasing surface hydrophobicity. Fusion molecules were generated wherein each of the six GDF15 mutein sequences was fused to HSA through the linker depicted in FIG. 1H (a non-cleavable 3×(4Gly- Ser) linker (SEQ ID NO:64); the sequences set forth in FIG. 3 neither depict the HSA component nor the linker component of the fusion molecules.

Thereafter, the fusion molecules were monitored for expression as secreted disulfide-linked homodimers (see FIG. 4). Data generated as described in the examples were used to evaluate solubility resulting from introduction of N-linked Glycosylation consensus site(s) along the sequence of mature human GDF15, and to address solubility limitations associated with surface hydrophobicities and hydrophilicities inherent to mature human GDF15. The evaluation entailed construction of GDF15/GDF15 muteins-N-terminal HSA fusion molecules containing a Factor Xa proteolytic-sensitive, cleavable linker. Each mutein was generated as a non-HSA fusion using the mature sequence of hGDF15 with an IgK signal peptide. Reduction of surface hydrophobicity of five GDF15 muteins (w29, w32, w52, w68 and w89; see FIG. 3) was assessed via selective mutagenesis of hydrophobic residues to alanine and were generated as either HSA-fusions containing a factor Xa proteolytic-sensitive cleavable linker or as a bacterial refold containing the 112 amino acid sequence of mature hGDF15 muteins containing an N-terminal Methionine. Comparison of the solubility of these five muteins relative to mature human GDF15 indicated that w52 and w89 were the only muteins exhibiting improved solubility.

In addition, the surface hydrophilicity of the following five GDF15 mutein sequences (see FIG. 5) was assessed via selective mutagenesis of acidic residues to alanine: w113, w114, w115, w116 and w117. Comparison of the relative solubility of these five muteins to mature human GDF15 indicated that w116 was the only mutein that exhibited improved solubility.

The mature human GDF15 sequence was then assessed for its ability to accommodate introduction of N-linked Glycosylation consensus site(s). In this context, a single amino acid substitution would impart the required consensus site within the mature human GDF15 sequence, the consensus site for N-linked glycosylation being defined as "Asn-Xxx-Ser/Thr", where "Xxx" cannot be a proline residue. Based on a scan of the mature human GDF15 sequence, 14 possible single-point muteins were identified that would accommodate introduction of the N-Glycan consensus site. FIG. 6 depicts the sequences of the 14 mono-glycosylation muteins, as well as additional combinatorial di-Glycosylation muteins. Each of these engineered N-Glycan muteins was evaluated for both N-glycan site occupancy and for secretion as a folded GDF15 homodimer into mammalian tissue culture media. As set forth in FIG. 7, 10 of the 14 mono-glycosylated muteins were secreted as folded GDF15 homodimers, whereas 4 (w123, w125, w127 and w129) did not result in dimer formation. Of the 10 mono-glycosylation muteins that secreted as homodimers, two (w121 and w124) exhibited low occupancy and their solubility was not subsequently evaluated (see FIG. 7).

Engineered human mono-glycosylated GDF15 muteins which were both secreted as homodimers and possessed high glycan occupancy within the consensus site exhibited improved solubility compared to mature human GDF15 (see Example 3; FIG. 8). These GDF15 muteins were assessed for their ability to effect a reduction in food intake, and the data are set forth in FIG. 9A.

Finally, hydrodynamic radii of engineered GDF15 N-Glycan muteins relative to mature human GDF15 were assessed utilizing analytical gel filtration chromatography (see Example 4). As indicated in FIG. 10, each of the N-linked glycan muteins increased the hydrodynamic radii of the human GDF15 disulfide-linked dimer. Thus, each mutein may potentially serve as a starting point for generating molecules having, for example, a favorable in vivo half-life.

Relative to mature human GDF15, many of the N-Glycosylation muteins exhibiting the most substantial improvements in physical properties (e.g., enhancement of solubility and increase in hydrodynamic radii) while maintaining an efficacious food intake reduction, appear to be localized to a specific epitope/region of human GDF15. Specifically, mutagenesis resulting in the introduction of N-Glycoyslation consensus sites appeared to be tolerated in the epitope/region spanning Gln90 to Leu98. Thus, though an understanding of preferred regions for mutagenesis is not required in order to practice the present disclosure, this epitope/region is believed to be advantageous for introduction of N-Glycosylation consensus sites.

Human serum albumin (HSA) as a cleavable fusion and expression partner was then further exploited for the production and purification of various different GDF15 orthologs and BMP/TGF family members as described in FIGS. 11A, 11B and 12. Based on expression profiling and characterization of secreted constructs it appears that human serum albumin (as per standardized expression template of IgK-HSA-2×(4Gly-Ser)-IEGR-GDF15 (SEQ ID NO:12)) as a fusion partner is well suited for the mature human GDF15 amino acid sequence. The expression template is optimized for human GDF15 and orthologs which retain at least 45%, at least 50%, at least 60% at least 65%, 70%, 75%, 80%, 85%, 90%, 95% or more sequence identity to the amino acid sequence of mature human GDF15.

Specific residues that are amenable to amino acid substitution were identified by Alanine scanning mutagenesis of the 112 amino acid sequence of mature human GDF15, with the results illustrated in FIGS. 7, 8, 9 and 10. The human serum albumin expression fusion was utilized to identify regions not tolerant of mutagenesis. Cysteine residues were not subjected to mutation to maintain cysteine knot folding (C7, C14, C15, C44, C48, C77, C78, C109 and C111). Five sites were identified that would not tolerate mutagenesis to Alanine: w36, w46, w62, w65 and w83 (P36, G46, K62, L65, and Y83, described in FIGS. 13 and 14). The resultant expression and purification of each Alanine mutein were assessed for aggregation state and homodimerization fidelity, and as a result identified residues amenable to mutagenesis without detriment to fold or biological function of GDF15. Examples of residues amenable to amino acid substitution include, but are not limited to: N3A, N3Q, N3E, N3S, N3T, G4P, D5S, D5T, Q40A, Q40E, Q40D, Q40H, M43A, M43V, M43F, Q51A, Q51E, Q51L, Q51H, N56A, N56S, M57A, M571, M57T, Q60A, Q60L, N84A, N84E, N84Q, N84T, M86A, M86V, Q90A, Q90E, Q90E, Q90H, Q95A, Q95E, Q95D, Q95H, Q95T, Q95S.

In particular embodiments, modifications to GDF15 were designed to address various undesirable effects, for example, deamidation at residue N3 and/or proteolysis at residue R2. In addition to addressing deamidation at N3, modifications (e.g., substitutions) may also be made to other asparagine residues (e.g., N84) within the mature GDF15 in order to prevent deamidation.

As discussed further in Example 6, having demonstrated that N3 is amenable to mutagenesis without substantial detriment to activity (as illustrated by the N3A mutation described herein), it is reasonable to expect that other amino acids can be substituted at this site, such as N3Q, N3E, N3T or N3S. The skilled artisan is familiar with techniques (e.g., alignment of mature human GDF15 with a non-human GDF15 ortholog) for identifying amino acid residues that tolerate substitution and amino acid residues that can be substituted for those in the native sequence.

Other modifications of Polypeptides are contemplated herein. For example, deamidation at N3 can create an unnatural Aspartate residue, which can result in an iso-aspartate isomerization due to the presence of G4 directly C-terminal to the deamidation event (i.e., Asp-Gly site). Deamidation at N3 may be prevented by mutating the isomerization partner Gly to a Pro (G4P) in order to disrupt the Asp-Gly pairing. Additionally, deamidation can be prevented via creation of an N-linked glycosylation site at N3 via mutagenesis of D5, e.g., to DST or DSS.

Other embodiments of the present disclosure contemplate elimination of deamidation at N3 of mature GDF15 through truncation of residues at the N-terminus. The first 3 residues are removed from the N-terminus in a particular embodiment, the first 4 residues are removed in a further embodiment, the first 5 residues are removed in a sill further embodiment, and 6 or more residues are removed in additional embodiments. Such truncations have the further benefit of correcting for proteolysis at R2 (as the arginine residue at that position has been cleaved off).

The present disclosure contemplates the combination of the modifications described above (e.g., truncation of amino acid residues at the N-terminus) with one or more other modifications C-terminal to residue three.

Finally, Example 7 describes engineering of genetic fusions to the N-terminus of mature human GDF15 amino acid sequence. These constructs include the design and implementation of fusions containing human Fc domains, albumin binding domains and maltose binding domains (see FIGS. 15 and 16). In each case, the expressed construct was assessed for secretion fidelity from an appropriate transient expression system, and purified for assessment of physical properties. In the case of Albumin Binding Domain (ABD) and Maltose Binding Domain (MBD), a significant increase to maximum solubility was observed which directly impacts formulation considerations for these molecules as pharmaceutical agents (i.e., maximal formulatable dose). Additionally, FIG. 16B illustrates the 2-week efficacy (body weight reduction) of an ABD fused to GDF15 (ABD-GDF15) following a single acute dose of 3 mg/kg in ob/ob mouse model. PK profiling of the ABD-GDF15 demonstrated a half-life in excess of 24 hrs in ob/ob mice, demonstrating a desirable improvement of GDF15 pharmaceutical properties.

Nucleic acid molecules encoding the Polypeptides are contemplated by the present disclosure, including their naturally-occurring and non-naturally occurring isoforms, allelic variants and splice variants. As previously noted, a Polypeptide also refers to polypeptides that have one or more alterations in the amino acid residues (e.g., at locations that are not conserved across variants or species) while retaining the conserved domains and having the same biological activity as the naturally-occurring Polypeptides. The present disclosure also encompasses nucleic acid sequences that vary in one or more bases from a naturally-occurring DNA sequence but still translate into an amino acid sequence that corresponds to a Polypeptide due to degeneracy of the genetic code. For example, GDF15 may refer to amino acid sequences that differ from the naturally-occurring sequence by one or more conservative substitutions, tags, or conjugates (e.g., a Polypeptide).

Thus, in addition to any naturally-occurring GDF15 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution (e.g., a Polypeptide).

By "conservative amino acid substitution" generally refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions preserve the activity of the protein by replacing an amino acid(s) in the protein with an amino acid with a side chain of similar acidity, basicity, charge, polarity, or size of the side chain. Guidance for substitutions, insertions, or deletions may be based on alignments of amino acid sequences of different variant proteins or proteins from different species.

The present disclosure also contemplates active fragments (e.g., subsequences) of the Polypeptides containing contiguous amino acid residues derived from the mature GDF15 polypeptide or a GDF15 mutein. The length of contiguous amino acid residues of a peptide or a polypeptide subsequence varies depending on the specific naturally-occurring amino acid sequence from which the subsequence is derived. In general, peptides and polypeptides may be from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, from about 40 amino acids to about 50 amino acids, from about 50 amino acids to about 75 amino acids, from about 75 amino acids to about 100 amino acids, or from about 100 amino acids up to the full-length peptide or polypeptide.

Additionally, the Polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable Polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 5 amino acids to about 10 amino acids, from about 10 amino acids to about 12 amino acids, from about 12 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, from about 90 amino acids to about 100 amino acids, or from about 100 amino acids to 112 amino acids or 113 amino acids, of one of the amino acid sequence depicted in FIGS. 1, 3, 5, and 6.

The Polypeptides may be isolated from a natural source (e.g., an environment other than its naturally-occurring environment) and also may be recombinantly made (e.g., in a genetically modified host cell such as bacteria; yeast; *Pichia*; insect cells; and the like), where the genetically modified host cell is modified with a nucleic acid comprising a nucleotide sequence encoding the polypeptide. The Polypeptides may also be synthetically produced (e.g., by cell-free chemical synthesis). Methods of productions are described in more detail below.

A Polypeptide may be generated using recombinant techniques to manipulate different GDF15-related nucleic acids known in the art to provide constructs capable of encoding the Polypeptide. It will be appreciated that, when provided a particular amino acid sequence, the ordinary skilled artisan will recognize a variety of different nucleic acid molecules encoding such amino acid sequence in view of her background and experience in, for example, molecular biology.

B. Modulators

The term "Modulators" refers to both Polypeptides and Activators. As indicated above, Activators are agents that, for example, stimulate, increase, activate, facilitate, enhance activation, sensitize or up-regulate the function or activity of one or more Polypeptides. In addition, Activators include agents that operate through the same mechanism of action as the Polypeptides (i.e., agents that modulate the same signaling pathway as the Polypeptides in a manner analogous to that of the Polypeptides) and are capable of eliciting a biological response comparable to (or greater than) that of the Polypeptides. An Activator may be, for example, a small molecule agonist compound, or other bioorganic molecule.

In some embodiments, the Activator is a small molecule agonist compound. Numerous libraries of small molecule compounds (e.g., combinatorial libraries) are commercially available and can serve as a starting point for identifying such an Activator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

In still further embodiments, the Activator is an agonistic polypeptide structurally distinguishable from the Polypeptides but having comparable activity. The skilled artisan is able to identify such polypeptides having desired properties.

Amide Bond Substitutions

In some cases, a Polypeptide includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of a Polypeptide can be substituted.

In another example, one or more amide linkages (—CO—NH—) in a Polypeptide can be replaced with a linkage which is an isostere of an amide linkage, such as —CH$_2$NH—, CH$_2$S—, —CH$_2$CH$_2$—, —CH=CH-(cis and trans), —COCH$_2$—, —CH(OH)CH$_2$— or —CH$_2$SO—. One or more amide linkages in a Polypeptide can also be replaced by, for example, a reduced isostere pseudopeptide bond. See Couder et al. (1993) Int. J. Peptide Protein Res. 41:181-184. Such replacements and how to effect are known to those of ordinary skill in the art.

Amino Acid Substitutions

One or more amino acid substitutions can be made in a Polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids;

e) substitution of side chain amide residue, including asparagine, glutamine, and alkyl or aromatic substituted derivatives of asparagine or glutamine; and f) substitution of hydroxyl containing amino acids, including serine, threonine, homoserine, 2,3-diaminopropionic acid, and alkyl or aromatic substituted derivatives of serine or threonine.

In some cases, a Polypeptide comprises one or more naturally occurring non-genetically encoded L-amino acids, synthetic L-amino acids or D-enantiomers of an amino acid. For example, a Polypeptide can comprise only D-amino acids. For example, a Polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into a Polypeptide to provide for linkage to another peptide via a disulfide linkage or to provide for cyclization of the Polypeptide. Methods of introducing a cysteine or cysteine analog are known in the art; see, e.g., U.S. Pat. No. 8,067,532.

A Polypeptide can be cyclized. One or more cysteine or cysteine analogs can be introduced into a Polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moiety) that can form a cyclizing bond can be used and/or introduced. A cyclizing bond can be generated with any combination of amino acids (or with amino acid and —(CH2)$_n$—CO— or —(CH2)$_n$—C$_6$H$_4$—CO—) with functional groups which allow for the introduction of a bridge. Some examples are disulfides, disulfide mimetics such as the —(CH2)$_n$— carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives of the modulator compounds of the present disclosure include C-terminal hydroxymethyl derivatives, O-modified derivatives (e.g., C-terminal hydroxymethyl benzyl ether), N-terminally modified derivatives including substituted amides such as alkylamides and hydrazides.

In some cases, one or more L-amino acids in a Polypeptide is replaced with a D-amino acid.

In some cases, a Polypeptide is a retroinverso analog. Sela and Zisman (1997) FASEB J. 11:449. Retro-inverso peptide analogs are isomers of linear polypeptides in which the direction of the amino acid sequence is reversed (retro) and the chirality, D- or L-, of one or more amino acids therein is inverted (inverso) e.g., using D-amino acids rather than L-amino acids. See, e.g., Jameson et al. (1994) Nature 368:744; and Brady et al. (1994) Nature 368:692.

A Polypeptide can include a "Protein Transduction Domain" (PTD), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a Polypeptide, while in other embodiments, a PTD is covalently linked to the carboxyl terminus of a Polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:177); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:178); Transportan GWTLNSAGYLLGKINL-KALAALAKKIL (SEQ ID NO:179); KALAWEAKLAKA-LAKALAKHLAKALAKALKCEA (SEQ ID NO:180); and RQIKIWFQNRRMKWKK (SEQ ID NO:181). Exemplary PTDs include, but are not limited to, YGRKKRRQRRR (SEQ ID NO:177), RKKRRQRRR (SEQ ID NO:182); an arginine homopolymer of from 3 arginine residues to 50 arginine residues; Exemplary PTD domain amino acid sequences include, but are not limited to, any of the following: YGRKKRRQRRR (SEQ ID NO:177); RKKRRQRR (SEQ ID NO:183); YARAAARQARA (SEQ ID NO:184); THRLPRRRRRR (SEQ ID NO:185); and GGRRAR-RRRRR (SEQ ID NO:186).

The carboxyl group COR$_3$ of the amino acid at the C-terminal end of a Polypeptide can be present in a free form (R$_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched C$_1$-C$_6$-alkyl alcohols, e.g., ethyl alcohol or tert-butanol. The carboxyl group can also be amidated with primary or secondary amines such as ammonia, branched or unbranched C$_1$-C$_6$-alkylamines or C$_1$-C$_6$ di-alkylamines, e.g., methylamine or dimethylamine.

The amino group of the amino acid NR$_1$R$_2$ at the N-terminus of a Polypeptide can be present in a free form (R$_1$=H and R$_2$=H) or in the form of a physiologically-tolerated salt such as, e.g., a chloride or acetate. The amino group can also be acetylated with acids such that R$_1$=H and R$_2$=acetyl, trifluoroacetyl, or adamantyl. The amino group can be present in a form protected by amino-protecting groups conventionally used in peptide chemistry such as, e.g., Fmoc, Benzyloxy-carbonyl (Z), Boc, or Alloc. The amino group can be N-alkylated in which R$_1$ and/or R$_2$=C$_1$-C$_6$ alkyl or C$_2$-C$_5$ alkenyl or C$_7$-C$_9$ aralkyl. Alkyl residues can be straight-chained, branched or cyclic (e.g., ethyl, isopropyl and cyclohexyl, respectively).

Particular Modifications to Enhance and/or Mimic GDF15 Function

A Polypeptide can include one or more modifications that enhance a property desirable in a protein formulated for therapy (e.g., serum half-life), that enable the raising of antibodies for use in detection assays (e.g., epitope tags), that provide for ease of protein purification, etc. Such modifications include, but are not limited to, including pegylation (covalent attachment of one or more molecules of polyethylene glycol (PEG), or derivatives thereof); glycosylation (N- and O-linked); polysialylation; albumin fusion; albumin binding through a conjugated fatty acid chain (acylation); Fc-fusion proteins; and fusion with a PEG mimetic.

As set forth herein, the present disclosure contemplates fusion molecules comprising mature GDF15 polypeptide (e.g., mature human GDF15) or a GDF15 mutein polypeptide (e.g., a mutein of mature human GDF15), wherein the mature GDF15 polypeptide or GDF15 mutein polypeptide comprises at least one modification that does not alter its amino acid sequence, and wherein the modification improves at least one physical property of the polypeptide or the mutein polypeptide. In one embodiment, the GDF15 polypeptide or GDF15 mutein polypeptide modification comprises conjugation with serum albumin (e.g., human serum albumin (HSA), cyno serum albumin, or bovine serum albumin (BSA)). In some embodiments, the physical property is solubility.

In embodiments wherein the fusion molecule comprises a modified GDF15 polypeptide or a GDF15 mutein polypeptide, either of which is conjugated to albumin, the solubility of the fusion molecule is improved relative to unconjugated recombinant human GDF15. In certain embodiments, the fusion molecule has a solubility of at least 1 mg/mL in phosphate buffered saline (PBS) at pH 7.0, In other embodiments, the fusion molecule has a solubility of at least 2 mg/mL, at least 3 mg/mL, at least 4 mg/mL, or at least 5 mg/mL. In other embodiments, the fusion molecule has a solubility of at least 6 mg/mL in phosphate buffered saline (PBS) at pH 7.0, at least 7 mg/mL, at least 8 mg/mL, at least 9 mg/mL, or at least 10 mg/mL. In particular embodiments, the fusion molecule has a solubility of greater than 0 mg/mL.

Pegylation:

The clinical effectiveness of protein therapeutics is often limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes (see, for example, typically via a linking moiety covalently bound to both the protein and the nonproteinaceous polymer, e.g., a PEG). Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, but certain embodiments have a molecular weight between 500 and 20,000 while other embodiments have a molecular weight between 4,000 and 10,000.

The present disclosure also contemplates compositions of conjugates wherein the PEGs have different n values and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. For example, cation exchange chromatography may be used to separate conjugates, and a fraction is then identified which contains the conjugate having, for example, the desired number of PEGs attached, purified free from unmodified protein sequences and from conjugates having other numbers of PEGs attached.

PEG may be bound to a polypeptide of the present disclosure via a terminal reactive group (a "spacer"). The spacer is, for example, a terminal reactive group which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments the reaction is terminated by acidifying the reaction mixture and freezing at, e.g., −20° C.

The present disclosure also contemplates the use of PEG Mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties of proteins and can also be important in protein stability, secretion, and subcellular localization. Indeed, glycosylation of the GDF15- and GDF15 mutein-related polypeptides described herein imparts beneficial improvements to their physical properties. By way of example, but not limitation, solubility of GDF15/GDF15 muteins can be improved by glycosylation, and such improvement may be substantial (see Examples). The solubility improvement exhibited by such modified GDF15/GDF15 muteins can, for example, enable the generation of formulations more suitable for pharmaceutical administration than non-glycosylated GDF15/GDF15 muteins. The glycosylated GDF15/GDF15 mutein polypeptides may also exhibit enhanced stability. Moreover, the polypeptides may improve one or more pharmacokinetic properties, such as half-life.

Proper glycosylation can be essential for biological activity. In fact, some genes from eucaryotic organisms, when expressed in bacteria (e.g., *E. coli*) which lack cellular processes for glycosylating proteins, yield proteins that are recovered with little or no activity by virtue of their lack of glycosylation.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants.

The polypeptide sequences of the present disclosure may optionally be altered through changes at the DNA level, particularly by mutating the DNA encoding the polypeptide at preselected bases such that codons are generated that will translate into the desired amino acids. Another means of increasing the number of carbohydrate moieties on the polypeptide is by chemical or enzymatic coupling of glycosides to the polypeptide. Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Dihydrofolate reductase (DHFR)-deficient Chinese Hamster Ovary (CHO) cells are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

Polysialylation:

The present disclosure also contemplates the use of polysialylation, the conjugation of peptides and proteins to the naturally occurring, biodegradable α-(2→8) linked polysialic acid ("PSA") in order to improve their stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of activity in vivo activity, and reduction in immunogenicity and antigenicity (see, e.g., G. Gregoriadis et al., Int. J. Pharmaceutics 300(1-2):125-30). As with modifications with other conjugates (e.g., PEG), various techniques for site-specific polysialylation are available (see, e.g., T. Lindhout et al., PNAS 108(18)7397-7402 (2011)).

Fusion Proteins.

The present disclosure contemplates fusion proteins of wildtype mature GDF15 (e.g., human GDF15), as well as fusion proteins of the Polypeptides of the present disclosure (e.g., modified human GDF15 molecules, muteins of human GDF15, modified GDF15 muteins, and the like). Such fusion proteins are generally comprised of a non-GDF15 polypeptide (e.g., albumin (e.g., HSA) or a fragment thereof: ABD; Fc polypeptide; MBD, which may be referred to herein as a "fusion partner", conjugated to the wildtype GDF15 polypeptide or Polypeptide of the present disclosure at its N-terminus or C-terminus. Optionally, the fusion partner may be conjugated to the wildtype GDF15 or Polypeptide through a linker polypeptide. The linker polypeptide may optionally be a cleavable linker, e.g., an enzymatically cleavable linker. Examples of fusion partners are described below.

Albumin Fusion:

Additional suitable components and molecules for conjugation include albumins such as human serum albumin (HSA), cyno serum albumin, and bovine serum albumin (BSA).

Mature HSA (see FIG. 1D), a 585 amino acid polypeptide (~67 kDa) having a serum half-life of ~20 days, is primarily responsible for the maintenance of colloidal osmotic blood pressure, blood pH, and transport and distribution of numerous endogenous and exogenous ligands. The protein has three structurally homologous domains (domains I, II and III), is almost entirely in the alpha-helical conformation, and is highly stabilized by 17 disulphide bridges. The three primary drug binding regions of albumin are located on each of the three domains within sub-domains IB, IIA and IIIA.

Albumin synthesis takes place in the liver, which produces the short-lived, primary product preproalbumin. Thus, the full-length HSA has a signal peptide of 18 amino acids (MKWVTFISLLFLFSSAYS; SEQ ID NO:164) followed by a pro-domain of 6 amino acids (RGVFRR; SEQ II) NO:165); this 24 amino acid residue peptide may be referred to as the pre-pro domain. HSA can be expressed and secreted using its endogenous signal peptide as a pre-pro-domain (see FIG. 1C). Alternatively, HSA can be expressed and secreted using a IgK signal peptide (SEQ ID NO:53) fused to a mature construct (D25-L609; of SEQ ID NO:5); in a construct used to generate the experimental data presented herein, the endogenous signal peptide was replaced with human IgK signal peptide, and the endogenous pro-domain was left out entirely. In turn, preproalbumin is rapidly co-translationally cleaved in the endoplasmic reticulum lumen at its amino terminus to produce the stable, 609-amino acid precursor polypeptide, proalbumin (see FIG. 1C). Proalbumin then passes to the Golgi apparatus, where it is converted to the 585 amino acid mature albumin by a furin-dependent amino-terminal cleavage. Unless otherwise indicated, reference herein to "albumin" or to "mature albumin" is meant to refer to HSA.

The primary amino acid sequences, structure, and function of albumins are highly conserved across species, as are the processes of albumin synthesis and secretion. Albumin serum proteins comparable to HSA are found in, for example, cynomolgus monkeys, cows, dogs, rabbits and rats. Of the non-human species, bovine serum albumin (BSA) is the most structurally similar to HSA. [See, e.g., Kosa et al., J Pharm Sci. 96(11):3117-24 (November 2007)]. The present disclosure contemplates the use of albumin from non-human species, including, but not limited to, those set forth above, in, for example, the drug development process. In certain embodiments, the non-human species is a cow. In other embodiments, the non-human species is a cynomolgus monkey.

According to the present disclosure, albumin may be conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701). Furthermore, the present disclosure contemplates albumin fusion proteins comprising more than one homologous (e.g., multiple GDF15 mutein molecules) or heterologous (e.g., a GDF15 mutein molecule and a distinct anti-diabetic agent) drug molecules.

In the HSA-drug molecule conjugates contemplated by the present disclosure, various forms of albumin may be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

In particular embodiments, the albumin, albumin variant, or albumin fragment is conjugated to a polypeptide comprising the 167 amino acid pro-domain and the 112 amino acid mature domain of the 308 amino acid GDF15 precursor polypeptide; thus, the present disclosure contemplates a GDF15 polypeptide that has a length of from about amino acid residue 30 to about amino acid residue 308 of the sequence depicted in FIG. 1A (SEQ ID NO:1).

The present disclosure contemplates direct expression and production of the 112 amino acid mature domain of GDF15 as depicted in FIG. 1B, absent the 167 amino acid pro-domain, using a signal peptide of appropriate length to confer secretion from mammalian tissue culture. An example of a suitable signal peptide to facilitate expression and secretion includes IgK. As indicated above, the art describes mechanisms by which other appropriate signal peptides can be identified.

In still other embodiments, albumin serves as an intracellular chaperon for the expression of a drug molecule. For example, a nucleic acid molecule (e.g., a vector) encoding a HSA-GDF15/GDF15 mutein fusion protein may be introduced into a cell. Cellular introduction can be by any means (e.g., transfection or electroporation) known in the art. The expressed HSA-GDF15/GDF15 mutein fusion protein may optionally be conjugated through a linker(s). Examples of suitable linkers are described herein. Some embodiments contemplate a peptide linker of, for example, four-to-six amino acids.

In embodiments wherein the fusion protein comprises a linker, the linker may be a non-cleavable linker. For example, in one embodiment the present disclosure contemplates a fusion molecule wherein the HSA precursor amino acid sequence is fused to the N-terminus of the mature human GDF15 or a GDF15 mutein amino acid sequence through a non-cleavable 3×(4Gly-Ser) linker (SEQ ID NO:64) (see, e.g., FIG. 1G), and in another embodiment the present disclosure contemplates a fusion molecule wherein the mature HSA amino acid sequence is fused to the N-terminus of the mature human GDF15 or a GDF15 mutein amino acid sequence through a non-cleavable 3×(4Gly-Ser) linker (SEQ ID NO:64) (see, e.g., FIG. 1H).

In other embodiments wherein the fusion protein comprises a linker, the linker is a cleavable linker. For example, the disclosure contemplates a fusion molecule wherein the HSA precursor amino acid sequence is fused to the N-terminus of the mature human GDF15 or a GDF15 mutein amino acid sequence through a protease-sensitive 2×(4Gly-Ser) Factor Xa-cleavable linker (SEQ ID NO:56) (see, e.g., FIG. 1E). In other embodiments, the disclosure contemplates a fusion molecule wherein the mature HSA amino acid sequence is fused to the N-terminus of the mature human GDF15 or a GDF15 mutein amino acid sequence through a protease-sensitive 2×(4Gly-Ser) Factor Xa-cleavable linker (SEQ ID NO:56) (see, e.g., FIG. 1F).

Construction of HSA-cleavable linker-mature recombinant GDF15/GDF15 mutein molecules, as well as construction of mature recombinant GDF15/GDF15 mutein-cleavable linker-HSA fusion molecules, may be used to facilitate the assessment of, for example, solubility and the determination of in vivo efficacy of the GDF15/GDF15 mutein. In such embodiments, the GDF15/GDF15 mutein may be excised from the HSA chaperone through intracellular cleavage or through in vitro enzymatic cleavage. In some embodiments, excision is effected by proteolytic digestion of the cleavable linker using any viable protease. In other embodiments, GDF15 muteins can also be generated as non-HSA fusions via construction of a signal peptide fused to the mature 112 amino acid sequence, as denoted in FIG. 1B.

Intracellular cleavage may be carried out enzymatically by, for example, furin or caspase. The cells express a low level of these endogenous enzymes, which are capable of cleaving a portion of the fusion molecules intracellularly; thus, some of the polypeptides are secreted from the cell without being conjugated to HSA, while some of the polypeptides are secreted in the form of fusion molecules that comprise HSA. Embodiments of the present disclosure contemplate the use of various furin fusion constructs. For example, constructs may be designed that comprise the sequence RGRR (SEQ ID NO:222), RKRKKR (SEQ ID NO:223), RKKR (SEQ ID NO:224), or RRRKKR (SEQ ID NO:225). Such constructs can have the following general structure: Igk-HSA(D25-L609 of SEQ ID NO:5)-2×(G4S)-furin sequence-hGDF15(A197-I308 of SEQ ID NO:1).

The present disclosure also contemplates extra-cellular cleavage (i.e., ex-vivo cleavage) whereby the fusion molecules are secreted from the cell, subjected to purification, then cleaved (e.g., using, for example, a Factor Xa proteolytic-sensitive linker or an enterokinase). It is understood that the excision may dissociate the entire HSA-linker complex from the mature GDF15 or GDF15 mutein, or less that the entire HSA-linker complex.

As alluded to above, fusion of albumin to one or more polypeptides of the present disclosure can, for example, be achieved by genetic manipulation, such that the DNA coding for HSA, or a fragment thereof, is joined to the DNA coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake, incorporation and expression of exogenous genetic material (exogenous DNA) from its surroundings and taken up through the cell membrane(s). Transformation occurs naturally in some species of bacteria, but it can also be effected by artificial means in other cells.

Furthermore, albumin itself may be modified to extend its circulating half-life. Fusion of the modified albumin to one or more Polypeptides can be attained by the genetic manipulation techniques described above or by chemical conjugation; the resulting fusion molecule has a half-life that exceeds that of fusions with non-modified albumin. [See WO2011/051489].

Well-established technology platforms exist for the genetic fusion and chemical conjugation of polypeptides (e.g., the Polypeptides described herein) and recombinant albumin. By way of example, the ALBUFUSE® flex platform (Novozymes Biopharma A/S; Denmark) can be used to effect the genetic fusion of one or more recombinant albumin molecules to one or more Polypeptides, thereby producing a contiguous cDNA encoding the Polypeptide(s) and the albumin(s) to generate a single homogeneous protein. The platform can be used with, for example, yeast and mammalian host expression systems. By way of further example, the RECOMBUMIN® Flex platform (Novozymes Biopharma A/S; Denmark) can be used to effect chemical conjugation of the Polypeptides of the present disclosure to recombinant albumin, without any further derivitization of the albumin. Although conjugation may be performed at several amino acid residues (e.g., lysine and tyrosine), the free thiol at Cys34 is a common strategy due to site specificity yielding a more homogenous final product.

Alternative Albumin Binding Strategies:

Several albumin-binding strategies have been developed as alternatives for direct fusion, including albumin binding through a conjugated fatty acid chain (acylation). Because serum albumin is a transport protein for fatty acids, these natural ligands with albumin-binding activity have been used for half-life extension of small protein therapeutics. For example, insulin determir (LEVEMIR), an approved product for diabetes, comprises a myristyl chain conjugated to a genetically-modified insulin, resulting in a long-acting insulin analog.

The present disclosure also contemplates fusion proteins which comprise an albumin binding domain (ABD) polypeptide sequence and the sequence of one or more of the polypeptides described herein. Any ABD polypeptide sequence described herein or in the literature can be a component of the fusion proteins. The components of the fusion proteins can be optionally covalently bonded through a linker, such as those linkers described herein. In some of the embodiments of the present disclosure, the fusion proteins comprise the ABD polypeptide sequence as an N-terminal moiety and the polypeptides described herein as a C-terminal moiety.

The present disclosure also contemplates fusion proteins comprising a fragment of an albumin binding polypeptide, which fragment substantially retains albumin binding; or a multimer of albumin binding polypeptides or their fragments comprising at least two albumin binding polypeptides or their fragments as monomer units.

Without wishing to be bound by any theory, it is believed that the polypeptides described herein bind to the ABD polypeptide sequence, thereby sequestering the polypeptides in a subject leading to increased duration of action in the subject.

For a general discussion of ABD and related technologies, see WO 2012/050923, WO 2012/050930, WO 2012/004384 and WO 2009/016043.

Fusion Proteins with Maltose Binding Protein or Fragments Thereof:

The present disclosure also contemplates fusion proteins which comprise a maltose binding protein (MBP), or fragment thereof, and the amino acid sequence of one or more of the Polypeptides described herein. In some embodiments, the MBP fragment comprises a maltose binding domain (MBD). Any MBP, or fragment thereof, or MBD polypeptide sequence described herein or known in the art can be a component of the fusion proteins of the present disclosure. The components of the fusion proteins can be optionally covalently bonded through a linker, such as those linkers described herein. In some of the embodiments of the present disclosure, the fusion proteins comprise the MBP, or fragment thereof, or MBD polypeptide sequence as an N-terminal moiety and the polypeptides described herein as a C-terminal moiety.

The present disclosure also contemplates fusion proteins comprising a fragment of a MBP or MBD polypeptide, which fragment substantially retains maltose binding activity; or a multimer of maltose binding polypeptides, or fragments thereof (e.g., multimer of a MBD) comprising at least two maltose binding polypeptides, or fragments thereof, as monomer units (e.g., two or more MBD polypeptides).

For a general discussion of MBP and MBD and related technologies, see, e.g., Kapust et al. (1999) Protein Sci 8(8):1668-74.

Fc Fusion Proteins.

The present disclosure also contemplates fusion proteins which comprise an Fc polypeptide or fragment thereof, and the amino acid sequence of one or more of the Polypeptides described herein (e.g., modified human GDF15 molecules, GDF15 muteins, and modified GDF15 muteins). Any Fc polypeptide sequence described herein or known in the art can be a component of the fusion proteins of the present disclosure. The components of the fusion proteins can be optionally covalently bonded through a linker, such as those linkers described herein. In some of the embodiments of the present disclosure, the fusion proteins comprise the Fc polypeptide sequence as an N-terminal moiety and the polypeptides described herein as a C-terminal moiety.

The present disclosure also contemplates Fc polypeptide fusion partners, and fusion proteins comprising such, where the Fc polypeptide fusion partner is modified to be one partner of a charged Fc pair. A "partner of a charged Fc pair" refers to a (i) a "negatively charged" Fc sequence (optionally lacking the hinge region) and comprising a charged pair mutation or (ii) a "positively charged" Fc sequence (optionally lacking the hinge region) and comprising a charged pair mutation. "Positively charged" and "negatively charged" are used herein for ease of reference to describe the nature of the charge pair mutations in the Fc sequences, and not to indicate that the overall sequence or construct necessarily has a positive or negative charge. Charged Fc amino acid sequences suitable for use in Polypeptide constructs (e.g., GDF15 mutein, modified GDF15 muteins) of the present disclosure are described in, for example WO 2013/113008.

Examples of a positively charged Fc ("Fc(+)") include an Fc comprising an aspartatic acid-to-lysine mutation (E356K) and a glutamic acid-to-lysine mutation (D399K) of an Fc sequence lacking the hinge region. Examples of a negatively charged Fc ("Fc(−)") include an Fc comprising two lysine-to-aspartate mutations (K392D, K409D) in an Fc sequence lacking the hinge region. The C-terminal lysine (K477) also may also be optionally deleted. When a Fc(+) Polypeptide fusion protein (e.g., Fc(+)GDF mutein fusion protein) and a Fc(−)Polypeptide fusion protein (e.g., Fc(−) GDF mutein fusion protein) GDF mutein are incubated together, the aspartate residues associate with the lysine residues through electrostatic force, facilitating formation of Fc heterodimers between the Fc(+) and the Fc(−) sequences of the Polypeptide fusion proteins.

The present disclosure also contemplates constructs designated "hemi" or "hemiFc" constructs, which comprise two Fc sequences joined in tandem by a linker that connects the N-terminus of a first Fc sequence to the C-terminus of a second Fc sequence. In some embodiments, a monomer comprises a Polypeptide (e.g., a mature modified GDF15 or mutein GDF15) sequence linked to the first Fc sequence by a first linker that connects the N-terminus of the GDF15 sequence to the C-terminus of the first Fc sequence, wherein the first Fc sequence is linked to the second Fc sequence by a second linker that connects the N-terminus of the first Fc sequence to the C-terminus of the second Fc sequence. The first and second Fc sequences also are associated by the Fc hinge regions. Two such monomers associate to form a dimer in which the monomers are linked via an interchain disulfide bond between the two Polypeptide sequences. For examples of hemiFc polypeptides suitable for use with the GDF muteins of the present disclosure see WO 2013/113008.

The present disclosure also contemplates fusion proteins having a multimer of Fc polypeptides, or fragments thereof, including a partner of a charged Fc pair (e.g., multimer of an Fc).

Conjugation with Other Molecules:

Additional suitable components and molecules for conjugation include, for example, thyroglobulin; tetanus toxoid; Diphtheria toxoid; polyamino acids such as poly(D-lysine: D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another protein (e.g., a protein having an amino acid sequence heterologous to the subject protein), or a carrier molecule. Thus, an exemplary polypeptide sequence can be provided as a conjugate with another component or molecule.

A conjugate modification may result in a polypeptide sequence that retains activity with an additional or complementary function or activity of the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disorder or disease as set forth herein (e.g., diabetes).

A Polypeptide may also be conjugated to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from about 3 to 5.5, e.g., at pH ~4.5. The content of the fractions obtained by cation exchange chromatography may be identified by molecular weight using conventional methods, for example, mass spectroscopy, SDS-PAGE, or other known methods for separating molecular entities by molecular weight.

Fc-Fusion Molecules:

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications:

The present disclosure contemplates the use of other modifications, currently known or developed in the future, of the Polypeptides to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the molecule's characteristics. Various aspects of hesylation are described in, for example, U.S. Patent Appln. Nos. 2007/0134197 and 2006/0258607.

The present disclosure also contemplates fusion molecules comprising SUMO as a fusion tag (LifeSensors, Inc.;

Malvern, Pa.). Fusion of a polypeptide described herein to SUMO may convey several beneficial effects on the polypeptide, including enhancement of expression, improvement in solubility, and/or assistance in the development of purification methods. SUMO proteases recognize the tertiary structure of SUMO and cleave the fusion protein at the C-terminus of SUMO, thus releasing a polypeptide described herein with the desired N-terminal amino acid.

Linkers:

Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 (e.g., Gly), 2, 3, 4, 5, 6, 7, 8, 9, 10, 10-20, 20-30, 30-50 amino acids (e.g., Gly).

Exemplary flexible linkers include glycine polymers $(G)_n$, glycine-serine polymers (for example, $(GS)_n$, $GSGGS_n$ and $GGGS_n$, where n is an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG (SEQ ID NO:226), GGSGG (SEQ ID NO:227), GSGSG (SEQ ID NO:228), GSGGG (SEQ ID NO:229), GGGSG (SEQ ID NO:230), and GSSSG (SEQ ID NO:231).

In some cases, the linker is a cleavable linker, e.g., an enzymatically cleavable linker. In other cases, the linker is a non-cleavable linker, e.g., a linker that is not cleaved enzymatically under normal physiological conditions in vivo.

Examples of suitable linkers include, e.g., $(GGGGS)_n$, where n is an integer from 1 to about 10 (SEQ ID NO:187) (e.g., n=3); GGGSGGGSIEGR (SEQ ID NO:188); GGGGG (SEQ ID NO:189); $(EGGGS)_n$, where n is an integer from 1 to about 10 (SEQ ID NO:190) (e.g., n=3).

For example, a proteolytically cleavable crosslinker can be a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue) (SEQ ID NO:191), e.g., Pro-X-X-Hy-(Ser/Thr) (SEQ ID NO:192), e.g., Pro-Leu/Gln-Gly-Met-Thr-Ser (SEQ ID NO:193) or Pro-Leu/Gln-Gly-Met-Thr (SEQ ID NO:194). Another example of a protease cleavage site is a plasminogen activator cleavage site, e.g., a uPA or a tissue plasminogen activator (tPA) cleavage site. Specific examples of cleavage sequences of uPA and tPA include sequences comprising Val-Gly-Arg. Another example is a thrombin cleavage site, e.g., CGLVPAGSGP (SEQ ID NO:195). Additional suitable linkers comprising protease cleavage sites include linkers comprising one or more of the following amino acid sequences: 1) SLLKSRMVPNFN (SEQ ID NO:196) or SLLIARRMPNFN (SEQ ID NO:197), cleaved by cathepsin B; SKLVQASASGVN (SEQ ID NO:198) or SSYLKAS-DAPDN (SEQ ID NO:199), cleaved by an Epstein-Barr virus protease; RPKPQQFFGLMN (SEQ ID NO:200) cleaved by MMP-3 (stromelysin); SLRPLALWRSFN (SEQ ID NO:201) cleaved by MMP-7 (matrilysin); SPQ-GIAGQRNFN (SEQ ID NO:202) cleaved by MMP-9; DVDERDVRGFASFL (SEQ ID NO:203) cleaved by a thermolysin-like MMP; SLPLGLWAPNFN (SEQ ID NO:204) cleaved by matrix metalloproteinase 2(MMP-2); SLLIFRSWANFN (SEQ ID NO:205) cleaved by cathespin L; SGVVIATVIVIT (SEQ ID NO:206) cleaved by cathepsin D; SLGPQGIWGQFN (SEQ ID NO:207) cleaved by matrix metalloproteinase 1(MMP-1); KKSPGRVVGGSV (SEQ ID NO:208) cleaved by urokinase-type plasminogen activator; PQGLLGAPGILG (SEQ ID NO:209) cleaved by membrane type 1 matrixmetalloproteinase (MT-MMP); HGPEGL-RVGFYESDVMGRGHARLVHVEEPHT (SEQ ID NO:210) cleaved by stromelysin 3 (or MMP-11), thermolysin, fibroblast collagenase and stromelysin-1; GPQGLAGQRGIV (SEQ ID NO:211) cleaved by matrix metalloproteinase 13 (collagenase-3); GGSGQRGRKALE (SEQ ID NO:212) cleaved by tissue-type plasminogen activator (tPA); SLSALLSSDIFN (SEQ ID NO:213) cleaved by human prostate-specific antigen; SLPRFKIIGGFN (SEQ ID NO:214) cleaved by kallikrein (hK3); SLLGIAVPGNFN (SEQ ID NO:215) cleaved by neutrophil elastase; and FFKNIVTPRTPP (SEQ ID NO:216) cleaved by calpain (calcium activated neutral protease).

Methods of Production of Polypeptides

A polypeptide of the present disclosure can be produced by any suitable method, including recombinant and non-recombinant methods (e.g., chemical synthesis).

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides of the present disclosure. Details of the chemical synthesis are known in the art (e.g., Ganesan A. 2006 Mini Rev. Med. Chem. 6:3-10; and Camarero J. A. et al., 2005 Protein Pept Lett. 12:723-8).

Solid phase peptide synthesis may be performed as described hereafter. The α functions (Nα) and any reactive side chains are protected with acid-labile or base-labile groups. The protective groups are stable under the conditions for linking amide bonds but can be readily cleaved without impairing the peptide chain that has formed. Suitable protective groups for the α-amino function include, but are not limited to, the following: t-butyloxycarbonyl (Boc), benzyloxycarbonyl (Z), o-chlorbenzyloxycarbonyl, bi-phenylisopropyloxycarbonyl, tert-amyloxycarbonyl (Amoc), α,α-dimethyl-3,5-dimethoxy-benzyloxycarbonyl, o-nitrosulfenyl, 2-cyano-t-butoxy-carbonyl, 9-fluorenylmethoxy-carbonyl (Fmoc), 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl (2-CIZ), 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers and the like. Polystyrene (1%)-divinylbenzene or TentaGel® derivatized with 4-benzyloxybenzyl-alcohol (Wang-anchor) or 2-chlorotrityl chloride can be used if it is intended to prepare the peptidic acid. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material with the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, o-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or also in the absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, e.g., in a 2-fold excess and at temperatures between about 10° C. and 50° C., e.g., 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride under the conditions described above.

The Nα-protected amino acid (e.g., the Fmoc amino acid) can be coupled to the 2-chlorotrityl resin in dichloromethane with the addition of DIEA with reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained may be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

B. Recombinant Production

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., E. coli) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV1) and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification methods. In one embodiment, the protein may be isolated using metal chelate chromatography methods. Proteins may contain modifications to facilitate isolation.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than 90%, less than 60%, less than 50%, less than 40%, less than 30%, less than 20%, less than 10%, less than 5%, or less than 1%, of the composition is made up of other expressed proteins.

Antibodies

The present disclosure provides antibodies, including isolated antibodies, that specifically bind a GDF15 polypeptide, e.g., a GDF15 mutein of the present disclosure. The term "antibody" encompasses intact monoclonal antibodies, polyclonal antibodies, multispecific antibodies (e.g., bispecific antibodies) formed from at least two intact antibodies, and antibody binding fragments including Fab and F(ab)'$_2$, provided that they exhibit the desired biological activity. The basic whole antibody structural unit comprises a tetramer, and each tetramer is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. In contrast, the carboxy-terminal portion of each chain defines a constant region primarily responsible for effector function. Human light chains are classified as kappa and lambda, whereas human heavy chains are classified as mu, delta, gamma, alpha, or epsilon, and define the antibody's isotype as IgM, IgD, IgG, IgA, and IgE, respectively. Binding fragments are produced by recombinant DNA techniques, or by enzymatic or chemical cleavage of intact antibodies. Binding fragments include Fab, Fab', F(ab')$_2$, Fv, and single-chain antibodies.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Within light and heavy chains, the variable and constant regions are joined by a "J" region of about 12 or more amino acids, with the heavy chain also including a "D" region of about 10 more amino acids. The antibody chains all exhibit the same general structure of relatively conserved framework regions (FR) joined by three hyper-variable regions, also called "complementarity-determining regions" or "CDRs". The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4.

An intact antibody has two binding sites and, except in bifunctional or bispecific antibodies, the two binding sites are the same. A bispecific or bifunctional antibody is an artificial hybrid antibody having two different heavy/light chain pairs and two different binding sites. Bispecific antibodies can be produced by a variety of methods including fusion of hybridomas or linking of Fab' fragments.

As set forth above, binding fragments may be produced by enzymatic or chemical cleavage of intact antibodies. Digestion of antibodies with the enzyme papain results in two identical antigen-binding fragments, also known as "Fab" fragments, and an "Fc" fragment which has no antigen-binding activity. Digestion of antibodies with the enzyme pepsin results in a F(ab')$_2$ fragment in which the two arms of the antibody molecule remain linked and comprise two-antigen binding sites. The F(ab')$_2$ fragment has the ability to crosslink antigen.

As used herein, the term "Fab" refers to a fragment of an antibody that comprises the constant domain of the light chain and the CH1 domain of the heavy chain.

When used herein, the term "Fv" refers to the minimum fragment of an antibody that retains both antigen-recognition and antigen-binding sites. In a two-chain Fv species, this region includes a dimer of one heavy-chain and one light-chain variable domain in non-covalent association. In a single-chain Fv species, one heavy-chain and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. While the six CDRs, collectively, confer antigen-binding specificity to the antibody, even a single variable domain (or half of an Fv comprising only three CDRs specific for an antigen) has the ability to recognize and bind antigen.

When used herein, the term "complementarity determining regions" or "CDRs" refers to parts of immunological receptors that make contact with a specific ligand and determine its specificity.

The term "hypervariable region" refers to the amino acid residues of an antibody which are responsible for antigen-binding. The hypervariable region generally comprises amino acid residues from a CDR and/or those residues from a "hypervariable loop".

As used herein, the term "epitope" refers to binding sites for antibodies on protein antigens. Epitopic determinants usually comprise chemically active surface groupings of molecules such as amino acids or sugar side chains, as well as specific three-dimensional structural and charge characteristics. An antibody is said to bind an antigen when the dissociation constant is ≤1 µM, ≤100 nM, or ≤10 nM. An increased equilibrium constant ("$K_D$") means that there is less affinity between the epitope and the antibody, whereas a decreased equilibrium constant means that there is more affinity between the epitope and the antibody. An antibody with a $K_D$ of "no more than" a certain amount means that the antibody will bind to the epitope with the given $K_D$ or more strongly. Whereas $K_D$ describes the binding characteristics of an epitope and an antibody, "potency" describes the effectiveness of the antibody itself for a function of the antibody. There is not necessarily a correlation between an equilibrium constant and potency; thus, for example, a relatively low $K_D$ does not automatically mean a high potency.

The term "selectively binds" in reference to an antibody does not mean that the antibody only binds to a single substance, but rather that the $K_D$ of the antibody to a first substance is less than the $K_D$ of the antibody to a second substance. An antibody that exclusively binds to an epitope only binds to that single epitope.

When administered to humans, antibodies that contain rodent (i.e., murine or rat) variable and/or constant regions are sometimes associated with, for example, rapid clearance from the body or the generation of an immune response by the body against the antibody. In order to avoid the utilization of rodent-derived antibodies, fully human antibodies can be generated through the introduction of human antibody function into a rodent so that the rodent produces fully human antibodies. Unless specifically identified herein, "human" and "fully human" antibodies can be used interchangeably. The term "fully human" can be useful when distinguishing antibodies that are only partially human from those that are completely, or fully, human. The skilled artisan is aware of various methods of generating fully human antibodies.

In order to address possible human anti-mouse antibody responses, chimeric or otherwise humanized antibodies can be utilized. Chimeric antibodies have a human constant region and a murine variable region, and, as such, human anti-chimeric antibody responses may be observed in some patients. Therefore, it is advantageous to provide fully human antibodies against multimeric enzymes in order to avoid possible human anti-mouse antibody or human anti-chimeric antibody responses.

Fully human monoclonal antibodies can be prepared, for example, by the generation of hybridoma cell lines by techniques known to the skilled artisan. Other preparation methods involve the use of sequences encoding particular antibodies for transformation of a suitable mammalian host cell, such as a CHO cell. Transformation can be by any known method for introducing polynucleotides into a host cell, including, for example, packaging the polynucleotide in a virus (or into a viral vector) and transducing a host cell with the virus (or vector) or by transfection procedures known in the art. Methods for introducing heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. Mammalian cell lines available as hosts for expression are well known in the art and include, but are not limited to, CHO cells, HeLa cells, and human hepatocellular carcinoma cells.

The antibodies can be used to detect a Polypeptide of the present disclosure. For example, the antibodies can be used as a diagnostic by detecting the level of one or more Polypeptides of the present disclosure in a subject, and either comparing the detected level to a standard control level or to a baseline level in a subject determined previously (e.g., prior to any illness).

Another embodiment of the present disclosure entails the use of one or more human domain antibodies (dAb). dAbs are the smallest functional binding units of human antibodies (IgGs) and have favorable stability and solubility characteristics. The technology entails a dAb(s) conjugated to HSA (thereby forming a "AlbudAb"; see, e.g., EP1517921B, WO2005/118642 and WO2006/051288) and a molecule of interest (e.g., a polypeptide sequence of the present disclosure). AlbudAbs are often smaller and easier to manufacture in microbial expression systems, such as bacteria or yeast, than current technologies used for extending the serum half-life of polypeptides. As HSA has a half-life of about three weeks, the resulting conjugated molecule improves the half-life of the molecule of interest. Use of the dAb technology may also enhance the efficacy of the molecule of interest.

Therapeutic and Prophylactic Uses

The present disclosure provides methods for treating or preventing hyperglycemia, hyperinsulinemia, glucose intolerance, glucose metabolism disorders, obesity and other body weight disorders, as well as other metabolic and metabolic-associated diseases, disorders and conditions by the administration of the Polypeptides, or compositions thereof, as described herein. Such methods may also have an advantageous effect on one or more symptoms associated with a disease, disorder or condition by, for example, decreasing the severity or the frequency of a symptom.

In order to determine whether a subject may be a candidate for the treatment or prevention of hyperglycemia, hyperinsulinemia, glucose intolerance, and/or glucose disorders by the methods provided herein, various diagnostic methods known in the art may be utilized. Such methods include those described elsewhere herein (e.g., fasting plasma glucose (FPG) evaluation and the oral glucose tolerance test (oGTT)).

In order to determine whether a subject may be a candidate for the treatment or prevention of a body weight disorder (e.g., obesity) by the methods provided herein, parameters such as, but not limited to, the etiology and the extent of the subject's condition (e.g., how overweight the subject is compared to reference healthy individual) should be evaluated. For example, an adult having a BMI between ~25 and ~29.9 kg/m$^2$ may be considered overweight (pre-obese), while an adult having a BMI of ~30 kg/m$^2$ or higher may be considered obese. For subjects who are overweight and/or who have poor diets (e.g., diets high in fat and calories), it is common to initially implement and assess the effect of modified dietary habits and/or exercise regimens before initiating a course of therapy comprising one or more of the Polypeptides of the present disclosure. As discussed herein, the Polypeptides can effect appetite suppression.

Pharmaceutical Compositions

The Modulators (e.g., Polypeptides) of the present disclosure may be in the form of compositions suitable for administration to a subject. In general, such compositions are "pharmaceutical compositions" comprising one or more Modulators and one or more pharmaceutically acceptable or physiologically acceptable diluents, carriers or excipients. In certain embodiments, the Modulators are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds (e.g., glucose lowering agents) as described herein in order to treat or prevent the diseases, disorders and conditions as contemplated by the present disclosure.

The pharmaceutical compositions typically comprise a therapeutically effective amount of at least one of the Modulators (e.g., Polypeptides) contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), and N-tris[Hydroxymethyl] methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver the Polypeptides, including implants (e.g., implantable pumps) and catheter systems, both of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

The pharmaceutical compositions containing the active ingredient may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods of preparing liposomes are described in, for example, U.S. Pat. Nos. 4,235,871, 4,501,728, and 4,837,028. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the Modulators in the form of suppositories for rectal administration of the drug. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The Modulators contemplated by the present disclosure may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of the disclosed Modulators (e.g., Polypeptides), and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation.

Depot injections, which are generally administered subcutaneously or intramuscularly, may also be utilized to release the Modulators disclosed herein over a defined period of time. Depot injections are usually either solid- or oil-based and generally comprise at least one of the formulation components set forth herein. One of ordinary skill in the art is familiar with possible formulations and uses of depot injections.

Regarding antibodies, in an exemplary embodiment an antibody or antibody fragment of the present disclosure is stored at 10 mg/ml in sterile isotonic aqueous saline solution for injection at 4° C. and is diluted in either 100 ml or 200 ml 0.9% sodium chloride for injection prior to administration to the subject. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via subcutaneous bolus injection.

Combination Therapy

The present disclosure contemplates the use of the Modulators (e.g., Polypeptides) in combination with one or more active therapeutic agents or other prophylactic or therapeutic modalities. In such combination therapy, the various active agents frequently have different mechanisms of action. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the Modulators are administered or applied sequentially, e.g., where one agent is administered prior to one or more other agents. In other embodiments, the Modulators are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The Modulators of the present disclosure can be used in combination with other agents useful in the treatment, prevention, suppression or amelioration of the diseases, disorders or conditions set forth herein, including those that are normally administered to subjects suffering from hyperglycemia, hyperinsulinemia, glucose intolerance, and other glucose metabolism disorders.

The present disclosure contemplates combination therapy with numerous agents (and classes thereof), including 1) insulin, insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., repaglinide (PRANDIN) and nateglinide (STARLIX)); 2) biguanides (e.g., metformin (GLUCOPHAGE)) and other agents that act by promoting glucose utilization, reducing hepatic glucose production and/or diminishing intestinal glucose output; 3) alpha-glucosidase inhibitors (e.g., acarbose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; 5) glucagon-like-peptides including DPP-IV inhibitors (e.g., vildagliptin (GALVUS) and sitagliptin (JANUVIA)) and Glucagon-Like Peptide-1 (GLP-1) and GLP-1 agonists and analogs (e.g., exenatide (BYETTA and ITCA 650 (an osmotic pump inserted subcutaneously that delivers an exenatide analog over a 12-month period; Intarcia, Boston, Mass.)); 6) and DPP-IV-resistant analogues (incretin mimetics), PPAR gamma agonists, dual-acting PPAR agonists, pan-acting PPAR agonists, PTP1B inhibitors, SGLT inhibitors, insulin secretagogues, RXR agonists, glycogen synthase kinase-3 inhibitors, immune modulators, beta-3 adrenergic receptor agonists, 11beta-HSD1 inhibitors, and amylin analogues.

Furthermore, the present disclosure contemplates combination therapy with agents and methods for promoting weight loss, such as agents that stimulate metabolism or decrease appetite, and modified diets and/or exercise regimens to promote weight loss.

The Modulators of the present disclosure may be used in combination with one or more other agent in any manner appropriate under the circumstances. In one embodiment, treatment with the at least one active agent and at least one Modulator of the present disclosure is maintained over a period of time. In another embodiment, treatment with the at least one active agent is reduced or discontinued (e.g., when the subject is stable), while treatment with the Modulator of the present disclosure is maintained at a constant dosing regimen. In a further embodiment, treatment with the at least one active agent is reduced or discontinued (e.g., when the subject is stable), while treatment with the Modulator of the present disclosure is reduced (e.g., lower dose, less frequent dosing or shorter treatment regimen). In yet another embodiment, treatment with the at least one active agent is reduced or discontinued (e.g., when the subject is stable), and treatment with the Modulator of the present disclosure is increased (e.g., higher dose, more frequent dosing or longer treatment regimen). In yet another embodiment, treatment with the at least one active agent is maintained and treatment with the Modulator of the present disclosure is reduced or discontinued (e.g., lower dose, less frequent dosing or shorter treatment regimen). In yet another embodiment, treatment with the at least one active agent and treatment with the Modulator of the present disclosure are reduced or discontinued (e.g., lower dose, less frequent dosing or shorter treatment regimen).

Dosing

The Modulators (e.g., Polypeptides) of the present disclosure may be administered to a subject in an amount that is dependent upon, for example, the goal of the administration (e.g., the degree of resolution desired); the age, weight, sex, and health and physical condition of the subject to be treated; the nature of the Modulator, and/or formulation being administered; the route of administration; and the nature of the disease, disorder, condition or symptom thereof (e.g., the severity of the dysregulation of glucose/insulin and the stage of the disorder). The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with absorption, distribution, metabolism, and excretion ("ADME"), taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the Modulators of the present disclosure may be an amount that, when administered in one or more doses to a subject, produces a desired result relative to a healthy subject. For example, an effective dose may be one that, when administered to a subject having elevated plasma glucose and/or plasma insulin, achieves a desired reduction relative to that of a healthy subject by at least about 10%, at least about 20%, at least about 25%, at least about 30%, at least about 40%, at least about 50%, at least about 60%, at least about 70%, at least about 80%, or more than 80%.

An appropriate dosage level will generally be about 0.001 to 100 mg/kg of patient body weight per day, which can be administered in single or multiple doses. In some embodiments, the dosage level will be about 0.01 to about 25 mg/kg per day, and in other embodiments about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The Modulators may be administered on a regimen of, for example, 1 to 4 times per day, and often once or twice per day.

The dosage of the Modulators of the present disclosure may be repeated at an appropriate frequency, which may be in the range of once per day to once every three months, depending on the pharmacokinetics of the Modulators (e.g. half-life) and the pharmacodynamic response (e.g. the duration of the therapeutic effect of the Modulator). In some embodiments where the Modulator is an antibody or a fragment thereof, or a polypeptide or variants thereof, dosing is frequently repeated between once per week and once every 3 months. In other embodiments, such Modulators are administered approximately once per month.

In certain embodiments, the dosage of the disclosed Modulators is contained in a "unit dosage form". The phrase "unit dosage form" refers to physically discrete units, each unit containing a predetermined amount of a Modulator of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising the disclosed Modulators (e.g., Polypeptides), and pharmaceutical compositions thereof. The kits are generally in the form of a physical structure housing various components, as described below, and may be utilized, for example, in practicing the methods described above (e.g., administration of a Modulator to a subject in need of restoring glucose homeostasis).

A kit can include one or more of the Modulators disclosed herein (provided in, e.g., a sterile container), which may be in the form of a pharmaceutical composition suitable for administration to a subject. The Modulators can be provided in a form that is ready for use or in a form requiring, for example, reconstitution or dilution prior to administration. When the Modulators are in a form that needs to be reconstituted by a user, the kit may also include buffers, pharmaceutically acceptable excipients, and the like, packaged with or separately from the Modulators. When combination therapy is contemplated, the kit may contain the several agents separately or they may already be combined in the kit. Each component of the kit can be enclosed within an individual container and all of the various containers can be within a single package. A kit of the present disclosure can be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampoule, tube or vial). Exemplary instructions include those for reducing or lowering blood glucose, treatment of hyperglycemia, treatment of diabetes, etc. with the disclosed Modulators, and pharmaceutical compositions thereof Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar;

kDa=kilodalton; i.m.=intramuscular(ly); i.p.=intraperitoneal (ly); s.c.=subcutaneous(ly); bid=twice daily; HPLC=high performance liquid chromatography; BW=body weight; U=unit; ns=not statistically significant; PG=fasting plasma glucose; FPI=fasting plasma insulin; ITT=insulin tolerance test; PTT=pyruvate tolerance test; oGTT=oral glucose tolerance test; GSIS=glucose-stimulated insulin secretion; PBS=phosphate-buffered saline; PCR=polymerase chain reaction; NHS=N-Hydroxysuccinimide; DMEM=Dulbeco's Modification of Eagle's Medium; GC=genome copy; EDTA=ethylenediaminetetraacetic acid.

Materials and Methods

The following methods and materials were used in the Examples below:

Animals.

Male, 7-15 week-old, B6.V-LEP$^{ob}$/J (leptin-deficient (ob/ob)) mice (The Jackson Laboratory, Bar Harbor, Me.) were used in the experiments described hereafter. Mice had free access to autoclaved distilled water and were fed ad libitum a commercial mouse chow (Irradiated 2018 Teklad Global 18% protein Rodent Diet, Harlan Laboratories, Dublin, Va.). Diet-induced obese (DIO) male C57BL/6J mice (The Jackson Laboratory, Bar Harbor, Me.) were maintained on a high-fat diet (D12492, Research Diets, Inc, New Brunswick, N.J.) containing 60 kcal % fat, 20 kcal % protein and 20 kcal % carbohydrate for 12-20 weeks. All animal studies were approved by the NGM Institutional Animal Care and Use Committee.

Nucleic Acid and Amino Acid Sequences.

GenBank Accession No. BC000529.2 sets forth the cDNA of ORF encoding human GDF15 variants, and GenBank Accession No. NP_004855.2 sets forth the amino acid sequence encoded by the cDNA. *Homo sapiens* serum albumin cDNA was purchased from Origene (SC319937), GeneBank Accession No. NM_000477.3, NP_000468).

Fusion PCR fragments for HSA and human GDF15 were generated by Sapphire (Clontech) enzyme, gel purified (Qiagen Gel Extraction kit) and assembled with Gibson Assembly Master Mix (NEB) into pTT5 vector containing the human IgK signal peptide digested with EcoRI and BamHI. Two PCR fragments were generated for cloning, the first encoding HSA and the second encoding human GDF15. The following primers were used for amplifying HSA: forward primer: 5'-tggctccgaggtgccagatgtgatgcacacaagagtgaggttgct-catcgg-3' (SEQ ID NO:217); reverse primer: 5'-gctaccgcctc-cacctaagcctaaggcagcttgacttgc-3' (SEQ ID NO:218). The following primers were used for amplifying GDF15: forward primer: 5'-gctgccttaggcttaggtggaggcggtagcggtggag-gtgggagtggaggtggaggcagtgcgcgcaacggggaccactgtccgctcg gg-3'(SEQ ID NO:219); reverse primer: 5'-cagaggtcgag-gtcgggggatcctcatatgcagtggcagtctttggctaacaa-3' (SEQ ID NO:220).

Colonies were plated and sequence confirmed. Primers were designed to mutate regions of interest, and mutagenesis was performed with Quikchange Lightning Site Directed Mutagenesis Kit (Agilent). Sequence-confirmed colonies were amplified and plasmid DNA was purified using Qiagen DNA-Maxi prep kit.

HSA-GDF15 Mutein Fusion Molecule Expression.

All muteins were transiently transfected in Expi 293F cells (Invitrogen Corporation, Carlsbad, Calif.). Cells were routinely subcultured in Expi expression medium (Invitrogen) and maintained as suspension cultures in shake flasks of varying sizes. Typically, cells were subcultured at a cell density of 5e5 viable cells/ml and grown for 3 days before subculturing. The flasks were maintained in a humidified $CO_2$ incubator (37° C. and 5% $CO_2$) on New Brunswick shaker platforms (New Brunswick Scientific Company, Edison, N.J.) at an agitation rate of 110 RPM.

Transfections were performed when the cell density of the culture reached 2.5e6 viable cells/mL at greater than 95% viability. Typically, for 50 mL transfection, 2.5e6 cells/mL× 50 mL cells were inoculated in a 250 mL shaker flask in 42.5 mL culture volume. Fifty micrograms (50 μg) plasmid DNA consisting of the expression vector containing the gene of interest was first diluted in 2.5 mL OPTI-MEM reduced-serum medium (Invitrogen). Simultaneously, Expifectamine transfection reagent (Invitrogen), 2.67 times the volume (of the amount of plasmid DNA) was also diluted in 2.5 mL OPTI-MEM reduced-serum medium. After a 5 min incubation at room temperature, the diluted transfection reagent was slowly added to the diluted plasmid DNA to form transfection competent complexes. After a further 20 min incubation period at room temperature, 5 mL of the transfection complex was added to the 42.5 mL cell culture. The transfected cells were then placed in the humidified $CO_2$ incubator on an orbital shaker maintained at 110 RPM. Twenty-four hours post-transfection, the transfected culture was fed with 250 μL enhancer 1 solution (Invitrogen) and 2.5 mL enhancer 2 solution (Invitrogen). The culture was then replaced in the humidified $CO_2$ incubator on an orbital shaker. Six-to-seven days post-transfection, cultures were harvested by centrifugation at 3000 RPM for 30 min before being filtered through a 0.2 μm filter (Nalgene). Samples were then analyzed on a commassie stain gel for expression.

Cleavage of HSA-GDF15 Fusion Molecules.

Human Serum Albumin hGDF15 fusion constructs were purified to greater than 95% homogeneity. Muteins were excised via overnight digestion at Room Temperature using Factor Xa obtained from New England Biolabs (P8010) using a 1:500 (w/w) addition (in 1× phosphate buffered saline). Following cleavage, GDF15 muteins were purified to greater than 95% homogeneity.

Production of Mature GDF15 Fusion Molecules.

hGDF15 muteins were also constructed and purified as non-HSA fusions via utilization of a IgK signal peptide fused to the mature (112 amino acid) sequence of GDF15 (FIG. 1B). Mature muteins were purified directly from media to greater than 95% homogeneity.

Production of Bacterially-Refolded Mature, Non-Glycosylated Molecules.

hGDF15 muteins set forth in FIG. 4 (w29, w32, w52, w68 and w89) were also generated as bacterial refolds from inclusion bodies and purified to greater than 95% homogeneity containing the mature (112 amino acid) sequence of GDF15 (FIG. 1B) with an N-terminal methionine.

Solubility Assessment of Human GDF15 Muteins.

Solubility of GDF15 muteins was assessed using two complementary assays, the results of which closely mirrored each other. In one assay format, muteins were dialyzed into 1× phosphate buffered saline and concentrated using Amicon Ultra Centrifugal Filters composed of Regenerated Nitrocellulose 10,000 NMWL (UFC901096). Following concentration, solubility assessments were performed on a NanoDrop ND-1000 spectrophotometer blanked in 1× Phosphate Buffered Saline using Absorbance at 280 nm wavelength and Beer's law (Extinction coefficient=14400, Molecular weight=12,287 Da). In a second assay format, muteins were dialyzed into 0.05% (v/v) formic acid (pH 2.0) and concentrated using Amicon Ultra Centrifugal Filters composed of Regenerated Nitrocellulose 10,000 NMWL (UFC901096) up to and greater than 20 mg/mL. The starting concentration for each mutein was determined using Absorbance at 280 nm wavelength and Beer's law (Extinction coefficient=14400, Molecular weight=12,287 Da). Each mutein was then serial diluted 2-fold back into 0.01% formic acid and 90 µL of each dilution was added to a 96-well plate. 10 µL of 10×PBS was added to each well and pH was confirmed to be 7.3. Following incubation at room temperature overnight with shaking, turbidity was measured at 370 nm. The inflection point at which turbidity begins to occur is accepted as the maximum solubility for each mutein.

Blood Glucose Assay.

Blood glucose from mouse tail snip was measured using ACCU-CHEK Active test strips read by ACCU-CHEK Active meter (Roche Diagnostics, Indianapolis, Ind.) following manufacturer's instruction.

Serum GDF15 Muteins Exposure Level Assay.

Whole blood (~50 µl/mouse) from mouse tail snips was collected into plain capillary tubes (BD Clay Adams SurePrep, Becton Dickenson, Sparks, Md.). Serum and blood cells were separated by spinning the tubes in an Autocrit Ultra 3 (Becton Dickinson, Sparks, Md.). GDF15 exposure levels in serum were determined using Human GDF-15 Quantikine ELISA Kit (R&D Systems, Minneapolis, Minn.) by following the manufacturer's instructions.

Analytical Gel Filtration.

Increases to hydrodynamic radii of engineered human GDF15 muteins was monitored via A280 elution absorbance on an Agilent 1200-series HPLC elution times (min) using a TOSOH Biosciences TSKgelG3000SW$_{XL}$ column (7.8 mm ID×30 cm, 5 µm), pre-equilibrated with 1× phosphate buffered saline with flow rate of 1 mL/min.

Production of Mature Platypus (Oa) GDF15 Molecule.

Referring to FIG. 17A, mature OaGDF15 was constructed from a precursor amino acid sequence containing a signal sequence, pro-domain (furin cut site underlined), followed by MatureOaGDF15 (bold) (see FIG. 17A).

The OaGDF15 construct was transiently transfected in Expi 293F cells (Invitrogen; Carlsbad, Calif.) in a manner as described herein for HSA-GDF15 mutein fusion molecules. Secreted OaGDF15 was purified to greater than 95% homogeneity from the cell media. The N-terminus of the mature form of OaGDF15 was confirmed via LC/MS analysis.

Example 1: Effects of a HSA-GDF15 Fusion Molecule on Body Weight, Food Intake and Fasted Blood The effects of a subcutaneously administered fusion molecule having recombinant HSA fused to recombinant human GDF15 on body weight, food intake, and fasted blood glucose were evaluated over a 22 day period post-delivery. Briefly, the fusion molecule depicted in FIG. 1H (mature HSA fused to the N-terminus of mature human GDF15 through a non-cleavable 3×(4Gly-Ser) linker (SEQ ID NO:64) was administered, at various doses, as a single, subcutaneous bolus injection to 7-15 week old male ob/ob mice weighing approximately 44 g and having non-fasted glucose serum levels of approximately 340 mg/dl. Following administration of vehicle control (PBS) or the fusion molecule at doses of 0.04 mg/kg, 0.12 mg/kg, 0.4 mg/kg and 1.2 mg/kg, the indicated parameters were determined over a 22-day period on days 0, 2, 3, 6, 8, 15 and 22. Serum exposure was monitored by Human GDF-15 Quantikine ELISA Kit (R&D Systems, Minneapolis, Minn.) following the manufacturer's instructions.

The fusion molecule demonstrated an improved half-life of 37 hours compared to a half-life of 2 hours for unconjugated, recombinant human GDF15. Additionally, whereas the solubility of human GDF15 is less than 0.2 mg/mL in vehicle control buffer (1×PBS), the fusion molecule improved solubility to more than 50 mg/mL in vehicle control buffer (1×PBS).

As depicted in FIG. 2, administration of the fusion molecule at doses of 0.04 mg/kg, 0.12 mg/kg, 0.4 mg/kg and 1.2 mg/kg resulted in significant improvement in body weight (FIG. 2A), food intake (FIG. 2B), and non-fasted blood glucose (FIG. 2C) compared to vehicle control. In each group of mice, n=7 and p-values (*, $p<0.05$; , $p<0.01$; *, $p<0.001$) were determined by student's unpaired T-test comparing the body weight, food intake and blood glucose groups at the various concentrations to vehicle control group at each specified time point.

Referring to FIG. 2A, 22 days post-administration of the fusion molecule at the indicated doses compared to 22 days post-administration of vehicle control (PBS-injected ob/ob mice (52.5 g)) resulted in the following body weight reductions: a decrease of 1.7 g comprising a percent decrease of 3.2% (ns) for the 0.04 mg/kg dose group; a decrease of 1.8 g comprising a percent decrease of 3.5% (ns) for the 0.12 mg/kg dose group; a decrease of 1.9 g comprising a percent decrease of 3.6% (*, $p<0.05$) for the 0.40 mg/kg dose group; and a decrease of 3.2 g comprising a percent decrease of 6.1% (**, $p<0.01$) for the 1.2 mg/kg dose group.

Food intake (grams/animal/day) in ob/ob mice administered vehicle control or the fusion molecule at the indicated doses was assessed at various times during the 22 day post-administration observation period. Referring to the 9-15 day time period in FIG. 2B, average food intake relative to vehicle control (PBS)-injected ob/ob mice (7.88 g/animal/day) was as follows: average food intake decreased 0.24 g/animal/day, which comprised a percent decrease of 3.0% (ns) for 0.04 mg/kg dose group; decreased 0.92 g/animal/day, which comprised a percent decrease of 11.7% (ns) for 0.12 mg/kg dose group; decreased 1.70 g/animal/day, which comprised a percent decrease of 21.5% (, $p<0.01$) for 0.40 mg/kg dose group; and decreased 2.31 g/animal/day, which comprised a percent decrease of 29.3% (, $p<0.01$) for 1.2 mg/kg dose group.

Non-fasted blood glucose (mg/dL) in ob/ob mice administered vehicle control or the fusion molecule at the indicated doses was assessed at various time points during the 22 day post-administration observation period. Referring to FIG. 2C, relative to vehicle control (PBS-injected ob/ob mice (day 8=357.4 mg/dL), non-fasted blood glucose levels on day 8 demonstrated a decrease of 3.9 mg/dl, which comprised a percent decrease of 1.1% (ns) for 0.04 mg/kg dose group; a decrease of 62.7 mg/dL, which comprised a percent decrease of 17.5% (ns) for 0.12 mg/kg dose group; a decrease of 106.1 mg/dL, which comprised a percent decrease of 29.7% (*, $p<0.05$) for 0.40 mg/kg dose group; and a decrease of 191.1 mg/dL, which comprised a percent decrease of 53.5% (**, $p<0.01$) for 1.2 mg/kg dose group.

The data in FIG. 2 demonstrate that an HSA fusion with GDF15 is active, and that such fusion molecules represent a viable approach for enhancing certain beneficial properties of GDF15 muteins. The data also indicate that measurement of the indicated parameters may be useful as a platform for high-throughput screening of muteins.

Example 2: Improvement of GDF15 Properties Via Reduction of Surface Hydrophobicity In an effort to identify means for improving the physical properties (e.g., solubility and stability) of mature human GDF15, a set of six hydrophobic residues predicted to be surface-accessible were mutated to alanine as a means of increasing surface hydrophobicity.

Fusion molecules were generated wherein each of the six GDF15 mutein sequences was fused to HSA through the linker depicted in FIG. 1H (a non-cleavable 3×(4Gly-Ser) linker (SEQ ID NO:64); the sequences set forth in FIG. 3 neither depict the HSA component nor the linker component of the fusion molecules.

The fusion molecules were then monitored for expression as secreted disulfide-linked homodimers. FIG. 4 summarizes the data for each fusion molecule. The first two columns identify the residue of the mature human GDF15 that was mutated, the third column identifies those native residues that were substituted by alanine, and the fourth column indicates whether each resultant fusion molecule was expressed as a secreted dimer. Five of the six hydrophobicity-reduction muteins expressed and secreted as disulfide linked homodimers and were further evaluated for improvements in physical properties (w65 was not expressed as a homodimer and was not pursued further).

Example 3: Human GDF15 Muteins with Improved Solubility Characteristics

The data set forth in Example 2 were used to address solubility limitations associated with surface hydrophobicities inherent to mature human GDF15. In addition, the effect on solubility of introducing N-linked Glycosylation consensus site(s) along the sequence of mature human GDF15 was evaluated.

In order to facilitate assessment of solubility and determination of in vivo efficacy, mature, recombinant human GDF15 and GDF15 muteins were constructed as N-terminal HSA fusion molecules containing a Factor Xa proteolytic-sensitive linker (a 2×(4Gly-Ser) Factor Xa cleavable linker (SEQ ID NO:56); as described in FIG. 1F) to allow for excision of the GDF15 or the GDF15 mutein from the HSA chaperone using Factor Xa digestion. Mature, recombinant human GDF15 and GDF15 muteins were also constructed utilizing IgK as a signal peptide directly fused with the mature 112 amino acid sequence of hGDF15 (FIG. 1B) or the mutein sequence of interest; or as bacterial refolds of muteins with an N-terminal methionine. Solubility assessments were performed in 1×PBS, a stringent buffer for which improvements in the solubility of a mutein can be assessed relative to mature human GDF15 (which has a maximum observed solubility of <0.2 mg/mL in 1×PBS).

Assessment of solubility was determined based on Absorbance at 280 nm using Beer's law calculated using Extinction Coefficient (mature human GDF15=14,400/monomer) and molecular weight (mature human GDF15=12,278 Da/monomer). Muteins were categorized into one of five groups depending on their level of solubility: 0.0-0.2 mg/mL=+; 0.2-0.5 mg/mL=++; 0.5-1.0 mg/mL=+++; 1.0-5.0 mg/mL=++++; and >5.0 mg/mL=+++++.

Reduction of surface hydrophobicity of five of the GDF15 muteins (w29, w32, w52, w68 and w89) set forth in FIG. 5 was assessed via selective mutagenesis of hydrophobic residues to alanine. Comparison of the relative solubility of these five muteins to mature human GDF15 indicated that w52 and w89 were the only muteins in this class that exhibited improved solubility (++) relative to mature human GDF15 (+). The other three muteins exhibited solubility within the same range as mature human GDF15.

Reduction of the surface hydrophilicity of human GDF15 was assessed via selective mutagenesis of acidic residues to alanine with the five sequences denoted in FIG. 5 and summarized hereafter: w113, w114, w115, w116 and w117. Comparison of the relative solubility of these five muteins to mature human GDF15 indicated w116 was the only mutein in this class that exhibited improved solubility (++) relative to mature human GDF15 (+). Of the other four muteins, w113 and w115 exhibited solubility within the same range as mature human GDF15, while muteins w114 and w117 were insoluble under the conditions employed.

Next, the mature human GDF15 sequence was assessed for its ability to accommodate introduction of N-linked Glycosylation consensus site(s). In this context, a single amino acid substitution would impart the required consensus site within the mature human GDF15 sequence, the consensus site for N-linked glycosylation being defined as "Asn-Xxx-Ser/Thr", where "Xxx" cannot be a proline residue. Based on a scan of the mature human GDF15 sequence, 14 possible single-point muteins were identified that would accommodate introduction of the N-Glycan consensus site. FIG. 6 depicts the sequences of the 14 mono-glycosylation muteins, as well as additional combinatorial di-Glycosylation muteins.

Before being assessed for solubility, each of the engineered N-Glycan muteins set forth in FIG. 6 was evaluated both for secretion as a folded GDF15 homodimer into mammalian tissue culture media and for N-glycan site occupancy. As set forth in FIG. 7, ten of the fourteen mono-glycosylated muteins were secreted as folded GDF15 homodimers, whereas muteins w123, w125, w127 and w129 did not result in dimer formation. The ten mono-glycosylation muteins that secreted as homodimers were then assessed by LC/MS and SDS-PAGE gel shift to determine occupancy of N-Glycan groups on the consensus site; two of these muteins (w121 and w124) exhibited low occupancy and their solubility was not subsequently evaluated.

Engineered N-Glycan GDF15 muteins which were both secreted as homodimers and possessed high glycan occupancy within the consensus site were monitored for improvements to solubility relative to mature human GDF15. As denoted in FIG. 8A, each of the N-Glycan GDF15 muteins that was assessed using the centrifugal assay format exhibited improved solubility compared to mature human GDF15: w118: +++; w120: ++++; w122: ++; w126: ++++; w128: ++++; w130: ++++; w131: ++++; w132n: ++++; w133: ++++; w134: ++++; w135: +++++; w136: ++++; w137: ++++; w138: +++++; w139: +++++; and w140: +++++. +++++. As denoted FIG. 8B, each of the N-Glycan GDF15 muteins that was assessed using the tubidity assay format exhibited improved solubility compared to mature human GDF15: w120: ++++; w122: ++; w126: ++++; w128: ++++; w130: +++++; w131: ++++.

Acute in vivo efficacy was confirmed for those human mono-glycosylated GDF15 muteins which displayed improved solubility compared to mature human GDF15.

Referring to FIG. 9A, following subcutaneous administration of a single 0.3 mg/kg dose of mature human GDF15 or a N-glycan mutein to 7-15 week-old male ob/ob mice (n=7), food intake (grams/animal) over a 16-hour overnight period was monitored relative to a vehicle (PBS) control group. Three cohorts of mice were evaluated, and p-values were determined by an unpaired student T-test.

As shown in FIG. 9A, in the first cohort of mice, food intake decreased an average of 0.82 g/animal (a percent decrease of 17.3% (*, p<0.001)), for the mature human GDF15 dose group; decreased 0.16 g/animal (a percent decrease of 3.4% (ns)) for the w120 dose group; decreased 0.87 g/animal (a percent decrease of 18.3% (*, p<0.001)) for the w128 dose group; decreased 0.77 g/animal (a percent decrease of 16.2% (***, p<0.001)) for the w130 dose group; and decreased 0.45 g/animal (a percent decrease of 9.4% (*, p<0.05)), for the w131 dose group. The average food intake for the vehicle control dose group was 4.76 g/animal.

For the second cohort of mice shown in FIG. 9A, food intake decreased an average of 0.77 g/animal (a percent decrease of 17.1% (*, p<0.05)) for the wild-type human GDF15 dose group; decreased 0.35 g/animal (a percent decrease of 7.9% (ns)) for the w118 dose group; and decreased 0.59 g/animal (a percent decrease of 13.0% (*, p<0.05)) for the w126 dose group. The average food intake for the vehicle control dose group was 4.53 g/animal.

For the third cohort of mice shown in FIG. 9A, food intake decreased an average of 1.10 g/animal (a percent decrease of 23.4% (*, p<0.001)) for the wild-type human GDF15 dose group; and decreased 1.29 g/animal (a percent decrease of 27.4% (*, p<0.001)) for the w122 dose group. The average food intake for the vehicle control dose group was 4.70 g/animal.

Referring to FIG. 9B, following an 8-hour fast, subcutaneous administration of a single 1.0 mg/kg dose of PBS vehicle, mature human GDF15 or a N-glycan mutein was given to 17 week-old male DIO mice (n=9). Food intake following refeeding (grams/animal) over a 16-hour overnight period was monitored relative to a vehicle (PBS) control group. P-values were determined by an unpaired student T-test. Referring to FIG. 9B, food intake decreases were monitored and are reported relative to PBS vehicle. For the mature human GDF15 dose group (*; p=0.0000003), w122 (*; p=0.000006), w120 (*; p=0.00003), w118 (*; p=0.000001), w126 (*; p=0.000008), w128 (ns; p>0.05), w130 (*; p=0.0000005) and w131 (ns; p>0.05).

Example 4: Analytical Gel Filtration Analysis of Engineered N-Glycan GDF15 Muteins Hydrodynamic radii of GDF15 N-Glycan muteins were assessed relative to mature human GDF15 utilizing analytical gel filtration chromatography (see FIG. 10). A TOSOH Biosciences TSKgelG3000SW$_{XL}$ (7.8 mm ID×30 cm, 5 μm) analytical sizing column pre-equilibrated in 1× phosphate buffered saline with flow rate of 1 mL/min was used in the evaluation. Two μg of each GDF15 mutein were injected in a 20 μL volume (0.1 mg/mL), and elution times were recorded at maximum absorbance during elution of the bell-shaped curve via measurement at 280 nm.

Analytical gel filtration chromatography of mature human GDF15 indicated a non-aggregated, disulfide-linked homodimer eluting at 10.837 minutes (FIG. 10). Each of the N-linked glycan muteins increased the hydrodynamic radii of the human GDF15 disulfide-linked dimer. Thus, each mutein may potentially serve as a starting point for generating molecules having, for example, a favorable in vivo half-life.

Example 5: Expression of GDF15 Orthologs Utilizing HSA as Fusion Partner

The data set forth in Example 5 highlight the utility of HSA as a fusion partner for expression and purification of GDF15 orthologs and other BMP family members.

FIG. 11A depicts the amino acid sequences of fusion molecules comprising HSA having an IgK signal sequence (signal sequence underlined; SEQ ID NO:53) fused to the N-terminus of species orthologs of mature GDF15 *Mus musculus* (bold; SEQ ID NO:54) and *Macaca mulatta* (bold; SEQ ID NO:55) through a cleavable linker (bold and underlined; SEQ ID NO:56). FIG. 11B depicts the amino acid sequences of fusion molecules comprising HSA having an IgK signal sequence (signal sequence underlined; SEQ ID NO:53) fused to the N-terminus of mature human TGF-β1 (bold; SEQ ID NO:59) and mature human BMP2 (bold; SEQ ID NO:60) through a cleavable linker (bold and underlined; SEQ ID NO:61).

The profiles for mouse GDF15 (NP_035949.2) and *Macaca* GDF15 (EHH29815.1) mirrored that observed for human GDF15 in that they were expressed and purified as folded homodimers in the context of a HSA fusion. Factor Xa cleavage of the purified HSA fusion constructs and release/purification of the GDF15 orthologs revealed homodimers with physical properties equivalent to that of the human sequence (data not shown). The homology of the mature forms for each of mouse and *Macaca* GDF15 molecules relative to the human sequence is 67% and 95% respectively, indicating that the HSA fusion molecule template can accommodate sequence diversity in the GDF15 fusion partner.

The folding and secretion properties appeared to be altered for lower homology sequences relative to human GDF15 for family members such as the BMP class and the TGF-β class of molecules. Indeed, when expression was attempted in the HSA template for secretion that was robust for human GDF15, mouse and *Macaca* GDF15; human BMP2 (27%% sequence identity relative to human GDF15) and human TGF-β1 (22%% sequence identity relative to human GDF15) displayed poor folding and secretion properties (FIG. 12).

The ability of human GDF15 to be expressed and secreted as a fully functional and biologically active molecule can be accomplished using a polypeptide having 45% amino acid sequence identity to human GDF15 (e.g., such as mouse and *Macaca* GDF15). The ability to express and purify HAS fused to the N-Terminus of human GDF15 (or closely related molecules) containing a linker of variable length and composition has direct implications for beneficial improvements to the pharmaceutical properties of GDF15 such as solubility, expression profile, formulation and stability.

Example 6: Identification of Residues Amenable to Mutagenesis within Human GDF15 to Allow for Engineering for Improved Physical Properties A comprehensive Alanine scan was performed in which each amino acid within the mature sequence of human GDF15 was individually mutated to Alanine (with the exception of Cysteine residues so as to maintain the cysteine-knot structure/fold of GDF15). The sequences for each mutein are set forth in FIG. 13, and the expression results are detailed in FIG. 14. Each mutein described in FIG. 14 was purified and assessed for physical properties, including homo-dimeric fold and aggregation state.

The results of the Alanine scan indicated that human GDF15 is amenable to mutagenesis at all residues with the exception of five muteins; w36, w46, w62, w65 and w83 (or additionally the introduction of a novel glycosylation consensus site(s) as defined in FIG. 7: w123, w125, w127 or w129). All other muteins expressed, folded and secreted in a manner similar to that of wild-type human GDF15.

The identification of specific residues within GDF15 that can accommodate mutagenesis as described herein aids in the design and engineering of a GDF15 molecule with improved physical properties. These properties include, but are not limited to, correction of unwanted sites of in vivo and/or in vitro proteolysis; and/or sites of chemical heterogeneities such as deamidation, dehydration, succinimide formation and/or sites of oxidation; which may lead to drug inactivation and/or decreased activity.

Experimentally defined chemical heterogeneities arising from accelerated stability studies (data not shown) of mature sequence of human GDF15 demonstrated evidence of deamidation events occurring at sites N3, Q40, Q51, N56, Q60, N84, Q90 and Q95; and oxidation events occurring at sites W29, W32, M43, M57 and M86.

The results from the Alanine scan and identification of sites available for mutagenesis can be used to produce engineered constructs so as to improve and correct the demonstrated chemical heterogeneities.

For example, the identification of sites amenable to mutageneis can be used to correct the deamidation event that occurs at N3 within the mature sequence of GDF15. Having demonstrated that N3 is amenable to mutagenesis without detriment as illustrated by the N3A mutation described above, it is reasonable to expect that other amino acids could be substituted at this site, such as N3Q, N3E, N3T or N3S. Amino acids suitable for substitution can be identified by, for example, alignment of human GDF15 with a non-human ortholog (e.g., *Otolemur garnettii* (XP_003796612.1; e.g., N3T) or *Felis catus* (XP_003982125.1; e.g., N3S). Finally, a deamidation event at N3 creates an unnatural Aspartate residue at position 3, which could result in an iso-aspartate isomerization due to the presence of G4 directly C-terminal to the deamidation event (i.e., Asp-Gly site). Deamidation at site N3 could be prevented by mutating the isomerization partner Gly to a Pro (G4P) to disrupt the Asp-Gly pairing. Additionally, deamidation can be reduced via creation of an N-linked Glycosylation site at N3 via mutagenesis of D5 to either DST or DSS. Further, the deaminidation can be by truncation of the N-terminus of the mature GDF15 by removal of the first 3 residues (ΔA1-N3), 4 residues (ΔA1-G4), 5 residues (ΔA1-D5), 6 residues (ΔA1-H6) or more.

Based on the Alanine scanning mutagenesis results described above, and applying similar analysis as applied to the site N3, corrective mutations to other observed sites of heterogeneity within the mature sequence of human GDF15 include, but are not limited to: N3A, N3Q, N3E, N3S, N3T, G4P, DSS, DST, Q40A, Q40E, Q40D, Q40H, M43A, M43V, M43F, Q51A, Q51E, Q51L, Q51H, N56A, N56S, M57A, M57I, M57T, Q60A, Q60L, N84A, N84E, N84Q, N84T, M86A, M86V, Q90A, Q90E, Q90E, Q90H, Q95A, Q95E, Q95D, Q95T, Q95S.

The data set forth in Example 6 highlighted residues that are amenable to mutagenesis so as not to significantly impact folding or secretion of GDF15 when expressed as a fusion protein comprising HSA fused to the N-terminus of mature GDF15 with a non-cleavable linker.

Example 7: Expression of Solubility Improved, Half-Life Extended Molecules Comprising N-Terminal Fusions of GDF15

The effect on solubility of introducing genetic fusions to the N-terminus of mature human GDF15 was evaluated. The data set forth in Example 7 were generated using several fusion constructs schematically depicted in FIG. 15A and having the amino acid sequences set forth in FIGS. 15B-15E.

FIG. 15B is a fusion molecule comprising a signal sequence (underlined)-Fc fused to the N-terminus of mature GDF15 (bold) through a 3×(Glu-3Gly-Ser) linker (bold and underlined);

FIG. 15C is a fusion molecule comprising a signal sequence [underlined]-(Fc(+)GDF15/Fc(−) charged pair containing Fc(+)-3×(Glu-3Gly-Ser)-GDF15 and Fc(−), wherein Fc(+)GDF15/Fc(−) charged pairs were designed as a Fc(+)GDF15 fusion containing positive charge mutations in the Fc domain (D356K and D399K, underlined and bold in FIG. 15C, which can be co-transfected with a Fc(−) domain containing negative charge mutations in the Fc domain (K392D and K409D), underlined and bold in FIG. 15C.

FIG. 15D is a fusion molecule comprising an Albumin Binding Domain (ABD) fused to the N-terminus of GDF15 (bold) through a 5×Gly linker (bold and underlined); the N-terminal methionine is underlined.

FIG. 15E is a fusion molecule comprising a signal sequence (underlined)-Maltose Binding Domain (MBD) fused to the N-terminus of GDF15 (bold) through an enterokinase-cleavable 5×Gly linker (bold and underlined).

Referring to the fusion constructs described above, those containing Fc and MBD were directly purified from transiently transfected 293 cell culture. ABD fusion was expressed and purified in a similar manner to that of Mature GDF15 from bacterially expressed inclusion bodies.

In the case of the homo-dimeric Fc fusion construct (FcGDF15), the observed secreted form was composed of high molecular weight oxidized aggregates in the culture media. To circumvent this observed aggregation, a Fc(+) GDF15/Fc(−) charged pairs were designed as a Fc(+)GDF15 fusion containing positive charge mutations in the Fc domain (D356K and D399K) that can be co-transfected with a Fc(−) domain containing negative charge mutations in the Fc domain (K392D and K409D).

Solubility assessments of ABD-GDF15, MBD-GDF15 and human GDF15 (control) were performed in 1×PBS, a stringent buffer for which improvements in the solubility of a mutein can be assessed relative to mature human GDF15 (which has a maximum solubility of <0.2 mg/mL). Assessment of solubility was determined based on Absorbance at 280 nm using Beer's law calculated using Extinction Coefficient and molecular weight for each respective fusion molecule. A280 Concentrations were confirmed with Bradford protein quant at 595 nm relative to a BSA standard control. Fusion molecules were categorized into one of five groups depending on their level of solubility: 0.0-0.2 mg/mL=+; 0.2-0.5 mg/mL=++; 0.5-1.0 mg/mL=+++; 1.0-5.0 mg/mL=++++; and >5.0 mg/mL=+++++. Each of the expressed and purified fusion molecules that were assessed exhibited improved solubility compared to mature human GDF15: hGDF15: +; ABD-GDF15: +++++; MBD-GDF15: ++++(see FIG. 16 (Panel A)).

Reduction in body weight over 15 days was confirmed in vivo for the ABD fusion which displayed improved solubility compared to mature human GDF15. Following subcutaneous administration of a single 3 mg/kg dose of ABD-GDF15 into 10 week-old male ob/ob mice (n=6), body weight (grams/animal) over a 15 day period was monitored relative to a vehicle control group and p-values were determined by a two-way anova analysis (*=p<0.05; =P<0.01; *=p<0.001). In the case of ABD-GDF15, a significant reduction in body weight was observed at day 15 indicating a molecule with extended efficacy. A follow-up PK profiling of the ABD-GDF15 molecule in ob/ob mice at 0.3 mg/kg and 3 mg/kg dose subcutaneously and monitored with time points taken over two weeks (data not shown) demonstrated a T1/2 of 54.2 hrs (0.3 mg/kg) and 28.4 hrs (3 mg/kg) (and see FIG. 16 (Panel B)).

Example 8: Expression of Platypus GDF15 Ortholog Recombinant Protein and Effects on Food Intake and Body Weight in DIO Mice The data set forth in Example 8 exemplify the utility of construction and expression of biologically active GDF15 orthologs using a signal peptide and furin-cleavable pro-domain.

Mature Platypus GDF15 (*Ornithorhynchus anatinus* (Oa); AFV61279) was recombinantly produced as described herein using the construct depicted in FIG. 17A. Mature platypus GDF15 polypeptide exhibits ~45% identity to mature human GDF15 polypeptide.

The effect on overnight food intake and body weight reduction was determined in 17 week-old DIO mice (n=8) following a single, subcutaneous dose of 0.001, 0.003, 0.01, 0.03, 0.1, 0.3 and 1.0 mg/kg of mature OaGDF15. Although mature platypus GDF15 polypeptide only exhibits 45% sequence identity to mature human GDF15 polypeptide, a similar in vivo effect was observed on food intake reduction (OaGDF15=0.03 mg/kg; hGDF15=0.04 mg/kg) and body weight reduction (OaGDF15=0.04 mg/kg; hGDF15=0.01 mg/kg) based on differences of pre-dose vs. 24 post-dose, respectively (see FIG. 17B (binding curves for human GDF15 are not shown).

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A dimer comprising two polypeptides, each of the two polypeptides comprising the amino acid sequence of SEQ ID NO: 32.

2. The dimer of claim 1, wherein at least one of the two polypeptides comprises an albumin fusion, wherein an albumin, an albumin variant, or an albumin fragment is conjugated to at least one of the two polypeptides.

3. The dimer of claim 2, wherein the albumin, albumin variant, or albumin fragment is human serum albumin, a human serum albumin variant, ora human serum albumin fragment, respectively, or bovine serum albumin, a bovine serum albumin variant, or a bovine serum albumin fragment, respectively, or cyno serum albumin, a cyno serum albumin variant, or a cyno serum albumin fragment, respectively.

4. The dimer of claim 2, wherein the albumin, albumin variant, or albumin fragment is conjugated to at least one of the two polypeptides at the carboxyl terminus or the amino terminus.

5. The dimer of claim 4, wherein the albumin, albumin variant, or albumin fragment is conjugated to at least one of the two polypeptides at the amino terminus.

6. The dimer of claim 4, wherein the albumin, albumin variant, or albumin fragment is conjugated to at least one of the two polypeptides via a linker.

7. The dimer of claim 6, wherein the linker is a cleavable linker.

8. The dimer of claim 7, wherein the cleavable linker can be cleaved by a protease.

9. The dimer of claim 6, wherein the linker is a non-cleavable linker.

10. The dimer of claim 1, wherein the dimer is N-glycosylated.

11. A genetically modified mammalian host cell that expresses the dimer of claim 1.

12. A pharmaceutical composition, comprising the dimer of claim 1, and a pharmaceutically acceptable diluent, carrier or excipient.

13. A pharmaceutical composition, comprising the dimer of claim 10, and a pharmaceutically acceptable diluent, carrier or excipient.

14. A sterile container comprising the pharmaceutical composition of claim 13.

15. The sterile container of claim 14, wherein the sterile container is a syringe.

16. A kit comprising the sterile container of claim 14.

17. A method of treating obesity in a mammalian subject, the method comprising administering to the subject the dimer of claim 1, wherein the dimer is administered in an amount effective to treat obesity in the subject.

18. The method of claim 17, wherein the administering is by parenteral injection.

19. The method of claim 18, wherein the parenteral injection is subcutaneous.

20. A method of treating hyperglycemia in a mammalian subject, the method comprising administering to the subject the dimer of claim 1, wherein the dimer is administered in an amount effective to treat the hyperglycemia in the subject.

21. The method of claim 20, wherein the subject has diabetes mellitus.

22. The method of claim 20, wherein the subject is human.

23. The method of claim 20, wherein the subject is obese.

24. The method of claim 20, wherein the administering is by parenteral injection.

25. The method of claim 24, wherein the parenteral injection is subcutaneous.

26. A method of treating obesity in a mammalian subject, the method comprising administering to the subject the dimer of claim 10, wherein the dimer is administered in an amount effective to treat obesity in the subject.

27. The method of claim 26, wherein the administering is by parenteral injection.

28. The method of claim 27, wherein the parenteral injection is subcutaneous.

29. A method of treating hyperglycemia in a mammalian subject, the method comprising administering to the subject the dimer of claim 10, wherein the dimer is administered in an amount effective to treat the hyperglycemia in the subject.

30. The method of claim 29, wherein the subject has diabetes mellitus.

31. The method of claim 29, wherein the subject is human.

32. The method of claim 29, wherein the subject is obese.

33. The method of claim 29, wherein the administering is by parenteral injection.

34. The method of claim 33, wherein the parenteral injection is subcutaneous.

* * * * *